(12) United States Patent
Protter et al.

(10) Patent No.: US 9,199,985 B2
(45) Date of Patent: Dec. 1, 2015

(54) COMPOUNDS AND METHODS FOR TREATMENT OF HYPERTENSION

(75) Inventors: Andrew Asher Protter, Palo Alto, CA (US); Sarvajit Chakravarty, Mountain View, CA (US)

(73) Assignee: Medivation Technologies, Inc., San Francisco, CA (US)

( * ) Notice: Subject to any disclaimer, the term of this patent is extended or adjusted under 35 U.S.C. 154(b) by 0 days.

(21) Appl. No.: 14/000,171

(22) PCT Filed: Feb. 17, 2012

(86) PCT No.: PCT/US2012/025752
§ 371 (c)(1),
(2), (4) Date: Nov. 27, 2013

(87) PCT Pub. No.: WO2012/112963
PCT Pub. Date: Aug. 23, 2012

(65) Prior Publication Data
US 2014/0296209 A1 Oct. 2, 2014

Related U.S. Application Data

(60) Provisional application No. 61/561,773, filed on Nov. 18, 2011, provisional application No. 61/444,622, filed on Feb. 18, 2011, provisional application No. 61/444,626, filed on Feb. 18, 2011, provisional application No. 61/561,761, filed on Nov. 18, 2011, provisional application No. 61/444,547, filed on Feb. 18, 2011.

(51) Int. Cl.
| | | |
|---|---|---|
| A61K 31/40 | (2006.01) |
| A61K 31/44 | (2006.01) |
| A61K 31/55 | (2006.01) |
| C07D 471/04 | (2006.01) |
| A61K 31/437 | (2006.01) |
| A61K 31/439 | (2006.01) |
| A61K 31/4985 | (2006.01) |
| A61K 31/506 | (2006.01) |
| A61K 31/519 | (2006.01) |
| A61K 45/06 | (2006.01) |
| C07D 471/14 | (2006.01) |
| C07D 471/18 | (2006.01) |
| C07D 487/04 | (2006.01) |
| C07D 487/14 | (2006.01) |
| C07D 471/08 | (2006.01) |
| C07D 487/08 | (2006.01) |
| C07D 487/18 | (2006.01) |

(52) U.S. Cl.
CPC ............ *C07D 471/04* (2013.01); *A61K 31/437* (2013.01); *A61K 31/439* (2013.01); *A61K 31/4985* (2013.01); *A61K 31/506* (2013.01); *A61K 31/519* (2013.01); *A61K 31/55* (2013.01); *A61K 45/06* (2013.01); *C07D 471/08* (2013.01); *C07D 471/14* (2013.01); *C07D 471/18* (2013.01); *C07D 487/04* (2013.01); *C07D 487/08* (2013.01); *C07D 487/14* (2013.01); *C07D 487/18* (2013.01)

(58) Field of Classification Search
CPC ...... A61K 31/55; A61K 45/06; A61K 31/437; A61K 31/506; A61K 31/4985; A61K 31/439; A61K 31/519; C07D 471/18; C07D 471/14; C07D 471/04; C07D 471/08; C07D 487/18; C07D 487/14; C07D 487/04; C07D 487/08
USPC ............ 514/214.02, 215, 250, 275, 285, 286, 514/292, 410; 540/578, 579; 544/331, 345; 546/63, 70, 85; 548/421
See application file for complete search history.

(56) References Cited

U.S. PATENT DOCUMENTS

| | | |
|---|---|---|
| 6,187,785 B1 | 2/2001 | Zefirov et al. |
| 7,071,206 B2 | 7/2006 | Zefirov et al. |
| 7,485,634 B2 | 2/2009 | Martin et al. |
| 8,338,408 B2 | 12/2012 | Hung et al. |
| 8,338,447 B2 | 12/2012 | Hung et al. |
| 8,362,277 B2 | 1/2013 | McKnight et al. |
| 8,541,437 B2 | 9/2013 | Ivashchenko et al. |
| 8,546,381 B2 | 10/2013 | Hung et al. |
| 8,569,287 B2 | 10/2013 | Hung et al. |
| 8,604,074 B2 | 12/2013 | McKnight et al. |

(Continued)

FOREIGN PATENT DOCUMENTS

| | | |
|---|---|---|
| EP | 2 236 511 A2 | 10/2010 |
| WO | WO-2005/055951 A2 | 6/2005 |
| WO | WO-2005/055951 A3 | 6/2005 |
| WO | WO-2007/041697 A2 | 4/2007 |
| WO | WO-2007/041697 A3 | 4/2007 |

(Continued)

OTHER PUBLICATIONS

Adham, N. et al. (Jun. 23, 1998). "Functional Characterization of the Recombinant Human 5-Hydroxytryptamine$_{7(a)}$ Receptor Isoform Coupled to Adenylate Cyclase Stimulation," *The Journal of Pharmacology and Experimental Therapeutics* 287(2):508-514.

(Continued)

*Primary Examiner* — My-Chau T Tran
(74) *Attorney, Agent, or Firm* — Morrison & Foerster LLP

(57) ABSTRACT

Hydrogenated pyrido[4,3-b]indoles, pyrido[3,4-b]indoles and azepino[4,5-b]indoles are described. The compounds may bind to and are adrenergic receptor $\alpha_{2B}$ antagonists. The compounds may also bind to and antagonize adrenergic receptor $\alpha_{1B}$—The compounds may find use in therapy, e.g., to (i) reduce blood pressure and/or (ii) promote renal blood flow and/or (iii) decrease or inhibit sodium reabsorption. The compounds may also be used to treat diseases or conditions that are, or are expected to be, responsive to a decrease in blood pressure. Use of the compounds to treat cardiovascular and renal disorders is particularly described.

25 Claims, No Drawings

(56) References Cited

U.S. PATENT DOCUMENTS

| | | |
|---|---|---|
| 8,735,440 B2 | 5/2014 | McKnight et al. |
| 8,741,919 B2 | 6/2014 | Jain et al. |
| 8,791,132 B2 | 7/2014 | Protter et al. |
| 8,815,843 B2 | 8/2014 | Protter et al. |
| 8,859,561 B2 | 10/2014 | Jain et al. |
| 8,877,797 B2 | 11/2014 | McKnight et al. |
| 8,906,925 B2 | 12/2014 | Hung et al. |
| 8,907,097 B2 | 12/2014 | Hung et al. |
| 8,927,571 B2 | 1/2015 | Jain et al. |
| 8,999,977 B2 | 4/2015 | Hung et al. |
| 8,999,978 B2 | 4/2015 | Hung et al. |
| 9,006,234 B2 | 4/2015 | Jain et al. |
| 9,006,263 B2 | 4/2015 | Protter et al. |
| 9,034,865 B2 | 5/2015 | Chakravarty et al. |
| 9,034,869 B2 | 5/2015 | Hung et al. |
| 9,034,880 B2 | 5/2015 | Hung et al. |
| 9,035,056 B2 | 5/2015 | Chakravarty et al. |
| 9,040,519 B2 | 5/2015 | Chakravarty et al. |
| 9,045,482 B2 | 6/2015 | Jain et al. |
| 9,051,314 B2 | 6/2015 | Hung et al. |
| 9,079,904 B2 | 7/2015 | Jain et al. |
| 9,085,580 B2 | 7/2015 | Jain et al. |
| 2001/0020028 A1 | 9/2001 | Zefirov et al. |
| 2002/0115682 A1 | 8/2002 | Zefirov et al. |
| 2003/0225058 A1 | 12/2003 | Frank et al. |
| 2004/0044022 A1 | 3/2004 | Zefirov, Jr. et al. |
| 2005/0054634 A1 | 3/2005 | Busch et al. |
| 2005/0234311 A1 | 10/2005 | Kouchi et al. |
| 2006/0140866 A1 | 6/2006 | Zefirov et al. |
| 2007/0117834 A1 | 5/2007 | Hung |
| 2007/0117835 A1 | 5/2007 | Hung |
| 2007/0179174 A1 | 8/2007 | Bachurin et al. |
| 2007/0225316 A1 | 9/2007 | Bachurin et al. |
| 2008/0234310 A1 | 9/2008 | Bachurin et al. |
| 2009/0221627 A1 | 9/2009 | Aksinenko et al. |
| 2010/0022580 A1 | 1/2010 | Hung et al. |
| 2010/0029706 A1 | 2/2010 | Miller et al. |
| 2010/0087471 A1 | 4/2010 | Schrimpf et al. |
| 2010/0099700 A1 | 4/2010 | Hung |
| 2010/0152108 A1 | 6/2010 | Hung et al. |
| 2010/0152225 A1 | 6/2010 | Hung |
| 2010/0178277 A1 | 7/2010 | Hung et al. |
| 2010/0249105 A1 | 9/2010 | Schrimpf et al. |
| 2010/0286188 A1 | 11/2010 | Bachurin et al. |
| 2011/0046368 A1 | 2/2011 | Ivashchenko et al. |
| 2011/0112132 A1 | 5/2011 | Bachurin et al. |
| 2011/0237582 A1 | 9/2011 | Jain et al. |
| 2011/0269777 A1 | 11/2011 | Bachurin et al. |
| 2012/0022096 A1 | 1/2012 | McKnight et al. |
| 2012/0101121 A1 | 4/2012 | Bachurin et al. |
| 2012/0136008 A1 | 5/2012 | Jain et al. |
| 2013/0040977 A1 | 2/2013 | McKnight et al. |
| 2013/0079352 A1 | 3/2013 | Hung et al. |
| 2013/0123277 A1 | 5/2013 | Jain et al. |
| 2013/0131054 A1 | 5/2013 | Hung et al. |
| 2013/0131077 A1 | 5/2013 | Hung et al. |
| 2013/0137705 A1 | 5/2013 | Jain et al. |
| 2013/0172320 A1 | 7/2013 | Chakravarty et al. |
| 2013/0172366 A1 | 7/2013 | Jain et al. |
| 2013/0184269 A1 | 7/2013 | Hung et al. |
| 2013/0184303 A1 | 7/2013 | Jain et al. |
| 2013/0184304 A1 | 7/2013 | Jain et al. |
| 2013/0184306 A1 | 7/2013 | Hung et al. |
| 2013/0190293 A1 | 7/2013 | Chakravarty et al. |
| 2013/0190294 A1 | 7/2013 | Protter et al. |
| 2013/0190295 A1 | 7/2013 | Hung et al. |
| 2013/0190303 A1 | 7/2013 | Hung et al. |
| 2013/0190304 A1 | 7/2013 | Hung et al. |
| 2013/0190308 A1 | 7/2013 | Jain et al. |
| 2013/0190323 A1 | 7/2013 | Hung et al. |
| 2013/0190328 A1 | 7/2013 | Jain et al. |
| 2013/0190331 A1 | 7/2013 | Jain et al. |
| 2013/0190344 A1 | 7/2013 | Jain et al. |
| 2013/0190347 A1 | 7/2013 | Hung et al. |
| 2013/0190348 A1 | 7/2013 | Hung et al. |
| 2013/0190359 A1 | 7/2013 | Jain et al. |
| 2013/0203746 A1 | 8/2013 | Hung et al. |
| 2013/0210803 A1 | 8/2013 | Chakravarty et al. |
| 2013/0217675 A1 | 8/2013 | Chakravarty et al. |
| 2013/0225558 A1 | 8/2013 | Chakravarty et al. |
| 2014/0024643 A1 | 1/2014 | Hung et al. |
| 2014/0088086 A1 | 3/2014 | Protter et al. |
| 2014/0088087 A1 | 3/2014 | Hung et al. |
| 2014/0155384 A1 | 6/2014 | Protter et al. |
| 2014/0194414 A1 | 7/2014 | Hung et al. |
| 2014/0206711 A1 | 7/2014 | Chakravarty et al. |
| 2014/0213577 A1 | 7/2014 | Hung et al. |
| 2014/0228353 A1 | 8/2014 | Protter et al. |
| 2014/0303144 A1 | 10/2014 | Protter et al. |
| 2015/0005322 A1 | 1/2015 | Jain et al. |
| 2015/0051218 A1 | 2/2015 | Hung et al. |
| 2015/0182509 A1 | 7/2015 | Hung et al. |

FOREIGN PATENT DOCUMENTS

| | | |
|---|---|---|
| WO | WO-2007/087425 A1 | 8/2007 |
| WO | WO-2008/036400 A2 | 3/2008 |
| WO | WO-2008/036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO-2008/051599 A3 | 5/2008 |
| WO | WO-2008/060190 A2 | 5/2008 |
| WO | WO-2008/060190 A3 | 5/2008 |
| WO | WO-2008/069963 A1 | 6/2008 |
| WO | WO-2008/073231 A1 | 6/2008 |
| WO | WO-2008/115098 A2 | 9/2008 |
| WO | WO-2008/115098 A3 | 9/2008 |
| WO | WO-2008/123796 A2 | 10/2008 |
| WO | WO-2008/123796 A3 | 10/2008 |
| WO | WO-2008/123800 A2 | 10/2008 |
| WO | WO-2008/123800 A3 | 10/2008 |
| WO | WO-2008/147551 A1 | 12/2008 |
| WO | WO-2009/005771 A1 | 1/2009 |
| WO | WO-2009/017836 A1 | 2/2009 |
| WO | WO-2009/039420 A1 | 3/2009 |
| WO | WO-2009/039420 A9 | 3/2009 |
| WO | WO-2009/055828 A1 | 4/2009 |
| WO | WO-2009/082268 A2 | 7/2009 |
| WO | WO-2009/082268 A3 | 7/2009 |
| WO | WO-2009/094668 A1 | 7/2009 |
| WO | WO-2009/094668 A8 | 7/2009 |
| WO | WO-2009/094668 C1 | 7/2009 |
| WO | WO-2009/111540 A1 | 9/2009 |
| WO | WO-2009/120717 A2 | 10/2009 |
| WO | WO-2009/120717 A3 | 10/2009 |
| WO | WO-2009/120720 A1 | 10/2009 |
| WO | WO-2009/135091 A1 | 11/2009 |
| WO | WO-2010/036998 A2 | 4/2010 |
| WO | WO-2010/036998 A3 | 4/2010 |
| WO | WO-2010/051501 A1 | 5/2010 |
| WO | WO-2010/051503 A1 | 5/2010 |
| WO | WO-2010/081115 A1 | 7/2010 |
| WO | WO-2010/127177 A1 | 11/2010 |
| WO | WO-2011/008312 A2 | 1/2011 |
| WO | WO-2011/008312 A3 | 1/2011 |
| WO | WO-2011/014695 A1 | 2/2011 |
| WO | WO-2011/019417 A1 | 2/2011 |
| WO | WO-2011/038161 A1 | 3/2011 |
| WO | WO-2011/038162 A1 | 3/2011 |
| WO | WO-2011/038163 A1 | 3/2011 |
| WO | WO-2011/038164 A1 | 3/2011 |
| WO | WO-2011/103430 A1 | 8/2011 |
| WO | WO-2011/103433 A1 | 8/2011 |
| WO | WO-2011/103448 A1 | 8/2011 |
| WO | WO-2011/103460 A1 | 8/2011 |
| WO | WO-2011/103485 A1 | 8/2011 |
| WO | WO-2011/103487 A1 | 8/2011 |
| WO | WO-2012/006419 A2 | 1/2012 |
| WO | WO-2012/006419 A3 | 1/2012 |
| WO | WO-2012/112961 A1 | 8/2012 |
| WO | WO-2012/112962 A1 | 8/2012 |
| WO | WO-2012/112964 A2 | 8/2012 |
| WO | WO-2012/112964 A3 | 8/2012 |

(56) References Cited

FOREIGN PATENT DOCUMENTS

| WO | WO-2012/112965 A1 | 8/2012 |
|---|---|---|
| WO | WO-2012/112966 A1 | 8/2012 |
| WO | WO-2012/154261 A1 | 11/2012 |
| WO | WO-2014/031125 A1 | 2/2014 |
| WO | WO-2014/031165 A1 | 2/2014 |
| WO | WO-2014/031167 A1 | 2/2014 |
| WO | WO-2014/031170 A1 | 2/2014 |
| WO | WO-2014/105958 A2 | 7/2014 |
| WO | WO-2014/105958 A3 | 7/2014 |

OTHER PUBLICATIONS

Bartolini, L. et al. (1996). "Aniracetam Restores Object Recognition Impaired by Age, Scopolamine, and Nucleus Basalis Lesions," *Pharmacology Biochemistry Behavior* 53(2):277-283.
Berge, S.M. et al. (Jan. 1977). "Pharmaceutical Salts," *J. Pharm. Sci.* 66(1):1-19.
Boess, F.G. et al. (1997). "Analysis of the Ligand Binding Site of the 5-HT$_3$ Receptor Using Site Directed Mutagenesis: Importance of Glutamate 106," *Neuropharmacology* 36(4/5):637-647.
Bonhaus, D.W. et al. (1995). "The Pharmacology and Distribution of Human 5-Hydroxytryptamine$_{2B}$ (5-HT$_{2B}$) Receptor Gene Products: Comparison with 5-HT$_{2A}$ and 5-HT$_{2C}$ Receptors," *British Journal of Pharmacology* 115:622-628.
Brown, C.M. et al. (1990). "$\alpha_2$-Adrenoceptor Subtypes and Imidazoline-Like Binding Sites in the Rat Brain," *Br. J. Pharmacol.* 99:803-809.
Bubber, P. et al. (May 2005). "Mitochondrial Abnormalities in Alzheimer Brain: Mechanistic Implications," *Ann Neurol.* 57(5):695-703.
Burke, S.L. et al. (2011). "Effects of Chronic Sympatho-Inhibition on Renal Excretory Function in Renovascular Hypertension," *J. Hypertension* 29(5):945-952.
Carter, J.D. et al. (2009). "A Practical Guide to Rodent Islet Isolation and Assesment." *Biological Procedures Online* 11(1):3-31.
Chen, B. et al. (2011). "Sitagliptin Lowers Glucagon and Improves Glucose Tolerance in Prediabetic Obese SHROB Rats," *Exp. Biol. Med.* 236:309-414.
Cheng, Y. et al. (Sep. 15, 1973). "Relationship Between the Inhibition Constant ($K_I$) and the Concentration of Inhibitor Which Causes 50 Per Cent Inhibition ($I_{50}$) of an Enzymatic Reaction," *Biochem. Pharmacol.* 22(18):3099-3108.
De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.
Duprez, D.A. (2008). "Systolic Hypertension in the Elderly: Addressing an Unmet Need," *Am. J. Med.* 121 :179-184.
Ennaceur, A. et al. (1988). "A New One-Trial Test for Neurobiological Studies of Memory in Rats. 1: Behavioral Data," *Behav. Brain. Res.* 31:47-59.
Franklin, S. S. et al. (2011). "The Significance of Low DBP in US Adults with Isolated Systolic Hypertension," *J. Hypertension* 29(6):1101-1108.
García-Sáinz, J.A. et al. (Jul. 31, 1992). "Species Heterogeneity of Hepatic $\alpha_1$-Adrenoceptors: $\alpha_{1A}$-, $\alpha_{1B}$- and $\alpha_{1C}$-Subtypes," *Biochemical and Biophysical Research Communications* 186(2):760-767.
Gilliland, S.L. et al. (2000, e-pub. Feb. 29, 2000). "Characterization of Dopaminergic Compounds at hD$_{2short}$, hD$_{4.2}$ and hD$_{4.7}$ Receptors in Agonist-Stimulated [$^{35}$S]GTPγS Binding Assays," *Naunyn-Schmiedeberg's Archives of Pharmacology* 361:498-504.
Grandy, D.K. et al. (Dec. 1989). "Cloning of the cDNA and Gene for a Human D$_2$ Dopamine Receptor," *Proc. Natl. Acad. Sci. USA* 86:9762-9766.
Grossman, C.J. et al. (1993). "Development of a Radioligand Binding Assay for 5-HT$_4$ Receptors in Guinea-Pig and Rat Brain," *Br. J. Pharmacol.* 109:618-624.
Hardy, J. (1996). "New Insights Into the Genetics of Alzheimer's Disease," *Annals of Medicine* 28:255-258.

Hardy, J. (1997). "Amyloid, the Presenilins and Alzheimer's Disease," *Trends Neurosci.* 20(4):154-159.
Hayes, G. et al. (1992). "Structural Subtypes of the Dopamine D2 Receptor are Functionally Distinct: Expression of the Cloned D2$_A$ and D2$_B$ Subtypes in a Heterologous Cell Line," *Mol. Endocrinol.* 6(6):920-926.
Hoyer, D. et al. (1985). "Characterization of the 5-HT$_{1B}$ Recognition Site in Rat Brain: Binding Studies with (-)[$^{125}$I]Iodocyanopindolol," *European Journal of Pharmacology* 118:1-12.
International Search Report mailed on Apr. 22, 2011 for PCT Patent Application No. PCT/US2011/025440, filed on Feb. 18, 2011, 3 pages.
International Search Report mailed on May 30, 2012, for PCT Application No. PCT/US2012/25752, filed on Feb. 17, 2012, 3 pages.
International Search Report mailed Jun. 14, 2012 for PCT Application No. PCT/US2012/025751, filed on Feb. 17, 2012, 3 pages.
Ivashchenko, A.V. et al. (2009). Synthesis of Substituted 1, 2, 3, 4, 5, 6-Hexahydroazepine [4,3-b] Indoles. *Abstracts* 52(10):164.
Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.
Jerman, J.C. et al. (2001). "Pharmacological Characterisation of Human 5-HT$_2$ Receptor Subtypes," *European Journal of Pharmacology* 414:23-30.
Kenny, B.A. et al. (1995). "Characterization of an $\alpha_{1D}$-Adrenoceptor Mediating the Contractile Response of Rat Aorta to Noradrenaline," *British Journal of Pharmacology* 115:981-986.
Kohen, R. et al. (1996). "Cloning, Characterization and Chromosomal Localization of a Human 5-HT$_6$ Serotonin Receptor," *J. Neurochem.* 66(1):47-56.
Krueger, K. et al. (2005). "G Protein-Dependent Pharmacology of Histamine H$_3$ Receptor Ligands: Evidence for Heterogeneous Active State Receptor Conformations," *J Pharmacol Exp Ther* 314(1):271-281.
Kuhn, C.M. et al. (1987). "Exaggerated Peripheral Responses to Catecholamines Contributes to Stress-Induced Hyperglycemia in the ob/ob Mouse," *Pharmacol. Biochem. Behav.* 26:491-495.
Lohr, J.B. et al. (Aug. 28, 1995). "Motor Asymmetry, a Neurobiologic Abnormality in the Major Psychoses," *Psychiatry Research* 57(3):279-282.
Makaritsis et al. (Jan. 1999). "Role of the$\alpha_{2B}$-Adrenergic Receptor in the Development of Salt-Induced Hypertension," *Hypertension* 33(1):14-17.
Martin, G.R. (1994). "Receptors for 5-Hydroxytryptamine: Current Perspectives on Classification and Nomenclature," *Neuropharmacology* 33(3/4):261-273.
May, J.A. et al. (2003). "Evaluation of the Ocular Hypotensive Response of Serotonin 5-HT$_{1A}$ and 5-HT$_2$ Receptor Ligands in Conscious Ocular Hypertenisve Cynomolgus Monkeys," *The Journal of Pharmacology and Experimental Therapeutics* 306(1):301-309.
Meister, B. et al. (1994). Patterns of Messenger RNA Expression for Adrenergic Receptor Subtypes in the Rat Kidney, *J. Pharmacol. Exp. Therapeutics* 268(3):1606-1611.
Michel, A.D. et al. (1989). "Identification of a Single $\alpha_1$-Adrenoceptor Corresponding to the $\alpha_{1A}$-Subtype in Rat Submaxillary Gland," *Br. J. Pharmacol.* 98:883-889.
Miller, K et al. (1992). "Membrane-Bound and Solubilized Brain 5HT$_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.
Miller, T.R. et al. (1999). "Analysis of Apparent Noncompetitive Responses to Competitive H$_1$-Histamine Receptor Antagonists in Fluorescent Imaging Plate Reader-Based Calcium Assays," *Journal of Biomolecular Screening* 4(5):249-258.
Monsma, F.J. Jr. et al. (1993). "Cloning and Expression of a Novel Serotonin Receptor with High Affinity for Tricyclic Psychotropic Drugs," *Molecular Pharmacology* 43:320-327.
Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.

(56) References Cited

OTHER PUBLICATIONS

Perrin, R.J. et al. (2003). Epitope Mapping and Specificity of the Anti-α-Synuclein Monoclonal Antibody Syn-1 in Mouse Brain and Cultured Cell Lines *Neurosci. Lett.* 349:133-135.

Pfaffl, M.W. (2001). "A New Mathematical Model for Relative Quantification in Real-Time RT-PCR," *Nucleic Acids Res.* 29(9):e45.

Piercey, M.F. et al. (1988). "Dramatic Limbic and Cortical Effects Mediated by High Affinity PCP Receptors," *Life Sciences* 43(4):379-385.

Pubchem CID 10954584. Compound Summary, created on Oct. 26, 2006, located at <http://pubchem.ncbi.nlm.nih.gov/summary/summary.cgi?cid=10954584&loc=ec_rcs>, last visited Apr. 4, 2011, 3 pages.

Prichep, L.S. et al. (1994). "Quantitative EEG Correlates of Cognitive Deterioration in the Elderly," *Neurobiology of Aging* 15(1):85-90.

Reddy, P.H. et al. (2005, e-pub. Apr. 19, 2005). "Are Mitochondria Critical in the Pathogenesis of Alzheimer's Disease?" *Brain Res Rev.* 49(3):618-632.

Rees, S. et al. (Oct. 11, 1994). "Cloning and Characterisation of the Human 5-HT$_{5A}$ Serotonin Receptor," *FEBS Letters* 355:242-246.

Regard, J.B. et al. (Oct. 31, 2008). "Anatomical Profiling of G Protein-Coupled Receptor Expression," *Cell* 135:561-571.

Reisberg, B. et al. (Sep. 1982). "The Global Deterioration Scale for Assessment of Primary Degenerative Dementia," *Am. J. Psychiatry* 139(9):1136-1139.

Rosengren, A.H. et al. (Jan. 8, 2010). "Overexpression of Alpha2A-Adrenergic Receptors Contributes to Type 2 Diabetes," *Science* 327:217-220.

Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.

Ruat, M. et al. (Mar. 1990). "Reversible and Irreversible Labeling and Autoradiographic Localization of the Cerebral Histamine $H_2$ Receptor Using [$^{125}$I]Iodinated Probes," *Proc. Natl. Acad. Sci. USA* 87(5):1658-1662.

Saperstein, R. et al., (May 1990). "Effects of an $\alpha_2$-Adrenoceptor Antagonist on Glucose Tolerance in the Genetically Obese Mouse (C57BL/6J ob/ob)," *Metabolism* 39(5):445-451.

Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.

Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.

Senogles, S.E. et al. (Mar. 15, 1990). "Specificity of Receptor-G Protein Interactions. Discrimination of $G_i$ Subtypes by the $D_2$ Dopamine Receptor in a Reconstituted System," *Journal of Biological Chemistry* 265(8):4507-4514.

Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.

Swerdlow, R.H. et al. (2002). "Mitochondria in Alzheimer's Disease," *International Review of Neurobiology* 53:341-385.

Tanzi, R.E. et al. (1996). "The Gene Defects Responsible for Familial Alzheimer's Disease," *Neurobiology of Disease* 3:159-168.

Uhlén, S. et al. (1994). "The Novel *Alpha*-2 Adrenergic RadioLigand [$^3$H]-MK912 is *Alpha*-2C Selective Among Human *Alpha*-2A, *Alpha*-2B and *Alpha*-2C Adrenoceptors," *Journal of Pharmacology and Experimental Therapeutics* 271(3):1558-1565.

Uhlén, S. et al. (1998). "[$^3$H]RS79948-197 Binding to Human, Rat, Guinea Pig and Pig $\alpha_{2A}$-, $\alpha_{2B}$- and $\alpha_{2C}$-Adrenoceptors. Comparison with MK912, RX821002, Rauwolscine and Yohimbine," *European Journal of Pharmacology* 343:93-101.

Vekrellis, K. et al. (2009). "Inducible Over-Expressing of α-Synuclein in Human Neuronal Cells Leads to Caspase-Dependent Non-Apoptotic Death," *J. Neurochem.* 109:1348-1362.

Velliquette, R.A. et al. (2003). "The Role of $I_1$-Imidazoline and $\alpha_2$-Adrenergic Receptors in the Modulation of Glucose Metabolism in the Spontaneously Hypertensive Obese Rat Model of Metabolic Syndrome X," *J. Pharmacol. Exp. Ther.* 306(2):646-657.

Wade, S.M. et al., (2001). "Inverse agonist Activity at the $\alpha_{(2A)}$-Adrenergic Receptor," *Mol. Pharmacol.* 59(3):532-542.

Wang, X. et al. (2007, e-pub. Sep. 21, 2007). "Insights Into Amyloid-β-Induced Mitochondrial Dysfunction in Alzheimer Disease," *Free Radical Biology & Medicine* 43:1569-1573.

Wolf, W.A. et al. (1997). "The Serotonin 5-HT$_{2C}$ Receptor Is a Prominent Serotonin Receptor in Basal Ganglia: Evidence from Functional Studies on Serotonin-Mediated Phosphoinositide Hydrolysis," *Journal of Neurochemistry* 69(4):1449-1458.

Written Opinion mailed on Apr. 22, 2011 for PCT Patent Application No. PCT/US2011/025440, filed on Feb. 18, 2011, 7 pages.

Written Opinion mailed on May 30, 2012, for PCT Application No. PCT/US2012/25752, filed on Feb. 17, 2012, 5 pages.

Written Opinion mailed Jun. 14, 2012 for PCT Application No. PCT/US2012/025751, filed on Feb. 17, 2012, 5 pages.

U.S. Appl. No. 14/485,238, filed Sep. 12, 2014, by Jain et al.

U.S. Appl. No. 14/531,915, filed Nov. 3, 2014, by Hung et al.

Non-Final Office Action mailed on Mar. 24, 2015, for U.S. Appl. No. 13/579,908, filed Feb. 28, 2013, 13 pages.

Mancia, G. et al. (2007). 2007 Guidelines for the management of arterial hypertension: The Task Force for the Management of Arterial Hypertension of the European Society of Hypertension (ESH) and of the European Society of Cardiology (ESC), *Eur. Heart J.*, 28(12):1462-1536.

Non-Final Office Action mailed on Jul. 2, 2015, for U.S. Appl. No. 14/000,184, filed Nov. 27, 2013, 13 pages.

U.S. Appl. No. 14/758,194, filed Jun. 26, 2015, by Chakravarty et al. Correspond to WO 2014/105,958 A2.

U.S. Appl. No. 14/423,027, filed Feb. 20, 2015, by Protter et al.

U.S. Appl. No. 14/641,232, filed Mar. 6, 2015, by Protter et al.

U.S. Appl. No. 14/666,101, filed Mar. 23, 2015, by Chakravarty et al.

U.S. Appl. No. 14/701,244, filed Apr. 30, 2015, by Chakravarty et al.

U.S. Appl. No. 14/738,465, filed Jun. 12, 2015, by Jain et al.

COMPOUNDS AND METHODS FOR TREATMENT OF HYPERTENSION

CROSS-REFERENCE TO RELATED APPLICATIONS

This application is a national phase application under 35 U.S.C. §371 of International Application No. PCT/US2012/025752, filed Feb. 17, 2012, which claims priority to U.S. Provisional Patent Application No. 61/444,626 filed Feb. 18, 2011, U.S. Provisional Patent Application No. 61/561,773 filed Nov. 18, 2011, U.S. Provisional Patent Application No. 61/444,622 filed Feb. 18, 2011, U.S. Provisional Patent Application No. 61/561,761 filed Nov. 18, 2011, and U.S. Provisional Patent Application No. 61/444,547 filed Feb. 18, 2011, the disclosures of each of which are incorporated herein by reference in their entireties.

BACKGROUND OF THE INVENTION

Hypertension is a serious condition that can damage vital organs, such as the heart and kidneys, and other parts of the body, such as the central nervous system. Individuals who have hypertension may have, or be at risk of developing, dangerous diseases such as coronary heart disease and kidney failure. Hypertension, which is the leading modifiable risk factor for cardiovascular disease mortality, causes more than 7 million deaths every year worldwide.

Hypertension is the most common chronic medical condition in developed countries as well as the most common indication for physician visits and prescription medication use. Hypertension affects more than 50 million individuals in the United States and over one billion individuals worldwide, and overall prevalence may continue to increase with the advancing age of the population.

Unfortunately, despite the importance of blood pressure control and the availability of multiple classes of antihypertensive agents, the treatment of hypertension remains suboptimal. Data from the most recent National Health and Nutrition Examination Survey demonstrate that only 34% of patients with hypertension have blood pressures at their therapeutic goal. Additionally, it was shown that the majority of patients with hypertension will require two or more antihypertensive agents to achieve their goal blood pressure. Even with optimal compliance with multiple antihypertensive agents of different classes, a significant fraction of patients will not be able to achieve their goal blood pressure. The overall prevalence of resistant hypertension, defined as elevated blood pressure in spite of the use of three or more antihypertensive agents, is unknown, but small studies suggest that it ranges from 5%-16% in primary care settings to greater than 50% in nephrology clinics. Given data suggesting that increasing age and obesity are important risk factors for the development of resistant hypertension, it is expected that the overall prevalence of this condition is likely to increase due to demographic changes in the population.

Systolic blood pressure tends to increase with age and systolic hypertension is an important health issue, prominent in the elderly (Duprez, Am. J. Med. 121:179-184 (2008)). It has been suggested that this occurs as large vessels such as the aorta lose their elasticity with age and is less able to buffer the pulsative nature of cardiac output. There exists a need for a treatment for patients in such clinical setting, for example, patients with systolic hypertension accompanied with low diastolic pressure (Franklin et al. J. Hypertension 29:1101-1108 (2011)).

Metabolic syndrome is a cluster of disorders including obesity, hypertension, hypertrigleridemia, hypercholesterolemia and elevated blood sugar. Individuals with this spectrum of disorders are at increased risk of diabetes, heart disease and stroke. Agents capable of treating more than one of these disorders are desirable.

Hypertensive emergencies are defined as severe elevations in blood pressure associated with resultant organ damage (i.e. pulmonary edema, renal impairment, visual impairment, intracranial hemorrhage, or encephalopathy). The treatment of hypertensive emergencies involves aggressive and controlled blood pressure lowering in a highly monitored intensive care setting using intravenous blood pressure lowering agents. Therapeutic agents and method of treatment is needed to gradually lower blood pressure and minimize damage of end organs such as the brain, kidney, heart, and eye.

The frequency of chronic kidney disease also continues to increase worldwide as does the prevalence of end-stage renal disease. Although chronic kidney disease is often caused by hypertension, other factors such as a decrease in renal blood flow and increase in sodium retention or reabsorption can lead to renal diseases. Increased age and diabetes can also contribute to renal disease. Especially the elderly, which are a growing segment of the world population, are at increased risk for renal disease. The presence of chronic kidney disease is also associated with a large increase in cardiovascular morbidity and mortality. Consequently, the identification and reduction of chronic kidney disease has become a vital public health priority.

Thus, there remains a need for new and useful agents that are capable of (i) reducing an individual's blood pressure and/or (ii) promoting renal blood flow and/or (iii) inhibiting or decreasing sodium reabsorption.

BRIEF SUMMARY OF THE INVENTION

Hydrogenated pyrido[4,3-b]indoles, pyrido[3,4-b]indoles and azepino[4,5-b]indoles are described. Compositions and kits comprising the compounds are also provided, as are methods of using and making the compounds. Compounds provided herein may find use in treating a disease or condition that is, or is believed to be responsive to any one or more of: (i) a decrease in blood pressure; (ii) an increase in renal blood flow and (iii) a decrease or inhibition of sodium reabsorption. In one aspect, compounds provided herein are selective adrenergic receptor $\alpha_{2B}$ antagonists that may find use in treating a disease or condition that is, or is believed to be responsive to any one or more of: (i) a decrease in blood pressure; (ii) an increase in renal blood flow and (iii) a decrease or inhibition of sodium reabsorption. Compounds provided may also find use in treating diseases and/or conditions such as hypertension, congestive heart failure or a renal disease or condition.

In another aspect, compounds that promote mitochondrial health and cellular viability are also described. The compounds provided herein are selective adrenergic receptor $\alpha_{2B}$ antagonists that may find use in treating a disease or condition that is associated with dysfunction of mitochondria in a renal or cardiac cell. Compounds provided may also find use in treating diseases and/or conditions selected from the group consisting of acute renal failure, chronic renal failure, coronary ischemia, acute congestive heart failure, chronic congestive heart failure, coronary artery disease, sleep apnea, respiratory distress, hypertension, and peripheral vascular disease.

In one aspect, a method is provided of lowering blood pressure in an individual in need thereof comprising administering to the individual an effective amount of a compound of formulae (IA), (IB), (J-1) or (K-1), or a salt, solvate or N-oxide thereof, wherein formula (IA) is:

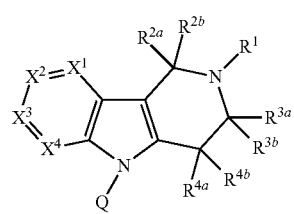
(IA)

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkyleneakoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^{2a}$ and $R^{4a}$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2CH_2$—) moiety or a propylene (—$CH_2CH_2CH_2$—) moiety, or $R^{4a}$ and $R^{2a}$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $X^1$, $X^2$, $X^3$ and $X^4$ is independently N, CH or $CR^6$;

Q is a substituted or unsubstituted aryl, substituted or unsubstituted heteroaryl, or substituted of unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and $R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkyleneakoxy, alkylsulfonylamino or acyl, provided that:
(1) at least one of $X^1$, $X^2$, $X^3$ and $X^4$ is CH or $CR^6$;
(2) when each $X^1$, $X^2$, $X^3$ and $X^4$ is independently CH or $CR^6$, none of $R^1$, $R^{2a}$, $R^{2b}$, $R^{3a}$, $R^{3b}$, $R^{4a}$ and $R^{4b}$ are taken together to form a ring and Q is an unsubstituted 6-membered aryl or an unsubstituted 6-membered heteroaryl, then Q is other than unsubstituted phenyl, unsubstituted pyridyl and unsubstituted pyrimidyl;
(3) when each $X^1$, $X^2$, $X^3$ and $X^4$ is independently CH or $CR^6$, none of $R^1$, $R^{2a}$, $R^{2b}$, $R^{3a}$, $R^{3b}$, $R^{4a}$ and $R^{4b}$ are taken together to form a ring and Q is a substituted phenyl, then Q is a phenyl substituted with a substituent selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl; and
(4) when each $X^1$, $X^2$, $X^3$ and $X^4$ is independently CH or $CR^6$, and $R^{2a}$ and $R^{3a}$ are taken together to form an ethylene (—$CH_2CH_2$—) moiety, then Q is a substituted aryl or substituted heteroaryl, where the substituted aryl or substituted heteroaryl is substituted with at least one substituent selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl;

formula (IB) is:

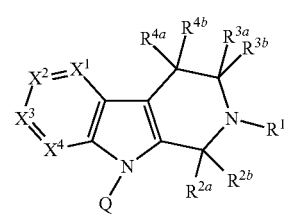
(IB)

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkyleneakoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^{2a}$ and $R^{4a}$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2CH_2$—) moiety or a propylene (—$CH_2CH_2CH_2$—) moiety, or $R^{4a}$ and $R^{2a}$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $X^1$, $X^2$, $X^3$ and $X^4$ is independently N, CH or $CR^6$;

Q is a substituted or unsubstituted aryl, substituted or unsubstituted heteroaryl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and $R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

provided that:
(1) at least one of $X^1$, $X^2$, $X^3$ and $X^4$ is $CR^6$;
(2) when none of $X^1$, $X^2$ and $X^3$ is N, and none of $R^1$, $R^{2a}$, $R^{2b}$, $R^{3a}$, $R^{3b}$, $R^{4a}$ and $R^{4b}$ are taken together to form a ring, then Q is other than an unsubstituted phenyl;
(3) when none of $X^1$, $X^2$, $X^3$ and $X^4$ is N, and $R^{2a}$ and $R^{2b}$ are taken together with the carbon to which they are attached to form a carbonyl moiety, then Q is other than a 4-substituted phenyl group; and
(4) when each $X^1$, $X^3$ and $X^4$ is CH, $X^2$ is $CR^6$ where $R^6$ is fluoro, and each $R^{2a}$, $R^{2b}$, $R^{3a}$, $R^{3b}$, $R^{4a}$ and $R^{4b}$ is H, then Q is other than 4-fluorophenyl;

formula (J-1) is:

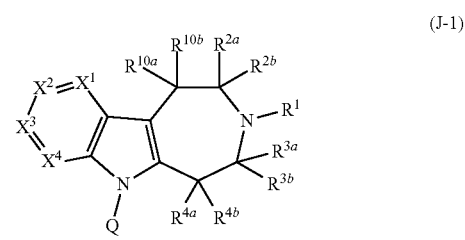

(J-1)

wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{2(a/b)}$, $R^{3(a/b)}$, $R^{4(a/b)}$ or $R^{10(a/b)}$ to form a carbonyl moiety or a cycloalkyl moiety;

each $X^1$, $X^2$ and $X^3$ is independently N, CH or $CR^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and $R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

provided that at least one of $X^1$, $X^2$, $X^3$ and $X^4$ is CH or $CR^6$;

and formula (K-1) is:

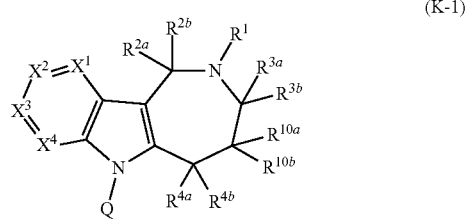

(K-1)

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$ $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{2(a/b)}$, $R^{3(a/b)}$, $R^{4(a/b)}$ or $R^{10(a/b)}$ to form a carbonyl moiety or a cycloalkyl moiety;

each $X^1$, $X^2$ and $X^3$ is independently N, CH or $CR^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and $R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thio alkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

provided that at least one of $X^1$, $X^2$, $X^3$ and $X^4$ is CH or $CR^6$.

In one variation, the individual has high blood pressure. In another variation, the method reduces one or more of the following: systolic blood pressure, diastolic blood pressure, mean arterial blood pressure, and pulse pressure of the individual, following administration of the compound. In another variation, the method does not substantially increase heart rate of the individual. In another variation, the individual has one or more risk factors for developing high blood pressure.

In another aspect of the invention, a method is provided for (i) increasing renal blood flow, and/or (ii) decreasing sodium reabsorption, in an individual in need thereof comprising administering to the individual an effective amount of a compound of the formula (IA), (IB), (J-1) or (K-1), described above.

In one variation, the method results in one of more of the following: increase in renal blood flow, decrease in sodium reabsorption, increase in urine sodium content and increase in urine volume. In another variation, the method results in any one or more of: (i) reducing edema, (ii) reducing elevated blood urea nitrogen to creatinine (BUN/Cr) ratio, and (iii) decreasing creatinine levels. In another variation, the individual has or is at risk of developing acute or chronic congestive heart failure, acute decompensated congestive heart failure, acute or chronic renal failure, or acute or chronic renal failure due to renal insufficiency.

In another aspect of the invention, a method is described for treating a disease or condition that is responsive to any one or more of: (i) a decrease in blood pressure; (ii) an increase in renal blood flow; and (iii) a decrease of sodium reabsorption, comprising administering to an individual in need thereof an effective amount of a compound of formula (IA), (IB), (J-1) or (K-1), described above.

In one variation, the disease or condition is hypertension. In another variation, the disease or condition is treatment-resistant hypertension. In another variation, the disease or condition is hypertensive emergency. In another variation, the disease or condition is a cardiac or renal disease or condition.

In the aspects described above, the compound is an adrenergic receptor $\alpha_{2B}$ antagonist. In one variation, the compound is also an adrenergic receptor $\alpha_{1B}$ antagonist. In another variation, the compound is also an adrenergic receptor $\alpha_{1D}$ antagonist.

In another aspect of the invention, a kit is described comprising (i) a compound of formula (IA) (IB), (J-1) or (K-1), described above, or a pharmaceutically acceptable salt thereof, and (ii) instructions for use according to the methods presented.

The invention also includes all salts of compounds referred to herein, such as pharmaceutically acceptable salts. The invention also includes N-oxides of the tertiary amines where one or more tertiary amine moieties are present in the compounds described. The invention also includes any or all of the stereochemical forms, including any enantiomeric or diastereomeric forms and geometric isomers of the compounds described, or mixtures thereof. Unless stereochemistry is explicitly indicated in a chemical structure or name, the structure or name is intended to embrace all possible stereoisomers, including geometric isomers, of a compound depicted. Unless olefin geometry is explicitly indicated, substituted olefinic bonds may be present as cis or trans or (Z) or (E) isomeric forms, or as mixtures thereof. In addition, where a specific stereochemical form is depicted, it is understood that other stereochemical forms are also embraced by the invention. For example, where only a Z form of a compound is specifically listed, it is understood that the E form of the compound is also embraced. All forms of the compounds are also embraced by the invention, such as crystalline or non-crystalline forms of the compounds. Compositions comprising a compound of the invention are also intended, such as a composition of substantially pure compound, which in some embodiments is a specific stereochemical form, including a specific geometric isomer. Compositions comprising a mixture of compounds of the invention in any ratio are also embraced by the invention, including mixtures of two or more stereochemical forms of a compound of the invention in any ratio, such that racemic, non-racemic, enantio-enriched and scalemic mixtures of a compound are embraced, or mixtures thereof.

The invention is also directed to pharmaceutical compositions comprising a compound of the invention and a pharmaceutically acceptable carrier or excipient. Kits comprising a compound of the invention and instructions for use are also embraced by this invention. Compounds as detailed herein or a pharmaceutically acceptable salt thereof are also provided for the manufacture of a medicament for the treatment of a disease or condition provided herein.

Also provided is use of a compound detailed herein, such as a compound of formula (IA), (IB), (J-1), (K-1) or any variations thereof, or a salt, solvate or N-oxide thereof, in lowering blood pressure, increasing renal blood flow, and/or decreasing or inhibiting sodium reabsorption. Further provided are uses of a compound detailed herein, such as a compound of formula (IA), (IB), (J-1), (K-1), or any variations thereof, or a salt, solvate or N-oxide thereof, for the manufacturing of a medicament for the treatment of a disease or condition that is responsive to any one or more of: (i) a decrease in blood pressure; (ii) an increase in renal blood flow; and (iii) a decrease of sodium reabsorption.

DETAILED DESCRIPTION OF THE INVENTION

Definitions

Unless clearly indicated otherwise, the terms "a," "an," and the like, refer to one or more.

It is also understood and clearly conveyed by this disclosure that reference to "the compound" or "a compound" includes and refers to any compounds (e.g., selective adrenergic receptor $\alpha_{2B}$ antagonists) or pharmaceutically acceptable salt or other form thereof as described herein.

Reference to "about" a value or parameter herein includes (and describes) embodiments that are directed to that value or parameter per se. For example, description referring to "about X" includes description of "X".

Unless clearly indicated otherwise, "an individual" as used herein intends a mammal, including but not limited to a human. The invention may find use in both human medicine and in the veterinary context.

As used herein, an "at risk" individual is an individual who is at risk of developing a disease or condition. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

As used herein, "treatment" or "treating" is an approach for obtaining a beneficial or desired result, including clinical results.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient, or compound which may be in a pharmaceutically acceptable carrier.

As used herein, by "pharmaceutically acceptable" is meant a material that is not biologically or otherwise undesirable, e.g., the material may be incorporated into a pharmaceutical composition administered to an individual without causing significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein includes an inert or inactive substance that may be used in the production of a drug or pharmaceutical, such as a tablet containing a compound detailed herein, or a pharmaceutically acceptable salt thereof, as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

An inverse agonist is a compound that binds to a receptor and inhibits the activity of the receptor in the absence of an agonist. An inverse agonist requires that the receptor have some constitutive basal activity in the absence of an agonist. While an agonist increases activity of the receptor over basal level an inverse agonist reduces receptor activity below basal level.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl and the like.

"Alkylene" refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—) and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —$CH_2$—CH=CH—$CH_3$ and —$CH_2$—$CH_2$-cyclohexenyl, where the ethyl group of the latter example can be attached to the cyclohexenyl moiety at any available position on the ring. Cycloalkenyl is a subset of alkenyl and can consist of one ring, such as cyclohexyl, or multiple rings, such as norbornenyl. A more preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl and the like.

"Alkynyl" refers to an unsaturated hydrocarbon group having at least one site of acetylenic unsaturation (i.e., having at least one moiety of the formula CC) and preferably having from 2 to 10 carbon atoms and more preferably 2 to 8 carbon atoms and the like.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, cycloalkyl-C(O)O—, substituted cycloalkyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. In one variation, an aralkyl is a fused ring system where at least one cycloalkyl moiety is fused with at least one aryl moiety. A "substituted aralkyl" refers to a residue in which an aryl moiety is attached to a substituted alkyl residue and wherein the aralkyl group may be attached to the parent structure at either the aryl or the alkyl residue. When an aralkyl is connected to the parent structure via the alkyl moiety, it may also be referred to as an "alkaryl". More particular alkaryl groups are those having 1 to 3 carbon atoms in the alkyl moiety (a "$C_1$-$C_3$ alkaryl").

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2- dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —NH$_2$.

"Substituted amino" refers to the group —NR$_a$R$_b$, where either (a) each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both R$_a$ and R$_b$ groups are not H; or (b) R$_a$ and R$_b$ are joined together with the nitrogen atom to form a heterocyclic or substituted heterocyclic ring.

"Acylamino" refers to the group —C(O)NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic or R$_a$ and R$_b$ groups can be joined together with the nitrogen atom to form a heterocyclic or substituted heterocyclic ring.

"Aminoacyl" refers to the group —NR$_a$C(O)R$_b$ where each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic or substituted heterocyclic. Preferably, R$_a$ is H or alkyl.

"Aminosulfonyl" refers to the groups —NRSO$_2$-alkyl, —NRSO$_2$ substituted alkyl, —NRSO$_2$-alkenyl, —NRSO$_2$-substituted alkenyl, —NRSO$_2$-alkynyl, —NRSO$_2$-substituted alkynyl, —NRSO$_2$-cycloalkyl, —NRSO$_2$-substituted cycloalkyl, —NRSO$_2$-aryl, —NRSO$_2$-substituted aryl, —NRSO$_2$-heteroaryl, —NRSO$_2$-substituted heteroaryl, —NRSO$_2$-heterocyclic, and —NRSO$_2$-substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —SO$_2$NH$_2$, —SO$_2$NR-alkyl, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$NR-heterocyclic, and —SO$_2$NR-substituted heterocyclic, where R is H or alkyl, or —SO$_2$NR$_2$, where the two R groups are taken together and with the nitrogen atom to which they are attached to form a heterocyclic or substituted heterocyclic ring.

"Sulfonyl" refers to the groups —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-aryl, —SO$_2$-substituted aryl, —SO$_2$-aralkyl, —SO$_2$-substituted aralkyl, —SO$_2$-heteroaryl, —SO$_2$-substituted heteroaryl, —SO$_2$-heterocyclic, and —SO$_2$-substituted heterocyclic.

"Aminocarbonylalkoxy" refers to the group —NR$_a$C(O) OR$_b$ where each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclyl.

"Carbonylalkylenealkoxy" refers to the group —C(O)—(CH$_2$)$_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Carbonyl" refers to the group C=O.

"Cyano" refers to the group —CN.

"Oxo" refers to the moiety =O.

"Nitro" refers to the group —NO$_2$.

"Thioalkyl" refers to the groups —S-alkyl.

"Alkylsulfonylamino" refers to the groups —R$^1$SO$_2$NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the R$_a$ and R$_b$ groups can be joined together with the nitrogen atom to form a heterocyclic or substituted heterocyclic ring and R$^1$ is an alkyl group.

"Carbonylalkoxy" refers to as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$.

"Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$.

Receptor Binding Profile

In some embodiments, compounds that bind to and are antagonists of the adrenergic receptor $\alpha_{2B}$, but which are not antagonists of the adrenergic receptor $\alpha_{2A}$, and pharmaceutically acceptable salts thereof, are provided. The compounds may find use in therapy for decreasing blood pressure in an individual and in treating diseases or conditions which are responsive to (i) a decrease in blood pressure and/or (ii) an increase in renal blood flow and/or (iii) a decrease or inhibition of sodium reabsorption or sodium retention. Thus, an individual who has a disease or condition that is responsive to (i) a decrease in blood pressure and/or (ii) an increase in renal blood flow and/or (iii) a decrease or inhibition of sodium reabsorption or sodium retention will experience one or more beneficial or desirable results upon administration of a compound provided herein, or pharmaceutically acceptable salt thereof. In one aspect, the beneficial or desirable result is a reduction in the individual's mean arterial blood pressure for a period of time following administration of the compound or pharmaceutically acceptable salt thereof. In another aspect, the beneficial or desirable result is a reduction in the individual's systolic blood pressure for a period of time following administration of the compound or pharmaceutically acceptable salt thereof. In a further aspect, the beneficial or desirable result is an increase in renal blood flow (e.g., by altering the vascular tone of renal efferent and afferent arterioles) for a period of time following administration of the compound or pharmaceutically acceptable salt thereof. In another aspect, the beneficial or desirable result is a decrease or inhibition in sodium reabsorption (e.g., thereby exerting a natriuretic and diuretic effect) for a period of time following administration of the compound or pharmaceutically acceptable salt thereof. In another aspect, the beneficial or desirable result is an increase in urine sodium and/or urine volume for a period of time following administration of the compound or pharmaceutically acceptable salt thereof. In one variation, the compounds may find use in therapy in treating diseases or conditions which are responsive to (i) a decrease in blood pressure and (ii) an increase in renal blood flow. In one variation, the compounds my find use in therapy in treating diseases or conditions which are responsive to (i) a decrease in blood pressure and (ii) a decrease or inhibition of sodium reabsorption. In one variation, the compounds may find use in treating diseases or conditions which are responsive to (i) an increase in renal blood flow and (ii) a decrease or inhibition of sodium reabsorption. In one variation, the compounds may find use in therapy in treating diseases or conditions which are responsive to (i) a decrease in blood pressure and (ii) an increase in renal blood flow and (iii) a decrease or inhibition of sodium reabsorption.

Compounds that bind to and are antagonists of the adrenergic receptor $\alpha_{2B}$ should reduce an individual's blood pressure. However, compounds that antagonize the adrenergic receptor $\alpha_{2A}$ in some instances may actually increase an individual's blood pressure. Thus, compounds that antagonize the adrenergic receptor $\alpha_{2B}$ but do not antagonize the adrenergic receptor $\alpha_{2A}$ (compounds referred to herein as "selective adrenergic receptor $\alpha_{2B}$ antagonists") are desirable agents in therapy. Selective adrenergic receptor $\alpha_{2B}$ antagonists find further use in therapy of cardiovascular and renal indications. The selective adrenergic receptor $\alpha_{2B}$ antagonists provided herein (i) bind to and are antagonists of the adrenergic receptor $\alpha_{2B}$, and (ii) are not antagonists of the adrenergic receptor $\alpha_{2A}$.

The selective adrenergic receptor $\alpha_{2B}$ antagonists may in some variations also bind to and be agonists of the adrenergic receptor $\alpha_{2A}$. The selective adrenergic receptor $\alpha_{2B}$ antagonists may also be used in conjunction with other agents that are agonists of the adrenergic receptor $\alpha_{2A}$.

The selective adrenergic receptor $\alpha_{2B}$ antagonists may in some variations also bind to and be antagonists of the adrenergic receptor $\alpha_{1D}$. The selective adrenergic receptor $\alpha_{2B}$ antagonists may also be used in conjunction with other agents that are antagonists of the adrenergic receptor $\alpha_{1B}$.

The selective adrenergic receptor $\alpha_{2B}$ antagonists may in some variations also bind to and be antagonists of the adrenergic receptor $\alpha_{1D}$. The selective adrenergic receptor $\alpha_{2B}$ antagonists may also be used in conjunction with other agents that are antagonists of the adrenergic receptor $\alpha_{1D}$.

The selective adrenergic receptor $\alpha_{2B}$ antagonists may in some variations both (i) bind to and be agonists of the adrenergic receptor $\alpha_{2A}$ and (ii) bind to and be antagonists of the adrenergic receptor $\alpha_{1B}$ and/or $\alpha_{1D}$.

In one variation, a selective adrenergic receptor $\alpha_{2B}$ antagonist exhibits (i) equal to or greater than about 60% inhibition of $\alpha_{2B}$ ligand binding at 0.03 μM and antagonist activity to adrenergic receptor $\alpha_{2B}$ and (ii) equal to or less than about 30% inhibition of $\alpha_{2A}$ ligand binding at 0.1 μM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.03 μM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.1 μM and absence of antagonist activity to adrenergic receptor $\alpha_{2A}$. In one variation, a selective adrenergic receptor $\alpha_{2B}$ antagonist exhibits (i) equal to or greater than about 60% inhibition of $\alpha_{2B}$ ligand binding at 0.1 μM and antagonist activity to adrenergic receptor $\alpha_{2B}$ and (ii) equal to or less than about 30% inhibition of $\alpha_{2A}$ ligand binding at 0.1 μM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.1 μM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.1 μM and absence of antagonist activity to adrenergic receptor $\alpha_{2A}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 μM and antagonist activity to adrenergic receptor $\alpha_{2B}$, and (ii) equal to or less than about 25% inhibition of $\alpha_{2A}$ ligand binding at 0.1 μM and absence of antagonist activity to adrenergic receptor $\alpha_{2A}$.

In one variation, a selective adrenergic receptor $\alpha_{2B}$ antagonist exhibits (i) equal to or greater than about 60% inhibition of $\alpha_{2B}$ ligand binding at 0.03 μM and antagonist activity to adrenergic receptor $\alpha_{2B}$ and (ii) equal to or less than about 30% inhibition of $\alpha_{2A}$ ligand binding at 0.03 μM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.03 μM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.03 μM and absence of antagonist activity to adrenergic receptor $\alpha_{2A}$. In one variation, a selective adrenergic receptor $\alpha_{2B}$ antagonist exhibits (i) equal to or greater than about 60% inhibition of $\alpha_{2B}$ ligand binding at 0.1 μM and antagonist activity to adrenergic receptor $\alpha_{2B}$ and (ii) equal to or less than about 30% inhibition of $\alpha_{2A}$ ligand binding at 0.03 μM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.1 μM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.03 µM and absence of antagonist activity to adrenergic receptor $\alpha_{2A}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 µM and antagonist activity to adrenergic receptor $\alpha_{2B}$, and (ii) equal to or less than about 25% inhibition of $\alpha_{2A}$ ligand binding at 0.03 µM and absence of antagonist activity to adrenergic receptor $\alpha_{2A}$.

In another variation, a selective adrenergic receptor $\alpha_{2B}$ antagonist has a Ki ratio of $\alpha_{2A}$ to $\alpha_{2B}$ that is greater than about any one of 5 or 15 or 50. Ki is the binding affinity from the Cheng-Prusoff equation: Ki=IC$_{50}$/(1+[S]/Kd), wherein [S] is the concentration of the radioligand and Kd is dissociation constant (affinity) of the radioligand for the protein (Cheng, Y., Prusoff, W. H., *Biochem. Pharmacol.* 22:3099-3108, 1973). It is understood that the Ki ratio of $\alpha_{2A}$ to $\alpha_{2B}$ may be combined with any binding and/or other activity profile details described herein for selective adrenergic receptor $\alpha_{2B}$ antagonists the same as if each were specifically and individually listed. For example, in one variation, a selective adrenergic receptor $\alpha_{2B}$ antagonist may exhibit (i) equal to or greater than about 65% inhibition of $\alpha_{2B}$ ligand binding at 0.03 µM and antagonist activity to adrenergic receptor $\alpha_{2B}$, and (ii) equal to or less than about 25% inhibition of $\alpha_{2A}$ ligand binding at 0.1 µM and absence of antagonist activity to adrenergic receptor $\alpha_{2A}$; and a Ki ratio of $\alpha_{2A}$ to $\alpha_{2B}$ that is greater than about any one of 5 or 15 or 50.

The selective adrenergic receptor $\alpha_{2B}$ antagonists may in some variations also bind to and be antagonists of the adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1B}$ ligand binding at 0.03 µM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1B}$ ligand binding at 0.03 µM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.1 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1B}$ ligand binding at 0.1 µM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1B}$ ligand binding at 0.1 µM and antagonist activity to adrenergic receptor $\alpha_{1B}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein and any of the adrenergic receptor $\alpha_{1B}$ binding profiles, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 µM and antagonist activity to adrenergic receptor $\alpha_{2B}$, (ii) equal to or less than about 25% inhibition of $\alpha_{2A}$ ligand binding at 0.1 µM and absence of antagonist activity to adrenergic receptor $\alpha_{2A}$, and (iii) equal to or greater than about 65% inhibition of $\alpha_{1B}$ ligand binding at 0.03 µM and antagonist activity to adrenergic receptor $\alpha_{1B}$. The selective adrenergic receptor $\alpha_{2B}$ antagonists may also be used in conjunction with other agents that antagonize the adrenergic receptor $\alpha_{1B}$. Administration in conjunction with another compound includes administration in the same or different composition, either sequentially, simultaneously, or continuously.

The selective adrenergic receptor $\alpha_{2B}$ antagonists may in some variations also bind to and be antagonists of the adrenergic receptor $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1D}$ ligand binding at 0.03 µM and antagonist activity to adrenergic receptor $\alpha_{1D}$. In another variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, (iii) equal to or greater than about 60% inhibition of $\alpha_{1B}$ ligand binding at 0.03 µM and antagonist activity to adrenergic receptor $\alpha_{1B}$ and (iv) equal to or greater than about 60% inhibition of $\alpha_{1D}$ ligand binding at 0.03 µM and antagonist activity to adrenergic receptor $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1D}$ and/or $\alpha_{1B}$ ligand binding at 0.03 μM and antagonist activity to adrenergic receptor $\alpha_{1D}$ and/or $\alpha_{1B}$. In one variation, the selective adrenergic receptor $\alpha_{2B}$ antagonists may exhibit (i) equal to or greater than about 60% inhibition of $\alpha_{2B}$ ligand binding at 0.1 μM and antagonist activity to adrenergic receptor $\alpha_{2B}$, (ii) equal to or less than about 30% inhibition of $\alpha_{2A}$ ligand binding at 0.1 μM and absence of antagonist activity to adrenergic receptor $\alpha_{2A}$, and (iii) equal to or greater than about 60% inhibition of $\alpha_{1B}$ and/or $\alpha_{1D}$ ligand binding at 0.1 μM and antagonist activity to adrenergic receptor $\alpha_{1B}$ and/or $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 μM and antagonist activity to adrenergic receptor $\alpha_{2B}$, (ii) equal to or less than about 30% inhibition of $\alpha_{2A}$ ligand binding at 0.1 μM and absence of antagonist activity to adrenergic receptor $\alpha_{2A}$, and (iii) equal to or greater than about 60% inhibition of $\alpha_{1B}$ and/or $\alpha_{1D}$ ligand binding at 0.1 μM and antagonist activity to adrenergic receptor $\alpha_{1B}$ and/or $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 μM and antagonist activity to adrenergic receptor $\alpha_{2B}$, (ii) equal to or less than about 30% inhibition of $\alpha_{2A}$ ligand binding at 0.1 μM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1B}$ and/or $\alpha_{1D}$ ligand binding at 0.1 μM and antagonist activity to adrenergic receptor $\alpha_{1B}$ and/or $\alpha_{1D}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein and any of the adrenergic receptor $\alpha_{1B}$ and/or $\alpha_{1D}$ binding profiles, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 μM and antagonist activity to adrenergic receptor $\alpha_{2B}$, (ii) equal to or less than about 25% inhibition of $\alpha_{2A}$ ligand binding at 0.1 μM and absence of antagonist activity to adrenergic receptor $\alpha_{2A}$, and (iii) equal to or greater than about 65% inhibition of $\alpha_{1D}$ ligand binding at 0.03 μM and antagonist activity to adrenergic receptor $\alpha_{1D}$. The selective adrenergic receptor $\alpha_{2B}$ antagonists may also be used in conjunction with other agents that antagonize the adrenergic receptor $\alpha_{1D}$. Administration in conjunction with another compound includes administration in the same or different composition, either sequentially, simultaneously, or continuously.

In some instances, compounds provided herein bind to and are antagonists of adrenergic receptor $\alpha_{2B}$ and may also be antagonists for the adrenergic receptor $\alpha_{2A}$. In such instances, it is preferable that the compound is more potent at inhibiting the adrenergic receptor $\alpha_{2B}$ compared to the adrenergic receptor $\alpha_{2A}$. In one variation, the compound inhibit both the adrenergic receptor $\alpha_{2B}$ and the adrenergic receptor $\alpha_{2A}$, and wherein the compound has limited of no brain bioavailability and so cannot easily activate adrenergic $\alpha_{2A}$ receptors in the brain. In one variation, the compound inhibit both the adrenergic receptor $\alpha_{2B}$ and the adrenergic receptor $\alpha_{2A}$, and wherein the compound has brain bioavailability. In some other instances, compounds provided herein bind to and are antagonists of adrenergic receptor $\alpha_{2B}$ and may be inverse agonists for the adrenergic receptor $\alpha_{2A}$. In some embodiments, the compound (1) binds to and is an antagonist of adrenergic receptor $\alpha_{2B}$, and (2) binds to and is an antagonist and/or inverse agonist of the adrenergic receptor $\alpha_{2A}$. In some embodiments, the compound (1) binds to and is an antagonist of adrenergic receptor $\alpha_{2B}$, (2) binds to and is an antagonist and/or inverse agonist of the adrenergic receptor $\alpha_{2A}$, and (3) binds to and is antagonist of the adrenergic receptor $\alpha_{1B}$ and/or the adrenergic receptor $\alpha_{1D}$. It is understood and clearly conveyed herein that an adrenergic receptor $\alpha_{2B}$ antagonist can exhibit any of the adrenergic receptor $\alpha_{2B}$ binding profiles (in terms of % inhibition at a given concentration and/or in terms of $K_i$) described herein in combination with any of the adrenergic receptor $\alpha_{1B}$ and/or $\alpha_{1D}$ binding profiles, as if each and every combination were listed separately.

The binding properties to adrenergic receptors of compounds disclosed herein may be assessed by methods known in the art, such as competitive binding assays. In one variation, compounds are assessed by the binding assays detailed herein. In one variation, inhibition of binding of a ligand to a receptor is measured by the assays described herein. In another variation, inhibition of binding of a ligand is measured in an assay known in the art.

Functional Assay Profile

Antagonist activity to the adrenergic receptor $\alpha_{2B}$ receptor may be assessed by methods known in the art, such as standard $\alpha_{2B}$ receptor cell membrane-based or intact cell-based activity assays. For example, the GTPγS binding or Aequorin-based assays may be used. In one variation, the selective adrenergic receptor $\alpha_{2B}$ antagonists exhibit an $IC_{50}$ value equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)) in an $\alpha_{2B}$ antagonist assay. In one variation, a selective adrenergic receptor $\alpha_{2B}$ antagonist exhibits an $IC_{50}$ value in an $\alpha_{2B}$ antagonist assay equal to or less than about 10 nM at a given concentration of agonist (e.g., concentration corresponding to $EC_{80}$ of oxymetazoline (for Aequorin assay) or guanfacine (for GTPγS assay)) in an $\alpha_{2B}$ antagonist assay. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of oxymetazoline corresponding to its $EC_{80}$ concentration as obtained by assay protocols described herein. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of oxymetazoline between about 50 nM and about 5000 nM. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of about 480 nM oxymetazoline. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of guanfacine between about 50 nM and about 5000 nM. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of about 500 nM guanfacine, which in a particular variation is 504 nM guanfacine.

The absence of antagonist activity to the adrenergic receptor $\alpha_{2A}$ may be assessed by methods known in the art, such as standard $\alpha_{2A}$ receptor intact cell-based activity assays. For example, the Aequorin-based assay may be used. It is understood and clearly conveyed that absence of antagonist activity to the adrenergic receptor $\alpha_{2A}$ intends activity that is sufficiently reduced, but not necessarily eliminated or undetectable, at the adrenergic receptor $\alpha_{2A}$. In one variation, a compound will exhibit an undetectable amount of antagonist activity to the adrenergic receptor $\alpha_{2A}$ In another variation, a compound will lack antagonist activity to the adrenergic receptor $\alpha_{2A}$ if it exhibits an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304). In one variation, the adrenergic receptor $\alpha_{2A}$ exhibits an $IC_{50}$ value in an $\alpha_{2A}$ antagonist assay that is greater than about 200 nM at a given concentration of agonist (e.g., concentration corresponding to $EC_{80}$ of UK14304). In one variation, a selective adrenergic receptor $\alpha_{2B}$ antagonist exhibits an $IC_{50}$ value in an $\alpha_{2A}$ antagonist assay greater than about any one of 50 nM, 100 nM or 200 nM at a concentration of UK14304 corresponding to its $EC_{80}$ concentration as obtained by assay protocols described herein. In one variation, a selective adrenergic receptor $\alpha_{2B}$ antagonist exhibits an $IC_{50}$ value in an $\alpha_{2A}$ antagonist assay greater than about any one of 50 nM, 100 nM or 200 nM at a concentration of UK14304 between about 0.4 nM and about 40 nM. In one variation, a selective adrenergic receptor $\alpha_{2B}$ antagonists exhibits an $IC_{50}$ value in an $\alpha_{2A}$ antagonist assay greater than about any one of 50 nM, 100 nM or 200 nM at a concentration of about 5 nM UK14304, which in a particular variation is 4.57 nM UK14304. Alternatively, a compound that does not bind the $\alpha_{2A}$ receptor will be neither an agonist nor antagonist of the $\alpha_{2A}$ receptor.

In some variations, regardless of $IC_{50}$ values obtained from $\alpha_{2B}$ and $\alpha_{2A}$ assays, a compound may nonetheless be a selective adrenergic receptor $\alpha_{2B}$ antagonist if it exhibits a Ki ratio of $\alpha_{2A}$ to $\alpha_{2B}$ that is higher than about any one of 5, 10, or 15. For example, where a compound exhibits an $IC_{50}$ value between about 50-100 nM in an $\alpha_{2B}$ antagonist assay at a given concentration of agonist (e.g., concentration corresponding to $EC_{80}$ of oxymetazoline) and an $IC_{50}$ value between about 50 and 100 nM in an $\alpha_{2A}$ antagonist assay at a given concentration of agonist (e.g., concentration corresponding to $EC_{80}$ of UK14304), the compound is considered, in one variation, a selective adrenergic receptor $\alpha_{2B}$ antagonist if it exhibits a Ki ratio of $\alpha_{2A}$ to $\alpha_{2B}$ higher than about any one of 5, 10, or 15.

Antagonist activity to adrenergic receptor $\alpha_{1B}$ may be assessed by methods known in the art, such as standard $\alpha_{1B}$ receptor intact cell-based activity assays, including the Aequorin-based assay. In one variation, a selective adrenergic receptor $\alpha_{2B}$ antagonist will also antagonize the adrenergic receptor $\alpha_{1B}$ and exhibit an $IC_{50}$ value equal to or less than about any one of 100 nM or 30 nM or 10 nM at a given concentration of agonist (e.g., concentration corresponding to $EC_{80}$ of cirazoline) in an adrenergic receptor $\alpha_{1B}$ antagonist assay. In one variation, a selective adrenergic receptor $\alpha_{2B}$ antagonist will also antagonize the adrenergic receptor $\alpha_{1B}$ and exhibit an $IC_{50}$ value equal or less than about 10 nM at a given concentration of agonist (e.g., concentration corresponding to $EC_{80}$ of cirazoline) in an adrenergic receptor $\alpha_{1B}$ antagonist assay. In one variation, the selective adrenergic receptor $\alpha_{2B}$ antagonists exhibit an $IC_{50}$ value in an $\alpha_{1B}$ antagonist assay equal to or less than about any one of 100 nM, 30 nM or 10 nM at a concentration of cirazoline corresponding to its $EC_{80}$ concentration as obtained by assay protocols described herein. In one variation, the selective adrenergic receptor $\alpha_{2B}$ antagonists exhibit an $IC_{50}$ value in an $\alpha_{1B}$ antagonist assay equal to or less than about any one of 100 nM, 30 nM or 10 nM at a concentration of cirazoline between about 2.3 nM and about 230 nM. In one variation, the selective adrenergic receptor $\alpha_{2B}$ antagonists exhibit an $IC_{50}$ value in an $\alpha_{1B}$ antagonist assay equal to or less than about any one of 100 nM, 30 nM or 10 nM at a concentration of about 25 nM cirazoline, which in a particular variation is 23.56 nM cirazoline.

Antagonist activity to adrenergic receptor $\alpha_{1D}$ may be assessed by methods known in the art, such as standard $\alpha_{1D}$ receptor intact cell-based activity assays, including the Aequorin-based assay. In one variation, a selective adrenergic receptor $\alpha_{2B}$ antagonist will also antagonize the adrenergic receptor $\alpha_{1D}$ and exhibit an $IC_{50}$ value equal to or less than about any one of 100 nM or 30 nM or 10 nM at a given concentration of agonist (e.g., concentration corresponding to $EC_{80}$ of cirazoline) in an adrenergic receptor $\alpha_{1D}$ antagonist assay. In one variation, a selective adrenergic receptor $\alpha_{2B}$ antagonist will also antagonize the adrenergic receptor $\alpha_{1D}$ and exhibit an $IC_{50}$ value equal or less than about 10 nM at a given concentration of agonist (e.g., concentration corresponding to $EC_{80}$ of cirazoline) in an adrenergic receptor $\alpha_{1D}$ antagonist assay. In one variation, the selective adrenergic receptor $\alpha_{2B}$ antagonists exhibit an $IC_{50}$ value in an $\alpha_{1D}$ antagonist assay equal to or less than about any one of 100 nM, 30 nM or 10 nM at a concentration of cirazoline corresponding to its $EC_{80}$ concentration as obtained by assay protocols described herein. In one variation, the selective adrenergic receptor $\alpha_{2B}$ antagonists exhibit an $IC_{50}$ value in an $\alpha_{1D}$ antagonist assay equal to or less than about any one of 100 nM, 30 nM or 10 nM at a concentration of cirazoline between about 2.3 nM and about 230 nM. In one variation, the selective adrenergic receptor $\alpha_{2B}$ antagonists exhibit an $IC_{50}$ value in an $\alpha_{1D}$ antagonist assay equal to or less than about any one of 100 nM, 30 nM or 10 nM at a concentration of about 25 nM cirazoline, which in a particular variation is 23.56 nM cirazoline.

In one variation, the selective adrenergic receptor $\alpha_{2B}$ antagonists exhibit (i) equal to or greater than about 60% inhibition of $\alpha_{2B}$ ligand binding at 0.03 µM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 µM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304). In some variations, the selective adrenergic receptor $\alpha_{2B}$ antagonists exhibit (i) equal to or greater than about 60% inhibition of $\alpha_{2B}$ ligand binding at 0.03 µM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 µM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304), and (iii) equal to or greater than about 60% inhibition of $\alpha_{1B}$ ligand binding at 0.03 µM and an $IC_{50}$ value in an $\alpha_{1B}$ antagonist assay equal or less than about any one of 100 nM or 30 nM or 10 nM at a given concentration of agonist (e.g., concentration corresponding to $EC_{80}$ of cirazoline). In some variations, the selective adrenergic receptor $\alpha_{2B}$ antagonists exhibit (i) equal to or greater than about 60% inhibition of $\alpha_{2B}$ ligand binding at 0.03 µM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 μM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304), and (iii) equal to or greater than about 60% inhibition of $\alpha_{1D}$ ligand binding at 0.03 μM and an $IC_{50}$ value in an $\alpha_{1D}$ antagonist assay equal or less than about any one of 100 nM or 30 nM or 10 nM at a given concentration of agonist (e.g., concentration corresponding to $EC_{80}$ of cirazoline). In some variations, the selective adrenergic receptor $\alpha_{2B}$ antagonists exhibit (i) equal to or greater than about 60% inhibition of $\alpha_{2B}$ ligand binding at 0.03 μM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 μM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304), (iii) equal to or greater than about 60% inhibition of $\alpha_{1B}$ ligand binding at 0.03 μM and an $IC_{50}$ value in an $\alpha_{1B}$ antagonist assay equal or less than about any one of 100 nM or 30 nM or 10 nM at a given concentration of agonist (e.g., concentration corresponding to $EC_{80}$ of cirazoline); and (iv) equal to or greater than about 60% inhibition of $\alpha_{1D}$ ligand binding at 0.03 μM and an $IC_{50}$ value in an $\alpha_{1D}$ antagonist assay equal or less than about any one of 100 nM or 30 nM or 10 nM at a given concentration of agonist (e.g., concentration corresponding to $EC_{80}$ of cirazoline).

In another variation, the selective adrenergic receptor $\alpha_{2B}$ antagonists exhibit (i) equal to or greater than about 60% inhibition of $\alpha_{2B}$ ligand binding at 0.03 μM and an $IC_{50}$ value in an $\alpha_{2B}$ antagonist assay equal to or less than any about one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) binding to and agonist activity to adrenergic receptor $\alpha_{2A}$.

In another variation, the adrenergic receptor $\alpha_{2B}$ antagonists exhibit (i) equal to or greater than about 60% inhibition of $\alpha_{2B}$ ligand binding at 0.03 μM and an $IC_{50}$ value in an $\alpha_{2B}$ antagonist assay equal to or less than any about one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) greater than or equal to about 50% inhibition of $\alpha_{2A}$ ligand binding at 0.1 μM and $IC_{50}$ value in an adrenergic receptor $\alpha_{2A}$ antagonist assay equal to or less than about any one of 100 nM, 30 nM or 10 nM at a concentration of UK14304 (for Aequorin assay) corresponding to its $EC_{80}$ concentration obtained by assay protocols described herein.

It is understood and clearly conveyed herein that compounds provided herein, including selective adrenergic receptor $\alpha_{2B}$ antagonists provided herein can exhibit any of the binding profiles and any of the antagonist or agonist activity profiles detailed herein, the same as if each and every combination were individually listed. For example, in one variation, the selective adrenergic receptor $\alpha_{2B}$ antagonists exhibit (i) greater than about 65% inhibition of $\alpha_{2B}$ ligand binding at 0.03 μM and an $IC_{50}$ value in an $\alpha_{2B}$ antagonist assay equal to or less than about 10 nM at a concentration of oxymetazoline corresponding to its $EC_{80}$ concentration as obtained by assay protocols described herein, and (ii) less than about 25% inhibition of $\alpha_{2A}$ ligand binding at 0.1 μM and an $IC_{50}$ value in an $\alpha_{2A}$ antagonist assay that is greater than 200 nM at a concentration of UK14304 corresponding to its $EC_{80}$ concentration as obtained by assay protocols described herein, and (iii) equal to or greater than about 60% inhibition of $\alpha_{1B}$ ligand binding at 0.03 μM and an $IC_{50}$ value in an $\alpha_{1B}$ antagonist assay equal or less than 10 nM at a concentration of cirazoline corresponding to its $EC_{80}$ concentration as obtained by assay protocols described herein. In one aspect, such a compound will also exhibit a Ki ratio of $\alpha_{2A}$ to $\alpha_{2B}$ that is greater than about any one of 5 or 15 or 50.

Medical Use

Without being bound by theory, it is believed that the compounds provided herein are capable of (i) reducing blood pressure and/or (ii) promoting renal blood flow and/or (iii) decreasing or inhibiting sodium reabsorption. In some embodiments, the compounds are adrenergic receptor $\alpha_{2B}$ antagonists (e.g., selective adrenergic receptor $\alpha_{2B}$ antagonists). In some embodiments, it is believed that the selective adrenergic receptor $\alpha_{2B}$ antagonists provided herein are capable of (i) reducing blood pressure and/or (ii) promoting renal blood flow and/or (iii) decreasing or inhibiting sodium reabsorption without concomitantly antagonizing the $\alpha_{2A}$ receptor, which would reduce or potentially eliminate the beneficial blood pressure lowering and renal effects modulated by antagonizing $\alpha_{2B}$. Furthermore, the selective adrenergic receptor $\alpha_{2B}$ antagonists provided herein may be capable of decreasing blood pressure sensitivity to salt, decreasing sodium retention, decreasing vasoconstriction in small arteries and veins, increasing insulin secretion, increasing basal metabolic rate, decreasing platelet aggregation and/or enhancing mitochondrial function. However, in certain cases where the compound has strong antagonist activities against adrenergic receptor $\alpha_{2B}$ and/or adrenergic receptor $\alpha_{1B}$, some antagonist activity against adrenergic receptor $\alpha_{2A}$ may be tolerated and even beneficial.

Compounds provided herein may be capable of mediating control of the renal function. Adrenergic $\alpha_{2B}$ receptors are located within the kidney. Regard et al. (Cell 2008; 135:561) have demonstrated that the gene for the adrenergic $\alpha_{2B}$ receptor is most abundantly expressed in the kidney. Meister et al. (J. Pharmacol. Exp. Therapeutics 1994; 268:1605) have shown by in situ hypbridization that expression predominates in the medulla outer stripe with extensions into the cortical S3 segment of the proximal tubules. Adrenergic $\alpha_{2B}$ receptor antagonists provided herein may be capable of disrupting sodium reabsorption resulting in natriuresis and diuresis. Methods to determine effects of adrenergic $\alpha_{2B}$ antagonists on renal function in a rabbit model of hypertension have been described by Burke et al. (J Hypertens 29:945-952).

In addition to reducing blood pressure, compounds disclosed herein, including adrenergic $\alpha_{2B}$ antagonists, are capable of a reduction in blood volume that might result from diueresis and/or the movement of fluid from the vascular space to the extravascular space. Reduction of blood volume results in increase in hematocrit levels which can be measured by methods known in the art, for example by estimation of erythrocyte volume fraction. Characterization of the effect of $\alpha_{2B}$ antagonists on renal function are determined by measuring urine volume, urine sodium and urine potassium using methods described by Burke et al. (Effects of chronic sympatho-inhibition on renal excretory function in renovascular hypertension Sandra L. Burke, Roger G. Evans and Geoffrey A. Head. Journal of Hypertens 29:945-952 (2011).

The compounds detailed herein are expected to find use in therapy, particularly in cardiac and renal diseases and conditions, in addition to hypertension and other conditions in which a (i) reduction in blood pressure and/or (ii) increase in renal blood flow and/or (iii) decrease in sodium reabsorption would be beneficial. In the methods provided herein, an effective amount of a compound detailed herein is administered to an individual. Methods of using compounds as described herein to (i) reduce blood pressure and/or (ii) promote renal blood flow and/or (iii) decrease or inhibit sodium reabsorption in an individual in need thereof are provided. The compounds may also find use in treating a disease or condition that is, or is expected to be, responsive to (i) a reduction in an individual's blood pressure and/or (ii) an increase in renal blood flow and/or (iii) a decrease or inhibition of sodium reabsorption. The individual may be a human who has been diagnosed with or is suspected of having high blood pressure or a disease or condition that is, or is expected to be, responsive to (i) a reduction in an individual's blood pressure and/or (ii) an increase in renal blood flow and/or (iii) a decrease or inhibition of sodium reabsorption. The individual may be a human who exhibits one or more symptoms associated with high blood pressure or a disease or condition that is, or is expected to be, responsive to (i) a reduction in an individual's blood pressure and/or (ii) an increase in renal blood flow and/or (iii) a decrease or inhibition of sodium reabsorption. The individual may be a human who is genetically or otherwise predisposed to developing high blood pressure or a disease or condition that is, or is expected to be, responsive to (i) a reduction in an individual's blood pressure and/or (ii) an increase in renal blood flow and/or (iii) a decrease or inhibition of sodium reabsorption. In one variation, the compounds may find use in treating metabolic syndrome. In some embodiments, the compounds are adrenergic receptor $\alpha_{2B}$ antagonists. In one variation, the adrenergic receptor $\alpha_{2B}$ antagonists are selective adrenergic receptor $\alpha_{2B}$ antagonists. In one variation, a compound that is an adrenergic receptor $\alpha_{2B}$ antagonist also showing adrenergic receptor $\alpha_{2A}$ antagonist and/or inverse agonist activity may find use reducing blood pressure in an individual with hypertension who is also suffering from obesity, type-2 diabetes and/or metabolic syndrome. Thus, provided is a method for lowering blood pressure in hypertensive patients with a disease or condition that is responsive to treatment using an antagonist or inverse agonist of adrenergic receptor $\alpha_{2A}$, such as obesity and/or type-2 diabetes and/or metabolic syndrome.

Compounds detailed herein may be used in a method of treating a disease or condition that is responsive to (i) a reduction in an individual's blood pressure and/or (ii) an increase in renal blood flow and/or (iii) a decrease or inhibition of sodium reabsorption. For example, the compounds may find use in treating hypertension, including treatment-resistant hypertension. In some embodiments, the compounds may be used in a method of treating hypertension in an individual not suffering from obesity or type-2 diabetes. In some embodiments, the compounds are adrenergic receptor $\alpha_{2B}$ antagonists. In some embodiments, the compounds are selective adrenergic receptor $\alpha_{2B}$ antagonists.

In one aspect, the disease or indication is a cardiac or renal disease or indication for which (i) a reduction in an individual's blood pressure and/or (ii) an increase in renal blood flow and/or (iii) a decrease or inhibition of sodium reabsorption would be, or would be expected to be, beneficial. Such cardiac indications include, but are not limited to, heart failure, such as compensated heart failure, decompensated heart failure, acute decompensated congestive heart failure and chronic congestive heart failure, coronary heart disease, cardiac arrhythmias, myocardial ischemia, and hypertrophy. Such renal indications include, but are not limited to, renal failure such as chronic renal failure, acute renal failure and endstage renal failure, renal ischemia and chronic kidney disease. Other indications for which (i) a reduction in an individual's blood pressure and/or (ii) an increase in renal blood flow and/or (iii) a decrease or inhibition of sodium reabsorption would be, or would be expected to be, beneficial include but are not limited to sleep apnea and ischemic attacks.

Compounds detailed herein may also ameliorate symptoms of a disease or condition that have a cardiac or renal component in which (i) a reduction in an individual's blood pressure and/or (ii) an increase in renal blood flow and/or (iii) a decrease or inhibition of sodium reabsorption would be, or would be expected to be, beneficial. For example, the compounds may reduce elevated blood pressure, improve shortness of breath, reduce tachycardia, reduce edema, reduce elevated blood urea nitrogen to creatinine (BUN/Cr) ratio, improve creatinine levels, improve the ability to lie flat, reduce the incidence or severity of high blood pressure, reduce the risk and/or number of acute cardiac events (e.g., acute decompensation or myocardial infarction) an individual experiences over a period of time (e.g., one year, 2 years, 5 years, etc.), reduce the incidence of acute heart failure an individual experiences over a period of time (e.g., one year, 2 years, 5 years, etc.), reduce the severity and/or incidence of pulmonary congestion and/or reduce the risk of stroke, reduce shortness of breath and/or tachycardia in individuals after myocardial infarction, improve left ventricular ejection fraction (LVEF) post infarct and/or lower weight and blood pressure in obese individuals (e.g., men and women) with prehypertension. In some embodiments, the compounds are adrenergic receptor $\alpha_{2B}$ antagonists. In some embodiments, the compounds are selective adrenergic receptor $\alpha_{2B}$ antagonists.

Compounds detailed herein (such as the adrenergic receptor $\alpha_{2B}$ antagonists detailed herein) may find use in the treatment of hypertensive emergencies. Provided is a method of treating hypertensive emergencies, comprising administering intravenously an effective amount of an adrenergic receptor $\alpha_{2B}$ antagonist to an individual in need thereof. In some embodiments, the method comprises administering intravenously an effective amount of an adrenergic receptor $\alpha_{2B}$ antagonist to an individual in need thereof in a highly monitored intensive care setting, wherein the administration results in aggressive and controlled blood pressure lowering in the individual. In some embodiments, intravenous administration of an adrenergic receptor $\alpha_{2B}$ antagonist in an individual results in gradually lowering of blood pressure in the individual and minimizing damage of end organs such as the brain, kidney, heart, and eye. Particularly useful in the treatment of hypertensive emergencies or crisis are parenteral formulations of an adrenergic receptor $\alpha_{2B}$ antagonist detailed herein. In one variation, the compound is an adrenergic receptor $\alpha_{2B}$ antagonist. In some variations, the compound is a selective adrenergic receptor $\alpha_{2B}$ antagonist. In one variation, the adrenergic receptor $\alpha_{2B}$ antagonist also exhibits adrenergic receptor $\alpha_{2A}$ antagonist and/or inverse agonist activity.

In one variation, a method of decreasing the severity and/or incidence of shortness of breath, tachycardia, edema, and/or the inability to lie flat is provided, comprising administering an effective amount of a compound detailed herein to an individual who has or is suspected of having heart failure (e.g., compensated heart failure and decompensated heart failure). In another variation, a method of decreasing the severity and/or incidence of elevated BUN/Cr, and/or edema is provided comprising administering an effective amount of a compound detailed herein to an individual who has or is suspected of having renal failure (e.g., acute or chronic renal failure). In another variation, a method of reducing blood pressure in an individual is provided comprising administering an effective amount of a compound detailed herein to an individual who has or is suspected of having hypertension (e.g., treatment-resistant hypertension). In another variation, a method of decreasing the severity and/or incidence of shortness of breath, tachycardia, and/or improving LVEF post infarct in an individual is provided comprising administering an effective amount of a compound detailed herein to an individual who has experienced myocardial infarction (e.g., an individual who has recently experienced myocardial infarction such as within 30 minutes, 1, 3, 6, 12, or 24 hours of treatment). In some of the variations, the adrenergic receptor $\alpha_{2B}$ antagonist is a selective adrenergic receptor $\alpha_{2B}$ antagonist. In some of the variations, the adrenergic receptor $\alpha_{2B}$ antagonist also exhibits antagonist activity for the adrenergic receptor $\alpha_{2A}$. In some embodiments, the compounds are adrenergic receptor $\alpha_{2B}$ antagonists. In some embodiments, the compounds are selective adrenergic receptor $\alpha_{2B}$ antagonists.

In one variation, provided is method for lowering the blood pressure in an individual in need thereof comprising administering to the individual a compound described herein, or a pharmaceutically acceptable salt thereof. Administration of an adrenergic receptor $\alpha_{2B}$ antagonist detailed herein lowers the blood pressure in the individual from a level considered above the desired level for such individual. The blood pressure lowering therapy such as administration of compounds detailed herein is intended to help hypertensive individuals reach their blood pressure goals defined by their individual cardiovascular risk factors. For example, for otherwise healthy individuals without diabetes or known cardiovascular disease, goal blood pressure is less than about 140/90 mmHg; for patients with known cardiovascular disease (e.g., prior myocardial infarction, peripheral vascular disease) goal blood pressure is less than about 130-135/85 mmHg; for patients with diabetes, goal blood pressure is less than about 130/80 mmHg.

In one variation, compounds provided herein may have any one or more of the following beneficial effects on an individual: (1) reduce arterial blood pressure (e.g., in an individual with hypertension, certain forms of heart failure and/or renal failure); (2) reduce pulse pressure (e.g., in an individual with hypertension, certain forms of heart failure and/or renal failure); (3) tachycardia-preserved baroreceptor activity (e.g., in an individual whose systolic blood pressure is expected to or does fall in response to an $\alpha_{2B}$ antagonist), which may suggest a lack of orthostatic hypotension; and (4) bradycardia-reduced cardiac work load and added reduction on blood pressure reduction by further reducing cardiac output (e.g., in an individual who has been administered a therapy that is an $\alpha_{2B}$ and $\alpha_{1B}$ mixed antagonist).

In another variation, compounds provided herein may exert their therapeutic effect with no or reduced side-effects, such as when compared to other therapies used in the treatment of the same or similar indication. In one aspect, compounds provided herein exhibit no or reduced side effects upon administration to an individual, wherein the side effects may be any one or more of: (i) reduced libido, (ii) orthostatic hypotension, (iii) muscle weakness, (iv) fatigue, (v) erectile dysfunction, (vi) constipation, (vii) depression, (viii) dizziness, (ix) dry mouth, (x) impaired thinking, (xi) weight gain, (xii) persistent cough, (xiii) chest pain, (xiv) headache, (xv) fluid retention, (xvi) racing pulse, and (xvii) emesis.

In one aspect, compounds are provided that do not bind appreciably any one or more of the histamine, dopamine and serotonin receptors. In any of the methods detailed herein, in one variation the individual does not have a cognitive disorder, psychotic disorder, neurotransmitter-mediated disorder and/or neuronal disorder. As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g., HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, mild cognitive impairment (MCI), stroke, traumatic brain injury (TBI) and age-associated memory impairment (AAMI). As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression. As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases. As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

Individuals who have high blood pressure, or a disease or condition that is, or is expected to be, responsive to (i) a reduction in an individual's blood pressure and/or (ii) an increase in renal blood flow and/or (iii) a decrease or inhibition of sodium reabsorption may benefit from the compounds detailed herein, including the adrenergic receptor $\alpha_{2B}$ antagonists (e.g., the selective adrenergic receptor $\alpha_{2B}$ antagonist) detailed herein.

An individual who does not have high blood pressure or a disease or condition that is, or is expected to be, responsive to (i) a reduction in an individual's blood pressure and/or (ii) an increase in renal blood flow and/or (iii) a decrease or inhibition of sodium reabsorption may nevertheless benefit from the compounds detailed herein if the individual has one or more risk factors for high blood pressure, or a disease or condition that is, or is expected to be, responsive to (i) a reduction in an individual's blood pressure and/or (ii) an increase in renal blood flow and/or (iii) a decrease or inhibition of sodium reabsorption. Risk factors for developing high blood pressure may include gender, race, ethnicity, age, family history, weight and/or lifestyle. For example, African-Americans, men (particularly if over age 45), woman over age 55, anyone over age 60, pre-hypertension individuals (individuals with a blood pressure of 120-130/80-89 mmHg), individuals who are overweight or obese, individuals with sleep apnea (such as obstructive sleep apnea), individuals who smoke, individuals who have a high salt diet, individuals who have a low potassium diet, individuals with chronic heavy alcohol use, individuals with a sedentary lifestyle, individuals with moderate to high stress, individuals with compromised renal function or renal failure and individuals with close relatives who have high blood pressure are each at an increased risk of developing high blood pressure themselves, or diseases or conditions associated with high blood pressure. Individuals with more than one such risk factor are particularly susceptible to developing high blood pressure. Risk factors for developing kidney disease may include diabetes, high blood pressure (hypertension), cardiovascular diseases, smoking, obesity, high cholesterol, a family history of kidney disease, and/or age 65 or older. Members of certain ethnic groups are also at higher risk for kidney disease including people of Aboriginal, Asian, south Asian, Pacific Island, African/Caribbean, American Indian and Hispanic origin.

Cell Viability and Mitochondrial Health

Methods of promoting cellular viability by promoting mitochondrial health are provided, the methods comprising contacting the cell with a compound detailed herein. The methods are applicable to various cells, such as neuronal and non-neuronal cells. In one variation, the cell is a non-neuronal cell, such as a renal or cardiac cell (e.g., myocardial muscle cell). In one aspect, methods of promoting cellular viability are provided wherein the cell is one whose viability would be, or would be expected to be, promoted by nutrient influx and/or oxygenation. Methods of promoting cellular viability in a cell experiencing, or exhibiting symptoms of, mitochondrial stress are also provided.

Methods of treating a disease or condition that is, or is expected to be, responsive to promoting mitochondrial health and cell viability are also described, the methods comprising administering to an individual in need thereof an effective amount of a compound provided herein. In one variation, the disease or condition is one which is associated with dysfunction of mitochondria in a non-neuronal cell. In a particular variation, the disease or condition is one which is associated with dysfunction of mitochondria in a renal or cardiac cell (e.g., myocardial muscle cell). In another variation, the disease or condition is one which would benefit from cellular (e.g., renal or cardiac) nutrient influx and/or oxygenation.

Thus, individuals who have a disease or condition that is associated with, or believed to be associated with, mitochondrial dysfunction may benefit from the compounds detailed herein, or pharmaceutically acceptable salts thereof. An individual who has a disease or condition that is associated with mitochondrial dysfunction should experience one or more beneficial or desirable results upon administration of an effective amount of a compound provided herein, or pharmaceutically acceptable salt thereof. In one aspect, the beneficial or desirable result is an increase in nutrient influx and/or oxygenation of a cell. In another aspect, the beneficial or desirable result is a reduction in the number and/or severity of symptoms associated with a disease or condition that is associated with mitochondrial dysfunction.

In one variation, a method of treating a renal or cardiac condition is provided, comprising administering to an individual in need thereof a compound as detailed herein. Such conditions include, but are not limited to, renal failure, such as acute renal failure and chronic renal failure, coronary (e.g., myocardial) ischemia, heart failure, such as acute and chronic congestive heart failure (including the muscle fatigue associated with these conditions), and coronary artery disease. Methods of treating other diseases and conditions are also described, such as methods of treating sleep apnea, acute respiratory distress syndrome (adult and infant) and peripheral vascular disease. The compounds as provided herein may also be used in a method of delaying the onset and/or development of a disease or condition associated with mitochondrial dysfunction, comprising administering a compound as provided herein, or a pharmaceutical salt thereof, to an individual who is at risk of developing a disease or condition associated with mitochondrial dysfunction.

Compounds that do not bind appreciably to neurotransmitter receptors but nevertheless enhance mitochondrial function, e.g., when administered to cells in the setting of mitochondrial stress (e.g., excess intracellular calcium), may be used in the methods herein to promote cell survival. In one aspect, the compounds exhibit the ability to enhance mitochondrial function by protecting against cell death mediated by mitochondrial dysfunction in an assay detailed herein. Thus, it is understood and clearly conveyed that enhancing mitochondrial function includes protecting a cell against cell death mediated by mitochondrial dysfunction. The compounds may also be assessed in assays known in the art.

It is understood and clearly conveyed that the binding and activity profiles detailed herein (e.g., in the disclosure above) in one variation apply to the formulae provided herein (e.g., the formulae for use in the methods). In one aspect, selective adrenergic receptor $\alpha_{2B}$ antagonists are of the formula (IA), (IA1), (IA2), (IA3), (IA4), (IA5), (IA6), (IA7), (IA8), (IA9), (A1), (A2), (B1), (B2), (B3), (B4), (B5), (B6), (C1), (C2) or (C3), (IB), (J-1), (J-1a), (J-1b), (J-1c), (J-2), (J-3), (J-4), (K-1), (K-1a), (K-1b), (K-1c), (K-2), (K-3), (K-4).

Compounds of the Invention

Compounds according to the invention are detailed herein, including in the Brief Summary of the Invention and elsewhere. The invention includes the use of all of the compounds described herein, including any and all stereoisomers, including geometric isomers (cis/trans or E/Z isomers), tautomers, salts and solvates of the compounds described herein, as well as methods of making such compounds.

In one aspect, compounds of the formula (IA) are provided:

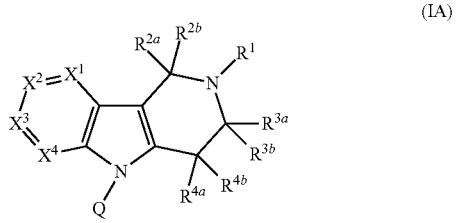

(IA)

or a salt or solvate thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^{2a}$ and $R^{4a}$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2CH_2$—) moiety or a propylene (—$CH_2CH_2CH_2$—) moiety, or $R^{4a}$ and $R^{2a}$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $X^1$, $X^2$, $X^3$ and $X^4$ is independently N, CH or $CR^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl; and each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl.

In one variation, compounds of the formula (IA) are provided:

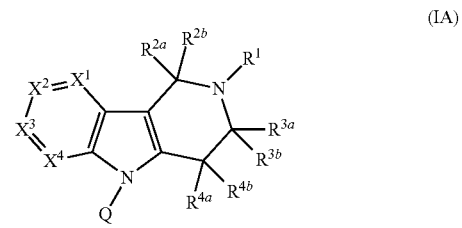

(IA)

or a salt or solvate thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^{2a}$ and $R^{4a}$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$CH$_2$—) moiety or a propylene (—CH$_2$CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;

each $X^1$, $X^2$, $X^3$ and $X^4$ is independently N, CH or $CR^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl; and each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkenyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl.

In one variation, compounds of the formula (IA), and salts and solvates thereof, are embraced, provided that at least one of $X^1$, $X^2$, $X^3$ and $X^4$ is CH or $CR^6$. In another variation, at least two of $X^1$, $X^2$, $X^3$ and $X^4$ is CH or $CR^6$.

In one variation, compounds of the formula (IA), and salts and solvates thereof, are embraced, provided that one or more of provisions (i)-(xiii) apply:

(i) when Q is an unsubstituted aryl, the aryl group is other than phenyl;

(ii) when Q is a mono-substituted aryl wherein the aryl group is phenyl, the phenyl group substituent is other than halo, nitro, methoxy, —NH$_2$, CF$_3$ and methyl;

(iii) when Q is a halo-substituted aryl wherein the aryl group is phenyl, the halo-substituted phenyl is not also substituted with a deuterium atom;

(iv) when none of $R^1$, $R^{2a}$, $R^{2b}$, $R^{3a}$, $R^{3b}$, $R^{4a}$ and $R^{4b}$ are taken together to form a ring and Q is a di-substituted phenyl wherein one of the phenyl substituents is bound to the ortho-position of the phenyl moiety via a nitrogen atom, then one or more of provisions (a)-(d) apply: (a) the phenyl moiety is not substituted with a chloro group; (b) the phenyl group is unsubstituted at the para position; (c) when $X^2$ is $CR^6$, then $R^6$ is other than an unsubstituted $C_1$-$C_8$ alkyl; (c) $R^1$ is other than an unsubstituted $C_1$-$C_8$ alkyl; and (d) the substituent bound to the ortho-position of the phenyl moiety via a nitrogen atom is other than an unsubstituted or substituted amino, —NO$_2$ or —NHOH moiety;

(v) when none of $R^1$, $R^{2a}$, $R^{2b}$, $R^{3a}$, $R^{3b}$, $R^{4a}$ and $R^{4b}$ are taken together to form a ring and Q is a di-substituted phenyl containing an ortho-chloro moiety and either a para-acylamino or a para-aminocarbonylamino moiety, then one or more of provisions (a)-(c) apply: (a) $R^{2a}$ and $R^{2b}$ are each H; (b) $R^1$ is other than an unsubstituted $C_1$-$C_8$ alkyl; and (c) at least one of $X^1$, $X^2$, $X^3$ and $X^4$ is N or $CR^6$;

(vi) when none of $R^1$, $R^{2a}$, $R^{2b}$, $R^{3a}$, $R^{3b}$, $R^{4a}$ and $R^{4b}$ are taken together to form a ring and Q is a mono-substituted phenyl wherein the substituent is bound to the meta-position of the phenyl moiety, then one or more of provisions (a)-(c) apply: (a) at least one of $X^1$, $X^2$, $X^3$ and $X^4$ is N or $CR^6$; (b) the substituent is bound to the phenyl moiety via an atom other than nitrogen; and (c) the substituent is other than a substituted amino moiety;

(vii) when none of $R^1$, $R^{2a}$, $R^{2b}$, $R^{3a}$, $R^{3b}$, $R^{4a}$ and $R^{4b}$ are taken together to form a ring and Q is a mono-substituted phenyl wherein the substituent is bound to the para-position of the phenyl moiety, then one or more of provisions (a)-(d) apply: (a) the substituent is bound to phenyl by an atom other than nitrogen or oxygen; (b) the substituent is other than an unsubstituted or substituted amino, —NO$_2$ and —OCH$_3$; (c) either each of $X^1$, $X^2$, $X^3$ and $X^4$ is CH or at least two of $X^1$, $X^2$, $X^3$ and $X^4$ are selected from N and $CR^6$; and (d) $R^1$ is other than an unsubstituted $C_1$-$C_8$ alkyl;

(viii) when none of $R^1$, $R^{2a}$, $R^{2b}$, $R^{3a}$, $R^{3b}$, $R^{4a}$ and $R^{4b}$ are taken together to form a ring and Q is an unsubstituted heteroaryl, then any one or more of provisions (a)-(e) apply: (a) at least one of $X^1$, $X^2$, $X^3$ and $X^4$ is N or $CR^6$; (b) Q is other than 2-pyridyl; (c) the heteroaryl moiety contains at least two annular nitrogen atoms; (d) the heteroaryl moiety contains an annular sulfur atom; and (e) the heteroaryl moiety contains an annular oxygen atom;

(ix) when none of $R^1$, $R^{2a}$, $R^{2b}$, $R^{3a}$, $R^{3b}$, $R^{4a}$ and $R^{4b}$ are taken together to form a ring and Q is a substituted cycloalkyl, then any one or more of provisions (a)-(g) apply: (a) at least two of $X^1$, $X^2$, $X^3$ and $X^4$ are N or $CR^6$; (b) $X^2$ is CH; (c) the substituted cycloalkyl moiety is not substituted with a hydroxyl group; (d) the substituted cycloalkyl group is substituted with more than one substituent, which may be the same or different; (e) the substituted cycloalkyl is a 3, 4 or 5-membered cycloalkyl moiety; (f) the substituted cycloalkyl is a 7, 8, 9 or 10-membered cycloalkyl moiety; and (g) at least one of $R^1$, $R^{2a}$, $R^{2b}$, $R^{3a}$, $R^{3b}$, $R^{4a}$ and $R^{4b}$ is other than H;

(x) when none of $R^1$, $R^{2a}$, $R^{2b}$, $R^{3a}$, $R^{3b}$, $R^{4a}$ and $R^{4b}$ are taken together to form a ring and Q is an unsubstituted cycloalkyl then at least one of $X^1$, $X^2$, $X^3$ and $X^4$ is N or $CR^6$;

(xi) Q is other than a substituted or unsubstituted $C_3$-$C_8$ cycloalkyl; a substituted or unsubstituted heterocyclyl moiety; and a substituted or unsubstituted $C_3$-$C_8$ cycloalkenyl moiety (xii) when none of $R^1$, $R^{2a}$, $R^{2b}$, $R^{3a}$, $R^{3b}$, $R^{4a}$ and $R^{4b}$ are taken together to form a ring and Q is a substituted heterocyclyl wherein the heterocyclyl is a 6-membered heterocyclyl group, then one or more of provisions (a)-(d) apply: (a) at least one of $X^1$, $X^2$, $X^3$ and $X^4$ is N or $CR^6$; (b) the 6-membered heterocyclyl group is a mono-substituted 6-membered heterocyclyl group; (c) the 6-membered heterocyclyl group contains at least one annular sulfur or oxygen atom; and (d) the 6-membered heterocyclyl group contains at least annular nitrogen atoms; and (xiii) when Q is a substituted heterocyclyl wherein the heterocyclyl is a 5-membered heterocyclyl group, then one or more of provisions (a)-(e) apply: (a) at least two of $X^1$, $X^2$, $X^3$ and $X^4$ are N or $CR^6$; (b) the 5-membered heterocyclyl group is a mono-substituted heterocyclyl group; (c) the 5-membered heterocyclyl group contains at least one annular sulfur or oxygen atom; (d) the 5-membered heterocyclyl group contains at least two annular nitrogen atoms; and (e) the 5-membered heterocyclyl group is not substituted with a carboxy group.

In some variations, provided are compounds of the formula (IA), where $R^1$, $R^{2a}$, $R^{2b}$, $R^{3a}$, $R^{3b}$, $R^{4a}$, $R^{4b}$, $X^1$, $X^2$, $X^3$ and $X^4$ are as defined for formula (IA), and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety. In some of these variations, one or more of provisions (i)-(xiii) apply.

In some variations, provided are compounds of the formula (IA), where $R^1$, $R^{2a}$, $R^{2b}$, $R^{3a}$, $R^{3b}$, $R^{4a}$, $R^{4b}$, $X^1$, $X^2$, $X^3$ and $X^4$ are as defined for formula (IA), and Q is a substituted or unsubstituted aryl, substituted or unsubstituted heteroaryl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety, provided that:

(xiv) when Q is substituted cycloalkenyl, any annular carbon atom of the cycloalkenyl which is adjacent to the carbon to which the parent structure is attached is not substituted with any substituent selected from the group consisting of substituted aryl, unsubstituted aryl, substituted heteroaryl, unsubstituted heteroaryl, substituted cycloalkyl, unsubstituted cycloalkyl, substituted cycloalkenyl, unsubstituted cycloalkenyl, substituted heterocyclyl, unsubstituted heterocyclyl, alkoxy, acyloxy, substituted amino, unsubstituted amino, aminoacyl, aminocarbonylalkoxy, cyano, alkynyl, carboxy, carbonylalkoxy and acylamino; and (xv) when Q is substituted heterocyclyl and the substituted heterocyclyl is attached to the parent structure at a annular carbon atom, then (a) Q is other than substituted or unsubstituted lactam; and (b) any annular carbon atom of the heterocyclyl which is adjacent to the carbon to which the parent structure is attached is not substituted with any substituent selected from the group consisting of substituted aryl, unsubstituted aryl, substituted heteroaryl, unsubstituted heteroaryl, substituted cycloalkyl, unsubstituted cycloalkyl, substituted cycloalkenyl, unsubstituted cycloalkenyl, substituted heterocyclyl, unsubstituted heterocyclyl, alkoxy, acyloxy, substituted amino, unsubstituted amino, aminoacyl, aminocarbonylalkoxy, cyano, alkynyl, carboxy, carbonylalkoxy and acylamino.

In some of these variations, one or more of provisions (i)-(xiii) further apply.

In one variation, compounds of the formula (IA), and salts and solvates thereof, are embraced, where $R^1$, $R^{2a}$, $R^{2b}$, $R^{3a}$, $R^{3b}$, $R^{4a}$, $R^{4b}$, $X^1$, $X^2$, $X^3$ and $X^4$ are as defined for formula (IA), and Q is a substituted or unsubstituted aryl, substituted or unsubstituted heteroaryl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety, provided that:

(1) at least one of $X^1$, $X^2$, $X^3$ and $X^4$ is CH or $CR^6$;

(2) when each $X^1$, $X^2$, $X^3$ and $X^4$ is independently CH or $CR^6$, none of $R^1$, $R^{2a}$, $R^{2b}$, $R^{3a}$, $R^{3b}$, $R^{4a}$ and $R^{4b}$ are taken together to form a ring and Q is an unsubstituted 6-membered aryl or an unsubstituted 6-membered heteroaryl, then Q is other than unsubstituted phenyl, unsubstituted pyridyl and unsubstituted pyrimidyl;

(3) when each $X^1$, $X^2$, $X^3$ and $X^4$ is independently CH or $CR^6$, none of $R^1$, $R^{2a}$, $R^{2b}$, $R^{3a}$, $R^{3b}$, $R^{4a}$ and $R^{4b}$ are taken together to form a ring and Q is a substituted phenyl, then Q is a phenyl substituted with a substituent selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl; and (4) when each $X^1$, $X^2$, $X^3$ and $X^4$ is independently CH or $CR^6$, and $R^{2a}$ and $R^{3a}$ are taken together to form an ethylene ($-CH_2CH_2-$) moiety, then Q is a substituted aryl or substituted heteroaryl, where the substituted aryl or substituted heteroaryl is substituted with at least one substituent selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl.

In another variation, provided is a compound of the formula (IA), provided that each of provisions (i)-(xi) applies. In another variation, the compound is of the formula (IA), provided that each of provisions (i)-(x), (xii) and (xiii) applies. In yet another variation, the compound is of the formula (IA), provided that each of provisions (i)-(xiii) applies.

In another aspect of the invention, compounds of the formula (IB) are provided:

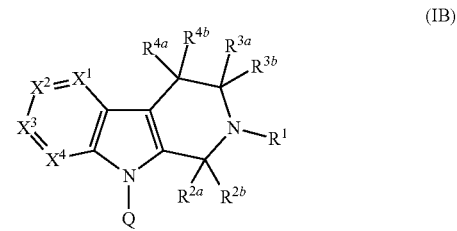

(IB)

or a salt or solvate thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene ($-CH_2CH_2CH_2-$) moiety or a butylene ($-CH_2CH_2CH_2CH_2-$) moiety, or $R^1$ and $R^{3a}$ are taken together to form a propylene ($-CH_2CH_2CH_2-$) moiety or a butylene ($-CH_2CH_2CH_2CH_2-$) moiety, or $R^1$ and $R^{4a}$ are taken together to form an ethylene ($-CH_2CH_2-$) moiety or a propylene ($-CH_2CH_2CH_2-$) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^{2a}$ and $R^{4a}$ are taken together to form a methylene (—CH$_2$—) moiety or an ethylene (—CH$_2$CH$_2$—) moiety;

each $R^{3a}$ and $R^{3b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$CH$_2$—) moiety or a propylene (—CH$_2$CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;

each $X^1$, $X^2$, $X^3$ and $X^4$ is independently N, CH or CR$^6$;

Q is a substituted or unsubstituted aryl, substituted or unsubstituted heteroaryl, substituted or unsubstituted cycloalkyl, substituted or unsubstituted cycloalkenyl, or substituted or unsubstituted heterocyclyl; and each $R^6$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl.

In one variation, compounds of the formula (IB) are provided:

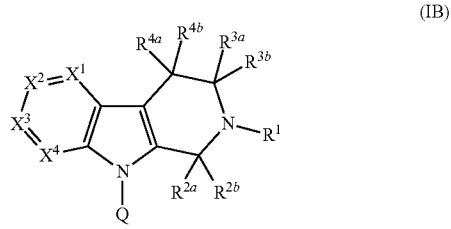

(IB)

or a salt or solvate thereof; wherein:

$R^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^{4a}$ are taken together to form an ethylene (—CH$_2$CH$_2$—) moiety or a propylene (—CH$_2$CH$_2$CH$_2$—) moiety;

each $R^{2a}$ and $R^{2b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^{2a}$ and $R^{4a}$ are taken together to form a methylene (—CH$_2$—) moiety or an ethylene (—CH$_2$CH$_2$—) moiety;

each $R^{3a}$ and $R^{3b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$CH$_2$—) moiety or a propylene (—CH$_2$CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;

each $X^1$, $X^2$, $X^3$ and $X^4$ is independently N, CH or CR$^6$;

Q is a substituted or unsubstituted aryl, substituted or unsubstituted heteroaryl, substituted or unsubstituted cycloalkyl, substituted or unsubstituted cycloalkenyl, or substituted or unsubstituted heterocyclyl; and each $R^6$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl.

In one variation, compounds of the formula (IB), and salts and solvates thereof, are embraced, provided that at least one of $X^1$, $X^2$, $X^3$ and $X^4$ is CH or $CR^6$. In another variation, at least two of $X^1$, $X^2$, $X^3$ and $X^4$ is CH or $CR^6$.

In one variation, compounds of the formula (IB), and salts and solvates thereof, are embraced, provided that on or more of provisions (xxi)-(xxix) apply:
  (xxi) when Q is an unsubstituted aryl, the aryl group is other than phenyl;
  (xxii) when Q is a mono-substituted aryl wherein the aryl group is phenyl, the phenyl group is substituted with a moiety other than halo and —C(=NH)NH$_2$;
  (xxiii) when Q is a substituted aryl wherein the aryl group is a phenyl substituted with two or more substituents which may be the same or different, then at least one of provisions (a)-(c) applies: (a) the phenyl group is substituted with at least one moiety other than methyl; (b) at least one of $X^1$, $X^2$, $X^3$ and $X^4$ is N or $CR^6$; and (c) none of $R^1$, $R^{2a}$, $R^{2b}$, $R^{3a}$, $R^{3b}$, $R^{4a}$ and $R^{4b}$ are taken together to form a ring;
  (xxiv) when none of $R^1$, $R^{2a}$, $R^{2b}$, $R^{3a}$, $R^{3b}$, $R^{4a}$ and $R^{4b}$ are taken together to form a ring and Q is a mono-substituted phenyl wherein the substituent is bound to the para-position of the phenyl moiety, then one or both of provisions (a) and (b) apply: (a) least one of $X^1$, $X^2$, $X^3$ and $X^4$ is N or $CR^6$; and (b) the phenyl substituent is other than —OCH$_3$ and a substituted pyridyl;
  (xxv) when none of $R^1$, $R^{2a}$, $R^{2b}$, $R^{3a}$, $R^{3b}$, $R^{4a}$ and $R^{4b}$ are taken together to form a ring and Q is a substituted aryl other than phenyl, then one or both of provisions (a) and (b) apply: (a) least one of $X^1$, $X^2$, $X^3$ and $X^4$ is N or $CR^6$; and (b) $R^1$ is a substituted or unsubstituted $C_1$-$C_8$ alkyl;
  (xxvi) when Q is an unsubstituted cycloalkyl, then at least one of provisions (a)-(c) applies: (a) at least one of $X^1$, $X^2$, $X^3$ and $X^4$ is $CR^6$; (b) none of $R^1$, $R^{2a}$, $R^{2b}$, $R^{3a}$, $R^{3b}$, $R^{4a}$ and $R^{4b}$ are taken together to form a ring; and (c) the unsubstituted cycloalkyl has greater than 3 annular carbon atoms;
  (xxvii) when Q is a substituted heterocyclyl wherein the heterocyclyl group is a 6-membered heterocyclyl, then at least one of provisions (a)-(d) applies: (a) at least one of $X^1$, $X^2$, $X^3$ and $X^4$ is $CR^6$; (b) $R^1$ is a substituted or unsubstituted $C_1$-$C_8$ alkyl; (c) the substituted heterocyclyl group contains an annular sulfur atom; and (d) the substituted heterocyclyl group contains at least two annular heteroatoms;
  (xxviii) when Q is a substituted heterocyclyl wherein the heterocyclyl group is a 5-membered heterocyclyl then at least one of provisions (a)-(c) applies: (a) at least one of $X^1$, $X^2$, $X^3$ and $X^4$ is $CR^6$; (b) the substituted heterocyclyl group does not contain a carboxyl moiety; and (c) the substituted heterocyclyl group is substituted with more than one substituents, which may be the same or different;
  (xxix) when none of $R^1$, $R^{2a}$, $R^{2b}$, $R^{3a}$, $R^{3b}$, $R^{4a}$ and $R^{4b}$ are taken together to form a ring and Q is an unsubstituted heterocyclyl then one or more of provisions (a)-(d) apply: (a) (a) at least two of $X^1$, $X^2$, $X^3$ and $X^4$ are N or $CR^6$; (b) the heterocyclyl group contains an annular nitrogen or sulfur atom; (c) the heterocyclyl group is a 3, 4 or 5-membered heterocyclyl group; and (d) the heterocyclyl group is a 7 or 8 membered heterocyclic group.

In some variations, provided are compounds of the formula (IB), where $R^1$, $R^{2a}$, $R^{2b}$, $R^{3a}$, $R^{3b}$, $R^{4a}$, $R^{4b}$, $X^1$, $X^2$, $X^3$ and $X^4$ are as defined for formula (IB), and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety. In some of these variations, one or more of provisions (xxi)-(xxix) apply.

In some variations, provided are compounds of the formula (IB), where $R^1$, $R^{2a}$, $R^{2b}$, $R^{3a}$, $R^{3b}$, $R^{4a}$, $R^{4b}$, $X^1$, $X^2$, $X^3$ and $X^4$ are as defined for formula (IB), and Q is a substituted or unsubstituted aryl, substituted or unsubstituted heteroaryl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety, provided that:
  (xxx) when Q is substituted cycloalkenyl, any annular carbon atom of the cycloalkenyl which is adjacent to the carbon to which the parent structure is attached is not substituted with any substituent selected from the group consisting of substituted aryl, unsubstituted aryl, substituted heteroaryl, unsubstituted heteroaryl, substituted cycloalkyl, unsubstituted cycloalkyl, substituted cycloalkenyl, unsubstituted cycloalkenyl, substituted heterocyclyl, unsubstituted heterocyclyl, alkoxy, acyloxy, substituted amino, unsubstituted amino, aminoacyl, aminocarbonylalkoxy, cyano, alkynyl, carboxy, carbonylalkoxy and acylamino; and
  (xxxi) when Q is substituted heterocyclyl and the substituted heterocyclyl is attached to the parent structure at a annular carbon atom, then (a) Q is other than substituted or unsubstituted lactam; and (b) any annular carbon atom of the heterocyclyl which is adjacent to the carbon to which the parent structure is attached is not substituted with any substituent selected from the group consisting of substituted aryl, unsubstituted aryl, substituted heteroaryl, unsubstituted heteroaryl, substituted cycloalkyl, unsubstituted cycloalkyl, substituted cycloalkenyl, unsubstituted cycloalkenyl, substituted heterocyclyl, unsubstituted heterocyclyl, alkoxy, acyloxy, substituted amino, unsubstituted amino, aminoacyl, aminocarbonylalkoxy, cyano, alkynyl, carboxy, carbonylalkoxy and acylamino.

In some of these variations, one or more of provisions (xxi)-(xxix) further apply.

In one variation, compounds of the formula (IB), and salts and solvates thereof, are embraced, where $R^1$, $R^{2a}$, $R^{2b}$, $R^{3a}$, $R^{3b}$, $R^{4a}$, $R^{4b}$, $X^1$, $X^2$, $X^3$ and $X^4$ are as defined for formula (IB), and Q is a substituted or unsubstituted aryl, substituted or unsubstituted heteroaryl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety, provided that:
  (1) at least one of $X^1$, $X^2$, $X^3$ and $X^4$ is $CR^6$;
  (2) when none of $X^1$, $X^2$ and $X^3$ is N, and none of $R^1$, $R^{2a}$, $R^{2b}$, $R^{3a}$, $R^{3b}$, $R^{4a}$ and $R^{4b}$ are taken together to form a ring, then Q is other than a unsubstituted phenyl;
  (3) when none of $X^1$, $X^2$, $X^3$ and $X^4$ is N, and $R^{2a}$ and $R^{2b}$ are taken together with the carbon to which they are attached to form a carbonyl moiety, then Q is other than a 4-substituted phenyl group; and (4) when each $X^1$, $X^3$ and $X^4$ is CH, $X^2$ is $CR^6$ where $R^6$ is fluoro, and each $R^{2a}$, $R^{2b}$, $R^{3a}$, $R^{3b}$, $R^{4a}$ and $R^{4b}$ is H, then Q is other than 4-fluorophenyl.

When Q is an unsubstituted or substituted heteroaryl, in one variation it is a heteroaryl containing an annular nitrogen atom. In one aspect, when Q is an unsubstituted or substituted heteroaryl the heteroaryl contains only nitrogen and carbon annular atoms. In a particular variation, Q is an unsubstituted pyridyl that may be bound to the parent structure at any available ring position. For example, in one variation of formula (IA) or (IB), Q is 4-pyridyl, 3-pyridyl or 2-pyridyl. When Q is a substituted heteroaryl in one aspect it is a substituted pyridyl. When Q is a substituted pyridyl, the pyridyl may be substituted with one or more than one substituent and the substituted pyridyl may be bound to the parent structure at any available ring position. For example, in one variation of formula (IA) or (IB), Q is a mono-substituted pyridyl where the substituent is a $C_1$-$C_8$ unsubstituted alkyl (e.g., methyl).

In another variation, the compound is of formula (IA) or (IB) where Q is a di- or tri-substituted aryl, substituted heteroaryl, or substituted or unsubstituted heterocyclyl. In one aspect, the compound is of formula (IA) or (IB) where Q is a di- or tri-substituted aryl. When Q is a di- or tri-substituted aryl, the substituents may be the same or different and may be located at any available position on the aryl ring. In one aspect, Q is a di- or tri-substituted phenyl (e.g., 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl and 2,4,6-trifluorophenyl). In another aspect, Q is a phenyl substituted with at least one chloro or methyl group (e.g., 4-chlorophenyl and 4-methylphenyl). In yet another aspect, the compound is of formula (IA) or (IB) where Q is a substituted heteroaryl (e.g., where Q is 6-methyl-3-pyridyl, 6-trifluoromethyl-3-pyridyl, 5-trifluoromethyl-3-pyridyl or pyrimidinyl). In one aspect, Q is a substituted pyridyl such as 6-methyl-3-pyridyl, 6-trifluoromethyl-3-pyridyl and 5-trifluoromethyl-3-pyridyl.

In some variations, the compound is of formula (IA) or (IB) where Q is a di- or tri-substituted aryl, substituted heteroaryl, or substituted or unsubstituted heterocyclyl, wherein each substituent is independently selected from the group consisting of hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, and sulfonylamino. In some of these variations, at least one of the substituent is selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl.

In one variation, the compound is of formula (IA) or (IB) where at least one of $X^1$, $X^2$, $X^3$ and $X^4$ is N. In another variation, one of $X^1$, $X^2$ and $X^3$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

In one variation, the compound is of formula (IA) or (IB) where at least one of $X^1$-$X^4$ is $CR^6$ where $R^6$ is chloro. In such variation, $X^2$ is $CR^6$ where $R^6$ is chloro. In another variation, $X^2$ is $CR^6$ where $R^6$ is chloro, and $X^1$ and $X^4$ are each CH. In one aspect, the compound is of formula (IA) or (IB) where at least one of $X^1$-$X^4$ is $CR^6$ where $R^6$ is chloro (e.g., when $X^2$ is $CR^6$ where $R^6$ is chloro) and Q is an unsubstituted aryl (e.g., phenyl), a substituted aryl (e.g., 4-fluorophenyl, 4-chlorophenyl, 4-methoxyphenyl, 3-fluoro-4-methoxyphenyl, 3,4-difluorophenyl, 4-chloro-3-fluorophenyl, 3,4-dichlorophenyl, 3-chloro-4-fluorophenyl, 2,4-difluorophenyl, 2,4,5-trifluorophenyl and 2,4-dichlorophenyl), an unsubstituted heteroaryl (e.g., 3-pyridyl and 4-pyridyl) or a substituted heteroaryl (e.g., 6-methyl-3-pyridyl, 6-trifluoromethyl-3-pyridyl and 5-trifluoromethyl-3-pyridyl). In a particular variation, $X^2$ is $CR^6$ where $R^6$ is chloro, $X^1$, $X^3$ and $X^4$ are each CH, $R^1$ is methyl or cyclopropyl and Q is an unsubstituted aryl, a substituted aryl, an unsubstituted heteroaryl or a substituted heteroaryl.

In specific variations, compounds of formula (IA) have the structure:

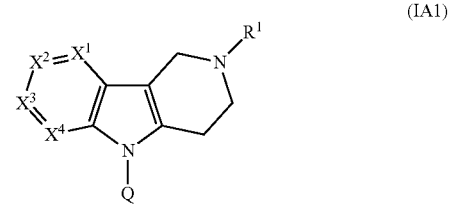

(IA1)

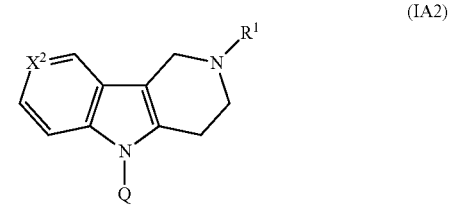

(IA2)

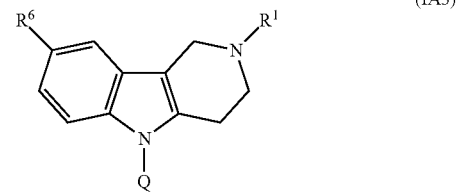

(IA3)

or a salt or solvate thereof; wherein $R^1$, $X^1$, $X^2$, $X^3$, $X^3$, $X^4$ and Q are defined as for formula (IA) and, where applicable, any variation thereof detailed herein. That is, variations of formula (IA) detailed throughout, where applicable, apply equally to any of formulae (IA1)-(IA3), the same as if each and every variation were specifically and individually listed for formula (IA1)-(IA3). Pharmaceutically acceptable salts of compounds of formulae (IA1)-(IA3) are also provided.

In one variation of formula (IA2), $X^2$ is CH or $CR^6$ where $R^6$ is halo or substituted or unsubstituted $C_1$-$C_8$ alkyl. In a particular variation of formula (IA2), $X^2$ is $CR^6$ where $R^6$ is halo (e.g., chloro). In another particular variation of formula (IA2), X² is CR⁶ where R⁶ is unsubstituted C₁-C₈ alkyl (e.g., methyl). In a particular variation of formula (IA2), X² is CH. In further variations of formula (IA2), Q is a substituted or unsubstituted heteroaryl. In one variation, Q is an unsubstituted heteroaryl (e.g., 4-pyridyl or 4-pyrimidyl). In still further variations of formula (IA2), X² is CH or CR⁶ where R⁶ is halo or substituted or unsubstituted C₁-C₈ alkyl and Q is a substituted or unsubstituted heteroaryl. In one aspect of formula (IA2), X² is CR⁶ where R⁶ is a C₁-C₈ alkyl (e.g., methyl) and Q is a substituted or unsubstituted heteroaryl. In another aspect of formula (IA2), X² is CR⁶ where R⁶ is halo (e.g., chloro) and Q is a substituted or unsubstituted heteroaryl. In another aspect of formula (IA2), X² is CH and Q is a substituted or unsubstituted heteroaryl. In a further aspect of formula (IA2), X² is CH or CR⁶ where R⁶ is methyl or chloro and Q is 4-pyridyl.

In one variation, compounds of the formula (IA3) are provided, or a salt or solvate thereof, where R¹ is a substituted or unsubstituted C₁-C₈ alkyl; R⁶ is H, halo, trifluoromethyl, a C₁-C₈ unsubstituted alkyl or a substituted amino; and Q is substituted aryl or a substituted or unsubstituted heteroaryl. In one variation of formula (IA3), R¹ is an unsubstituted C₁-C₈ alkyl or a C₁-C₈ alkyl substituted with a halo or hydroxyl group. In one such variation, R¹ is methyl, 2-haloethyl (e.g., 2-fluoroethyl), 2,2,2-trifluoroethyl, or a hydroxyl-substituted pentyl group. In a particular variation of formula (IA3), R¹ is —CH₃, —CH₂CH₂F, —CH₂CF₃, or —CH₂CH₂C(CH₃)₂OH. In another variation of formula (IA3), R⁶ is H, halo, methyl, trifluoromethyl, or a substituted amino of the formula —N(H)(C₁-C₈ unsubstituted alkyl). When R⁶ is a halo (e.g., fluoro or chloro), in one aspect R⁶ is chloro. In one variation of formula (IA3), R⁶ is H, methyl or chloro. In one variation of formula (IA3), R⁶ is methyl or chloro. When R⁶ is a substituted amino of the formula —N(H)(C₁-C₈ unsubstituted alkyl), in one aspect C₁-C₈ unsubstituted alkyl is a linear C₁-C₈ unsubstituted alkyl such as methyl or ethyl. In a particular variation of formula (IA3), R⁶ is —N(H)(CH₃). It is understood that any R¹ for formula (IA3) may be combined with any R⁶ of formula (IA3) the same as if each and every combination were specifically and individually listed. For example, compounds of the formula (IA3) are provided where R¹ is —CH₃, —CH₂CH₂F, —CH₂CF₃, or —CH₂CH₂C(CH₃)₂OH and R⁶ is H, chloro, fluoro, methyl, trifluoromethyl, or —N(H)(CH₃). Likewise, compounds of the formula (IA3) are provided where R¹ is methyl and R⁶ is H, halo, methyl or a substituted amino of the formula —N(H)(C₁-C₈ unsubstituted alkyl). In one such aspect, compounds of the formula (IA3) are provided where R¹ is methyl and R⁶ is H, halo or methyl. In one such aspect, compounds of the formula (IA3) are provided where R¹ is methyl and R⁶ is halo (e.g., fluoro or chloro), trifluoromethyl, or methyl. When each Q of formula (IA3) is independently a substituted aryl, in one aspect Q is a substituted phenyl. In one aspect, Q is a mono-substituted phenyl. In a particular aspect, each Q of formula (IA3) is independently a halo-substituted phenyl, alkoxy-substituted phenyl or an acylamino-substituted phenyl. Thus, compounds of the formula (IA3) are provided where each Q in one variation is independently a phenyl mono-substituted with a fluoro, C₁-C₈ alkoxy (e.g., methoxy), an acylamino moiety of the formula —C(O)NH(C₁-C₈ unsubstituted alkyl) or an acylamino moiety of the formula —C(O)N(C₁-C₈ unsubstituted alkyl)₂, such as 2-fluoro-phenyl, 4-fluoro-phenyl, 4-methoxy-phenyl, 4-(C(O)NH(CH₃) and 4-(C(O)N(CH₃)₂)-phenyl. In one aspect, Q is a di-substituted phenyl. In one aspect, each Q of formula (IA3) is independently a di-halo substituted phenyl group such as 3,4-difluoro-phenyl. In a particular aspect, each Q of formula (IA3) is independently a phenyl group substituted with one halo group and one C₁-C₈ alkoxy group (e.g., methoxy). Thus, compounds of the formula (IA3) are provided where each Q in one variation is independently a phenyl substituted with a fluoro and a C₁-C₈ alkoxy group, such as 3-fluoro-4-methoxy-phenyl. When each Q of formula (IA3) is independently a substituted or unsubstituted heteroaryl, in one variation the substituted or unsubstituted heteroaryl is a pyridyl or pyrimidyl moiety. Thus, in one aspect of formula (IA3), Q is an unsubstituted pyridyl or pyrimidyl, such as 3-pyridyl, 4-pyridyl and 4-pyrimidyl. In another aspect of formula (IA3), Q is a substituted pyridyl, such as 6-methyl-3-pyridyl. In another aspect of formula (IA3), Q is a substituted or unsubstituted aryl having multiple condensed rings, such as naphthyl, quinolinyl and isoquinolinyl. It is understood that any Q for formula (IA3) may be combined with any R¹ and/or R⁶ of formula (IA3) the same as if each and every combination were specifically and individually listed. For example, compounds of the formula (IA3) are provided where R¹ is —CH₃, —CH₂CH₂F, —CH₂CF₃, or —CH₂CH₂C(CH₃)₂OH; R⁶ is H, chloro, fluoro, methyl, trifluoromethyl, or —N(H)(CH₃) and Q is 4-pyridyl, 3-pyridyl, 6-methyl-3-pyridyl, 6-pyrimidyl, 4-fluoro-phenyl, 4-methoxy-phenyl, 3-fluoro-4-methoxy-phenyl or 4-dimethylcarbamoyl-phenyl. Likewise, compounds of the formula (IA3) are provided where R¹ is methyl; R⁶ is H, halo or methyl and Q is an unsubstituted pyridyl.

In one variation, compounds of formulae (IA) and (IA1)-(IA3) are provided wherein Q is a substituted or unsubstituted aromatic moiety such as, for example, phenyl, naphthyl, anthracenyl, and the like. In another variation, Q is a substituted or unsubstituted heteroaromatic moiety such as, for example, thiophenyl, pyridyl, pyrimidyl, imidazolyl, oxazolyl, and the like. In another variation, Q is a substituted or unsubstituted cycloalkenyl, such as cyclobutenyl, cyclopentenyl, cyclohexenyl, and the like, with the requirement that the carbon atom linking the cycloalkenyl group to the indole nitrogen atom of the pyrido[4,3-b]indole or pyrido[3,4-b]indole is sp³ hybridized. Particular cycloalkenyl groups comprise, for example, cyclobut-2-enyl, cyclopent-2-enyl, cyclopent-3-enyl, cyclohexa-2,4-dienyl, and the like. In another variation, Q is a substituted or unsubstituted aralkyl such as, for example, a tetrahydronaphthyl moiety linked to the parent structure through the cyclohexyl or the phenyl portion.

All variations referring to the formulae herein, such as formulae (IA), (IA1), (IA2), (IA3), where applicable, may apply equally to formula (IB), the same as if each and every variation were specifically and individually listed.

In one variation, compounds of the formula (IA) are provided where R²ᵃ, R²ᵇ, R³ᵃ, R³ᵇ, R⁴ᵃ and R⁴ᵇ are each H; and the compounds are of the formula (IA4):

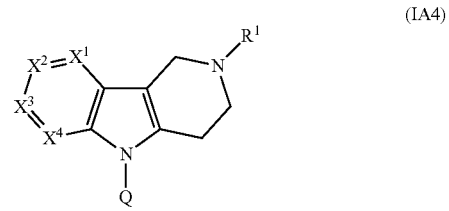

(IA4)

or a salt or solvate thereof, wherein X¹, X², X³ and X⁴ are as defined in formula (IA) and wherein:

R¹ is H, hydroxyl, substituted or unsubstituted C₁-C₈ alkyl, substituted or unsubstituted C₂-C₈ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

either (i) one or more of $X^1$, $X^2$, $X^3$ and $X^4$ is N or (ii) $X^1$ and $X^3$ are CH, $X^2$ is $CR^6$ and $X^4$ is N, CH or $CR^6$; and Q is an aromatic ring of the formula:

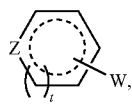

where

Z is C, NH, N—CH$_3$, O or S and the Z-containing aromatic ring is attached to the parent structure at any available ring position;

t is 0 or 1; and

W is: (i) a substituted or unsubstituted aryl, or a substituted or unsubstituted heteroaryl that is bound to the Z-containing ring via a single bond at any available ring position or is fused to the Z-containing ring at any available adjacent ring positions, (ii) a substituted amino, provided that when $X^1$, $X^2$, $X^3$ and $X^4$ are each independently CH or $CR^6$, then $R^1$ is an unsubstituted $C_1$-$C_8$ alkyl when W is a substituted amino, or (iii) H, provided that when $X^1$, $X^2$, $X^3$ and $X^4$ are each independently CH or $CR^6$, then W is H only when the Z-containing ring is a 5-membered heteroaryl moiety.

In one variation, compounds of the formula (IA4) are provided where at least one of $X^1$, $X^2$, $X^3$ and $X^4$ is N and W is (i) a substituted or unsubstituted aryl, or a substituted or unsubstituted heteroaryl that is bound to the Z-containing ring via a single bond at any available ring position or is fused to the Z-containing ring at any available adjacent ring positions, (ii) a substituted amino, or (iii) H. In one such variation, at least one of $X^1$, $X^2$, $X^3$ and $X^4$ is N and the Z-containing ring bearing W is selected from the group consisting of a substituted or unsubstituted phenyl, naphthalenyl, isoquinolinyl, thiophenyl and pyridyl.

In another variation, compounds of the formula (IA4) are provided wherein $X^1$ and $X^3$ are CH, $X^2$ is $CR^6$ and $X^4$ is N, CH or $CR^6$ and W is a substituted or unsubstituted aryl, or a substituted or unsubstituted heteroaryl that is bound to the Z-containing ring via a single bond at any available ring position or is fused to the Z-containing ring at any available adjacent ring positions. In one such variation, the Z-containing ring bearing W is a phenyl, naphthalenyl, isoquinolinyl, thiophenyl or pyridyl ring substituted with a substituted or unsubstituted aryl or a substituted or unsubstituted heteroaryl. In some variations, $X^1$, $X^3$ and $X^4$ are CH and $X^2$ is $CR^6$. When $X^2$ is $CR^6$, in one variation, $R^6$ is selected from the group consisting of a substituted or unsubstituted $C_1$-$C_8$alkyl, a substituted or unsubstituted $C_3$-$C_7$cycloalkyl, halo, cyano and trifluoromethyl. When $X^2$ is $CR^6$, in one variation $R^6$ is an unsubstituted $C_1$-$C_8$ alkyl (such as methyl) or halo (such as chloro). In some variations of formula (IA4), $R^1$ is selected from the group consisting of H, a substituted or unsubstituted $C_1$-$C_8$alkyl, a substituted or unsubstituted $C_3$-$C_7$cycloalkyl, and an alkaryl, wherein the alkaryl is bound to the parent structure via the alkyl portion of the moiety. In one aspect, the alkyl portion of the $R^1$ alkaryl moiety is a $C_4$-$C_8$alkyl. In some variations, $R^1$ is an unsubstituted $C_1$-$C_8$ alkyl (such as methyl). In a particular variation, compounds of the formula (IA4) are provided wherein $X^1$, $X^3$ and $X^4$ are CH and $X^2$ is $CR^6$, where $R^6$ is selected from the group consisting of a substituted or unsubstituted $C_1$-$C_8$alkyl, a substituted or unsubstituted $C_3$-$C_7$cycloalkyl, halo, cyano and trifluoromethyl, and $R^1$ is selected from the group consisting of H, a substituted or unsubstituted $C_1$-$C_8$alkyl, a substituted or unsubstituted $C_3$-$C_7$cycloalkyl, and an alkaryl, wherein the alkaryl is bound to the parent structure via the alkyl portion of the moiety. In one aspect, compounds of the formula (IA4) are provided wherein $X^1$, $X^3$ and $X^4$ are CH; $X^2$ is $CR^6$ where $R^6$ is an unsubstituted $C_1$-$C_8$ alkyl; and the Z-containing ring bearing W is a phenyl, naphthalenyl, isoquinolinyl, thiophenyl or pyridyl ring substituted with a substituted or unsubstituted aryl or a substituted or unsubstituted heteroaryl. In one aspect, the Z-containing ring (such as phenyl, thiophenyl and pyridyl) is substituted with a W where W is a substituted or unsubstituted aryl or a substituted or unsubstituted heteroaryl that is bound to the Z-containing ring via a single bond at any available ring position. For example, in one aspect, the Z-containing ring (such as phenyl, thiophenyl and pyridyl) is substituted with a W where W is selected from the group consisting of a substituted or unsubstituted pyridyl, phenyl, thiophenyl, pyrrolyl, imidazolyl, pyrazolyl, pyrimidinyl and isooxazolyl, where W is bound to the Z-containing ring via a single bond at any available ring position.

In another variation, compounds of the formula (IA4) are provided wherein $X^1$ and $X^3$ are CH; $X^2$ is $CR^6$; $X^4$ is N, CH or $CR^6$; and W a substituted amino, provided that when $X^1$, $X^2$, $X^3$ and $X^4$ are each independently CH or $CR^6$, then $R^1$ is an unsubstituted $C_1$-$C_8$ alkyl. In one such variation, $X^1$, $X^3$ and $X^4$ are CH; $X^2$ is $CR^6$; $R^1$ is an unsubstituted $C_1$-$C_8$ alkyl and W is a substituted amino (e.g., dimethylamino). In another such variation, $X^1$ and $X^3$ are CH, $X^2$ is $CR^6$; $X^4$ is CH or $CR^6$; $R^1$ is an unsubstituted $C_1$-$C_8$ alkyl and W is a substituted amino. When $X^2$ is $CR^6$, in one variation $R^6$ is an unsubstituted $C_1$-$C_8$ alkyl (such as methyl) or a halo (such as chloro). When $R^1$ is an unsubstituted $C_1$-$C_8$ alkyl, in one variation $R^1$ is methyl. In another such variation, the Z-containing ring bearing W is a phenyl, thiophenyl or pyridyl substituted with W where W is a substituted amino group. Thus, in one aspect, compounds of the formula (IA4) are provided wherein $X^1$, $X^3$ and $X^4$ are CH; $X^2$ is $CR^6$ where $R^6$ is an unsubstituted $C_1$-$C_8$ alkyl or halo; and the Z-containing ring is a phenyl, thiophenyl or pyridyl ring substituted with a substituted amino group (e.g., dimethylamino).

In another variation, compounds of the formula (IA4) are provided wherein $X^1$, $X^2$, $X^3$ and $X^4$ are each independently CH or $CR^6$; the Z-containing ring is a 5-membered heteroaryl moiety (where Z is NH, N—CH$_3$, O or S and t is 0) and W is H. In one such variation, the Z-containing ring is thiophene. In another variation, $X^1$, $X^3$ and $X^4$ are each CH and $X^2$ is $CR^6$. When $X^2$ is $CR^6$, in one aspect $R^6$ is selected from the group consisting of a substituted or unsubstituted $C_1$-$C_8$alkyl, a substituted or unsubstituted $C_3$-$C_7$cycloalkyl, halo, cyano and trifluoromethyl, and in another aspect is an unsubstituted $C_1$-$C_8$alkyl (such as methyl) or a halo (such as chloro). In a further such variation, $X^1$, $X^3$ and $X^4$ are each CH; $X^2$ is $CR^6$ where $R^6$ is an unsubstituted $C_1$-$C_8$alkyl (such as methyl) or a halo (such as chloro); $R^1$ is an unsubstituted $C_1$-$C_8$alkyl (such as methyl); the Z-containing ring is a 5-membered heteroaryl moiety and W is H.

In one variation, compounds of the formula (IA4) are provided where $X^1$ and $X^3$ are each CH, $X^2$ is $CR^6$; and the compounds are of the formula (IA5):

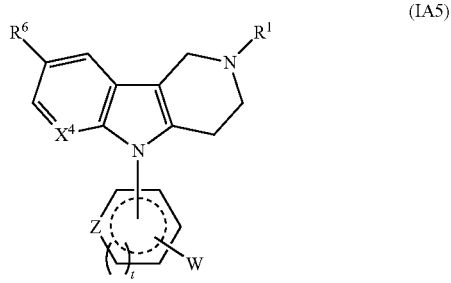

or a salt or solvate thereof, where $R^6$ and $X^4$ are as defined in formula (IA) and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

Z is C, NH, N—$CH_3$, O or S;

t is 0 or 1;

W is: (i) a substituted or unsubstituted aryl, or a substituted or unsubstituted heteroaryl that is bound to the Z-containing ring via a single bond at any available position or is fused to the Z-containing ring at two adjacent positions, (ii) a substituted amino, provided that $R^1$ is a $C_1$-$C_8$ alkyl when W is a substituted amino, or (iii) H, provided that W is only H when the Z-containing ring is a 5-membered heteroaryl moiety; and wherein the Z-containing ring is aromatic and is attached to the parent structure at any available ring position.

Compound of the formula (IA5) may in certain variations have any one or more of the following structural features, provided that features (iii) and (iv) cannot be combined and features (vi) and (vii) cannot be combined: (i) $X^4$ is CH; (ii) $R^1$ is an unsubstituted $C_1$-$C_8$ alkyl; (iii) t is 0; (iv) t is 1; (iv) Z is C, S or N; (v) the Z-containing ring is selected from the group consisting of phenyl, thiophenyl and pyridyl; (vi) W is selected from the group consisting of a substituted or unsubstituted: pyridyl, phenyl, thiophenyl, pyrrolyl, imidazolyl, pyrazolyl, pyrimidinyl and isooxazolyl, where W is bound to the Z-containing ring via a single bond at any available ring position; (vii) W is fused to the Z-containing ring at any available adjacent ring positions, thereby providing multiple condensed rings (e.g., naphthalenyl and isoquinolinyl); and (viii) $R^6$ is an unsubstituted $C_1$-$C_8$ alkyl or halo.

In some embodiments, in compounds of the formulae (IA), (IB), (J-1) and (K-1), and any variations thereof detailed herein, Q is a group having the formula -$Q^A$-$Q^B$, wherein $Q^A$ is substituted aryl or substituted heteroaryl and $Q^B$ is substituted or unsubstituted aryl or substituted or unsubstituted heteroaryl. In some embodiments, $Q^A$ is aryl (e.g., phenyl). In some embodiments, $Q^A$ is a 6-membered heteroaryl containing one annular heteroatom (e.g., pyridyl). In some embodiments, $Q^A$ is a 6-membered heteroaryl containing more than one annular heteroatoms, such as a 6-membered heteroaryl containing two annular heteroatoms (e.g., pyrimidyl and pyrazinyl). In some embodiments, $Q^A$ is a 5-membered heteroaryl containing one annular heteroatom (e.g., thiophenyl, furanyl and pyrrolyl). In some embodiments, $Q^A$ is a 5-membered heteroaryl containing more than one annular heteroatoms such as a 5-membered heteroaryl containing two annular heteroatoms (e.g., thiazolyl, oxazolyl, imidazolyl, isothiazolyl, isooxazolyl and pyrazolyl). In some embodiments, $Q^B$ is a substituted or unsubstituted aryl (e.g., phenyl, fluorophenyl and chlorophenyl). In some embodiments, $Q^B$ is a substituted or unsubstituted heteroaryl such as a substituted or unsubstituted pyridyl, pyrimidyl, pyrazinyl, thiophenyl, furanyl, pyrrolyl, thiazolyl, oxazolyl, imidazolyl, isothiazolyl, isooxazolyl, pyrazolyl, naphthyl, quinolinyl, isoquinolinyl, indolyl, benzofuranyl, benzothiophenyl, and the like. In some embodiments, the $Q^A$ moiety may be attached to the parent structure at any viable annular atom of $Q^A$. In some embodiments, the bond between $Q^A$ and $Q^B$ is between any viable annular atom of $Q^A$ and any viable annular atom of $Q^B$.

Examples of Q moieties that are contemplated for the formulae herein, such as formulae (IA) and (IB) and any variations detailed herein (for example formula (IA4) and (IA5) where the Q group is also referred to as the Z-containing ring bearing a W moiety), include but are not limited to the following:

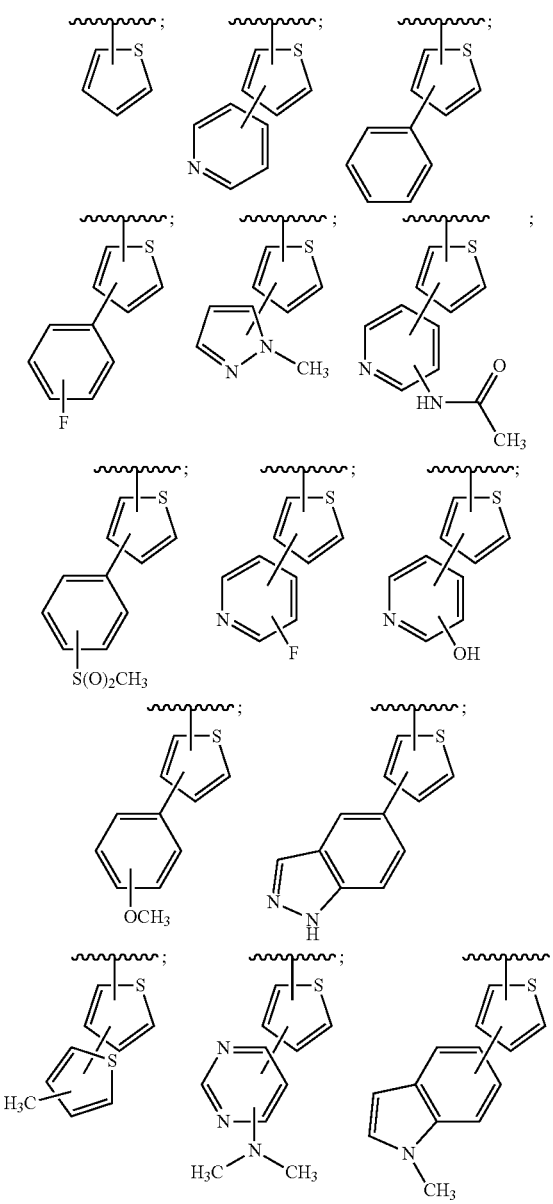

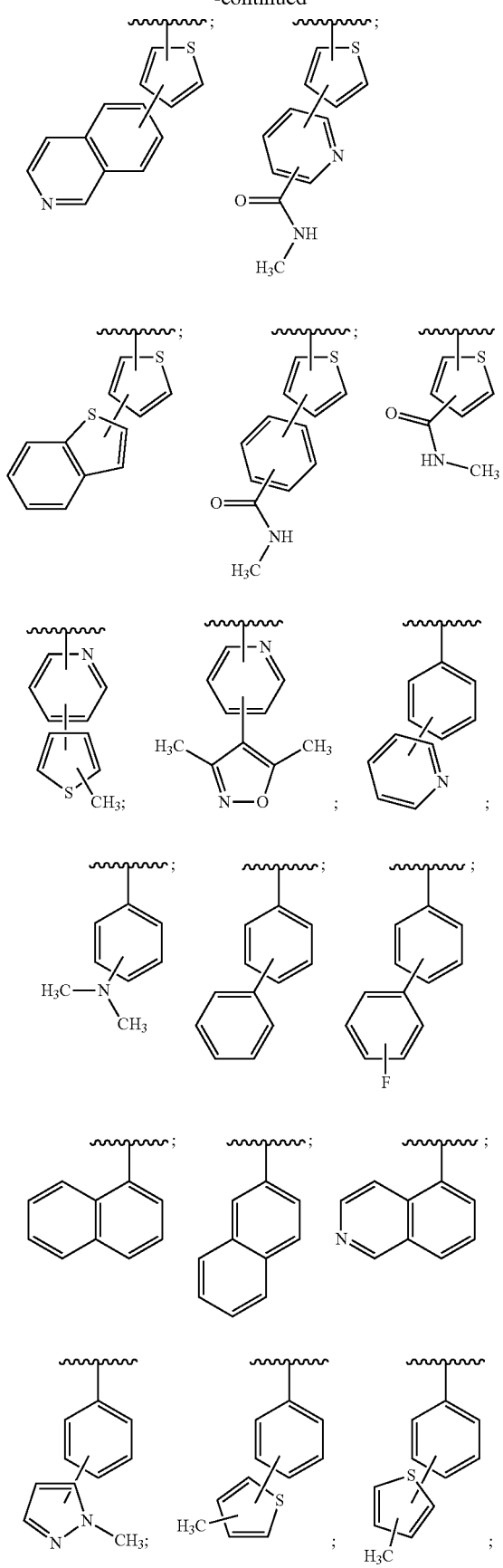
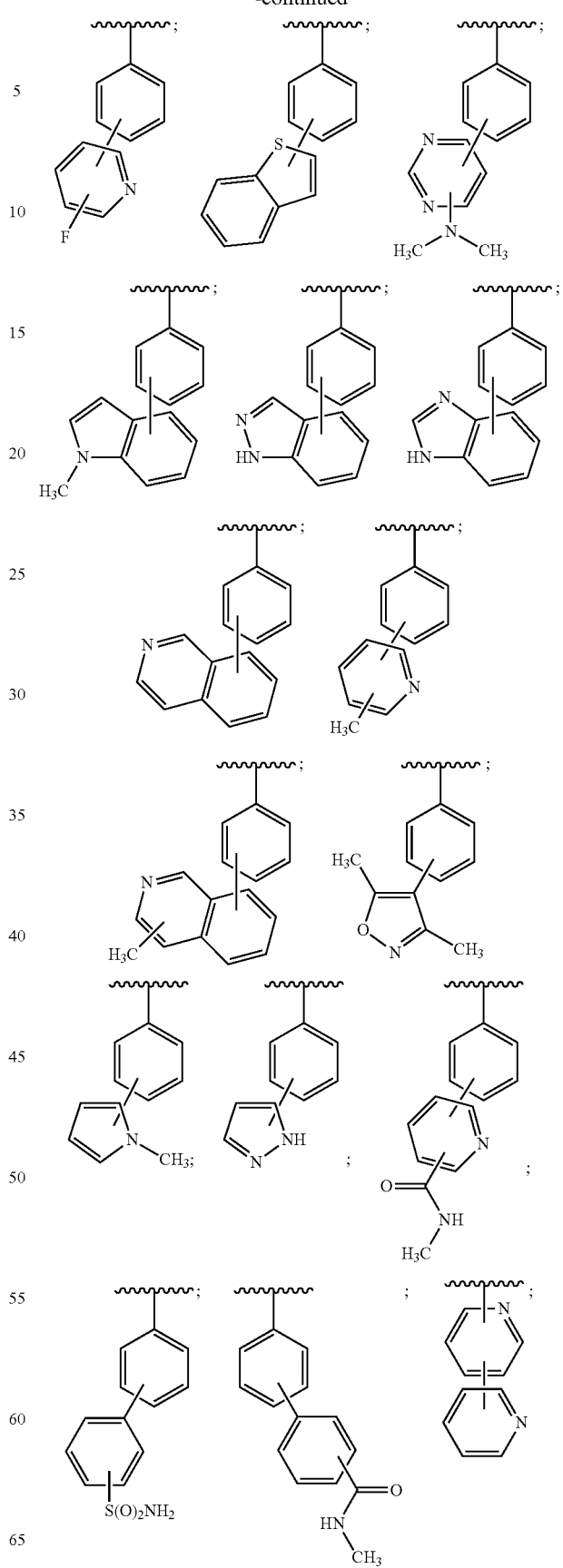

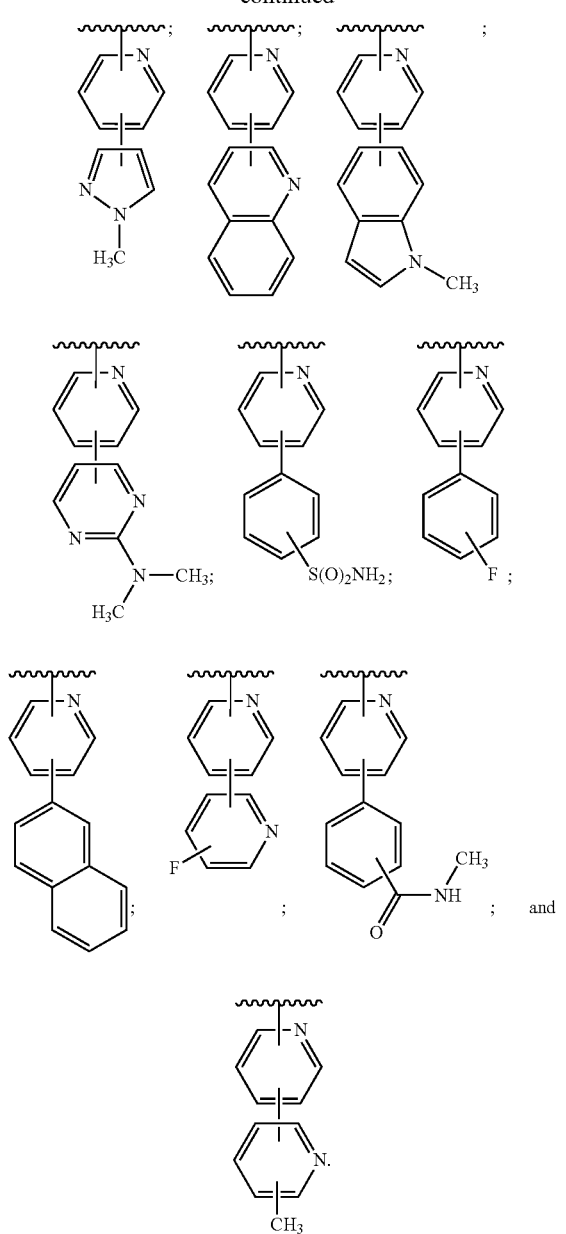

In one variation, compounds of the formula (IA) are provided, where $R^{2a}$, $R^{2b}$, $R^{3a}$, $R^{3b}$, $R^{4a}$ and $R^{4b}$ are each H; and the compounds have the structure (IA6):

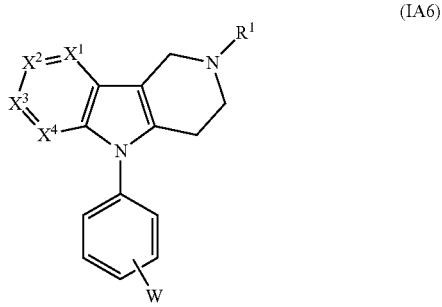
(IA6)

or a salt or solvate thereof, where $R^6$ and $X^1$, $X^2$, $X^3$ and $X^4$ are as defined in formula (IA) and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

either (i) one or more of $X^1$, $X^2$, $X^3$ and $X^4$ is N or (ii) $X^1$ and $X^3$ are CH, $X^2$ is $CR^6$ and $X^4$ is N, CH or $CR^6$; and W is: (i) a substituted or unsubstituted aryl, or a substituted or unsubstituted heteroaryl that is bound to the parent structure via a single bond located at any available ring position or (ii) a substituted amino, provided that $R^1$ is a $C_1$-$C_8$ unsubstituted alkyl when W is a substituted amino.

In one aspect of formula (IA6), one or more of $X^1$, $X^2$, $X^3$ and $X^4$ is N. In one aspect, $X^1$ is N and $X^2$, $X^3$ and $X^4$ are each CH. In another aspect, $X^2$ is N and $X^1$, $X^3$ and $X^4$ are each CH. In another aspect, $X^3$ is N and $X^1$, $X^2$ and $X^4$ are each CH. In a further aspect, $X^4$ is N and $X^1$, $X^2$ and $X^3$ are each CH. In one variation of formula (IA6), one of $X^1$, $X^2$, $X^3$ and $X^4$ is N, one of $X^1$, $X^2$, $X^3$ and $X^4$ is $CR^6$ and two of $X^1$, $X^2$, $X^3$ and $X^4$ are CH. In one variation, $X^4$ is N, $X^1$ and $X^3$ are each CH and $X^2$ is $CR^6$.

In another aspect of formula (IA6), $X^1$ and $X^3$ are CH, $X^2$ is $CR^6$ and $X^4$ is N, CH or $CR^6$. In one such aspect, $X^2$ is $CR^6$ where $R^6$ is selected from the group consisting of a substituted or unsubstituted $C_1$-$C_8$alkyl, a substituted or unsubstituted $C_3$-$C_7$cycloalkyl, halo, cyano and trifluoromethyl. In another variation, $X^1$, $X^3$ and $X^4$ are each CH and $X^2$ is $CR^6$. In another variation, $X^1$, $X^3$ and $X^4$ are each CH and $X^2$ is $CR^6$ where $R^6$ is a $C_1$-$C_8$ unsubstituted alkyl (e.g., methyl) or halo (e.g., chloro).

In any variation of formula (IA6), such as but not limited those provided herein above, the compound may further have any one or more of the following structural features: (i) $X^2$ is $CR^6$ (where in one particular variation $R^6$ is selected from the group consisting of a substituted or unsubstituted $C_1$-$C_8$alkyl, a substituted or unsubstituted $C_3$-$C_7$cycloalkyl, halo, cyano and trifluoromethyl); (ii) $R^1$ is selected from the group consisting of H, a substituted or unsubstituted $C_1$-$C_8$alkyl, a substituted or unsubstituted $C_3$-$C_7$cycloalkyl, and an alkaryl, wherein the alkaryl is bound to the parent structure via the alkyl portion of the moiety; (iii) $X^1$ and $X^3$ are each CH; (iv) W is a substituted or unsubstituted pyridyl, phenyl, thiophenyl, pyrrolyl, imidazolyl, pyrazolyl, pyrimidinyl and isooxazolyl; (v) W is bound at the ortho position of the phenyl ring; and (vi) W is bound to the meta position of the phenyl ring; (vii) W is bound to the para position of the phenyl ring. Thus, in one aspect of formula (IA6), $X^1$, $X^3$ and $X^4$ are each CH; $X^2$ is $CR^6$ where $R^6$ is a $C_1$-$C_8$ unsubstituted alkyl (e.g., methyl) or halo (e.g., chloro); $R^1$ is selected from the group consisting of H, a substituted or unsubstituted $C_1$-$C_8$alkyl, a substituted or unsubstituted $C_3$-$C_7$cycloalkyl, and an alkaryl, wherein the alkaryl is bound to the parent structure via the alkyl portion of the moiety; and W is bound at the ortho or meta position of the phenyl ring.

In some instances, compounds of the formula (IA6) are provided wherein $X^1$ and $X^3$ are each CH and the compound is of the formula (A1) or (A2):

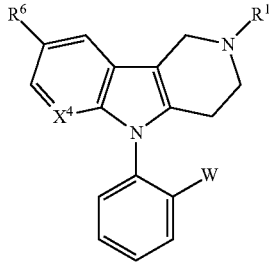

(A1)

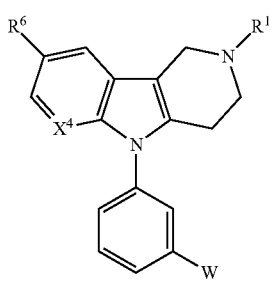

(A2)

or a salt or solvate thereof; wherein $R^6$ and $X^4$ are defined as for formulae (IA) and, where applicable, any variation thereof detailed herein, and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

W is a substituted amino, substituted or unsubstituted aryl, or substituted or unsubstituted heteroaryl. In one particular aspect of this variation, $X^4$ is N. In another particular aspect of this variation, $X^4$ is CH. In another aspect of this variation, $R^1$ and $R^6$ are each a substituted or unsubstituted $C_1$-$C_8$ alkyl. In one particular aspect of this variation, $R^1$ and $R^6$ are methyl. Variations of formula (IA) detailed throughout, where applicable, apply to formulae (A1)-(A2) the same as if each and every variation were specifically and individually listed for formulae (A1)-(A2). Pharmaceutically acceptable salts of compounds of formulae (A1)-(A2) are also provided.

All variations referring to the formulae (IA), such as formulae (A1)-(A2), where applicable, may apply equally to formulae (IB), the same as if each and every variation were specifically and individually listed.

In one variation, compounds of the formula (IA) are provided wherein $X^1$ and $X^3$ are each CH, $R^1$, $R^{2a}$, $R^{2b}$, $R^{3a}$, $R^{3b}$, $R^{4a}$ and $R^{4b}$ are each H and the compounds are of the formula (IA7):

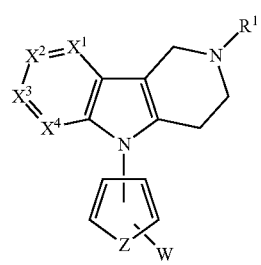

(IA7)

or a salt or solvate thereof, where $R^6$ and $X^1$, $X^2$, $X^3$ and $X^4$ are as defined in formula (IA) and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

either (i) one or more of $X^1$, $X^2$, $X^3$ and $X^4$ is N or (ii) $X^1$ and $X^3$ are CH, $X^2$ is $CR^6$ and $X^4$ is N, CH or $CR^6$;

W is H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl or sulfonylamino; and Z is NH, N—$CH_3$, O or S.

In one aspect of formula (IA7), one or more of $X^1$, $X^2$, $X^3$ and $X^4$ is N. In one aspect, $X^1$ is N and $X^2$, $X^3$ and $X^4$ are each CH. In another aspect, $X^2$ is N and $X^1$, $X^3$ and $X^4$ are each CH. In another aspect, $X^3$ is N and $X^1$, $X^2$ and $X^4$ are each CH. In a further aspect, $X^4$ is N and $X^1$, $X^2$ and $X^3$ are each CH. In one variation of formula (IA7), one of $X^1$, $X^2$, $X^3$ and $X^4$ is N, one of $X^1$, $X^2$, $X^3$ and $X^4$ is $CR^6$ and two of $X^1$, $X^2$, $X^3$ and $X^4$ are CH. In one variation, $X^4$ is N, $X^1$ and $X^3$ are each CH and $X^2$ is $CR^6$.

In another aspect of formula (IA7), $X^1$ and $X^3$ are CH, $X^2$ is $CR^6$ and $X^4$ is N, CH or $CR^6$. In one such aspect, $X^2$ is $CR^6$ where $R^6$ is selected from the group consisting of a substituted or unsubstituted $C_1$-$C_8$alkyl, a substituted or unsubstituted $C_3$-$C_7$cycloalkyl, halo, cyano and trifluoromethyl. In another variation, $X^1$, $X^3$ and $X^4$ are each CH and $X^2$ is $CR^6$. In another variation, $X^1$, $X^3$ and $X^4$ are each CH and $X^2$ is $CR^6$ where $R^6$ is a $C_1$-$C_8$ unsubstituted alkyl (e.g., methyl) or halo (e.g., chloro).

In any variation of formula (IA7), such as but not limited those provided herein above, the compound may further have any one or more of the following structural features: (i) $X^2$ is $CR^6$ (where in one particular variation $R^6$ is selected from the group consisting of a substituted or unsubstituted $C_1$-$C_8$alkyl, a substituted or unsubstituted $C_3$-$C_7$cycloalkyl, halo, cyano and trifluoromethyl); (ii) $R^1$ is selected from the group consisting of H, a substituted or unsubstituted $C_1$-$C_8$alkyl, a substituted or unsubstituted $C_3$-$C_7$cycloalkyl, and an alkaryl, wherein the alkaryl is bound to the parent structure via the alkyl portion of the moiety; (iii) $X^1$ and $X^3$ are each CH; (iv) $X^4$ is CH; (v) Z is S; (vi) W is bound to a position adjacent to Z; (vii) the Z-containing ring is bound to the parent structure at a carbon adjacent to Z; (viii) W is H, substituted or unsubstituted aryl, or substituted or unsubstituted heteroaryl; (ix) $R^1$ and $R^6$ are each a substituted or unsubstituted $C_1$-$C_8$ alkyl; and (x) $R^1$ is methyl and $R^6$ is halo.

In particular variations of formula (IA7), compounds are provided wherein $X^1$ and $X^3$ are each CH and the compounds are of the formulae (B1)-(B6):

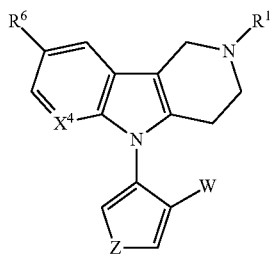
(B1)

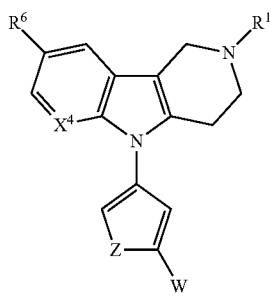
(B2)

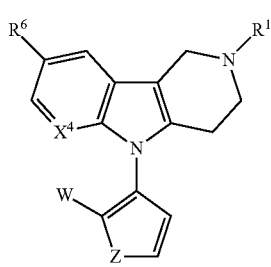
(B3)

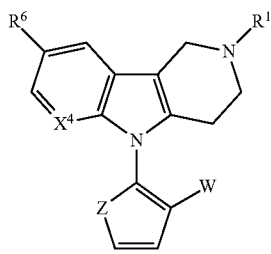
(B4)

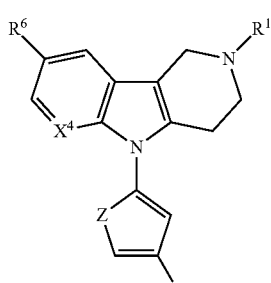
(B5)

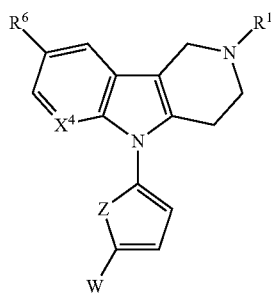
(B6)

or a salt or solvate thereof; wherein $R^6$ and $X^4$ are defined as for formulae (IA) and, where applicable, any variation thereof detailed herein, and wherein;

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

Z is NH, N—CH$_3$, O or S, and W is H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl or sulfonylamino. In one particular aspect of this variation, W is H, substituted or unsubstituted aryl, or substituted or unsubstituted heteroaryl. In one particular aspect of this variation, Z is S. In another particular aspect of this variation, $X^4$ is N. In another particular aspect of this variation, $X^4$ is CH. In another aspect of this variation, $R^1$ and $R^6$ are each a substituted or unsubstituted $C_1$-$C_8$ alkyl. In another particular aspect of this variation, $R^1$ and $R^6$ are methyl. In another particular aspect of this variation, $R^1$ is methyl and $R^6$ is halo. Variations of formula (IA) detailed throughout, where applicable, apply to formulae (B1)-(B6) the same as if each and every variation were specifically and individually listed for formulae (B1)-(B6). Pharmaceutically acceptable salts of compounds of formulae (B1)-(B6) are also provided.

All variations referring to the formulae (IA), such as formulae (B1)-(B6), where applicable, may apply equally to formulae (IB), the same as if each and every variation were specifically and individually listed.

In another variation, compounds of the formula (IA) are provided wherein $X^1$ and $X^3$ are each CH, $R^{2a}$, $R^{2b}$, $R^{3a}$, $R^{3b}$, $R^{4a}$ and $R^{4b}$ are ach H and the compound is of the formula (IA8):

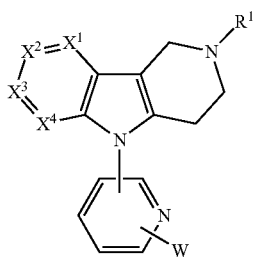

(IA8)

or a salt or solvate thereof, where $R^6$ and $X^1$, $X^2$, $X^3$ and $X^4$ are as defined in formula (IA) and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;
either (i) one or more of $X^1$, $X^2$, $X^3$ and $X^4$ is N or (ii) $X^1$ and $X^3$ are CH, $X^2$ is $CR^6$ and $X^4$ is N, CH or $CR^6$; and W is H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl or sulfonylamino, provided that when $X^1$, $X^3$ and $X^4$ are each H and $X^2$ is $CR^6$ where $R^6$ is H or fluoro, W is other than H.

In one aspect of formula (IA8), one or more of $X^1$, $X^2$, $X^3$ and $X^4$ is N. In one aspect, $X^1$ is N and $X^2$, $X^3$ and $X^4$ are each CH. In another aspect, $X^2$ is N and $X^1$, $X^3$ and $X^4$ are each CH. In another aspect, $X^3$ is N and $X^1$, $X^2$ and $X^4$ are each CH. In a further aspect, $X^4$ is N and $X^1$, $X^2$ and $X^3$ are each CH. In one variation of formula (IA8), one of $X^1$, $X^2$, $X^3$ and $X^4$ is N, one of $X^1$, $X^2$, $X^3$ and $X^4$ is $CR^6$ and two of $X^1$, $X^2$, $X^3$ and $X^4$ are CH. In one variation, $X^4$ is N, $X^1$ and $X^3$ are each CH and $X^2$ is $CR^6$.

In another aspect of formula (IA8), $X^1$ and $X^3$ are CH, $X^2$ is $CR^6$ and $X^4$ is N, CH or $CR^6$. In one such aspect, $X^2$ is $CR^6$ where $R^6$ is selected from the group consisting of a substituted or unsubstituted $C_1$-$C_8$alkyl, a substituted or unsubstituted $C_3$-$C_7$cycloalkyl, halo, cyano and trifluoromethyl. In another variation, $X^1$, $X^3$ and $X^4$ are each CH and $X^2$ is $CR^6$. In another variation, $X^1$, $X^3$ and $X^4$ are each CH and $X^2$ is $CR^6$ where $R^6$ is a $C_1$-$C_8$ unsubstituted alkyl (e.g., methyl) or halo (e.g., chloro).

In any variation of formula (IA8), such as but not limited those provided herein above, the compound may further have any one or more of the following structural features: (i) $X^2$ is $CR^6$ (where in one particular variation $R^6$ is selected from the group consisting of a substituted or unsubstituted $C_1$-$C_8$alkyl, a substituted or unsubstituted $C_3$-$C_7$cycloalkyl, halo, cyano and trifluoromethyl); (ii) $R^1$ is selected from the group consisting of H, a substituted or unsubstituted $C_1$-$C_8$alkyl, a substituted or unsubstituted $C_3$-$C_7$cycloalkyl, and an alkaryl, wherein the alkaryl is bound to the parent structure via the alkyl portion of the moiety; (iii) $X^1$ and $X^3$ are each CH; (iv) $X^4$ is CH; (v) W is H, substituted or unsubstituted aryl, or substituted or unsubstituted heteroaryl; (vi) $R^1$ and $R^6$ are each a substituted or unsubstituted $C_1$-$C_8$ alkyl; and (vii) $R^1$ is methyl and $R^6$ is halo.

In particular variations of formula (IA8), compounds are provided wherein $X^1$ and $X^3$ are each CH, and the compounds are of the formulae (C1)-(C3):

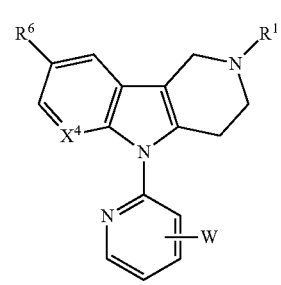

(C1)

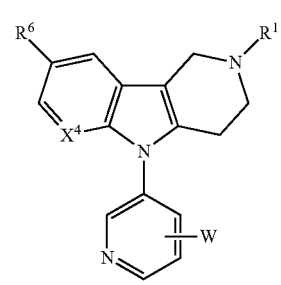

(C2)

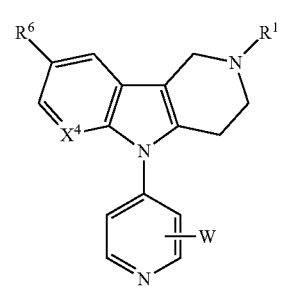

(C3)

or a salt or solvate thereof; wherein $R^6$ and $X^4$ are defined as for formulae (IA) and, where applicable, any variation thereof detailed herein, and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

W is, H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl or sulfonylamino, provided that when $X^4$ if CH and $R^6$ is H or fluoro, then W is other than H.

In one particular aspect of this variation, W is a substituted or unsubstituted aryl, or substituted or unsubstituted heteroaryl. In another particular aspect of this variation, $X^4$ is N. In another particular aspect of this variation, $X^4$ is CH. In another aspect of this variation, $R^1$ and $R^6$ are each a substituted or unsubstituted $C_1$-$C_8$ alkyl. In one particular aspect of this variation, $R^1$ and $R^6$ are methyl. In another particular aspect of this variation, $R^1$ is methyl and $R^6$ is halo. Variations of formula (IA) detailed throughout, where applicable, apply to formulae (C1)-(C3) the same as if each and every variation were specifically and individually listed for formulae (C1)-(C3). Pharmaceutically acceptable salts of compounds of formulae (C1)-(C3) are also provided.

All variations referring to the formulae (IA), such as formulae (C1)-(C3), where applicable, may apply equally to formulae (IB), the same as if each and every variation were specifically and individually listed.

In one variation, compounds of the formula (IA) are provided wherein $R^{2a}$, $R^{2b}$, $R^{3a}$, $R^{3b}$, $R^{4a}$ and $R^{4b}$ are each H and the compounds are of the formula (IA9):

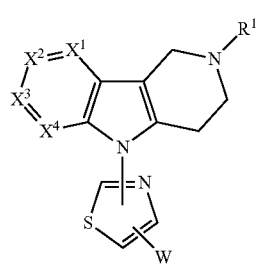

(IA9)

or a salt or solvate thereof, wherein $R^6$ and $X^1$, $X^2$, $X^3$ and $X^4$ are as defined in formula (IA) and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

either (i) one or more of $X^1$, $X^2$, $X^3$ and $X^4$ is N or (ii) $X^1$ and $X^3$ are CH, $X^2$ is $CR^6$ and $X^4$ is N, CH or $CR^6$; and W is H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl or sulfonylamino.

In one aspect of formula (IA9), one or more of $X^1$, $X^2$, $X^3$ and $X^4$ is N. In one aspect, $X^1$ is N and $X^2$, $X^3$ and $X^4$ are each CH. In another aspect, $X^2$ is N and $X^1$, $X^3$ and $X^4$ are each CH. In another aspect, $X^3$ is N and $X^1$, $X^2$ and $X^4$ are each CH. In a further aspect, $X^4$ is N and $X^1$, $X^2$ and $X^3$ are each CH. In one variation of formula (IA9), one of $X^1$, $X^2$, $X^3$ and $X^4$ is N, one of $X^1$, $X^2$, $X^3$ and $X^4$ is $CR^6$ and two of $X^1$, $X^2$, $X^3$ and $X^4$ are CH. In one variation, $X^4$ is N, $X^1$ and $X^3$ are each CH and $X^2$ is $CR^6$.

In another aspect of formula (IA9), $X^1$ and $X^3$ are CH, $X^2$ is $CR^6$ and $X^4$ is N, CH or $CR^6$. In one such aspect, $X^2$ is $CR^6$ where $R^6$ is selected from the group consisting of a substituted or unsubstituted $C_1$-$C_8$alkyl, a substituted or unsubstituted $C_3$-$C_7$cycloalkyl, halo, cyano and trifluoromethyl. In another variation, $X^1$, $X^3$ and $X^4$ are each CH and $X^2$ is $CR^6$. In another variation, $X^1$, $X^3$ and $X^4$ are each CH and $X^2$ is $CR^6$ where $R^6$ is a $C_1$-$C_8$ unsubstituted alkyl (e.g., methyl) or halo (e.g., chloro).

In any variation of formula (IA9), such as but not limited those provided herein above, the compound may further have any one or more of the following structural features: (i) $X^2$ is $CR^6$ (where in one particular variation $R^6$ is selected from the group consisting of a substituted or unsubstituted $C_1$-$C_8$alkyl, a substituted or unsubstituted $C_3$-$C_7$cycloalkyl, halo, cyano and trifluoromethyl); (ii) $R^1$ is selected from the group consisting of H, a substituted or unsubstituted $C_1$-$C_8$alkyl, a substituted or unsubstituted $C_3$-$C_7$cycloalkyl, and an alkaryl, wherein the alkaryl is bound to the parent structure via the alkyl portion of the moiety; (iii) $X^1$ and $X^3$ are each CH; (iv) $X^4$ is CH; (v) W is bound to the 4-position of the thiazole ring; (vii) the thiazole ring is bound to the parent structure at the 2-position; (viii) W is H, substituted or unsubstituted aryl, or substituted or unsubstituted heteroaryl; (ix) $R^1$ and $R^6$ are each a substituted or unsubstituted $C_1$-$C_8$ alkyl; and (x) $R^1$ is methyl and $R^6$ is halo.

All variations referring to the formula (IA) detailed herein, such as formulae (IA9), where applicable, may apply equally to formula (IB), the same as if each and every variation were specifically and individually listed.

The invention also embraces compounds of formula (J-1):

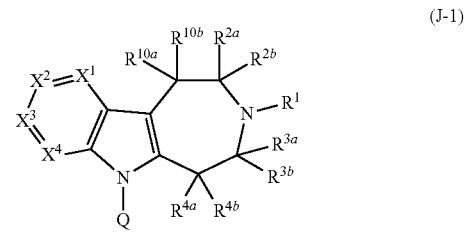

(J-1)

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted C₂-C₈ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{2(a/b)}$, $R^{3(a/b)}$, $R^{4(a/b)}$ or $R^{10(a/b)}$ to form a carbonyl moiety or a cycloalkyl moiety;

each $X^1$, $X^2$ and $X^3$ is independently N, CH or $CR^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl.

In one variation, provided are compounds of the formula (J-1), wherein at least one of $X^1$, $X^2$, $X^3$ and $X^4$ is CH or $CR^6$. In another variation, at least two of $X^1$, $X^2$, $X^3$ and $X^4$ is CH or $CR^6$.

In a particular embodiment, compounds of formula (J-1) are provided wherein the ring comprising $X^1$, $X^2$, $X^3$ and $X^4$ is a phenyl, pyridyl, pyrimidinyl or pyrazinyl ring, optionally substituted with 0-3 $R^6$ groups (i.e., $(R^6)_n$ where n is 0, 1, 2 or 3). In some such embodiments, n is 1, 2 or 3 and each $R^6$ is independently halo, methyl or $CF_3$.

In a particular variation, compounds of formula (J-1) have the structure:

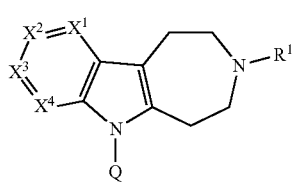

(J-1a)

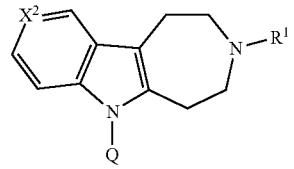

(J-1b)

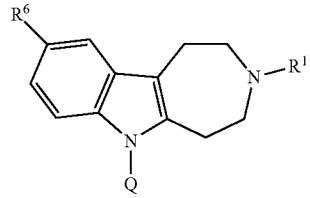

(J-1c)

or a salt or solvate thereof; wherein $R^1$, $R^6$, $X^1$, $X^2$, $X^3$, $X^4$ and Q are defined as for formula (J-1) and, where applicable, any variation thereof detailed herein. That is, variations of formula (J-1) detailed throughout, where applicable, apply equally to any of formulae (J-1a)-(J-1c), the same as if each and every variation were specifically and individually listed for formula (J-1a)-(J-1c). Pharmaceutically acceptable salts of compounds of formulae (J-1a)-(J-1c) are also provided.

In one variation, compounds of the formula (J-1) have the structure:

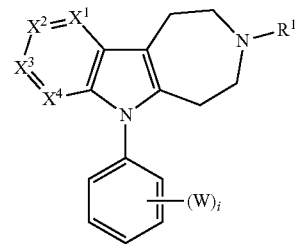

(J-2)

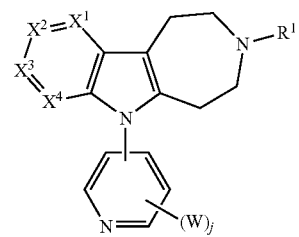

(J-3)

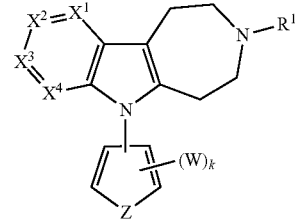

(J-4)

or a salt or solvate thereof; wherein $R^1$, $R^6$, $X^1$, $X^2$, $X^3$ and $X^4$ are defined as for formula (IA) and, where applicable, any variation thereof detailed herein, i is 0-5, j is 0-4, k is 0-3, Z is NH, N—$CH_3$, O or S, and W is H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino. In one particular aspect of this variation, W is H, substituted or unsubstituted aryl, or substituted or unsubstituted heteroaryl. In one particular aspect of this variation, Z is S. In another particular aspect of this variation, one of $X^1$, $X^2$, $X^3$ or $X^4$ (where present) is N. Variations of formula (J-1) detailed throughout, where applicable, apply equally to any of formulae (J-2)-(J-4), the same as if each and every variation were specifically and individually listed for formula (J-2)-(J-4). Pharmaceutically acceptable salts of compounds of formulae (J-2)-(J-4) are also provided.

The invention also embraces compounds of formula (K-1):

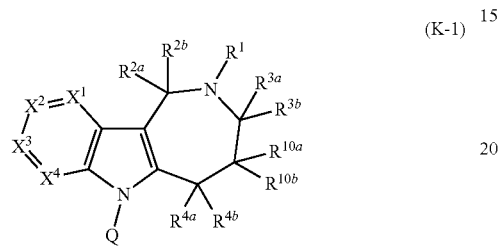

(K-1)

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{2(a/b)}$, $R^{3(a/b)}$, $R^{4(a/b)}$ or $R^{10(a/b)}$ to form a carbonyl moiety or a cycloalkyl moiety;

each $X^1$, $X^2$ and $X^3$ is independently N, CH or $CR^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl.

In one variation, provided are compounds of the formula (K-1), wherein at least one of $X^1$, $X^2$, $X^3$ and $X^4$ is CH or $CR^6$. In another variation, at least two of $X^1$, $X^2$, $X^3$ and $X^4$ is CH or $CR^6$.

In a particular variation, compounds of formula (K-1) have the structure:

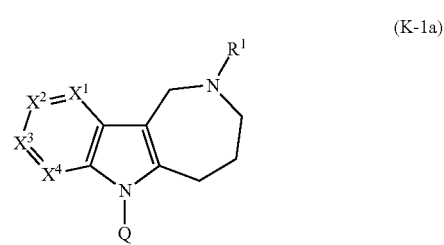

(K-1a)

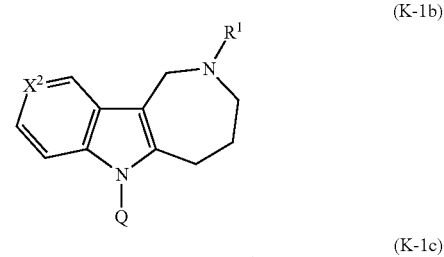

(K-1b)

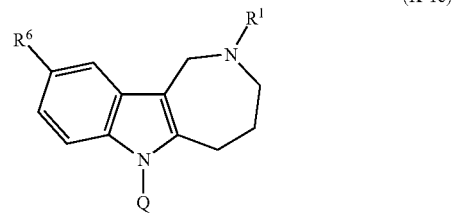

(K-1c)

or a salt or solvate thereof; wherein $R^1$, $X^1$, $X^2$, $X^3$, $X^4$ and Q are defined as for formula (K-1) and, where applicable, any variation thereof detailed herein. That is, variations of formula (K-1) detailed throughout, where applicable, apply equally to any of formulae (K-1a)-(K-1c), the same as if each and every variation were specifically and individually listed for formula (K-1a)-(K-1c). Pharmaceutically acceptable salts of compounds of formulae (K-1a)-(K-1c) are also provided.

In one variation, compounds of the formula (K-1) have the structure:

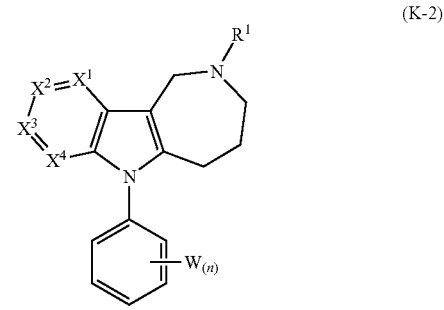

(K-2)

-continued

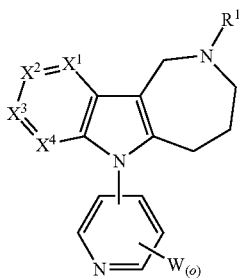

(K-3)

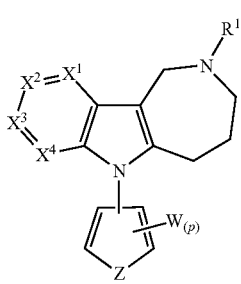

(K-4)

or a salt or solvate thereof; wherein $R^1$, $R^6$, $X^1$, $X^2$, $X^3$ and $X^4$ are defined as for formula (IA) and, where applicable, any variation thereof detailed herein, n is 0-5, o is 0-4, p is 0-3, Z is NH, N—$CH_3$, O or S, and W is H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino. In one particular aspect of this variation, W is H, substituted or unsubstituted aryl, or substituted or unsubstituted heteroaryl. In one particular aspect of this variation, Z is S. In another particular aspect of this variation, one of $X^1$, $X^2$, $X^3$ or $X^4$ is N. Variations of formula (K-1) detailed throughout, where applicable, apply equally to any of formulae (K-2)-(K-4), the same as if each and every variation were specifically and individually listed for formula (K-2)-(K-4). Pharmaceutically acceptable salts of compounds of formulae (K-2)-(K-4) are also provided.

All variations referring to formula (J-1), such as formulae (J-1a)-(J-1c) and (J-2)-(J-4), where applicable, may apply equally to formula (K-1), the same as if each and every variation were specifically and individually listed.

In certain embodiments, compounds are provided, such as compounds of the formulae (IA), (IB), (J-1) and (K-1), and any variations thereof detailed herein, wherein $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In specific embodiments, $R^1$ is a substituted or unsubstituted $C_1$-$C_8$ alkyl, acyl, acyloxy, carbonylalkoxy, substituted or unsubstituted heterocyclyl or substituted or unsubstituted aryl. In more specific embodiments, $R^1$ is an unsubstituted $C_1$-$C_8$ alkyl such as methyl and cyclopropyl.

In certain embodiments, compounds are provided wherein $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy. In more specific embodiments, $R^1$ is a sulfonyl such as —$SO_2$-alkyl, —$SO_2$-aryl and —$SO_2$-aralkyl.

In certain embodiments, compounds are provided where $R^1$ is selected from the following moieties:

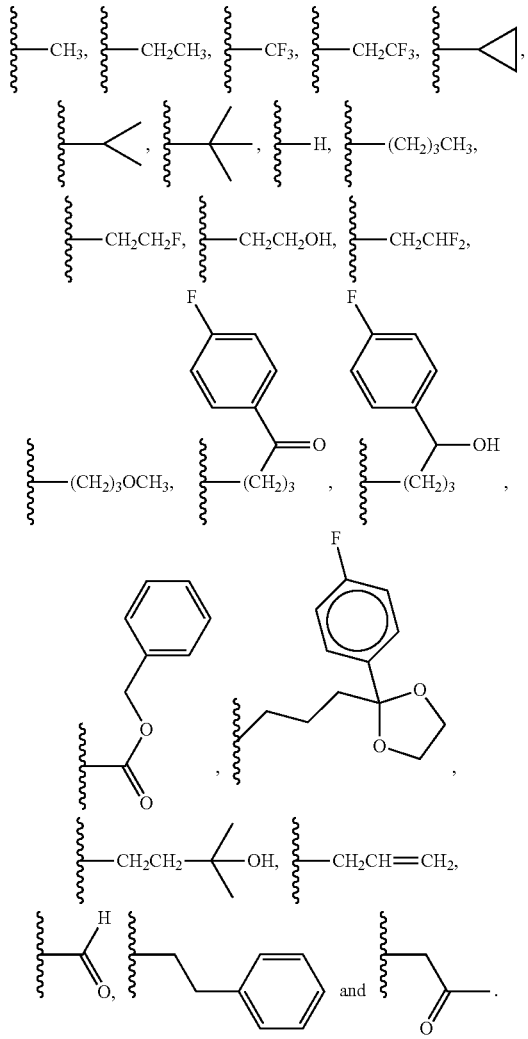

In certain embodiments, compounds are provided where each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety. In specific embodiments, each $R^{2a}$ and $R^{2b}$ is independently H, methyl, fluoro or $R^{2a}$ and $R^{2b}$ are taken together to form a carbonyl moiety. In a specific embodiment, $R^{2a}$ and $R^{2b}$ are both H.

In certain embodiments, compounds are provided where each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together to form a carbonyl moiety. In specific embodiments, each $R^{3a}$ and $R^{3b}$ is independently H or fluoro. In another specific embodiment, $R^{3a}$ and $R^{3b}$ are both H. In a further specific embodiment, $R^{3a}$ and $R^{3b}$ are both H and $R^{4a}$ and $R^{4b}$ are both H.

In certain embodiments, compounds are provided where each $R^{4a}$ and $R^{4b}$ is independently H, substituted or unsubstituted $C_1$-$C_8$ alkyl, halo, cyano, hydroxyl, alkoxy, nitro or $R^{4a}$ and $R^{4b}$ are taken together to form a carbonyl moiety. In specific embodiments, each $R^{4a}$ and $R^{4b}$ is independently H, halo, hydroxyl or methyl or $R^{4a}$ and $R^{4b}$ are taken together to form a carbonyl moiety. In another specific embodiment, $R^{4a}$ and $R^{4b}$ are both H. In a further specific embodiment, $R^{2a}$ and $R^{2b}$ are both H and $R^{3a}$, $R^{3b}$, $R^{4a}$ and $R^{4b}$ are each H.

In certain embodiments, compounds are provided where each $X^1$, $X^2$, $X^3$ and $X^4$ is independently N, CH or $CR^6$. In certain embodiments, each $X^1$, $X^2$, $X^3$ and $X^4$ is CH or $CR^6$, such that the ring comprising $X^1$, $X^2$, $X^3$ and $X^4$ is an optionally substituted phenyl ring. In specific embodiments, $X^2$ is $CR^6$ where $R^6$ is halo or alkyl and $X^1$, $X^3$ and $X^4$ are each CH. In other embodiments, one of $X^1$, $X^2$, $X^3$ and $X^4$ is N, and the others are CH or $CR^6$, such that the ring is an optionally substituted pyridine ring. In further embodiments, two of $X^1$, $X^2$, $X^3$ and $X^4$ are N, and the other is CH or $CR^6$, such that the ring is an optionally substituted pyrimidine or pyrazine ring.

In certain embodiments, compounds are provided where each $R^6$, where present, is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl. In one variation, at least one of $X^1$-$X^4$ is $CR^6$ where $R^6$ is halo. In a particular variation, one of $X^1$-$X^4$ is $CR^6$ where $R^6$ is chloro and the others are CH. In a specific variation, $X^1$, $X^3$ and $X^4$ are each CH and $X^2$ is $CR^6$ where $R^6$ is chloro.

In certain embodiments, compounds are provided where each $R^6$, where present, is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl. In further embodiments, each $R^6$, where present, is independently hydroxyl, halo, $C_1$-$C_4$ perhaloalkyl, substituted or unsubstituted $C_1$-$C_4$ alkyl, substituted or unsubstituted aryl, substituted or unsubstituted heteroaryl, or $C_1$-$C_4$ alkoxy; or in still a further variation, each $R^6$, where present, is independently halo, unsubstituted $C_1$-$C_4$ alkyl or $C_1$-$C_4$ perhaloalkyl.

In specific embodiments, the ring comprising $X^1$-$X^4$ is a phenyl, pyridyl, pyrimidinyl or pyrazinyl ring, optionally substituted with 0-2 $R^6$ groups (i.e., $(R^6)_n$) where n is 0, 1 or 2. In some such embodiments, n is 1 or 2 and each $R^6$ is independently halo, methyl or $CF_3$.

In certain embodiments, compounds are provided where Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy or acylamino. In one variation, compounds are of the formula (IA) or (IB) where Q is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl. In certain embodiments, Q is a substituted or unsubstituted 5- or 6-membered aryl or heteroaryl. In some such embodiments, Q is a substituted or unsubstituted phenyl, pyridyl or pyrimidinyl ring. When Q is substituted, it is frequently substituted with from 1-3 substituents selected from group consisting of halo, $C_1$-$C_4$ alkyl, $C_1$-$C_4$ perhaloalkyl, and $C_1$-$C_4$ alkoxy.

In a particular variation, Q is a substituted heteroaryl, a mono-substituted aryl group substituted with a chloro or alkyl group or a di- or tri-substituted aryl moiety. For instance, Q in one variation is selected from the group consisting of 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl, 2,4,6-trifluorophenyl, 4-chlorophenyl, 4-methylphenyl, 6-methyl-3-pyridyl, 6-trifluoromethyl-3-pyridyl, 5-trifluoromethyl-3-pyridyl and pyrimidinyl. In one aspect, Q is a substituted pyridyl such as 6-methyl-3-pyridyl, 6-trifluoromethyl-3-pyridyl and 5-trifluoromethyl-3-pyridyl.

In certain embodiments, $R^1$ is a substituted or unsubstituted $C_1$-$C_8$ alkyl, acyl, acyloxy, carbonylalkoxy, substituted or unsubstituted heterocyclyl or substituted or unsubstituted aryl; each $R^{2a}$ and $R^{2b}$ is independently H, methyl, fluoro or $R^{2a}$ and $R^{3b}$ are taken together to form a carbonyl moiety; each $R^{3a}$ and $R^{3b}$ is independently H or fluoro; and each $R^{4a}$ and $R^{4b}$ is independently H, halo, hydroxyl or methyl or $R^{4a}$ and $R^{4b}$ are taken together to form a carbonyl moiety. In particular variations, $R^1$ is an unsubstituted $C_1$-$C_8$ alkyl and $R^{2a}$, $R^{2b}$, $R^{3a}$, $R^{3b}$, $R^{4a}$ and $R^{4b}$ are each H. In still a further variation, $R^1$ is an unsubstituted $C_1$-$C_8$ alkyl, $R^{2a}$, $R^{2b}$, $R^{3a}$, $R^{3b}$, $R^{4a}$ and $R^{4b}$ are each H and Q is selected from the group consisting of 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl, 2,4,6-trifluorophenyl, 4-chlorophenyl, 4-methylphenyl, 6-methyl-3-pyridyl, 6-trifluoromethyl-3-pyridyl, 5-trifluoromethyl-3-pyridyl and pyrimidinyl. In still a further variation, $R^1$ is an unsubstituted $C_1$-$C_8$ alkyl, $R^{2a}$, $R^{2b}$, $R^{3a}$, $R^{3b}$, $R^{4a}$ and $R^{4b}$ are each H and $X^2$ is $CR^6$ where $R^6$ is chloro. In yet a further variation, $R^1$ is an unsubstituted $C_1$-$C_8$ alkyl, $R^{2a}$, $R^{2b}$, $R^{3a}$, $R^{3b}$, $R^{4a}$ and $R^{4b}$ are each H, $X^2$ is $CR^6$ where $R^6$ is chloro and Q is a substituted or unsubstituted aryl or a substituted or substituted heteroaryl. In one such variation, Q is a substituted phenyl.

In certain embodiments, compounds are provided where each $X^1$, $X^2$, $X^3$ and $X^4$ is CH or $CR^6$. In other embodiments, at least one of $X^1$, $X^2$, $X^3$ and $X^4$ is N. Another variation provides a compound where at least two of $X^1$, $X^2$, $X^3$ and $X^4$ are N. A further variation provides a compound where two of $X^1$, $X^2$, $X^3$ and $X^4$ are N and one of $X^1$, $X^2$, $X^3$ and $X^4$ is CH or $CR^6$. Compounds where one of $X^1$, $X^2$, $X^3$ and $X^4$ is N and two of $X^1$, $X^2$, $X^3$ and $X^4$ are CH or $CR^6$ are also embraced by this invention.

In another variation, compounds are provided where wherein the ring comprising $X^1$-$X^4$ is an aromatic moiety selected from the following structures:

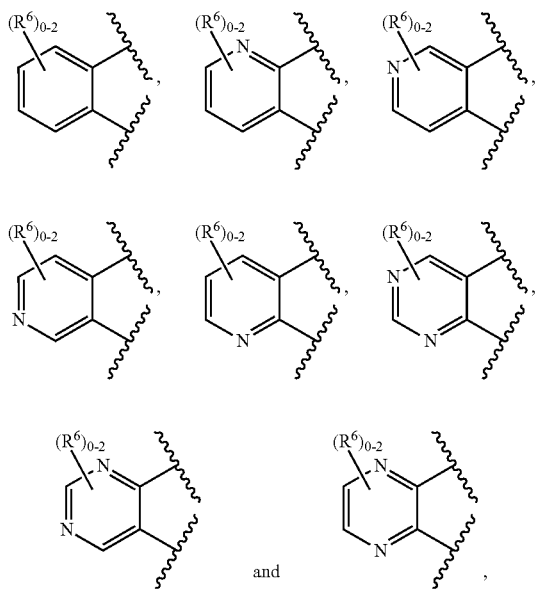

where each $R^6$ is as defined herein. In a particular variation, each $R^6$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl. In a further variation, each $R^6$ is independently halo, unsubstituted $C_1$-$C_4$ alkyl, $C_1$-$C_4$ perhaloalkyl, or $C_1$-$C_4$ alkoxy.

In still a further variation, compounds are provided wherein the ring comprising $X^1$-$X^4$ is an aromatic moiety selected from the following structures:

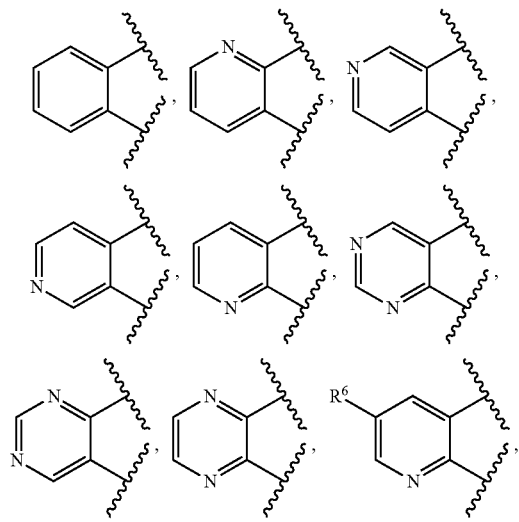

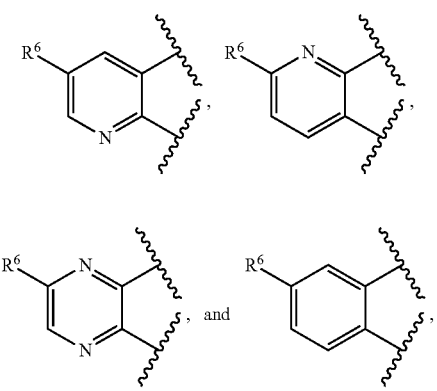

wherein $R^6$ is as defined herein; or in a particular variation, where $R^6$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl; or in still a further variation, where each $R^6$ is independently halo, unsubstituted $C_1$-$C_4$ alkyl, $C_1$-$C_4$ perhaloalkyl, or $C_1$-$C_4$ alkoxy.

In a further variation, compounds are provided wherein the ring comprising $X^1$-$X^4$ is an aromatic moiety selected from the following structures:

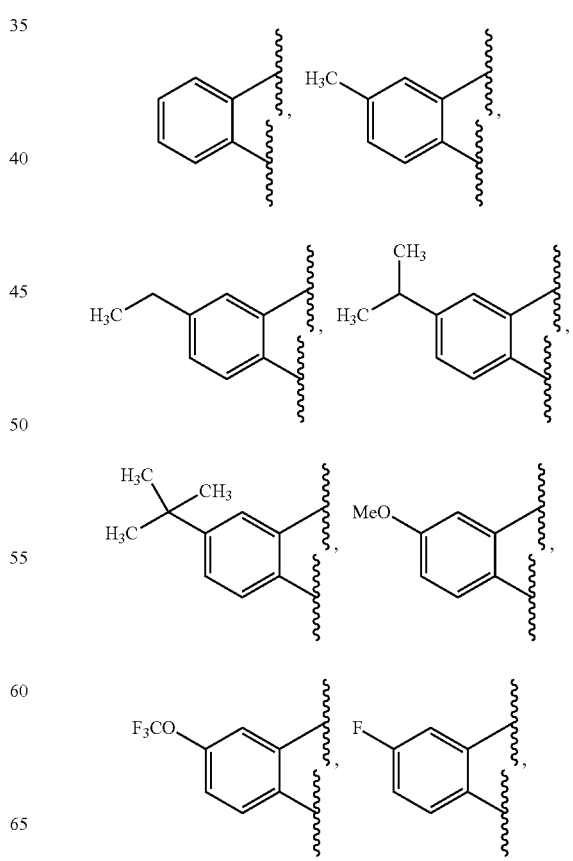

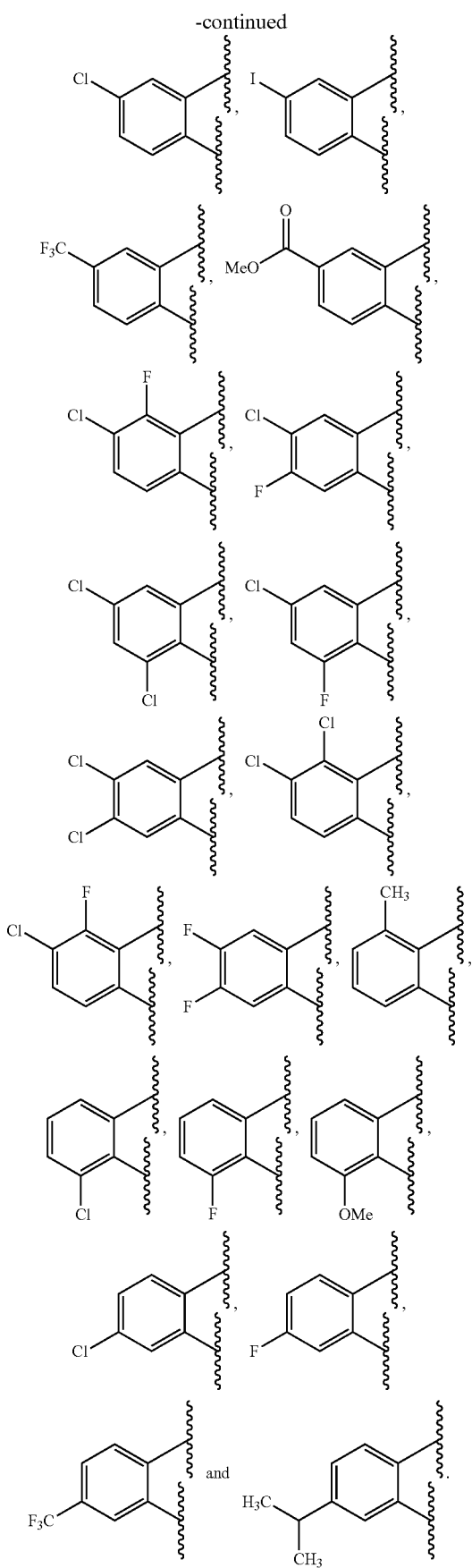

Any formula detailed herein, where applicable, may in one variation have $X^1$, $X^2$, $X^3$ and $X^4$ taken together to provide an aromatic moiety detailed herein above. It is understood that by "where applicable" it is intended that in one variation such $X^1$, $X^2$, $X^3$ and $X^4$ groups are taken together to provide a moiety hereinabove if the formula encompasses such a structure. For example, if a given formula does not encompass structures wherein $X^1$, $X^2$, $X^3$ and $X^4$ groups are taken together provide a pyridyl moiety, then a pyridyl moiety as detailed hereinabove is not applicable to that particular formula, but remains applicable to formulae that do encompass structures where $X^1$, $X^2$, $X^3$ and $X^4$ groups are taken together provide a pyridyl moiety.

In another embodiment, compounds are provided wherein $X^1$-$X^4$ are as defined herein or as detailed in any variation herein, where $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, compounds are provided wherein $X^1$-$X^4$ are as defined herein or as detailed in any variation herein, where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, compounds are provided wherein $X^1$-$X^4$ are as defined herein or as detailed in any variation herein, where $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In another variation, the compound of the invention is provided where $X^1$-$X^4$ and $R^1$ are as defined herein or as detailed in any variation herein, where $R^{2a}$ and $R^{2b}$ are independently H, substituted or unsubstituted $C_1$-$C_8$ alkyl, halo, cyano, nitro or $R^{2a}$ and $R^{3b}$ are taken together to form a carbonyl moiety and each $R^{3a}$ and $R^{3b}$ is independently H, substituted or unsubstituted $C_1$-$C_8$ alkyl, halo, cyano or nitro. In another variation, the compound of the invention is provided where $X^1$-$X^3$ and $R^1$ are as defined herein or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety and each $R^{3a}$ and $R^{3b}$ is independently H, unsubstituted $C_1$-$C_8$ alkyl, halo or $R^{3a}$ and $R^{3b}$ are taken together to form a carbonyl moiety. In still a further variation, the compound of the invention is provided where $X^1$-$X^4$ and $R^1$ are as defined herein or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety; and each $R^{3a}$ and $R^{3b}$ is independently H, unsubstituted $C_1$-$C_8$ alkyl, halo or $R^{3a}$ and $R^{3b}$ are taken together to form a carbonyl moiety. The invention also embraces compounds of the invention where $X^1$-$X^4$ and $R^1$ are as defined herein or as detailed in any variation herein, where each $R^{2a}$ and $R^{2b}$ is independently H, methyl, halo or $R^{2a}$ and $R^{2b}$ are taken together to form a carbonyl moiety and each $R^{3a}$ and $R^{3b}$ is independently H, methyl, halo or $R^{3a}$ and $R^{3b}$ are taken together to form a carbonyl moiety.

The invention further embraces compounds of the invention according to formula (IA) or (IB), where $X^1$-$X^4$ and $R^1$ are as defined herein or as detailed in any variation herein, where each $R^{2a}$, $R^{2b}$, $R^{3a}$ and $R^{3b}$ is H. In one variation, a compound of the invention is of the formula (IA) or (IB) where $X^1$-$X^4$ and $R^1$ are as defined herein or as detailed in any variation herein, where at least one of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety.

In another variation, a compound of the invention is of the formula (IA) or (IB) where $X^1$-$X^4$ and $R^1$ are as defined herein or as detailed in any variation herein, where at least two of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In yet another variation, a compound of the invention is of the formula (IA) or (IB) where $X^1$-$X^4$ and $R^1$ are as defined herein or as detailed in any variation herein, where at least one of $R^{2a}$, $R^{2b}$, $R^{3a}$ and $R^{3b}$ is fluoro or methyl or is taken together with a geminal $R^2$ or $R^3$ to form a carbonyl moiety.

In still another variation, a compound of the invention is of the formula (IA) or (IB) where $X^1$-$X^4$ and $R^1$ are as defined herein or as detailed in any variation herein, where either $R^{2a}$ and $R^{2b}$ or $R^{3a}$ and $R^{3b}$ are each methyl or fluoro (e.g., both $R^{2a}$ and $R^{2b}$ are methyl or one is fluoro and one is methyl) or are taken together to form a carbonyl moiety. In one variation, $R^{2a}$ and $R^{2b}$ are taken together to form a carbonyl moiety. In another variation, at least one of $R^{2a}$ and $R^{2b}$ is hydroxyl or alkoxy. In a particular variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl moiety. In another variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl moiety.

The invention also embraces compounds according to formula (IA) or (IB), where $X^1$-$X^4$, $R^1$, $R^{2a}$, $R^{2b}$, $R^{3a}$ and $R^{3b}$ are as defined herein or as detailed in any variation herein, where each $R^{4a}$ and $R^{4b}$ is independently H, halo, an unsubstituted $C_1$-$C_8$ alkyl, hydroxyl or $R^{4a}$ and $R^{4b}$ are taken together to form a carbonyl moiety. Also embraced are compounds according to formula (IA) or (IB), where $X^1$-$X^4$, $R^1$, $R^{2a}$, $R^{2b}$, $R^{3a}$ and $R^{3b}$ are as defined herein or as detailed in any variation herein, where each $R^{4a}$ and $R^{4b}$ is independently H, halo, an unsubstituted $C_1$-$C_4$ alkyl, hydroxyl or $R^{4a}$ and $R^{4b}$ are taken together to form a carbonyl moiety. In another variation, a compound of the invention is of the formula (IA) or (IB), where $X^1$-$X^4$, $R^1$, $R^{2a}$, $R^{2b}$, $R^{3a}$ and $R^{3b}$ are as defined herein or as detailed in any variation herein, where each $R^{4a}$ and $R^{4b}$ is independently H, bromo, methyl, hydroxyl or $R^{4a}$ and $R^{4b}$ are taken together to form a carbonyl moiety.

In yet another variation, a compound of the invention is of the formula (IA) or (IB), where $X^1$-$X^4$, $R^1$, $R^{2a}$, $R^{2b}$, $R^{3a}$ and $R^{3b}$ are as defined herein or as detailed in any variation herein, where at least one of $R^{4a}$ and $R^{4b}$ is an unsubstituted $C_1$-$C_8$ alkyl, hydroxyl, halo or $R^{4a}$ and $R^{4b}$ are taken together to form a carbonyl moiety. In still a further variation, a compound of the invention is of the formula (IA) or (IB), where $X^1$-$X^4$, $R^1$, $R^{2a}$, $R^{2b}$, $R^{3a}$ and $R^{3b}$ are as defined herein or as detailed in any variation herein, where at least one of $R^{4a}$ and $R^{4b}$ is methyl, bromo, hydroxyl or $R^{4a}$ and $R^{4b}$ are taken together to form a carbonyl moiety.

In another variation, a compound of the invention is of the formula (IA) or (IB), where $X^1$-$X^4$, $R^1$, $R^{2a}$, $R^{2b}$, $R^{3a}$ and $R^{3b}$ are as defined herein or as detailed in any variation herein, where both $R^{4a}$ and $R^{4b}$ are methyl. In another variation, a compound of the invention is of the formula (IA) or (IB), where $X^1$-$X^4$, $R^1$, $R^{2a}$, $R^{2b}$, $R^{3a}$ and $R^{3b}$ are as defined herein or as detailed in any variation herein, where $R^{4a}$ and $R^{4b}$ are taken together to form a carbonyl moiety. In another variation, a compound of the invention is of the formula (IA) or (IB), where $X^1$-$X^4$, $R^1$, $R^{2a}$, $R^{2b}$, $R^{3a}$ and $R^{3b}$ are as defined herein or as detailed in any variation herein, where $R^{4a}$ is H and $R^{4b}$ is methyl. In another variation, a compound of the invention is of the formula (IA) or (IB), where $X^1$-$X^4$, $R^1$, $R^{2a}$, $R^{2b}$, $R^{3a}$ and $R^{3b}$ are as defined herein or as detailed in any variation herein, where $R^{4a}$ is H and $R^{4b}$ is bromo. When the carbon of formula (IA) or (IB) bearing $R^{4a}$ and $R^{4b}$ is optically active, it may be in the (R)- or (S)-configuration and compositions comprising substantially pure (R) or (S) compound or mixtures thereof in any amount are embraced by this invention.

In one variation, a compound of the invention is of the formula (IA) or (IB) wherein the ring comprising N, $R^{2a}$, $R^{2b}$, $R^{3a}$, $R^{3b}$, $R^{4a}$ and $R^{4b}$ is a moiety selected from the following structures:

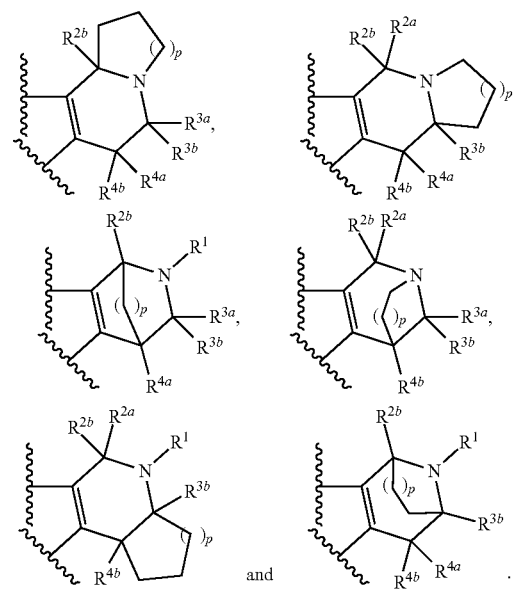

wherein $R^1$, $R^{2a}$, $R^{2b}$, $R^{3a}$, $R^{3b}$, $R^{4a}$ and $R^{4b}$ are as defined for formula (IA) or (IB), and p is 1 or 2.

In another variation, a compound of the invention is of the formula (IA) or (IB) wherein the ring comprising N, $R^{2a}$, $R^{2b}$, $R^{3a}$, $R^{3b}$, $R^{4a}$ and $R^{4b}$ is a moiety selected from the following structures:

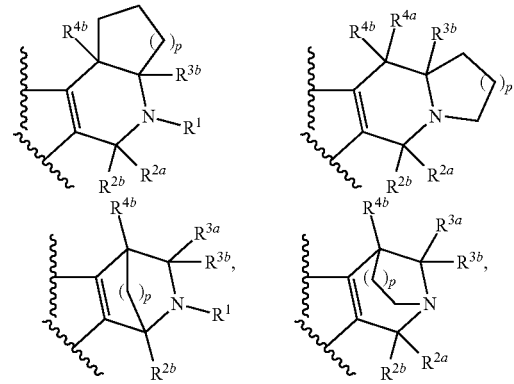

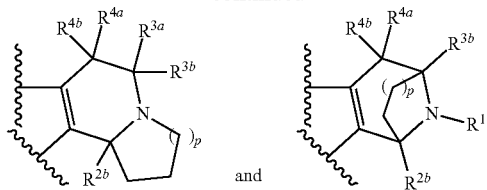

wherein $R^1$, $R^{2a}$, $R^{2b}$, $R^{3a}$, $R^{3b}$, $R^{4a}$ and $R^{4b}$ are as defined for formula (Ia), and p is 1 or 2.

In another variation, a compound of the invention is of the formula (IA) or (IB) wherein the ring comprising N, $R^{2a}$, $R^{2b}$, $R^{3a}$, $R^{3b}$, $R^{4a}$ and $R^{4b}$ is a moiety selected from the following structures:

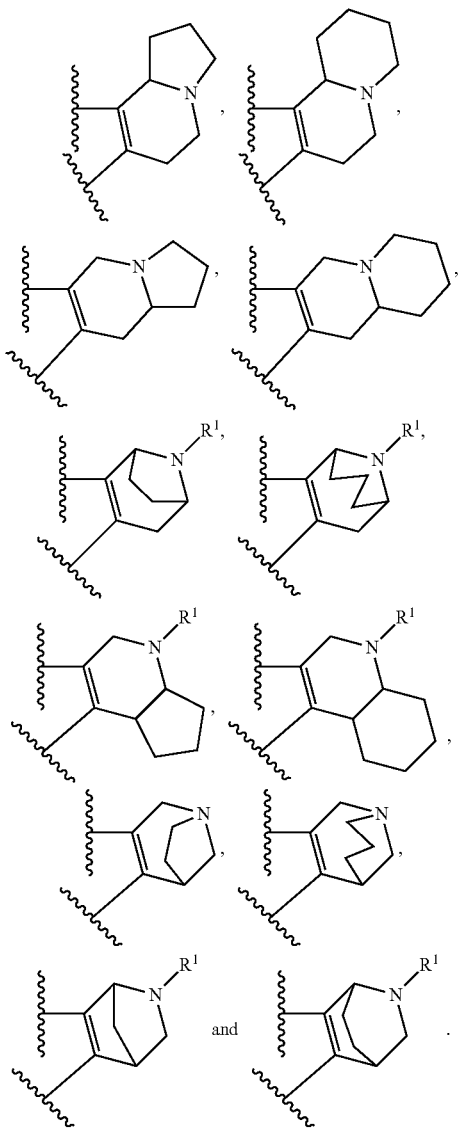

In another variation, a compound of the invention is of the formula (IA) or (IB) wherein the ring comprising N, $R^{2a}$, $R^{2b}$, $R^{3a}$, $R^{3b}$, $R^{4a}$ and $R^{4b}$ is a moiety selected from the following structures:

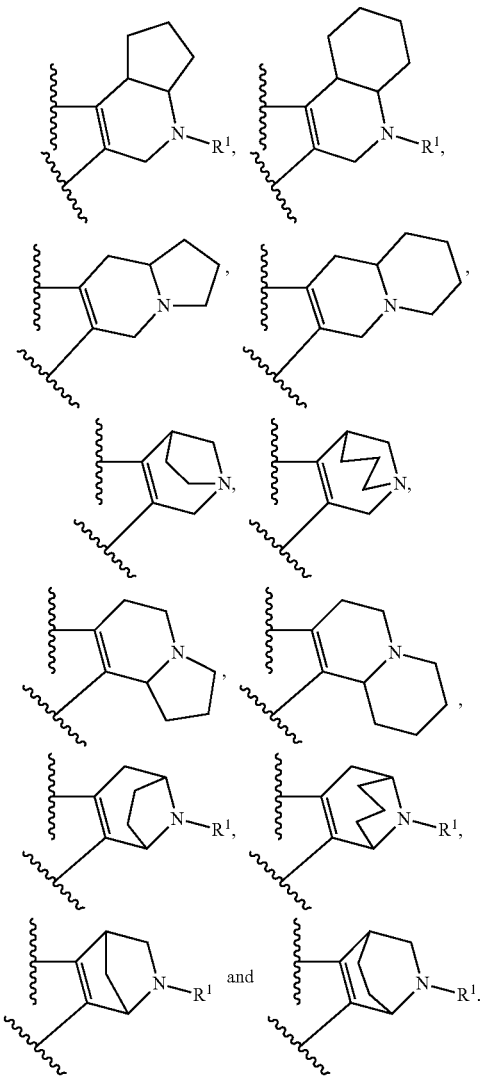

In any one of the variations of compounds of the formulae described herein, all stereoisomers are intended. For example, the C-ring can be either

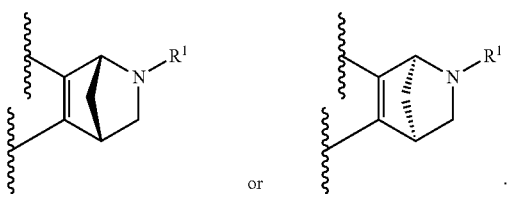

Where more than one stereocenter is present, it is understood that all such stereoisomers are intended. For example, a compound having two stereocenters may be present in the (S), (S); (S), (R); (R), (R); and (R), (S) forms. Compositions comprising a single stereoisomer or mixtures of more than one stereoisomer are also intended. Compositions comprising a mixture of stereoisomers in any ratio are embraced, including mixtures of two or more stereochemical forms of a compound of the invention in any ratio, such that racemic, non-racemic, enantioenriched and scalemic mixtures of a compound are embraced.

In some embodiments, the ring comprising N, $R^{2a}$, $R^{2b}$, $R^{3a}$, $R^{3b}$, $R^{4a}$ and $R^{4b}$ is a moiety selected from the following structures:

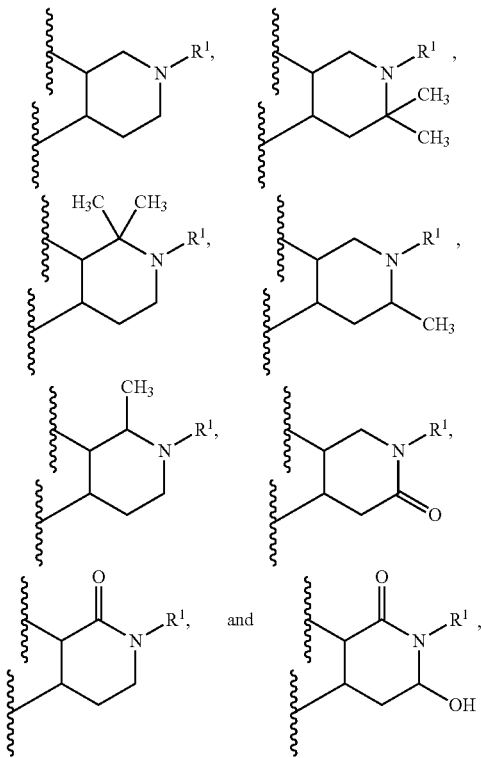

where $R^1$ in the structures above is as defined for formula (IA) or (IB) or any particular variation detailed herein. In some embodiments, the ring comprising N, $R^{2a}$, $R^{2b}$, $R^{3a}$, $R^{3b}$, $R^{4a}$ and $R^{4b}$ is a moiety selected from the following structures:

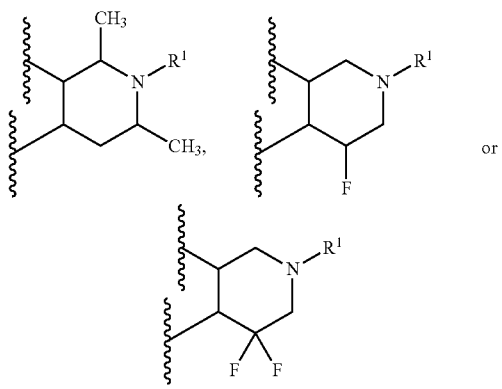

where $R^1$ is as defined for formula (IA) or (IB) or any particular variation detailed herein. Any formula detailed herein, where applicable, may in one variation have a ring according to the structures above.

In compounds of formula (IA) or (IB), Q is a substituted or unsubstituted aryl, substituted or unsubstituted heteroaryl, which may be but is not limited to a substituted or unsubstituted pyridyl, phenyl, pyrimidinyl, pyrazinyl, imidazolyl, furanyl, pyrrolyl or thiophenyl group. In one variation, a compound of the invention is of the formula (IA) or (IB) or any variation of the foregoing detailed herein, where Q is a substituted or unsubstituted phenyl or pyridyl group. In a particular variation, Q is a phenyl or pyridyl group substituted with at least one methyl, trifluoromethyl, methoxy or halo substituent. In another variation, a compound of the invention is of the formula (IA) or (IB) or any variation of the foregoing detailed herein, where Q is a pyridyl, phenyl, pyrimidinyl, pyrazinyl, imidazolyl, furanyl, pyrrolyl or thiophenyl group substituted with at least one substituted or unsubstituted $C_1$-$C_4$ alkyl, $C_1$-$C_4$ alkoxy, halo or $C_1$-$C_4$ perhaloalkyl moiety.

In still another variation, a compound of the invention is of the formula (IA) or (IB) or any variation of the foregoing detailed herein, where Q is a substituted or unsubstituted $C_3$-$C_8$ cycloalkyl or a substituted or unsubstituted heterocyclyl. In another variation, Q is a substituted or unsubstituted $C_3$-$C_8$ cycloalkyl or a substituted or unsubstituted heterocyclyl. In yet another variation, a compound of the invention is of the formula (IA) or (IB) or any variation of the foregoing detailed herein, where Q is a substituted or unsubstituted pyridyl, phenyl, pyrazinyl, piperazinyl, pyrrolidinyl or thiomorpholinyl group. In a particular variation, Q is a pyridyl, phenyl, pyrazinyl, piperazinyl, pyrrolidinyl or thiomorpholinyl group substituted with at least one methyl, $CF_3$, methoxy or halo group.

In one variation, a compound of the invention is of the formula (IA) or (IB) or any variation of the foregoing detailed herein, where Q is an unsubstituted cycloalkyl or an unsubstituted heterocyclyl. In another variation, Q is an unsubstituted $C_3$-$C_8$ cycloalkyl or an unsubstituted heterocyclyl. In another variation, a compound of the invention is of the formula (IA) or (IB) or any variation of the foregoing detailed herein, where Q is a substituted or unsubstituted cyclohexyl, morpholinyl, piperazinyl, thiomorpholinyl, cyclopentyl or pyrrolidinyl moiety. In yet another variation, a compound of the invention is of the formula (IA) or (IB) or any variation of the foregoing detailed herein, where Q is a substituted cyclohexyl, morpholinyl, piperazinyl, thiomorpholinyl, cyclopentyl or pyrrolidinyl moiety substituted with at least one carbonyl, hydroxymethyl, methyl or hydroxyl group. Q groups may be attached to the parent structure at any available position on the Q moiety. Thus, although specific attachment points for certain Q moieties are depicted herein, it is understood that such Q moieties, may also be connected to the parent structure at any available position. For example, if a mono-fluoro-phenyl is depicted herein, it is understood that each of the available mono-fluoro-phenyls are embraced, e.g., 2-fluoro-phenyl, 3-fluoro-phenyl and 4-fluoro-phenyl. It is also understood that any formula detailed herein, where applicable, may in one variation have a Q moiety as detailed herein and below.

In still another variation, a compound of the invention is provided where Q is a moiety selected from the structures:

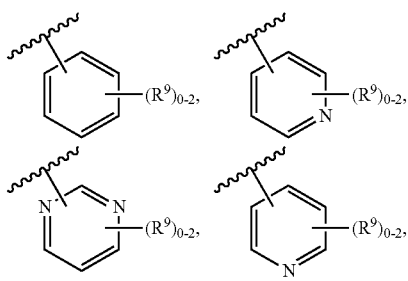

-continued

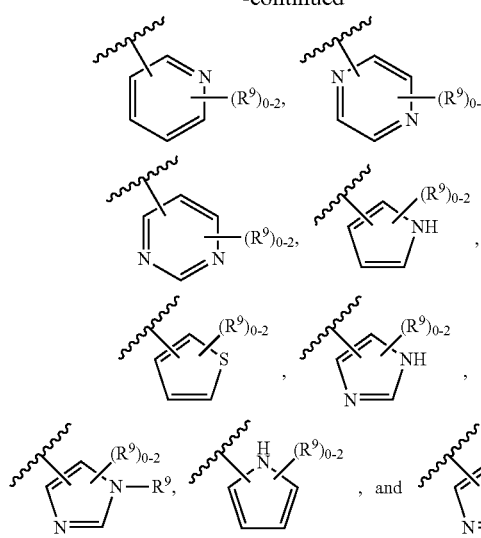

wherein each $R^9$ is independently a halo, cyano, nitro, perhaloalkyl ($C_1$-$C_8$), perhaloalkoxy ($C_1$-$C_8$), substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In one variation, Q is substituted with two $R^9$ groups. In another variation, Q is substituted with two vicinal $R^9$ groups that are taken together with the annular atoms to which they are attached to form a second fused ring. In a further variation, Q is selected from the aromatic structures detailed where the residue has the moiety $(R^9)_0$ such that each Q either contains no $R^9$ functionality or a moiety of the formula N—$R^9$.

In another variation, a compound of the invention is provided where Q is a moiety selected from the structures:

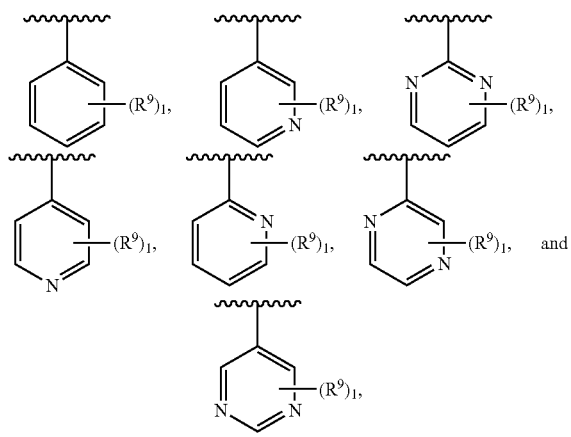

and wherein $R^9$ is connected to Q ortho or para to the position at which Q is connected to the indole nitrogen of the pyrido[4,3-b]indole or pyrido[3,4-b]indole. In a particular variation, Q is a structure of the formula:

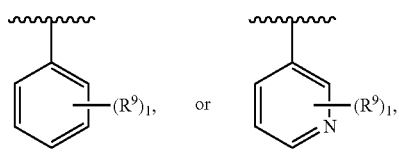

and $R^9$ is connected to Q para to the position at which Q is connected to the indole nitrogen of the pyrido[4,3-b]indole or pyrido[3,4-b]indole. In another particular variation, Q is a structure of the formula

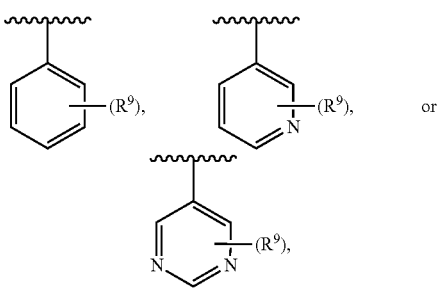

where each $R^9$ is independently alkyl, perhaloalkyl or halo.

In another variation, a compound of the invention is provided where Q is a moiety selected from the structures:

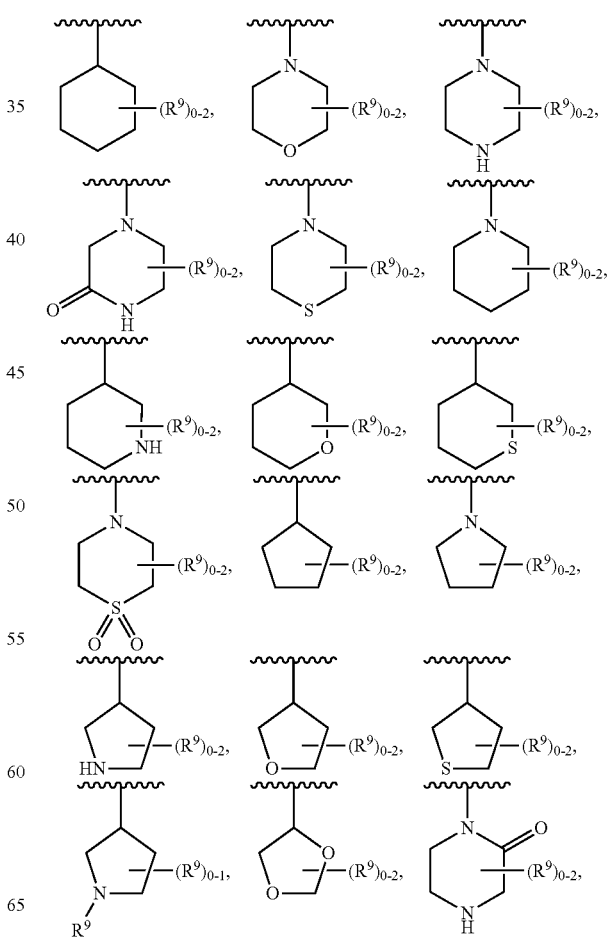

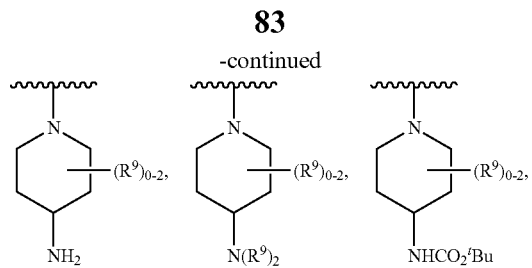
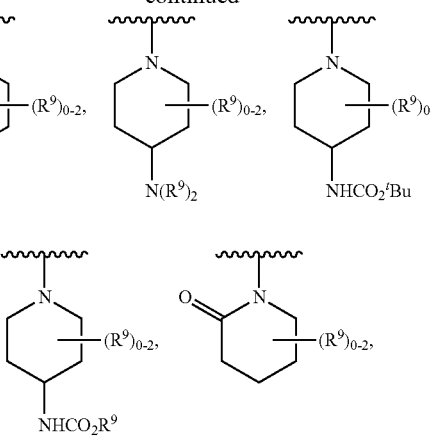

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In yet another variation, Q is substituted with two $R^9$ groups. In another variation, Q is substituted with two vicinal $R^9$ groups which are taken together with the annular atoms to which they are attached to form a second fused ring. In a particular variation, Q is selected from the carbocyclic and heterocyclic structures detailed where the residue has the moiety $(R^9)_0$ such that each Q either contains no $R^9$ functionality or a moiety of the formula N—$R^9$.

In any structure or variation detailed herein containing an $R^9$ group, in one variation, each $R^9$ is independently a substituted or unsubstituted $C_1$-$C_4$ alkyl, halo, trifluoromethyl or hydroxyl. In another variation, each $R^9$ is independently methyl, —$CH_2OH$, isopropyl, halo, trifluoromethyl or hydroxyl.

In another variation, a compound of the invention is provided where Q is an aromatic moiety selected from the structures:

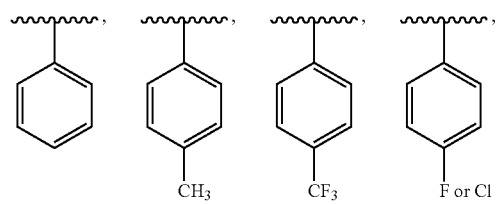
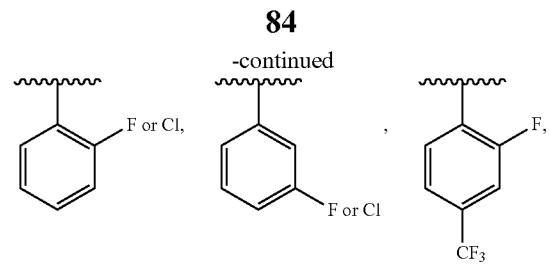
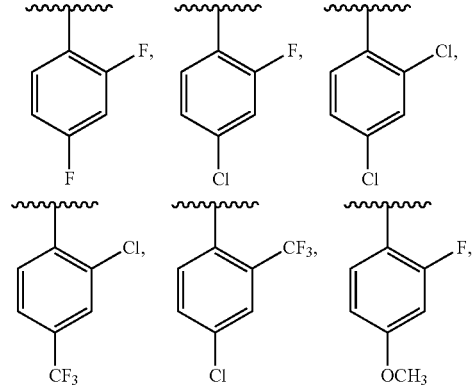
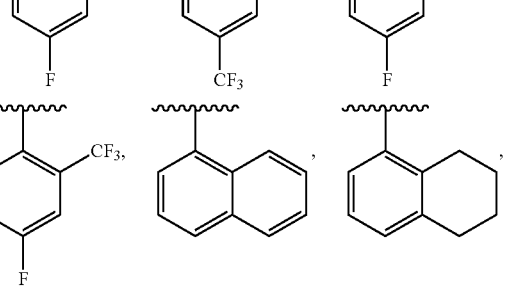
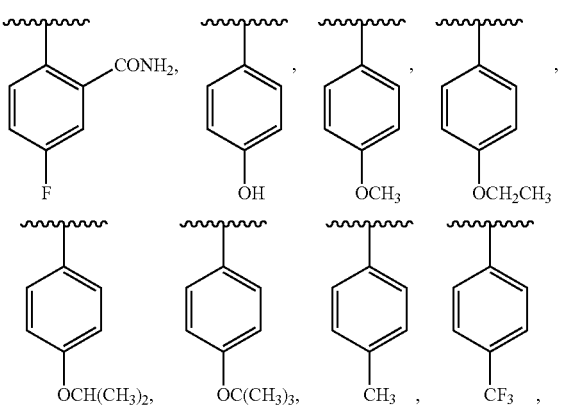
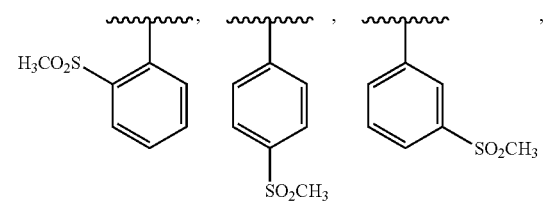

-continued
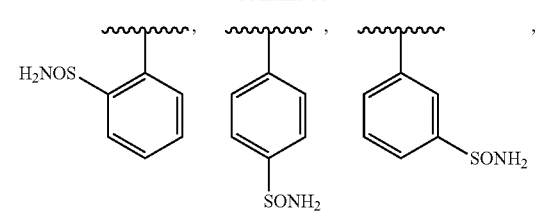
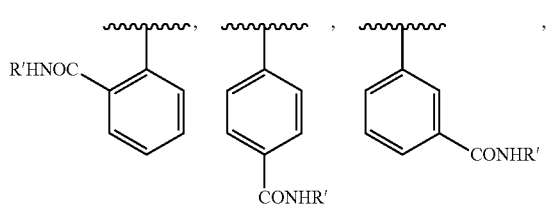
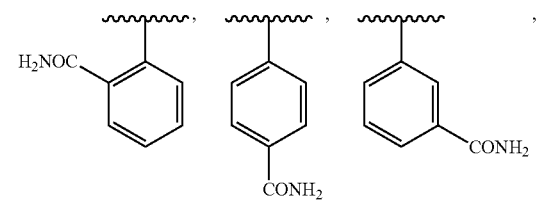
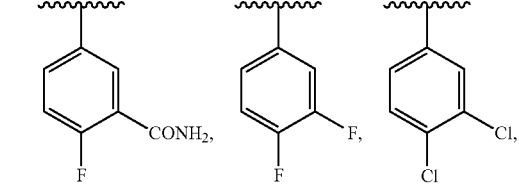
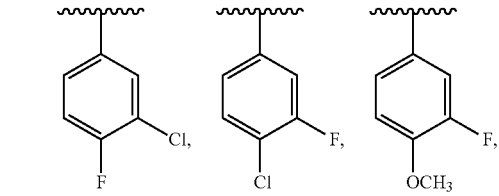
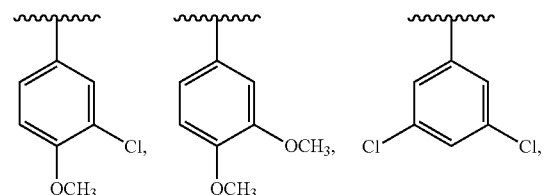
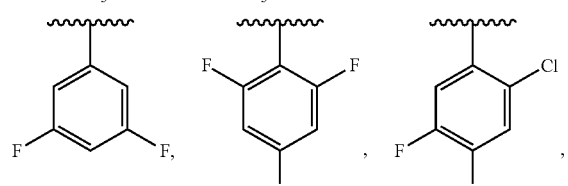
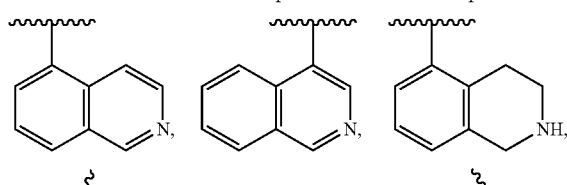
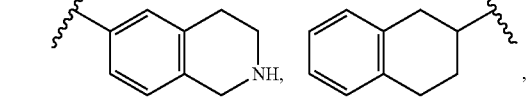
-continued
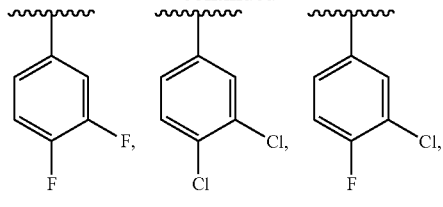
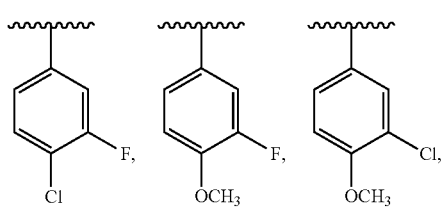
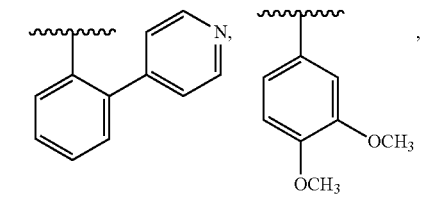
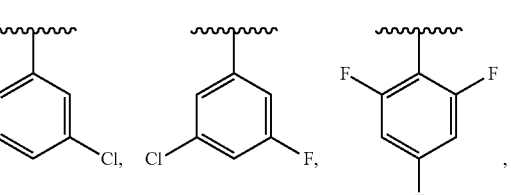
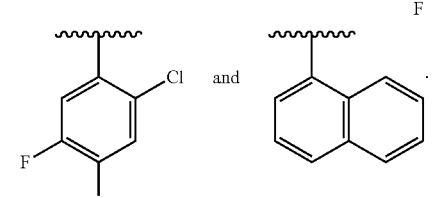
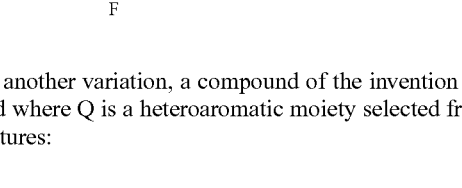
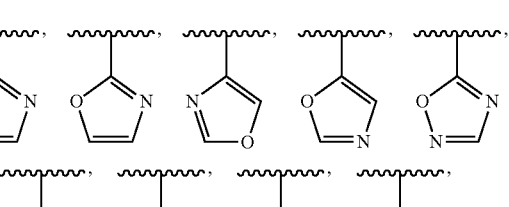
In another variation, a compound of the invention is provided where Q is a heteroaromatic moiety selected from the structures:
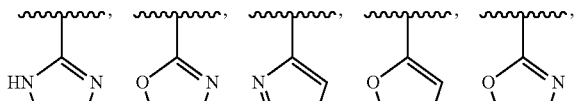
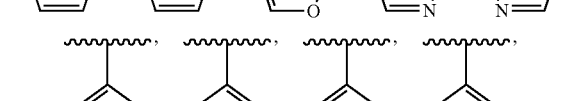
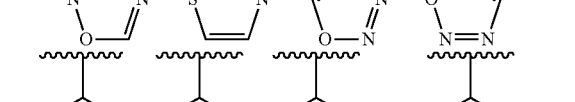
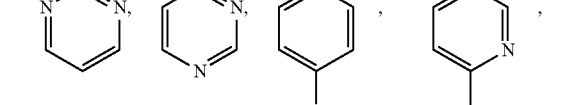

-continued
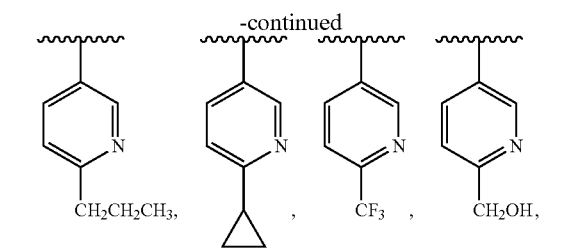
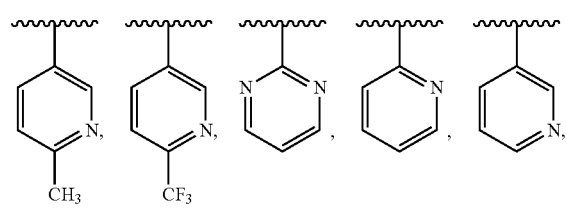
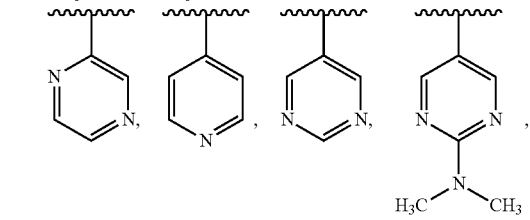
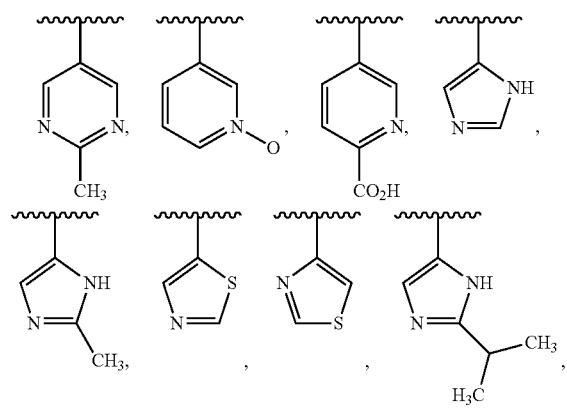
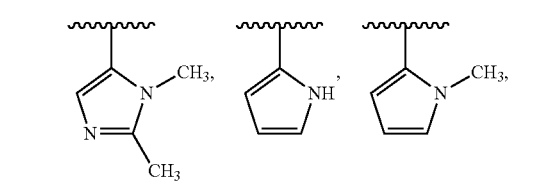
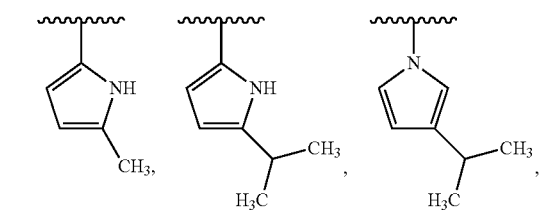
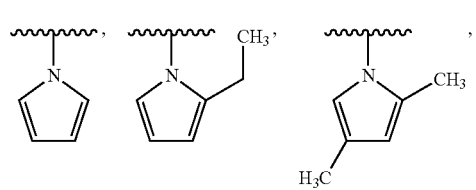
-continued
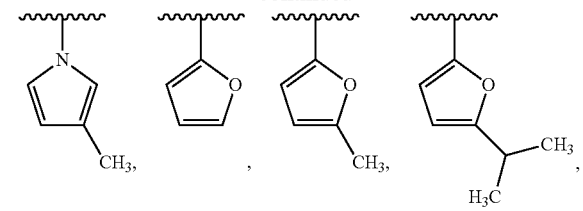
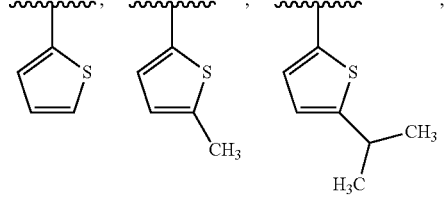
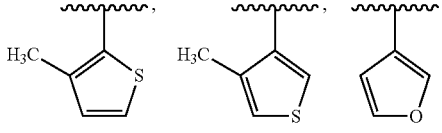
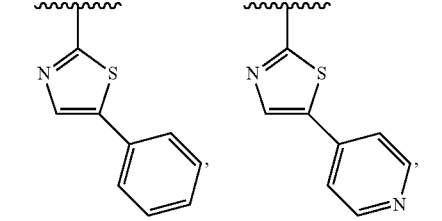
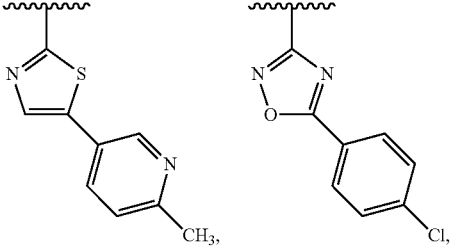
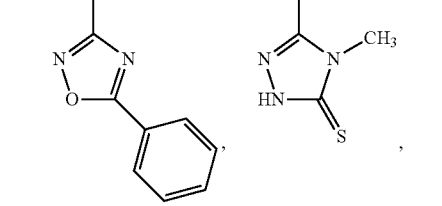
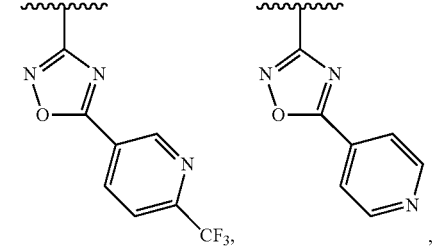

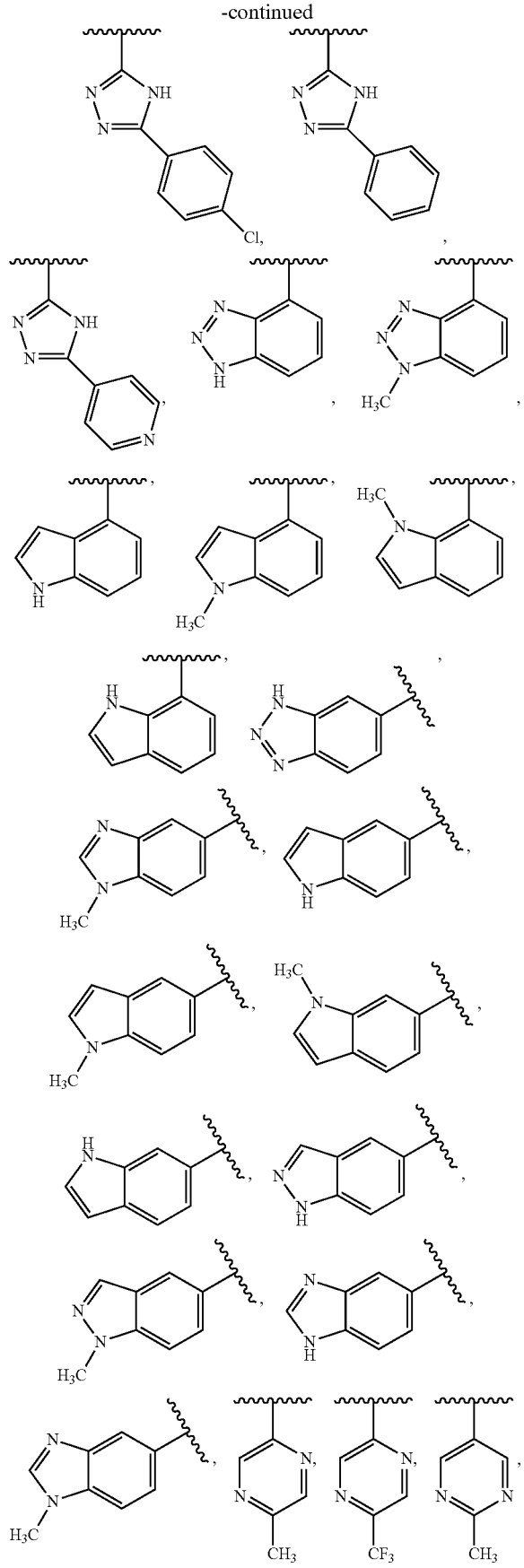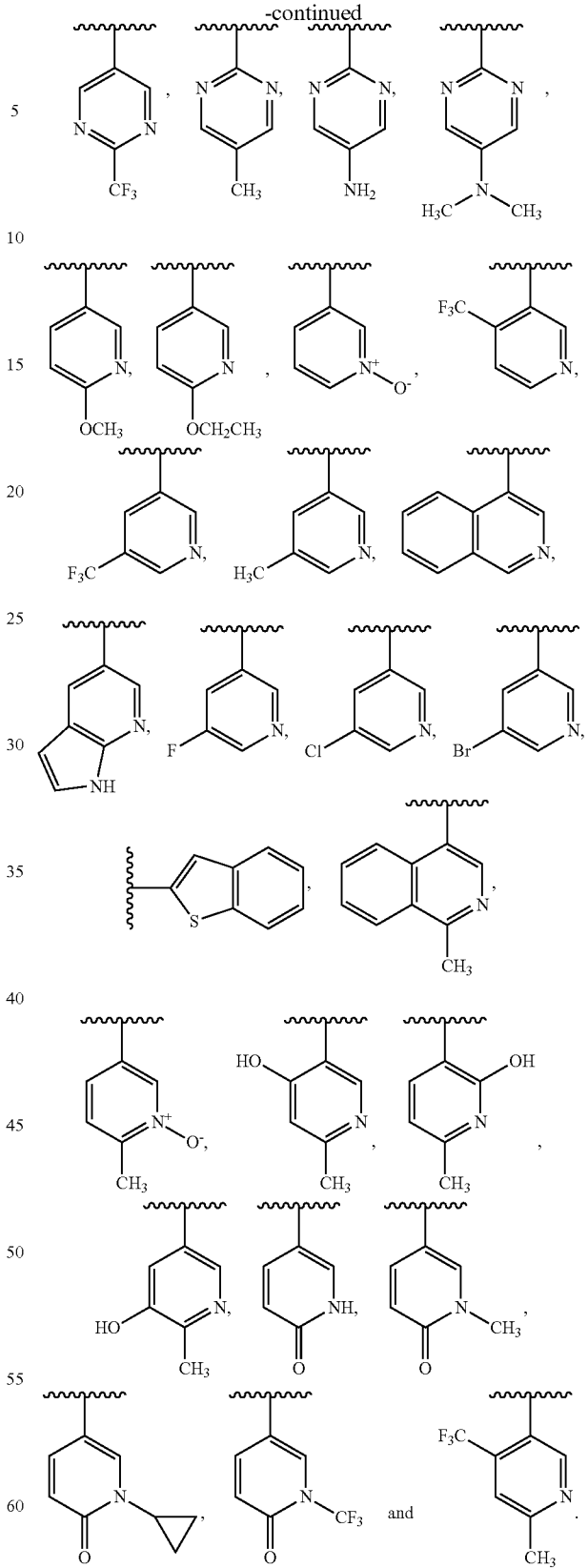
In yet another variation, a compound of the invention is provided where Q is a substituted or unsubstituted cycloalkyl or heterocyclyl selected from the structures:

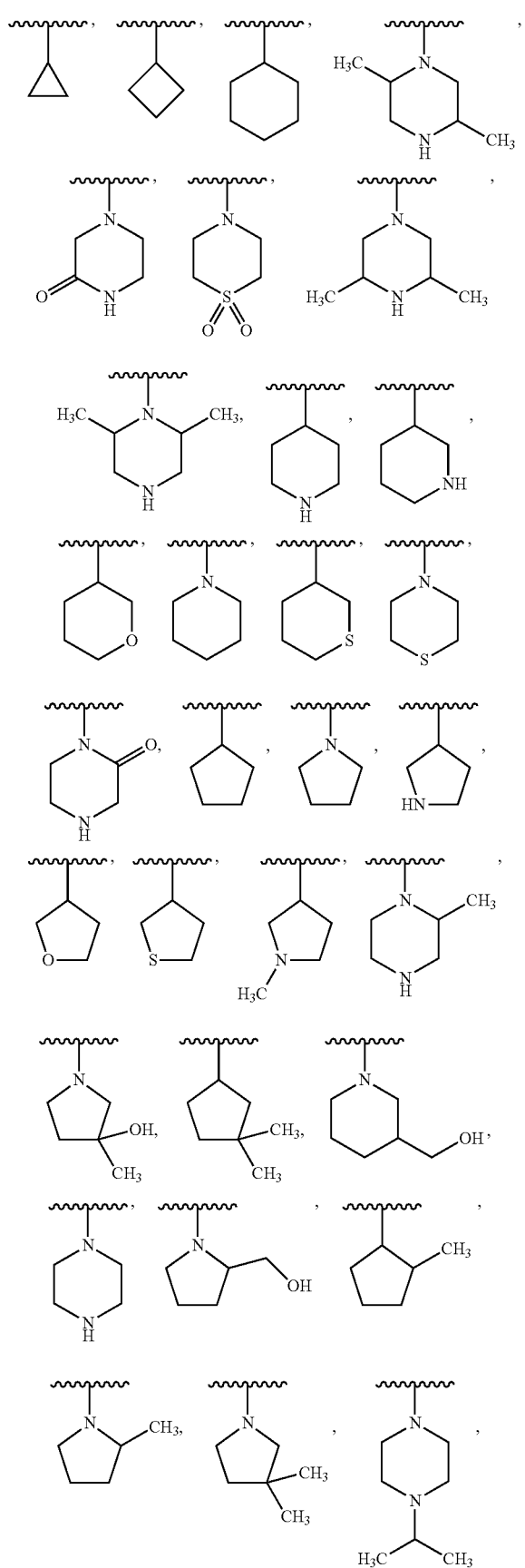
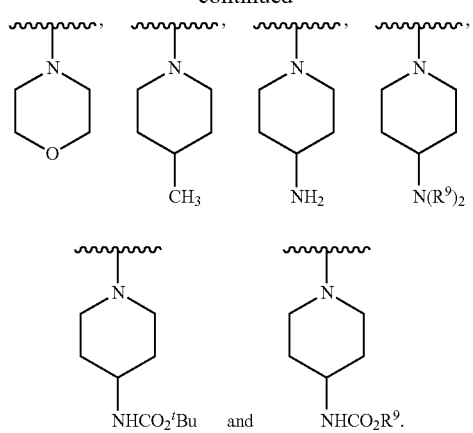
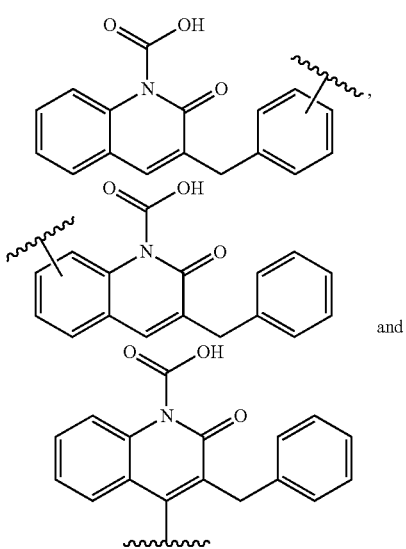
In yet another variation, a compound of the invention is provided where Q is a substituted or unsubstituted cycloalkyl or heterocyclyl selected from the structures:
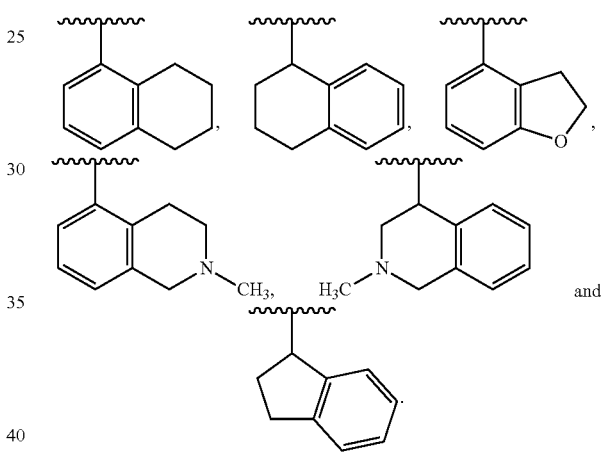
In yet another variation, a compound of the invention is provided where Q is selected from the structures:

In a further variation, a compound of the invention is provided where $R^1$ is an unsubstituted alkyl, $R^{2a}$, $R^{2b}$, $R^{3a}$, $R^{3b}$ and $R^4$ are each H, each $X^1$, $X^2$, $X^3$ and $X^4$ is independently N or CH, and Q is a substituted or unsubstituted aryl, substituted or unsubstituted heteroaryl, including but not limited to a substituted or unsubstituted phenyl or pyridyl group. Where Q is a substituted phenyl or pyridyl group, in one variation it is substituted with at least one methyl or halo group.

In yet a further variation, a compound of the invention is provided where $R^1$ is a substituted or unsubstituted $C_1$-$C_8$ alkyl, acyl, acyloxy, carbonylalkoxy, substituted or unsubstituted heterocyclyl, substituted or unsubstituted aryl; each $R^{2a}$ and $R^{2b}$ is independently H, unsubstituted $C_1$-$C_8$ alkyl or halo; each $R^{3a}$ and $R^{3b}$ is independently H or halo; each $X^1$, $X^2$ and $X^3$ is CH or $CR^6$, where $R^6$ is as defined or as detailed in a particular variation, $R^6$ is halo, pyridyl, methyl or trifluoromethyl; $R^{4a}$ and $R^{4b}$ are both H, and Q is a substituted or unsubstituted aryl, substituted or unsubstituted heteroaryl, including but not limited to a substituted or unsubstituted pyridyl, phenyl, pyrimidinyl, pyrazinyl, imidazolyl, furanyl, pyrrolyl or thiophenyl group. In a particular variation, Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In one variation, a compound of the variation detailed herein is provided wherein $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In still a further variation, a compound of the invention is provided where $R^1$ is a substituted or unsubstituted $C_1$-$C_8$ alkyl; each $R^{2a}$, $R^{2b}$, $R^{3a}$ and $R^{3b}$ is independently H or halo; each $R^6$ is independently halo, $C_1$-$C_8$ perhaloalkyl, substituted or a unsubstituted $C_1$-$C_8$ alkyl; and Q is a substituted or unsubstituted cyclohexyl, morpholinyl, piperazinyl, thiomorpholinyl, cyclopentyl or pyrrolidinyl moiety. The invention also embraces a compound where $R^1$ is a methyl; at least one of $X^1$ and $X^2$ is $CR^6$, and each $R^6$ is independently halo, methyl or trifluoromethyl. The invention embraces compounds where each Q in any variation detailed, where applicable, is independently substituted with at least one carbonyl, hydroxymethyl, methyl or hydroxyl group.

In a particular variation, a compound is provided where $R^1$ is a substituted or unsubstituted $C_1$-$C_8$ alkyl; each $R^{2a}$ and $R^{2b}$ is independently H, a substituted or unsubstituted $C_1$-$C_8$ alkyl or $R^{2a}$ and $R^{2b}$ are taken together to form a carbonyl moiety; $R^{3a}$ and $R^{3b}$ are both H; each $R^6$ is independently halo or a substituted or unsubstituted $C_1$-$C_8$ alkyl; each $R^{4a}$ and $R^{4b}$ is independently H, halo, a substituted or unsubstituted $C_1$-$C_8$ alkyl, hydroxyl, alkoxy or $R^{4a}$ and $R^{4b}$ are taken together to form a carbonyl moiety, provided that at least one of $R^{4a}$ and $R^{4b}$ is other than H. In one aspect of this variation, each Q may independently be a substituted or unsubstituted pyridyl, phenyl, pyrazinyl, piperazinyl, pyrrolidinyl or thiomorpholinyl group. In another aspect of this variation, Q is a pyridyl, phenyl, pyrazinyl, piperazinyl, pyrrolidinyl or thiomorpholinyl group substituted with at least one methyl or halo group. In yet another aspect of this variation, $X^1$, $X^2$ and $X^3$ are CH or $CR^6$ and each $R^6$ is independently halo or methyl.

The embodiments and variations described herein are suitable for compounds of any formulae detailed herein, where applicable. For instance, all variations referring to the formula (IA) detailed herein, such as formulae (IA), (IA1), (IA2), (IA3), (IA4), (IA5), (IA6), (IA7), (IA8), (IA9), (A1), (A2), (B1), (B2), (B3), (B4), (B5), (B6), (C1), (C2) and (C3), where applicable, may apply to formulae (IB), (J-1), (J-1a), (J-1b), (J-1c), (J-2), (J-3), (J-4), (K-1), (K-1a), (K-1b), (K-1c), (K-2), (K-3), (K-4) the same as if each and every variation were specifically and individually listed. In another instance, all variations referring to the formulae herein, such as formulae (IA), (IA1), (IA2) and (IA3), where applicable, may apply to formula (IA4), (IA5), (IA6), (IA7), (IA8), (IA9), (A1), (A2), (B1), (B2), (B3), (B4), (B5), (B6), (C1), (C2) or (C3), (IB), (J-1), (J-1a), (J-1b), (J-1c), (J-2), (J-3), (J-4), (K-1), (K-1a), (K-1b), (K-1c), (K-2), (K-3), (K-4) the same as if each and every variation were specifically and individually listed.

The embodiments and variations described herein for Formula (IA) are also suitable for compounds of formula (IA) or (IB). The embodiments and variations described herein for Formula (IB) are also suitable for compounds of formula (IA) or (IB).

In one embodiment, the invention relates to Compounds described in Table 1, and uses thereof.

In another embodiment, the invention relates to Compounds 1-231, and uses thereof.

In another embodiment, the invention relates to Compounds 1-88, 100, 102-105 and 131-164, and uses thereof.

Representative examples of compounds detailed herein, including intermediates and final compounds according to the invention are depicted in the tables below. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the invention embraces all salts and solvates of the compounds depicted here, as well as the non-salt and non-solvate form of the compound, as is well understood by the skilled artisan. In some embodiments, the salts of the compounds of the invention are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. For example, when a 2-hydroxypyridyl moiety is depicted, the corresponding 2-pyridone tautomer is also intended. The tautomeric forms specifically depicted may or may not be the predominant forms in solution or when used according to the methods described herein.

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. Taking compound 1 as an example, a composition of substantially pure compound 1 intends a composition that contains no more than 35% impurity, wherein the impurity denotes a compound other than compound 1 or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of "substantially pure" compound contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Kits comprising a compound of the invention, or a salt or solvate thereof, and suitable packaging are provided. In one embodiment, a kit further comprises instructions for use. In one aspect, a kit comprises a compound of the invention, or a salt or solvate thereof, and instructions for use of the compounds in the treatment of a disease or condition for which a reduction in blood pressure and/or promoting renal blood flow and/or inhibiting or decreasing sodium reabsorption is expected to be or is beneficial.

Articles of manufacture comprising a compound of the invention, or a salt or solvate thereof, in a suitable container are provided. The container may be a vial, jar, ampoule, preloaded syringe, i.v. bag, and the like.

In one aspect, a compounds detailed herein as provided herein exhibits the ability to cross the blood-brain barrier. In another aspect, a compounds detailed herein as provided herein is not able to cross the blood-brain barrier. In one aspect, a compounds detailed herein as provided herein exerts its therapeutic effect in the brain only. In one aspect, a compounds detailed herein as provided herein exerts its therapeutic effect in the periphery only. In one aspect, a compounds detailed herein as provided herein exerts its therapeutic effect both in the brain and peripherally. In some embodiments, the adrenergic receptor $\alpha_{2B}$ antagonist is a selective adrenergic receptor $\alpha_{2B}$ antagonist. In some embodiments, the adrenergic receptor $\alpha_{2B}$ antagonist also exhibits adrenergic receptor $\alpha_{2A}$ antagonist and/or inverse agonist activity.

Blood brain barrier permeability can be measured in rodents or dog by administering the compound orally or intravenously, recovering a blood and brain tissue sample at different time points and comparing how much compound is in each sample. Blood fraction is typically processed to plasma for determination of compound content. Brain exposure can be described from the ratio of brain to plasma levels of drug. In one variation, a compound that poorly crosses the blood brain barrier has a brain to plasma ratio of compound of about 0.1 or less. In another variation, the compound has a brain to plasma ratio of about 0.2 or less, about 0.3 or less, about 0.4 or less, about 0.5 or less, about 0.8 or less, or about 1.0 or less.

Preferably, the compounds detailed herein are orally bioavailable. However, the compounds may also be formulated for parenteral (e.g., intravenous) administration. In some settings, parenteral administration of an adrenergic receptor $\alpha_{2B}$ antagonists (e.g., selective adrenergic receptor $\alpha_{2B}$ antagonist) may be desired. For example, intra-renal delivery may offer treatment options for acute and chronic renal failure, end stage renal failure and acute decompensated congestive heart failure. Parenteral formulation may be preferred in the treatment of hypertensive urgency and emergency. In some embodiments, the adrenergic receptor $\alpha_{2B}$ antagonist is a selective adrenergic receptor $\alpha_{2B}$ antagonist. In some embodiments, the adrenergic receptor $\alpha_{2B}$ antagonist also exhibits adrenergic receptor $\alpha_{2A}$ antagonist and/or inverse agonist activity.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., reducing the blood pressure of an individual, promoting renal blood flow and/or decreasing or inhibiting sodium reabsorption.

Methods as provided herein may comprise administering to an individual a pharmacological composition that contains an effective amount of a compound and a pharmaceutically acceptable carrier. The effective amount of the compound may in one aspect be a dose of between about 0.01 and about 100 mg.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

The compound may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Compositions comprising a compound provided herein are also described. In one variation, the composition comprises a compound and a pharmaceutically acceptable carrier or excipient. In another variation, a composition of substantially pure compound is provided.

The invention further provides kits for carrying out the methods of the invention, which comprises one or more compounds described herein or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for any one or more of the following uses: treating, preventing, and/or delaying the onset and/or development of hypertension and/or a disease or condition which is responsive, or expected to be responsive, to (i) a reduction in an individual's blood pressure and/or (ii) an increase in renal blood flow and/or (iii) a decrease or inhibition of sodium reabsorption.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention also provides compositions (including pharmacological compositions) as described herein for the use in treating, preventing, and/or delaying the onset and/or development of hypertension and/or a disease or condition which is responsive, or expected to be responsive, to (i) a reduction in an individual's blood pressure and/or (ii) an increase in renal blood flow and/or (iii) a decrease or inhibition of sodium reabsorption and other methods described herein. In certain embodiments, the composition comprises a pharmaceutical formulation which is present in a unit dosage form. As used herein, the term "unit dosage form" refers to a formulation that contains a predetermined dose of a compound as disclosed herein and optionally a second pharmaceutically active compound useful for treatment of a disease or condition detailed herein (e.g., hypertension).

Representative compounds of the invention are shown in Table 1.

TABLE 1

Representative Compounds of the Invention

| Compound No. | Structure |
|---|---|
| 1 | 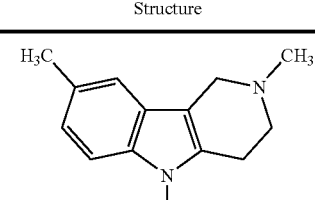 |

TABLE 1-continued

Representative Compounds of the Invention

| Compound No. | Structure |
|---|---|
| 2 | 7-methyl-2-methyl-5-(pyridin-4-yl)-2,3,4,5-tetrahydro-1H-pyrido[4,3-b]indole |
| 3 | 7-methyl-2-methyl-5-(6-methylpyridin-3-yl)-2,3,4,5-tetrahydro-1H-pyrido[4,3-b]indole |
| 4 | 7-methyl-2-methyl-5-(6-(trifluoromethyl)pyridin-3-yl)-2,3,4,5-tetrahydro-1H-pyrido[4,3-b]indole |
| 5 | 7-methyl-2-methyl-5-(2-(pyridin-4-yl)phenyl)-2,3,4,5-tetrahydro-1H-pyrido[4,3-b]indole |
| 6 | 7-methyl-2-methyl-5-(2-(dimethylamino)phenyl)-2,3,4,5-tetrahydro-1H-pyrido[4,3-b]indole |
| 7 | 7-methyl-2-methyl-5-(3-(dimethylamino)phenyl)-2,3,4,5-tetrahydro-1H-pyrido[4,3-b]indole |
| 8 | 7-methyl-2-methyl-5-(biphenyl-2-yl)-2,3,4,5-tetrahydro-1H-pyrido[4,3-b]indole |
| 9 | 7-methyl-2-methyl-5-(isoquinolin-5-yl)-2,3,4,5-tetrahydro-1H-pyrido[4,3-b]indole |
| 10 | 7-methyl-2-methyl-5-(4'-fluorobiphenyl-2-yl)-2,3,4,5-tetrahydro-1H-pyrido[4,3-b]indole |
| 11 | 7-methyl-2-methyl-5-(naphthalen-1-yl)-2,3,4,5-tetrahydro-1H-pyrido[4,3-b]indole |

TABLE 1-continued
Representative Compounds of the Invention
| Compound No. | Structure |
|---|---|
| 12 | 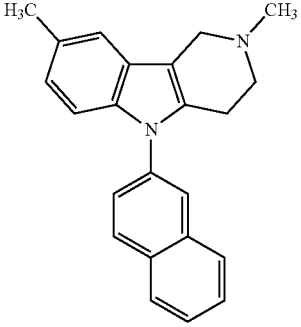 |
| 13 | 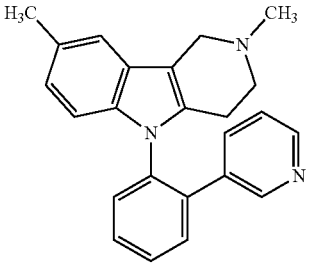 [SMILES: Cc1ccc2c(c1)c1c(n2-c2ccccc2-c2cccnc2)CCN(C)C1] |
| 14 | 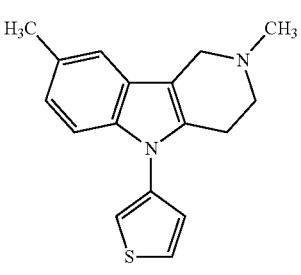 |
| 15 | 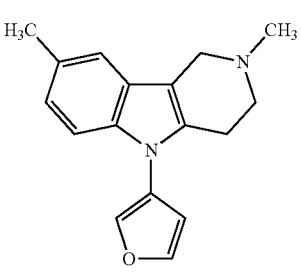 |
| 16 | 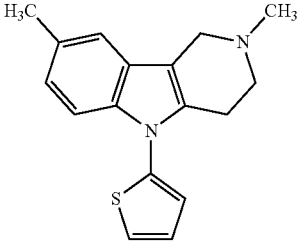 |
| 17 | 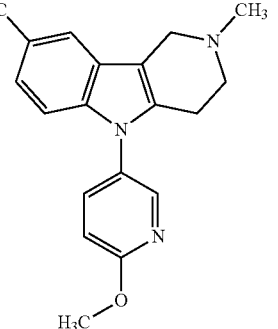 |
| 18 | 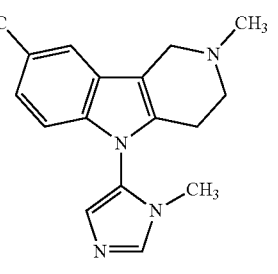 |
| 19 | 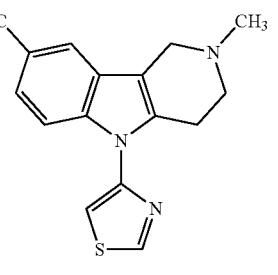 |
| 20 | 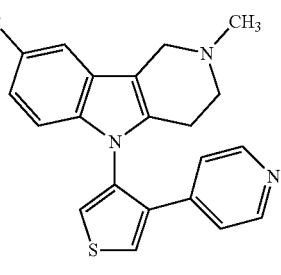 |
| 21 | 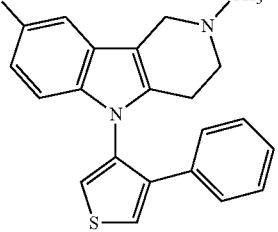 |

TABLE 1-continued

Representative Compounds of the Invention

| Compound No. | Structure |
|---|---|
| 22 | 6-methyl-2-methyl-tetrahydro-pyrido[4,3-b]indole with N-(4-(pyridin-3-yl)thiophen-3-yl) substituent |
| 23 | 7-methyl-2-methyl-tetrahydro-pyrido[4,3-b]indole with N-(4-(4-fluorophenyl)thiophen-3-yl) substituent |
| 24 | 8-methyl-2-methyl-tetrahydro-pyrido[4,3-b]indole with N-(quinolin-6-yl) substituent |
| 25 | 8-chloro-2-methyl-tetrahydro-pyrido[4,3-b]indole with N-(4-(4-fluorophenyl)thiophen-3-yl) substituent |
| 26 | 8-chloro-2-methyl-tetrahydro-pyrido[4,3-b]indole with N-(4-phenylthiophen-3-yl) substituent |
| 27 | 7-chloro-2-methyl-tetrahydro-pyrido[4,3-b]indole with N-(4-(pyridin-3-yl)thiophen-3-yl) substituent |
| 28 | 7-chloro-2-methyl-tetrahydro-pyrido[4,3-b]indole with N-(4-(pyridin-4-yl)thiophen-3-yl) substituent |
| 29 | 7-chloro-2-methyl-tetrahydro-pyrido[4,3-b]indole with N-(thiophen-3-yl) substituent |
| 30 | 7-methyl-2-methyl-tetrahydro-pyrido[4,3-b]indole with N-(4-(1-methyl-1H-pyrazol-4-yl)thiophen-3-yl) substituent |
| 31 | 8-methyl-2-methyl-tetrahydro-pyrido[4,3-b]indole with N-(2-(5-(dimethylamino)pyrimidin-... phenyl) substituent |

TABLE 1-continued

Representative Compounds of the Invention

| Compound No. | Structure |
|---|---|
| 32 | 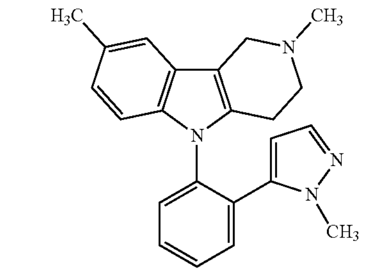 |
| 33 | 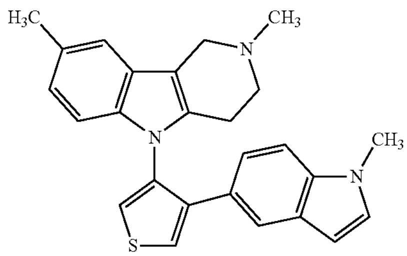 |
| 34 | 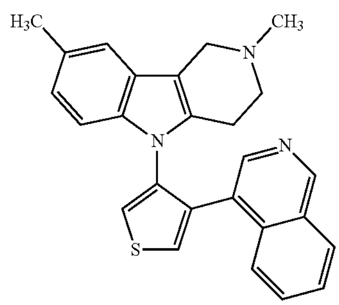 |
| 35 | 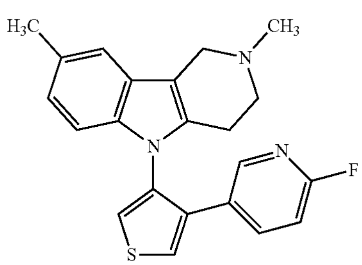 [SMILES: Cc1ccc2c(c1)c1c(n2-c2cscc2-c2ccc(F)nc2)CCN(C)C1] |
| 36 | 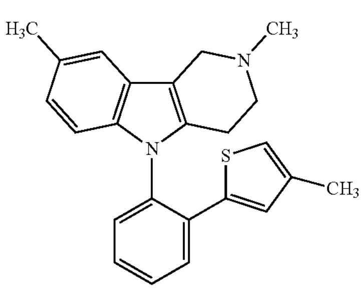 |
| 37 | |
| 38 | |
| 39 | |
| 40 | |
| 41 | |

TABLE 1-continued

Representative Compounds of the Invention

| Compound No. | Structure |
|---|---|
| 42 | (structure) |
| 43 | (structure) |
| 44 | (structure) |
| 45 | (structure) |
| 46 | (structure) |
| 47 | (structure) |
| 48 | (structure) |
| 49 | (structure) |
| 50 | (structure) |

TABLE 1-continued

Representative Compounds of the Invention

| Compound No. | Structure |
|---|---|
| 51 | (structure) |
| 52 | (structure) |
| 53 | (structure) |
| 54 | (structure) |
| 55 | (structure) |
| 56 | (structure) |
| 57 | (structure) |
| 58 | (structure) |
| 59 | (structure) |

TABLE 1-continued
Representative Compounds of the Invention
| Compound No. | Structure |
|---|---|
| 60 | 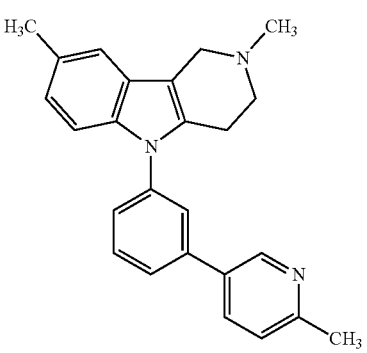 |
| 61 | 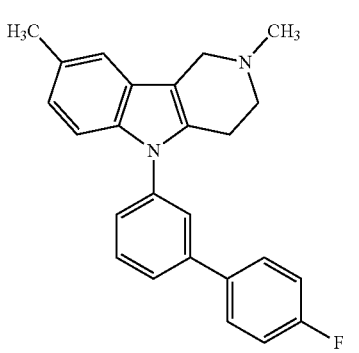 [SMILES: Cc1ccc2c(c1)c1c(n2-c2cccc(-c3ccc(F)cc3)c2)CCN(C)C1] |
| 62 | 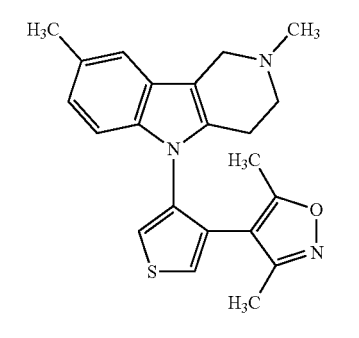 [SMILES: Cc1ccc2c(c1)c1c(n2-c2cscc2-c2c(C)noc2C)CCN(C)C1] |
| 63 | 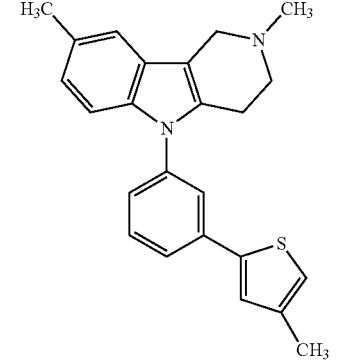 [SMILES: Cc1csc(-c2cccc(-n3c4c(c5cc(C)ccc53)CN(C)CC4)c2)c1] |
| 64 | 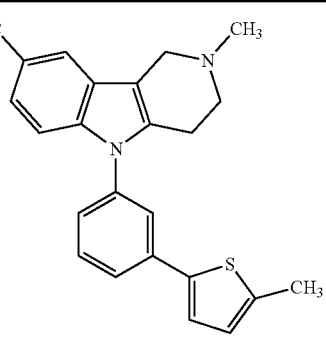 |
| 65 | 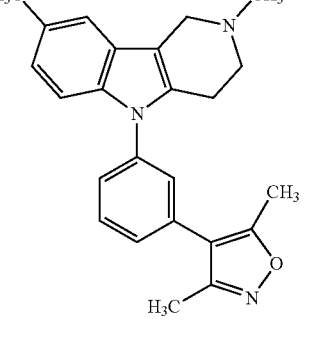 |
| 66 | 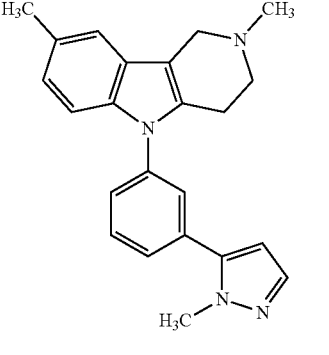 [SMILES: Cc1ccc2c(c1)c1c(n2-c2cccc(-c3ccnn3C)c2)CCN(C)C1] |
| 67 | 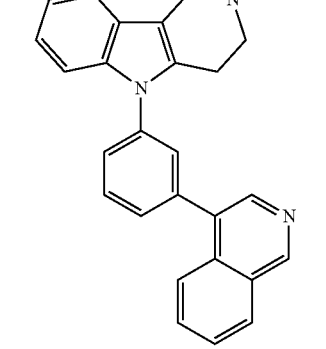 |

TABLE 1-continued

Representative Compounds of the Invention

| Compound No. | Structure |
|---|---|
| 68 | (structure) |
| 69 | (structure) |
| 70 | (structure) |
| 71 | (structure) |
| 72 | (structure) |
| 73 | (structure) |
| 74 | (structure) |
| 75 | (structure) |
| 76 | (structure) |

TABLE 1-continued

Representative Compounds of the Invention

| Compound No. | Structure |
|---|---|
| 77 | (structure) |
| 78 | (structure) |
| 79 | (structure) |
| 80 | (structure) |
| 81 | (structure) |
| 82 | (structure) |
| 83 | (structure) |
| 84 | (structure) |
| 85 | (structure) |
| 86 | (structure) |

TABLE 1-continued

Representative Compounds of the Invention

| Compound No. | Structure |
|---|---|
| 87 | (structure) |
| 88 | (structure) |
| 89 | (structure) |
| 90 | (structure) |
| 91 | (structure) |
| 92 | (structure) |
| 93 | (structure) |
| 94 | (structure) |
| 95 | (structure) |
| 96 | (structure) |

TABLE 1-continued

Representative Compounds of the Invention

| Compound No. | Structure |
|---|---|
| 97 | 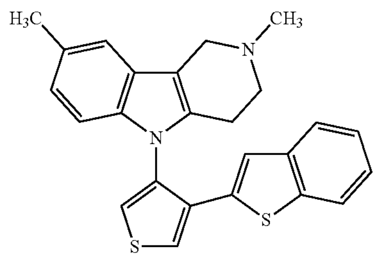 [SMILES: Cc1ccc2c(c1)c1c(n2-c2cscc2-c2cc3ccccc3s2)CCN(C)C1] |
| 98 | 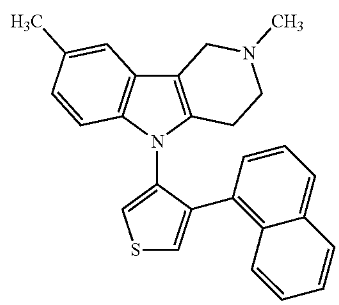 [SMILES: Cc1ccc2c(c1)c1c(n2-c2cscc2-c2cccc3ccccc23)CCN(C)C1] |
| 99 | 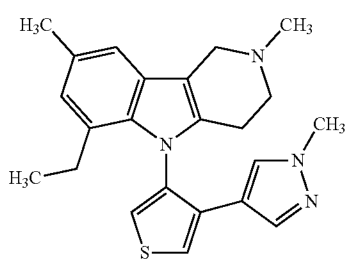 [SMILES: CCc1cc(C)cc2c3c(n(-c4cscc4-c4cnn(C)c4)c12)CCN(C)C3] |
| 100 | 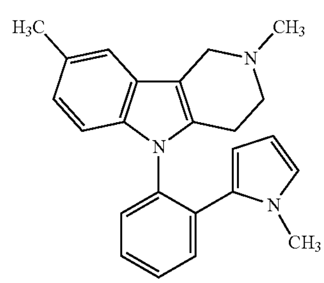 [SMILES: Cc1ccc2c(c1)c1c(n2-c2ccccc2-c2cccn2C)CCN(C)C1] |
| 101 | 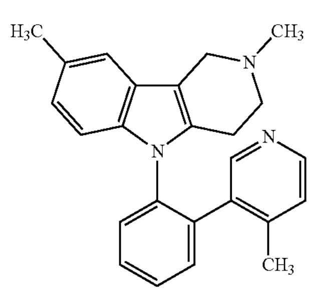 [SMILES: Cc1ccc2c(c1)c1c(n2-c2ccccc2-c2cnccc2C)CCN(C)C1] |
| 102 | |
| 103 | |
| 104 | |
| 105 | |
| 106 | |

TABLE 1-continued

Representative Compounds of the Invention

| Compound No. | Structure |
|---|---|
| 107 | (structure) |
| 108 | (structure) |
| 109 | (structure) |
| 110 | (structure) |
| 111 | (structure) |
| 112 | (structure) |
| 113 | (structure) |
| 114 | (structure) |

TABLE 1-continued

Representative Compounds of the Invention

| Compound No. | Structure |
|---|---|
| 115 | (structure) |
| 116 | (structure) |
| 117 | (structure) |
| 118 | (structure) |
| 119 | (structure) |
| 120 | (structure) |
| 121 | (structure) |
| 122 | (structure) |
| 123 | (structure) |
| 124 | (structure) |

TABLE 1-continued

Representative Compounds of the Invention

| Compound No. | Structure |
|---|---|
| 125 | (structure) |
| 126 | (structure) |
| 127 | (structure) |
| 128 | (structure) |
| 129 | (structure) |
| 130 | (structure) |
| 131 | (structure) |
| 132 | (structure) |

TABLE 1-continued
Representative Compounds of the Invention
| Compound No. | Structure |
|---|---|
| 133 | 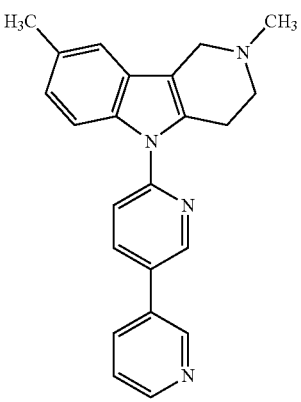 |
| 134 | 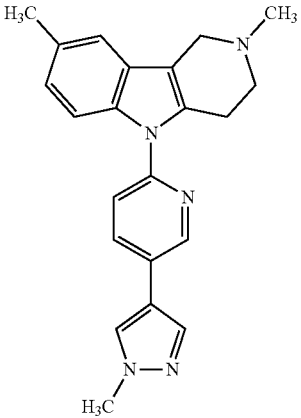 |
| 135 | 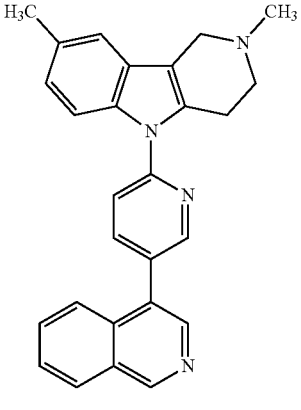 |
| 136 | 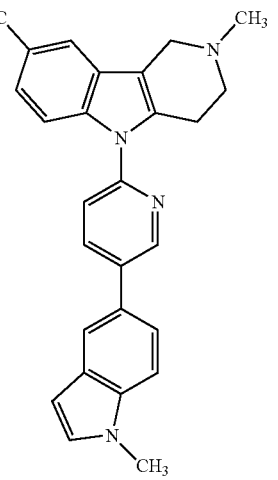 |
| 137 | 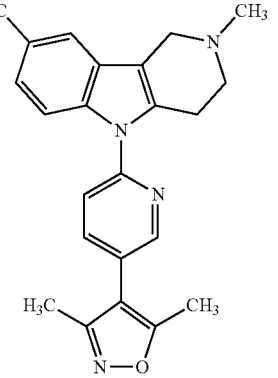 |
| 138 | 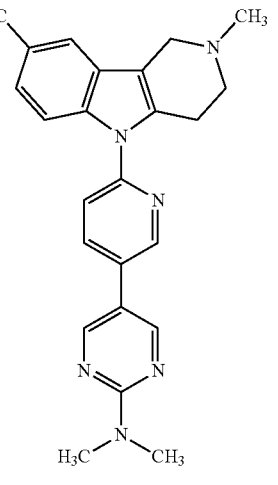 |

TABLE 1-continued

Representative Compounds of the Invention

| Compound No. | Structure |
|---|---|
| 139 | (8-methyl-2-methyl-tetrahydro-β-carboline linked via N to pyridine-pyridine-NHC(O)CH₃) |
| 140 | (8-methyl-2-methyl-tetrahydro-β-carboline linked via N to pyridine-(4-fluorophenyl)) |
| 141 | (8-methyl-2-methyl-tetrahydro-β-carboline linked via N to pyridine-(1-naphthyl)) |
| 142 | (8-methyl-2-methyl-tetrahydro-β-carboline linked via N to pyridine-(5-fluoropyridin-3-yl)) |
| 143 | (8-methyl-2-methyl-tetrahydro-β-carboline linked via N to pyridine-(3-acetamidophenyl)) |
| 144 | (8-methyl-2-methyl-tetrahydro-β-carboline linked via N to pyridine-(4-methylthiophen-2-yl)) |

TABLE 1-continued
Representative Compounds of the Invention
| Compound No. | Structure |
|---|---|
| 145 | 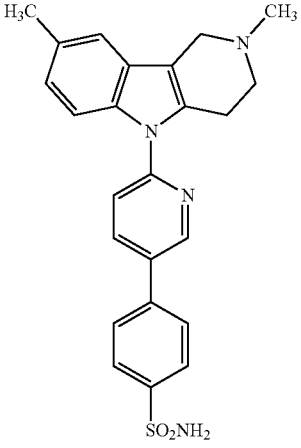 |
| 146 | 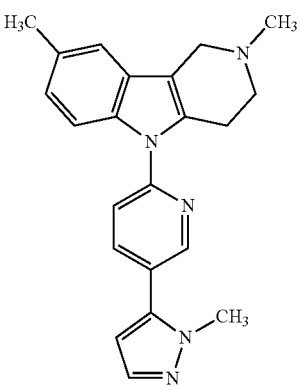 |
| 147 | 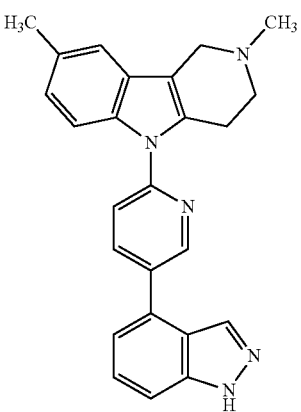 |
| 148 | 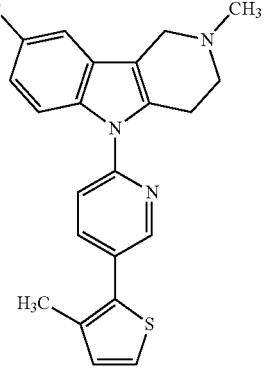 |
| 149 | 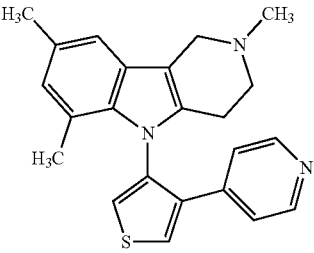 [SMILES: Cc1cc(C)c2c(c1)c1c(n2-c2cscc2-c2ccncc2)CCN(C)C1] |
| 150 | 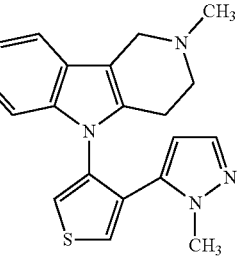 |
| 151 | 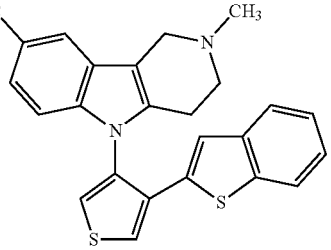 |
| 152 | 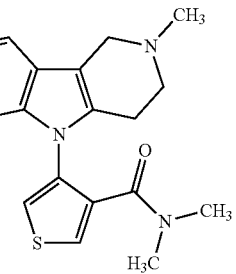 |

TABLE 1-continued

Representative Compounds of the Invention

| Compound No. | Structure |
|---|---|
| 153 | (structure) |
| 154 | (structure) |
| 155 | (structure) |
| 156 | (structure) |
| 157 | (structure) |
| 158 | (structure) |
| 159 | (structure) |
| 160 | (structure) |

TABLE 1-continued
Representative Compounds of the Invention
| Compound No. | Structure |
|---|---|
| 161 | 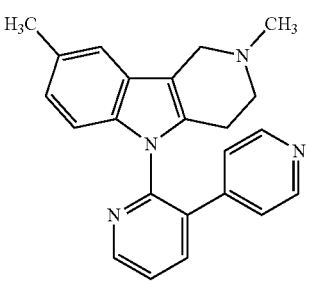 [SMILES: Cc1ccc2c(c1)c1c(n2-c2ncccc2-c2ccncc2)CCN(C)C1] |
| 162 | 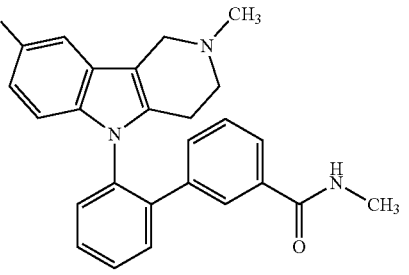 |
| 163 | 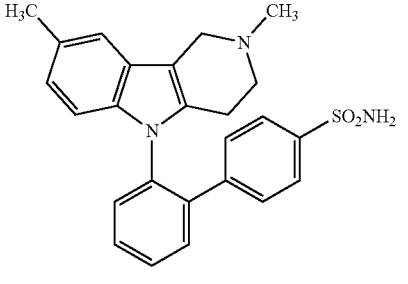 [SMILES: Cc1ccc2c(c1)c1c(n2-c2ccccc2-c2ccc(S(N)(=O)=O)cc2)CCN(C)C1] |
| 164 | 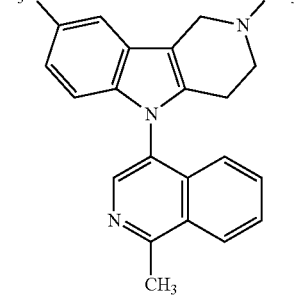 |
| 165 | 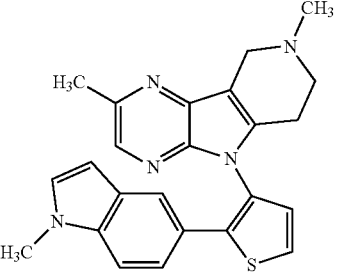 [SMILES: Cc1cnc2c(n1)c1c(n2-c2ccsc2-c2ccc3c(ccn3C)c2)CCN(C)C1] |
| 166 | 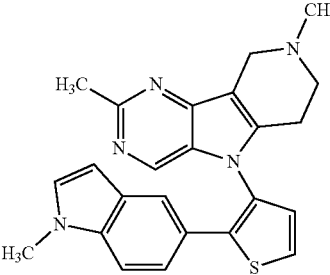 |
| 167 | 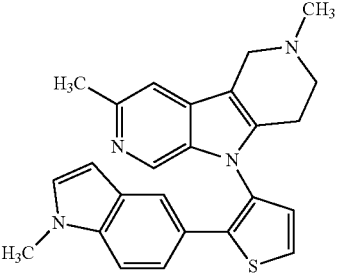 [SMILES: Cc1cc2c3c(n(-c4ccsc4-c4ccc5c(ccn5C)c4)c2cn1)CCN(C)C3] |
| 168 | 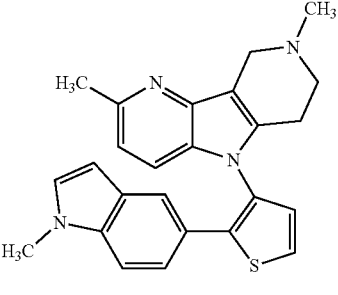 |
| 169 | 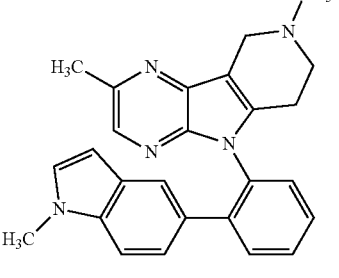 |
| 170 | 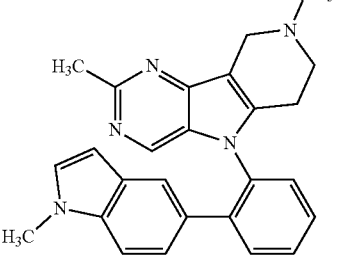 |

TABLE 1-continued
Representative Compounds of the Invention
| Compound No. | Structure |
|---|---|
| 171 | 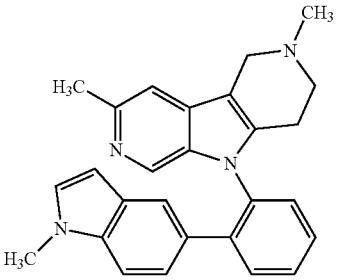 [SMILES: Cc1cc2c3c(n(-c4ccccc4-c4ccc5c(ccn5C)c4)c2cn1)CCN(C)C3] |
| 172 | 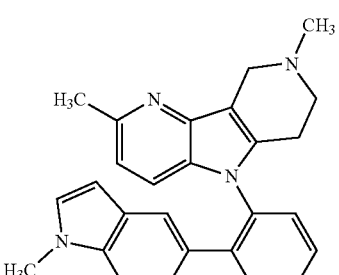 |
| 173 | 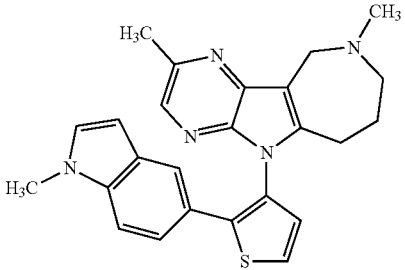 [SMILES: Cc1ncc2c(n1)c1c(n2-c2ccsc2-c2ccc3c(ccn3C)c2)CCCN(C)C1] |
| 174 | 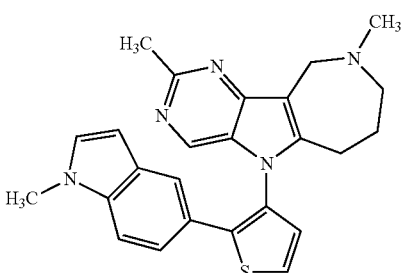 |
| 175 | 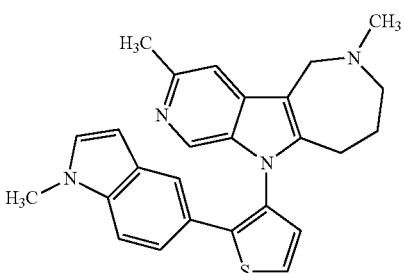 |
| 176 | 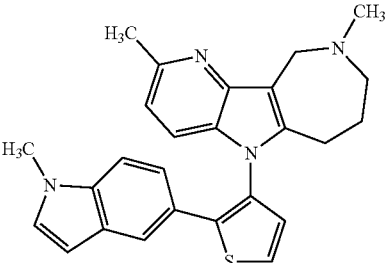 |
| 177 | 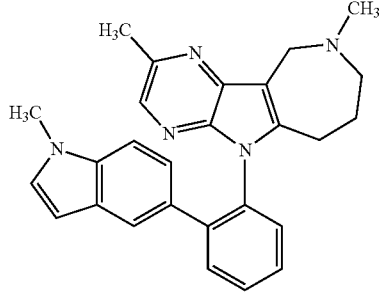 |
| 178 | 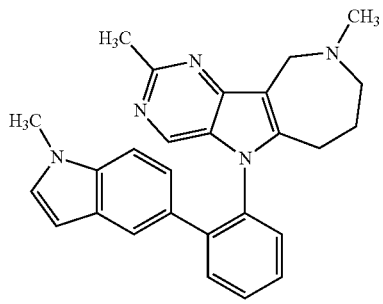 [SMILES: Cc1ncc2c(n1)c1c(n2-c2ccccc2-c2ccc3c(ccn3C)c2)CCCN(C)C1] |
| 179 | 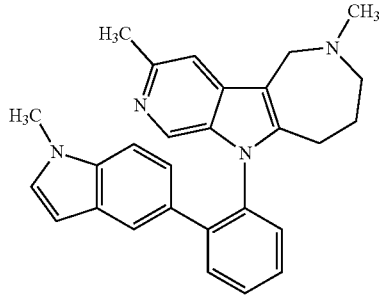 |
| 180 | 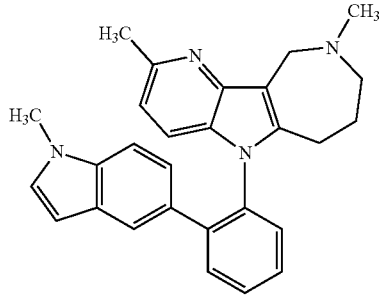 [SMILES: Cc1ccc2c(n1)c1c(n2-c2ccccc2-c2ccc3c(ccn3C)c2)CCCN(C)C1] |

TABLE 1-continued
Representative Compounds of the Invention
| Compound No. | Structure |
|---|---|
| 181 | 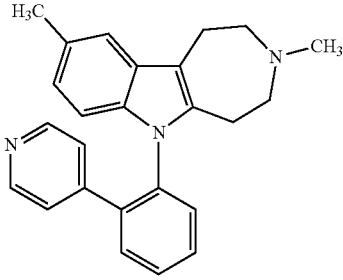 [SMILES: Cc1ccc2c(c1)c1c(n2-c2ccccc2-c2ccncc2)CCN(C)CC1] |
| 182 | 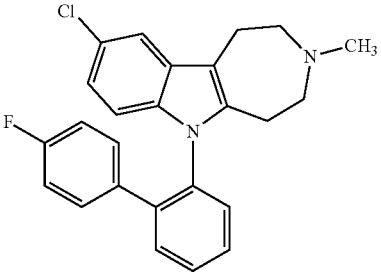 [SMILES: CN1CCc2c(n(-c3ccccc3-c3ccc(F)cc3)c3ccc(Cl)cc23)CC1] |
| 183 | 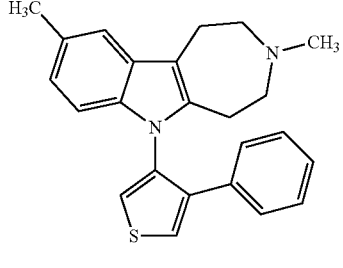 [SMILES: Cc1ccc2c(c1)c1c(n2-c2cscc2-c2ccccc2)CCN(C)CC1] |
| 184 | 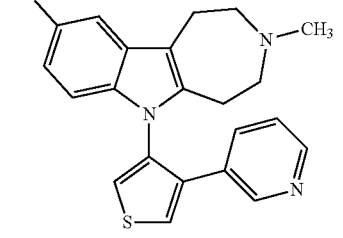 |
| 185 | 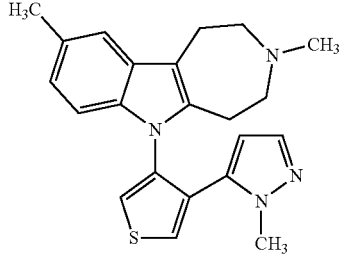 |
| 186 | 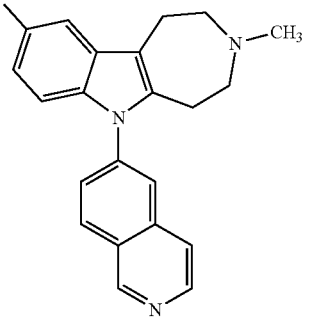 |
| 187 | 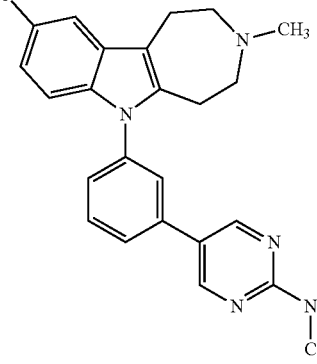 |
| 188 | 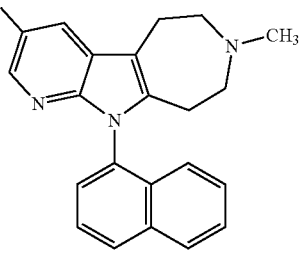 |
| 189 | 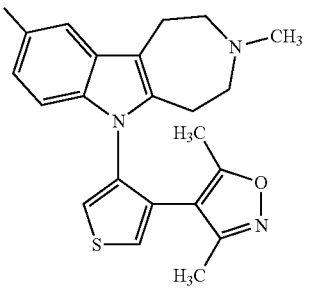 |

TABLE 1-continued
Representative Compounds of the Invention
| Compound No. | Structure |
|---|---|
| 190 | 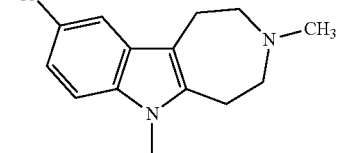 |
| 191 | 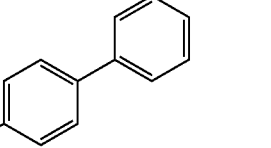 |
| 192 | 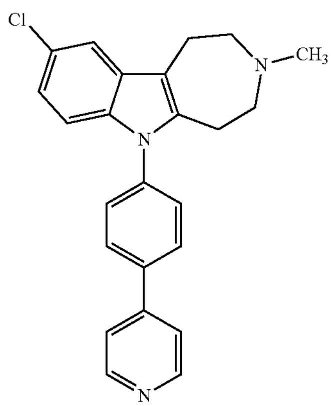 [SMILES: CN1CCc2c(n(-c3ccc(-c4ccncc4)cc3)c3ccc(Cl)cc23)CC1] |
| 193 | 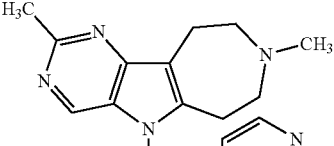 |
| 194 | 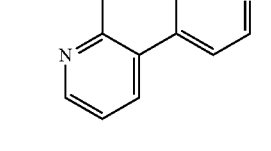 |
| 195 |  |
| 196 | 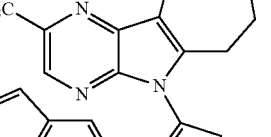 |
| 197 | 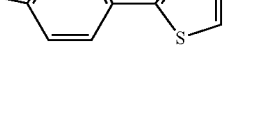 |
| 198 | 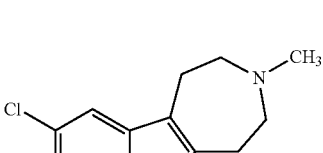 |

TABLE 1-continued

Representative Compounds of the Invention

| Compound No. | Structure |
|---|---|
| 199 | 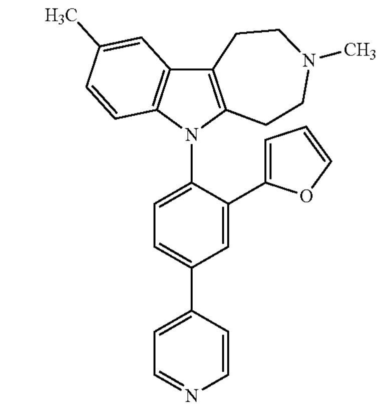 |
| 200 | 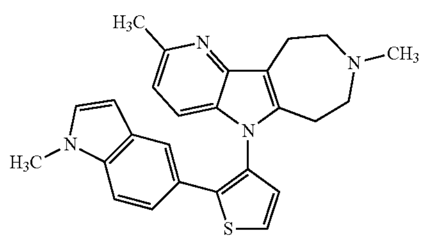 |
| 201 | 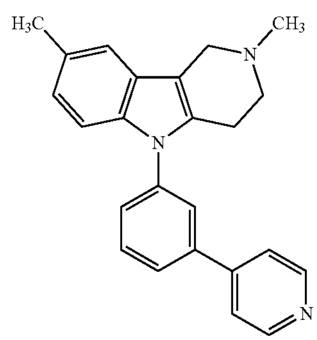 [SMILES: Cc1ccc2c(c1)c1c(n2-c2cccc(-c3ccncc3)c2)CCN(C)C1] |
| 202 | 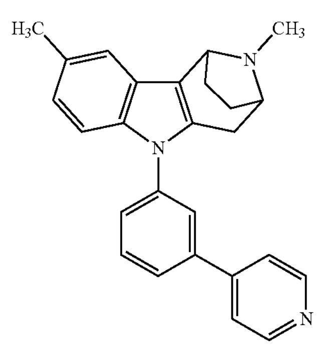 [SMILES: Cc1ccc2c(c1)c1c(n2-c2cccc(-c3ccncc3)c2)CC2CCC1N2C] |
| 203 | |
| 204 | |
| 205 | |
| 206 | |

TABLE 1-continued
Representative Compounds of the Invention
| Compound No. | Structure |
|---|---|
| 207 | 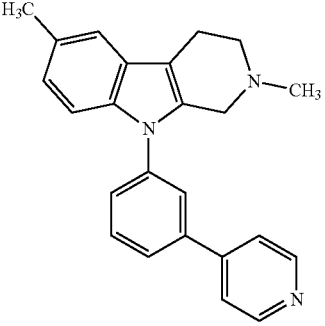 [SMILES: Cc1ccc2c(c1)c1c(n2-c2cccc(-c3ccncc3)c2)CN(C)CC1] |
| 208 | 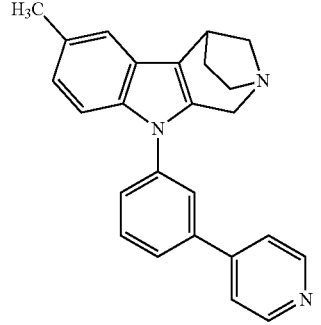 [SMILES: Cc1ccc2c(c1)c1c(n2-c2cccc(-c3ccncc3)c2)CN2CCC1C2] |
| 209 | 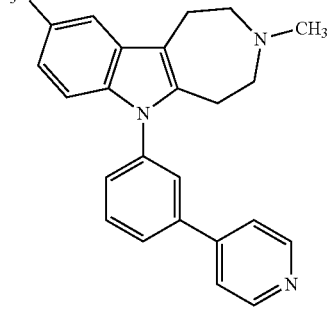 |
| 210 | 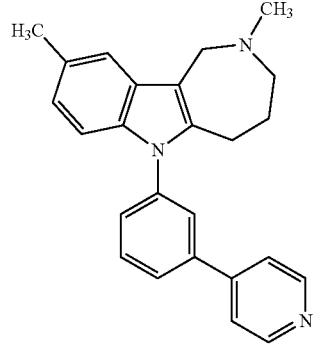 [SMILES: Cc1ccc2c(c1)c1c(n2-c2cccc(-c3ccncc3)c2)CCCN(C)C1] |
| 211 | 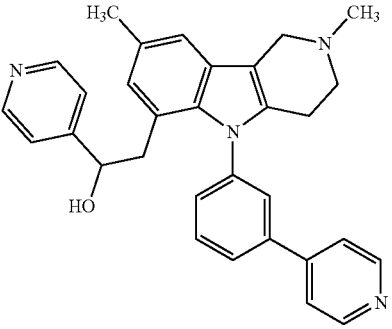 [SMILES: Cc1cc(CC(O)c2ccncc2)c2c(c1)c1c(n2-c2cccc(-c3ccncc3)c2)CCN(C)C1] |
| 212 | 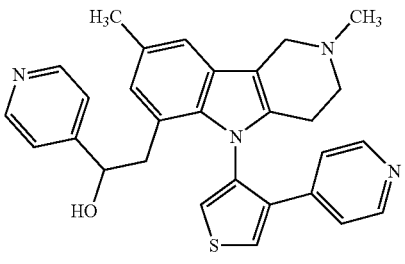 [SMILES: Cc1cc(CC(O)c2ccncc2)c2c(c1)c1c(n2-c2cscc2-c2ccncc2)CCN(C)C1] |
| 213 | 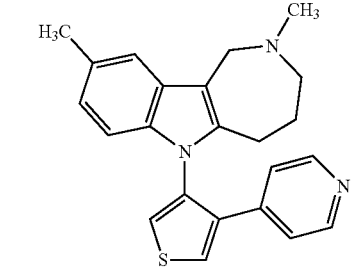 [SMILES: Cc1ccc2c(c1)c1c(n2-c2cscc2-c2ccncc2)CCCN(C)C1] |
| 214 | 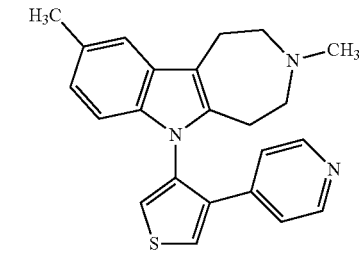 [SMILES: Cc1ccc2c(c1)c1c(n2-c2cscc2-c2ccncc2)CCN(C)CC1] |
| 215 | 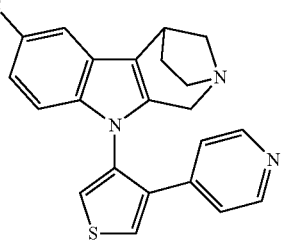 |

TABLE 1-continued
Representative Compounds of the Invention
| Compound No. | Structure |
|---|---|
| 216 | 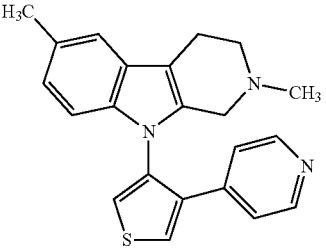 [SMILES: Cc1ccc2c(c1)c1c(n2-c2cscc2-c2ccncc2)CN(C)CC1] |
| 217 | 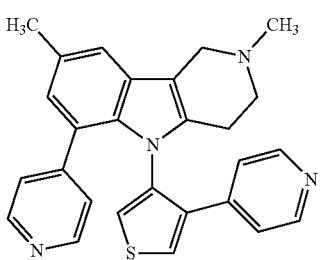 [SMILES: Cc1cc(-c2ccncc2)c2c(c1)c1c(n2-c2cscc2-c2ccncc2)CCN(C)C1] |
| 218 | 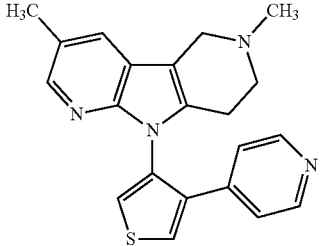 [SMILES: Cc1cnc2c(c1)c1c(n2-c2cscc2-c2ccncc2)CCN(C)C1] |
| 219 | 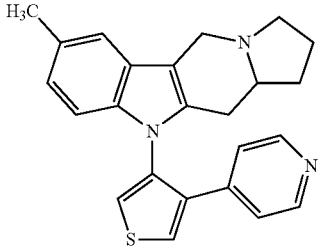 [SMILES: Cc1ccc2c(c1)c1c(n2-c2cscc2-c2ccncc2)CC2CCCN2C1] |
| 220 | 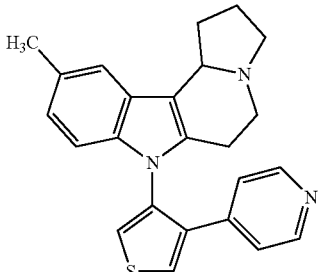 |
| 221 | 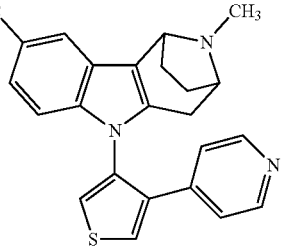 |
| 222 | 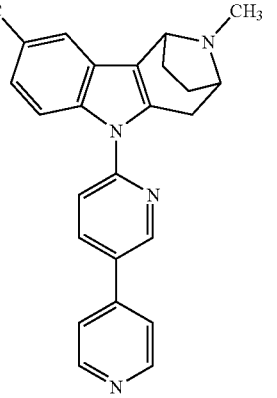 |
| 223 | 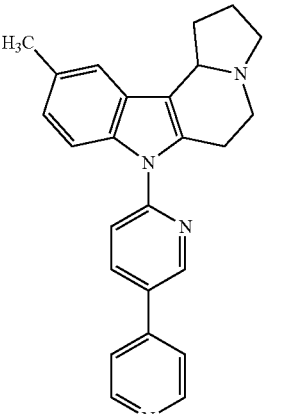 |
| 224 | 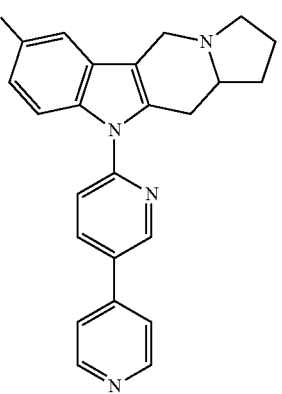 |

TABLE 1-continued

Representative Compounds of the Invention

| Compound No. | Structure |
|---|---|
| 225 | 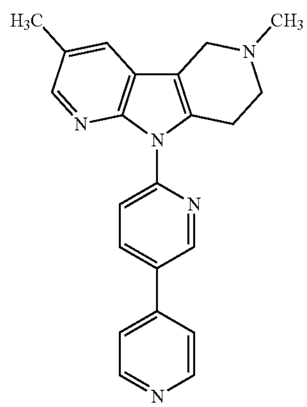 |
| 226 | 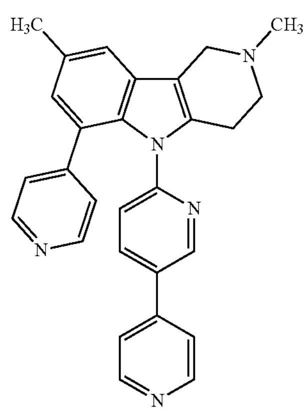 [SMILES: Cc1cc(-c2ccncc2)c2c(c1)c1c(n2-c2ccc(-c3ccncc3)cn2)CCN(C)C1] |
| 227 | 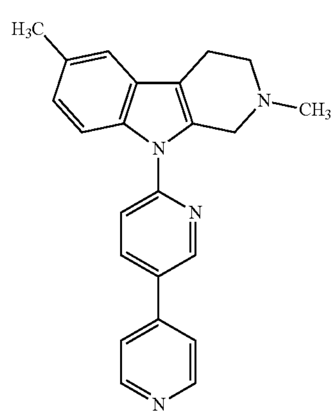 |
| 228 | |
| 229 | |
| 230 | |

TABLE 1-continued

Representative Compounds of the Invention

| Compound No. | Structure |
|---|---|
| 231 | 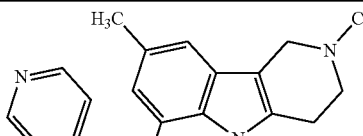 |

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to formula (IA) or (IB) or a variation thereof unless otherwise indicated.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General Protocol for Chiral Preparative HPLC Separation of Racemic Compounds

For chiral separations, samples were dissolved in MeOH and EtOH according to the solubility of sample and filtered through 0.22μ. PTFE filters. The columns used were CHIRALPAK-AD; 20*250 mm, 10μ and CHIRALCEL-ODH; 20*250 mm, 5μ. A flow rate of 12 mL/min-17 mL/min was used according to the resolution. Alkanes such as n-Pentane, Hexane and Heptane (40%-95%) and alcohols such as EtOH, Isopropyl alcohol and t-Butanol (5%-60%) were used as mobile phase. In some cases alcohol combinations i.e. (EtOH+MeOH), (EtOH+IPA), (IPA+MeOH), (t-Butanol+MeOH), (t-Butanol+EtOH) were used instead of a single alcohol. Diethyl amine (up to 0.3%) was used as modifier in the mobile phase.

The following abbreviations are used herein: thin layer chromatography (TLC); hour (h); minute (min); second (sec); ethanol (EtOH); dimethylsulfoxide (DMSO); N,N-dimethylformamide (DMF); 1,2-dimethoxyethane (DME); trifluoroacetic acid (TFA); tetrahydrofuran (THF); Normal (N); aqueous (aq.); methanol (MeOH); dichloromethane (DCM); ethyl acetate (EtOAc); Retention factor (Rf); room temperature (RT).

General methods of preparing compounds according to the invention are depicted in exemplified methods below. Other compounds of the invention may be prepared by similar methods. Compounds detailed herein may be prepared by those of skill in the art by referral to General Methods and Examples described in published PCT applications WO2009/055828 (see e.g., General Methods 1-24 and Examples 1-325), WO2010/127177 (General Methods 1-3 and Examples 1-58), WO2009/120720 (General Methods 1-15C and Examples 1-134), WO2009/120717 (General Methods 1-17 and Examples 1-134), WO2010/051501 (General Methods 1-10 and Examples 1-450) and WO2010/051503 (General Methods 1-15 and Examples 1-111), WO2011/019417 (General Methods 1-9 and Examples 1-10), WO2011/038164 (General Methods 1-19), WO2011/038162 (General Methods 1-21 and Examples 1-6), WO2011/038163 (General Methods 1-19 and Examples 1-49) and WO2011/038161 (General Methods 1-15B and Examples 1-22). The PCT publications described above are incorporated herein by reference in their entireties. Particular methods of synthesizing compounds of the invention are described in the Examples below and in the PCT Publication No. WO2011/103430 (General Methods 1-10 and Examples 1-132).

Routes to synthesizing aryl-linked compounds of the invention are shown below as General Methods 1 to 10. Although identifiers such as $R^1$ and $R^6$ are shown in the method below, it is understood that these moieties apply to the compounds detailed herein even if different identifiers or variations thereof are used elsewhere (e.g., it is understood that compounds may include more than one $R^1$, $R^6$ etc.).

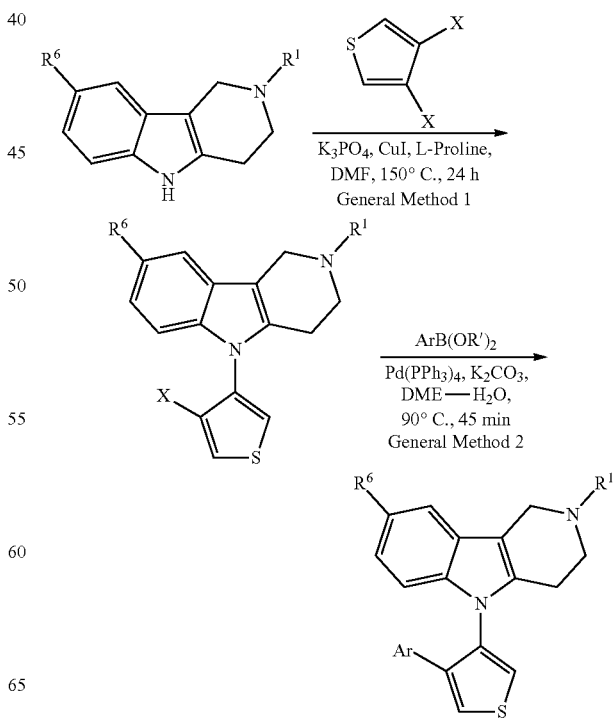

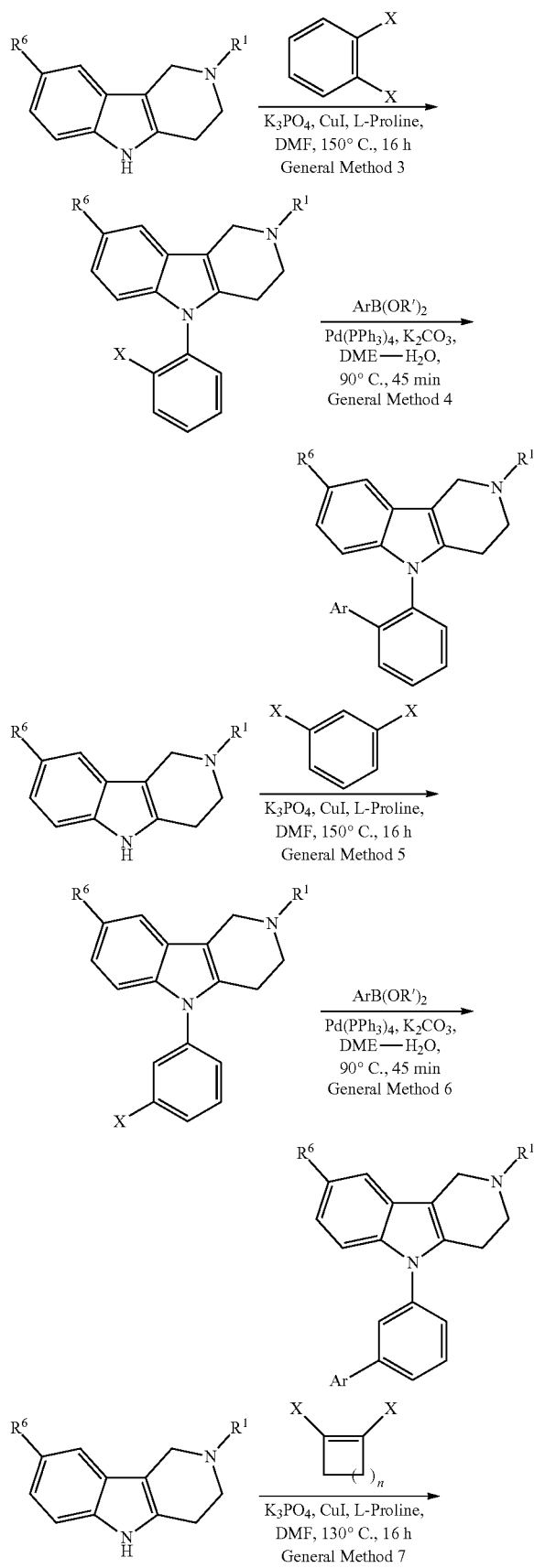

General Method 1

A solution of 2,3,4,5-tetrahydro-1H-pyrido[4,3-b]indole (9.09 mmol), 3,4-dihalo-thiophene (10.90 mmol), potassium phosphate (27.27 mmol), CuI (0.909 mmol) and L-Proline (1.81 mmol) in dry DMF (12 mL) was stirred at 150° C. for 24 h. The reaction mixture was diluted with water and extracted with EtOAc. The organic layer was dried over anhydrous sodium sulfate and concentrated under vacuum to afford the crude product, which was purified by column chromatography using neutral alumina and 3% EtOAc-Hexane as eluant to yield 0.3 g of 5-(4-halothiophen-3-yl)-2,3,4,5-tetrahydro-1H-pyrido[4,3-b]indole as an oil.

General Method 2

To a de-aerated solution of 5-(4-halothiophen-3-yl)-2,3,4,5-tetrahydro-1H-pyrido[4,3-b]indole (0.217 mmol), aryl-boronic acid or aryl-4,4,5,5-tetramethyl-1,3,2-dioxaborolane (0.431 mmol) and $K_2CO_3$ (0.845 mmol) in DME (4 mL)-water (2 mL) was added Pd(PPh$_3$)$_4$ (0.013 mmol). The reaction mixture was purged with $N_2$ for 5 min and stirred at 90° C. for 45 min. The reaction mixture was concentrated under vacuum and the residue dissolved in EtOAc (50 mL) and washed with water (20 mL). The organic layer was dried over anhydrous sodium sulfate and concentrated under vacuum to afford the crude product, which was purified by reverse phase HPLC to yield 5-(4-arylthiophen-3-yl)-2,3,4,5-tetrahydro-1H-pyrido[4,3-b]indole.

General Method 3

A solution of 2,3,4,5-tetrahydro-1H-pyrido[4,3-b]indole (9.09 mmol), 1,2-dihalobenzene (13.65 mmol), potassium phosphate (27.27 mmol), CuI (0.909 mmol) and L-Proline (1.81 mmol) in dry DMF (12 mL) was stirred at 150° C. for 16 h. The reaction mixture was diluted with water and extracted with EtOAc. The organic layer was dried over anhydrous sodium sulfate and concentrated under vacuum to afford the crude product, which was purified by column chromatography using neutral alumina and 3% EtOAc-Hexane as eluant to yield 5-(2-halophenyl)-2,3,4,5-tetrahydro-1H-pyrido[4,3-b]indole as an oil.

General Method 4

A solution of 5-(2-halophenyl)-2,3,4,5-tetrahydro-1H-pyrido[4,3-b]indole (0.281 mmol), aryl-boronic acid or aryl-4,4,5,5-tetramethyl-1,3,2-dioxaborolane (0.557 mmol) and K₂CO₃ (0.845 mmol) in DME (4 mL)-water (2 mL) was purged with nitrogen followed by addition of Pd(PPh₃)₄ (0.013 mmol). The reaction mixture was stirred at 90° C. for 45 min. The reaction mixture was concentrated under vacuum, the residue diluted with water (20 mL) and extracted with EtOAc (50 mL). The organic layer was dried over anhydrous sodium sulfate, concentrated under vacuum to obtain the crude product, which was purified by reverse phase HPLC to yield 5-(2-(aryl)phenyl)-2,3,4,5-tetrahydro-1H-pyrido[4,3-b]indole.

General Method 5

A solution of 2,3,4,5-tetrahydro-1H-pyrido[4,3-b]indole (9.09 mmol), 1,3-dihalobenzene (13.65 mmol), potassium phosphate (27.27 mmol), CuI (0.909 mmol) and L-Proline (1.81 mmol) in dry DMF (12 mL) was stirred at 150° C. for 16 h. The reaction mixture was diluted with water and extracted with EtOAc. The organic layer was dried over anhydrous sodium sulfate and concentrated under vacuum to afford crude material, which was purified by column chromatography using neutral alumina and 3% EtOAc-Hexane as eluant to yield 5-(3-halophenyl)-2,3,4,5-tetrahydro-1H-pyrido[4,3-b]indole as an oil.

General Method 6

A solution of 5-(3-halophenyl)-2,3,4,5-tetrahydro-1H-pyrido[4,3-b]indole (0.281 mmol), aryl-boronic acid or aryl-4,4,5,5-tetramethyl-1,3,2-dioxaborolane (0.557 mmol) and K₂CO₃ (0.845 mmol) in DME (4 mL)-water (2 mL) was purged with nitrogen followed by addition of Pd(PPh₃)₄ (0.013 mmol). The reaction mixture was stirred at 90° C. for 45 min. The reaction mixture concentrated under vacuum, residue diluted with water (20 mL) and extracted with EtOAc (50 mL). The organic layer was dried over anhydrous sodium sulfate, concentrated under vacuum to obtain crude which was purified by reverse phase HPLC to yield 5-(3-(aryl)phenyl)-2,3,4,5-tetrahydro-1H-pyrido[4,3-b]indole.

General Method 7

A solution of 2,3,4,5-tetrahydro-1H-pyrido[4,3-b]indole (5 mmol), 1,2-dihalocycloalkene (6.4 mmol), potassium phosphate (10 mmol), CuI (0.5 mmol) and L-Proline (1 mmol) in dry DMF (7 mL) was stirred at 130° C. for 16 h. The reaction mixture was diluted with water and extracted with EtOAc. The organic layer was dried over anhydrous sodium sulfate and concentrated under vacuum to afford crude product, which was purified by column chromatography using neutral alumina and 3% EtOAc-Hexane as eluant to yield 5-(2-halocycloalk-1-en-1-yl)-2,3,4,5-tetrahydro-1H-pyrido[4,3-b]indole.

General Method 8

A solution of 5-(2-halocycloalk-1-en-1-yl)-2,3,4,5-tetrahydro-1H-pyrido[4,3-b]indole (0.29 mmol), aryl-boronic acid or aryl-4,4,5,5-tetramethyl-1,3,2-dioxaborolane (0.579 mmol) and K₂CO₃ (0.87 mmol) in DME (4 mL)-water (2 mL) was purged with nitrogen followed by addition of Pd(PPh₃)₄ (0.0147 mmol). The reaction mixture was stirred at 90° C. for 45 min. The reaction mixture was concentrated under vacuum, residue diluted with water (20 mL) and extracted with EtOAc (50 mL). The organic layer was dried over anhydrous sodium sulfate, concentrated under vacuum to obtain crude, which was purified by reverse phase HPLC to yield 5-(2-arylcycloalk-1-en-1-yl)-2,3,4,5-tetrahydro-1H-pyrido[4,3-b]indole.

General Method 9

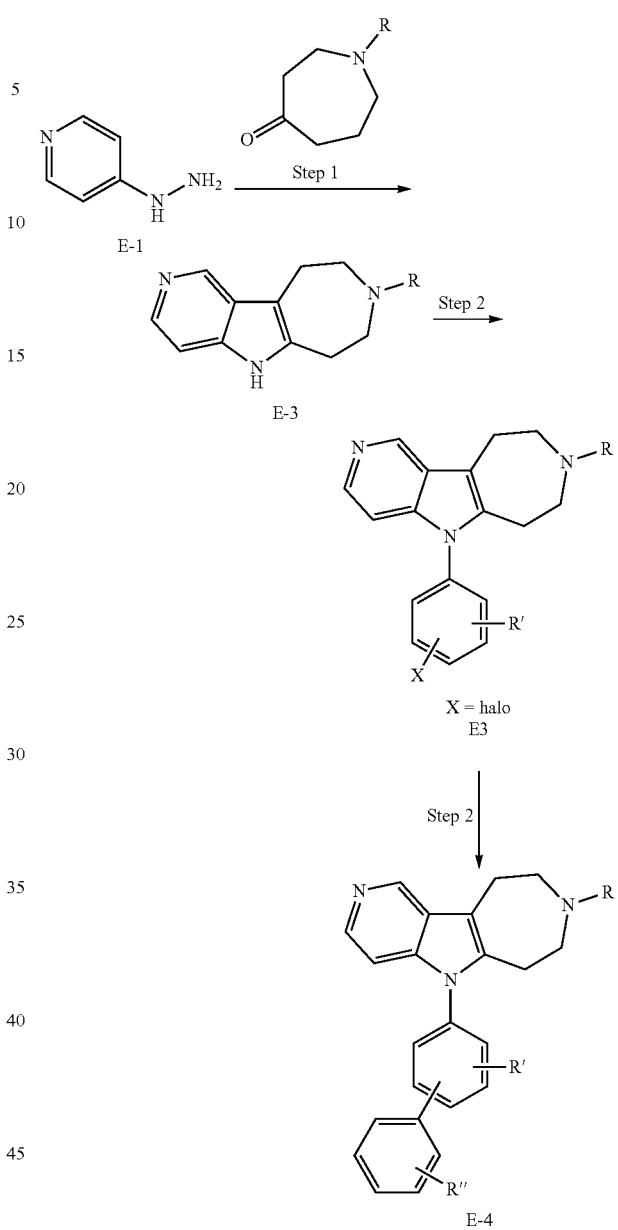

Condensation of appropriately functionalized 4-hydrazino pyridine E-1 with functionalized azepan-4-ones in step 1 yields the 9-aza-hexahydroazepino[5,4-b]indole intermediate E-2. The indole nitrogen atom can be coupled in step 2 with appropriately functionalized aromatic or heteroaromatic reagents known to those skilled in the art to give E-3. When necessary, further conversion of substituents such as X, for example halo, with reagents such as aryl boronic acids under the Suzuki reaction, leads to derivative E-4. Although the Scheme depicts phenyl or pyridyl rings in the compounds, it is understood that a number of aromatic and heteroaromatic analogs are conceivable for such synthetic routes, including but not limited to pyrimidine, pyrazine, thiophene, furan, pyrrolo, imidazole, thiazole, and the like. Similarly, the point of attachment of groups such as R' to the aromatic or heteroaromatic groups can be envisioned in a variety of chemically feasible locations. All possible attachment locations of functional groups on the aromatic ring(s) should be considered.

General Method 10

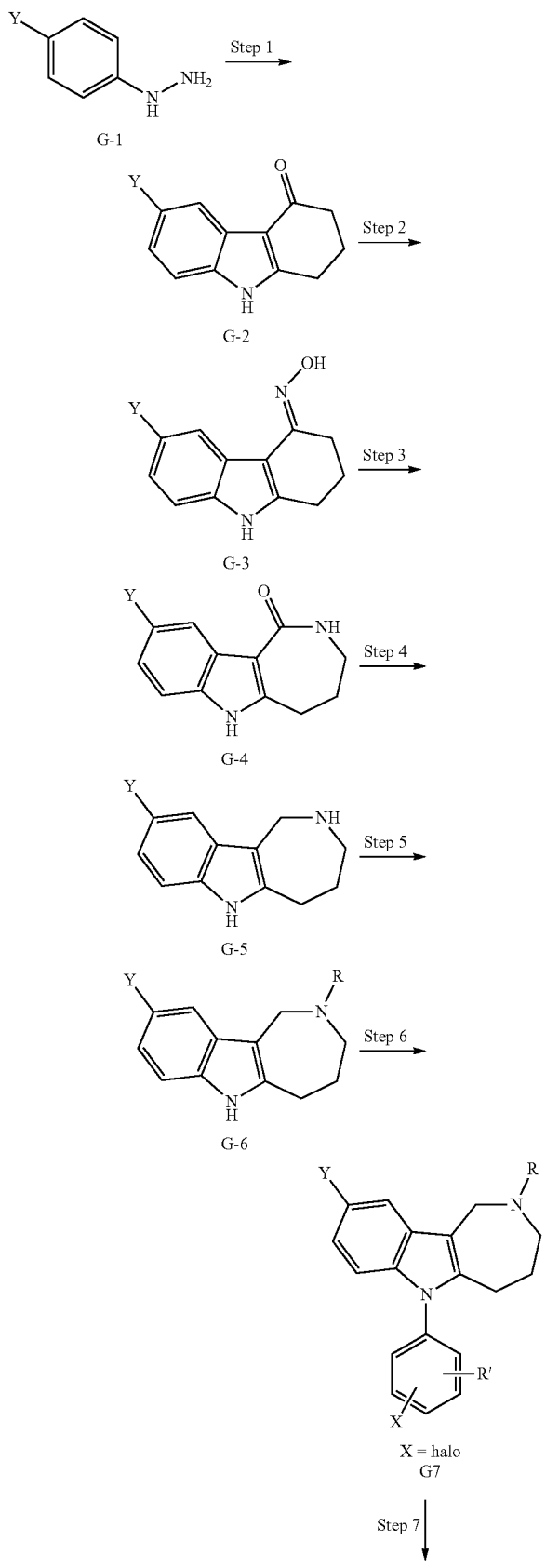

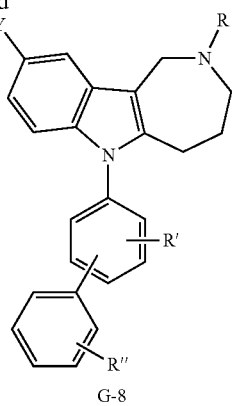

Condensation of appropriately functionalized aryl hydrazine G-1 with cyclohexane-1,3-dione in step 1 yields the dihydrocarbazolone intermediate G-2. The keto group is then converted in step 2 using standard conditions to give oxime G-3 that can undergo a Beckmann rearrangement in step 3 to yield the tetrahydroazepinoindolone G-4. Reduction of the amide in step 4 provides hexahydroazepinoindole G-5, the secondary amino group of which can be functionalized in step 5 to provide functionalized tertiary amine G-6. The indole nitrogen atom can be coupled in step 6 with appropriately functionalized aromatic or heteroaromatic reagents known to those skilled in the art to give G-7. When necessary, further conversion of substituents such as X, for example halo, with reagents such as aryl boronic acids under the Suzuki reaction in step 7, leads to derivative G-8. Although the Scheme depicts phenyl or pyridyl rings in the compounds, it is understood that a number of aromatic and heteroaromatic analogs are conceivable for such synthetic routes, including but not limited to pyrimidine, pyrazine, thiophene, furan, pyrrolo, imidazole, thiazole, and the like. Similarly, the point of attachment of groups such as R' to the aromatic or heteroaromatic groups can be envisioned in a variety of chemically feasible locations. All possible attachment locations of functional groups on the aromatic ring(s) should be considered.

The methods detailed above may be adapted as known by those of skill in the art to make compounds detailed herein. Particular examples of each of the General Methods are provided in the Examples below. One or more of the General Methods detailed above may be adapted or combined as required by those of skill in the art to make compounds detailed herein. Particular examples of each of the General Methods are provided in the Examples below. Compounds 1-88, 100-105 and 131-164 were prepared according to Example Nos. 1-88 and 92-130 respectively.

The following Examples are provided to illustrate but not to limit the invention.

All references disclosed herein are incorporated by reference in their entireties.

EXAMPLES

Example No. 1

Preparation of Compound No. 1

A solution of 2,8-dimethyl-2,3,4,5-tetrahydro-1H-pyrido[4,3-b]indole (0.2 g, 1 mmol), bromobenzene (0.314 g, 2 mmol), $K_3PO_4$ (0.424 g, 2 mmol), CuI (19 mg, 0.1 mmol) and L-Proline (23 mg, 0.2 mmol) in dry DMF (3 mL) was stirred at 150° C. for 12 h. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-phenyl-2,3,4,5-tetrahydro-1H-pyrido[4,3-b]indole as an off white solid (83 mg). $^1$H NMR (HCl salt, CD$_3$OD) δ (ppm): 7.60 (t, 2H), 7.5 (t, 1H), 7.4 (d, 2H), 7.35 (s, 1H), 7.1 (d, 1H), 7.05 (d, 1H), 4.8 (d, 1H), 4.4 (d, 1H), 3.85-3.8 (m, 1H), 3.6-3.59 (m, 1H), 3.2-3.19 (m, 1H), 3.18 (s, 3H), 3-2.95 (m, 1H), 2.4 (s, 3H).

Example No. 2

Preparation of Compound No. 2

A solution of 2,8-dimethyl-2,3,4,5-tetrahydro-1H-pyrido[4,3-b]indole (0.2 g, 1 mmol), 4-bromopyridine (0.316 g, 2 mmol), K$_3$PO$_4$ (0.424 g, 2 mmol), CuI (19 mg, 0.1 mmol) and L-Proline (23 mg, 0.2 mmol) in dry DMF (3 mL) was stirred at 150° C. for 12 h. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-pyridin-4-yl-2,3,4,5-tetrahydro-1H-pyrido[4,3-b]indole as an off white solid (30 mg). $^1$H NMR (HCl salt, CD$_3$OD) δ (ppm): 8.95 (d, 2H), 8.21 (d, 2H), 7.65 (d, 1H), 7.21 (s, 1H), 7.21 (d, 1H), 4.8 (d, 1H), 4.4 (d, 1H), 3.95-3.9 (m, 1H), 3.6-3.50 (m, 2H), 3.25 (m, 1H), 3.2 (s, 3H), 2.5 (s, 3H).

Example No. 3

Preparation of Compound No. 3

A solution of 2,8-dimethyl-2,3,4,5-tetrahydro-1H-pyrido[4,3-b]indole (0.2 g, 1 mmol), 5-bromo-2-methyl-pyridine (0.348 g, 2 mmol), K$_3$PO$_4$ (0.424 g, 2 mmol), CuI (19 mg, 0.1 mmol) and L-Proline (23 mg, 0.2 mmol) in dry DMF (3 mL) was stirred at 150° C. for 12 h. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-(6-methyl-pyridin-3-yl)-2,3,4,5-tetrahydro-1H-pyrido[4,3-b]indole as semisolid (8.6 mg). $^1$H NMR (HCl salt, CD$_3$OD) δ (ppm): 8.6 (s, 1H), 8.05 (d, 1H), 7.7 (d, 1H), 7.19 (s, 1H), 7.19-7.05 (dd, 2H), 4.8 (m, 1H), 4.4 (m, 1H), 3.90-3.8 (m, 1H), 3.6-3.50 (m, 1H), 3.25-3.20 (m, 1H), 3.2 (s, 3H), 3.05-3.0 (m, 1H), 2.75 (s, 3H), 2.45 (s, 3H).

Example No. 4

Preparation of Compound No. 4

A solution of 2,8-dimethyl-2,3,4,5-tetrahydro-1H-pyrido[4,3-b]indole (0.4 g, 2 mmol), 5-bromo-2-trifluoromethyl-pyridine (1.356 g, 6 mmol), K$_3$PO$_4$ (1.272 g, 6 mmol), CuI (38 mg, 0.2 mmol) and L-Proline (70 mg, 0.4 mmol) in dry DMF (5 mL) was stirred at 150° C. for 4 h. The reaction mixture was diluted with water and extracted with EtOAc. The organic layer was dried over anhydrous sodium sulfate and concentrated under reduced pressure to afford crude material, which was purified by column chromatography using silica (100-200 mesh) and 3% MeOH:DCM to yield 2,8-dimethyl-5-(6-trifluoromethyl-pyridin-3-yl)-2,3,4,5-tetrahydro-1H-pyrido[4,3-b]indole as an off white solid (150 mg). $^1$H NMR (HCl salt, CD$_3$OD) δ (ppm): 8.85 (s, 1H), 8.2 (d, 1H), 8.1 (d, 1H), 7.4 (s, 1H), 7.2 (d, 1H), 7.1 (d, 1H), 4.8 (m, 1H), 4.4 (m, 1H), 3.9-3.85 (m, 1H), 3.6-3.59 (m, 1H), 3.25-3.2 (m, 1H), 3.2 (s, 3H), 3.1-3.0 (m, 1H), 2.41 (s, 3H).

Example No. 5

Preparation of Compound No. 5

To a de-aerated solution of 5-(2-bromo-phenyl)-2,8-dimethyl-2,3,4,5-tetrahydro-1H-pyrido[4,3-b]indole (180 mg, 0.508 mmol), 4-pyridinylboronic acid (93.8 mg, 0.762 mmol) and K$_3$PO$_4$ (270 mg, 1.27 mmol) in DMF-water (9:1 mL) was added PdCl$_2$(PPh$_3$)$_2$ (18 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-(2-pyridin-4-yl-phenyl)-2,3,4,5-tetrahydro-1H-pyrido[4,3-b]indole as semisolid (14 mg). $^1$H NMR (Freebase, CDCl$_3$) δ (ppm): 8.38 (d, 2H), 7.58 (m, 3H), 7.40 (d, 1H), 7.20 (s, 1H), 6.90 (m, 4H), 3.75 (m, 2H), 2.76 (m, 1H), 2.60 (m, 1H), 2.50 (m, 1H), 2.48 (s, 3H), 2.42 (s, 3H), 2.20 (m, 1H).

Example No. 6

Preparation of Compound No. 6

A solution of 2,8-dimethyl-2,3,4,5-tetrahydro-1H-pyrido[4,3-b]indole (0.2 g, 1 mmol), (2-bromo-phenyl)-dimethyl-amine (600 mg, 3 mmol), K$_3$PO$_4$ (636 mg, 3 mmol), L-Proline (69 mg, 0.6 mmol) and CuI (57 mg, 0.3 mmol) in dry DMF (4 mL) was stirred at 150° C. for 16 h. The reaction mixture was cooled to RT, diluted with water and extracted with EtOAc. The organic layer was dried over anhydrous sodium sulfate and concentrated under reduced pressure to afford crude material, which was purified by column chromatography using neutral alumina and 10% EtOAc-Hexane followed by reverse phase HPLC purification to yield [2-(2,8-dimethyl-1,2,3,4-tetrahydro-pyrido[4,3-b]indol-5-yl)-phenyl]-dimethyl-amine (20 mg). $^1$H NMR (TFA salt, CD$_3$OD) δ (ppm): 7.50 (m, 1H), 7.38 (m, 2H), 7.18 (m, 2H), 7.0 (m, 2H), 4.75 (d, 1H), 4.40 (m, 1H), 3.80 (m, 1H), 3.58 (m, 1H), 3.15 (s, 3H), 3.0 (m, 1H), 2.70 (m, 1H), 2.56 (s, 6H), 2.42 (s, 3H).

Example No. 7

Preparation of Compound No. 7

A solution of 2,8-dimethyl-2,3,4,5-tetrahydro-1H-pyrido[4,3-b]indole (0.2 g, 1 mmol), (3-bromo-phenyl)-dimethyl-amine (600 mg, 3 mmol), K$_3$PO$_4$ (636 mg, 3 mmol), L-Proline (69 mg, 0.6 mmol) and CuI (57 mg, 0.3 mmol) in dry DMF (4 mL) was stirred at 150° C. for 16 h. The reaction mixture was cooled to RT, diluted with water and extracted with EtOAc. The organic layer was dried over anhydrous sodium sulfate and concentrated under reduced pressure to afford crude material, which was purified by column chromatography using neutral alumina and 10% EtOAc-Hexane to yield [3-(2,8-dimethyl-1,2,3,4-tetrahydro-pyrido[4,3-b]indol-5-yl)-phenyl]-dimethyl-amine as an off white solid (11 mg). $^1$H NMR (Oxalate salt, CD$_3$OD) δ (ppm): 7.40 (t, 1H), 7.30 (s, 1H), 7.10 (d, 1H), 7.86 (d, 1H), 6.64 (m, 2H), 4.58 (m, 2H), 3.64 (m, 2H), 3.16 (s, 3H), 3.08 (m, 2H), 2.96 (s, 6H), 2.42 (s, 3H).

Example No. 8

Preparation of Compound No. 8

To a de-aerated solution of 5-(2-bromo-phenyl)-2,8-dimethyl-2,3,4,5-tetrahydro-1H-pyrido[4,3-b]indole (100 mg, 0.282 mmol), phenylboronic acid (51.7 mg, 0.423 mmol) and $K_3PO_4$ (149.7 mg, 0.706 mmol) in DMF-water (4:1 mL) was added $PdCl_2(PPh_3)_2$ (10 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under reduced pressure to afford crude material, which was purified by reverse phase HPLC to yield 5-biphenyl-2-yl-2,8-dimethyl-2,3,4,5-tetrahydro-1H-pyrido[4,3-b]indole (18 mg). $^1$H NMR (Freebase, $CDCl_3$) δ (ppm): 7.58 (d, 1H), 7.44 (m, 2H), 7.30 (d, 1H), 7.18 (m, 4H), 6.98 (m, 3H), 6.82 (d, 1H), 3.70 (d, 1H), 3.60 (d, 1H), 3.64 (m, 1H), 2.50 (m, 1H), 2.44 (s, 3H), 2.40 (s, 3H), 2.18 (m, 2H).

Example No. 9

Preparation of Compound No. 9

A solution of 2,8-dimethyl-2,3,4,5-tetrahydro-1H-pyrido[4,3-b]indole (0.1 g, 1 mmol), 5-bromoisoquinoline (208 mg, 1 mmol), $K_3PO_4$ (318 mg, 1.5 mmol), L-Proline (11.5 mg, 0.2 mmol) and CuI (9.5 mg, 0.05 mmol) in dry DMF (2 mL) was stirred at 150° C. for 24 h. The reaction mixture was cooled to RT, diluted with water and extracted with EtOAc. The organic layer was dried over anhydrous sodium sulfate and concentrated under reduced pressure to afford crude material, which was purified by reverse phase HPLC to yield 5-isoquinolin-5-yl-2,8-dimethyl-2,3,4,5-tetrahydro-1H-pyrido[4,3-b]indole as an off white solid (20 mg). $^1$H NMR (Oxalate salt, $CD_3OD$) δ (ppm): 9.42 (s, 1H), 8.40 (m, 2H), 7.90 (m, 2H), 7.40 (s, 1H), 7.08 (d, 1H), 6.99 (d, 1H), 6.70 (d, 1H), 4.65 (m, 2H), 3.70 (m, 2H), 3.18 (s, 3H), 3.0 (m, 1H), 2.72 (m, 1H), 2.42 (s, 3H).

Example No. 10

Preparation of Compound No. 10

To a de-aerated solution of 5-(2-bromo-phenyl)-2,8-dimethyl-2,3,4,5-tetrahydro-1H-pyrido[4,3-b]indole (100 mg, 0.282 mmol), 4-fluorophenylboronic acid (59 mg, 0.423 mmol) and $K_3PO_4$ (149 mg, 0.706 mmol) in DMF-water (4:1 mL) was added $PdCl_2(PPh_3)_2$ (10 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under reduced pressure to yield crude, which was purified by reverse phase HPLC to yield 5-(4'-fluoro-biphenyl-2-yl)-2,8-dimethyl-2,3,4,5-tetrahydro-1H-pyrido[4,3-b]indole as semisolid (19.23 mg). $^1$H NMR (Oxalate salt, $CD_3OD$) δ (ppm): 7.65-7.59 (m, 3H), 7.41 (d, 1H), 7.25 (s, 1H), 7.15 (m, 1H), 7.05-6.85 (m, 5H), 4.5-3.39 (m, 2H), 3.6-3.5 (m, 1H), 3.2-3.19 (m, 1H), 2.95 (s, 3H), 2.85-2.8 (m, 1H), 2.59-2.50 (m, 1H), 2.4 (s, 3H).

Example No. 11

Preparation of Compound No. 11

A solution of 2,8-dimethyl-2,3,4,5-tetrahydro-1H-pyrido[4,3-b]indole (0.4 g, 4 mmol), 1-bromonaphthalene (0.828 g, 4 mmol), $K_3PO_4$ (0.848 g, 4 mmol), CuI (38 mg, 0.2 mmol) and L-Proline (46 mg, 0.39 mmol) in dry DMF (6 mL) was stirred at 150° C. for 16 h. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-naphthalen-2-yl-2,3,4,5-tetrahydro-1H-pyrido[4,3-b]indole as an off white solid (20 mg). $^1$H NMR (HCl salt, $CD_3OD$) δ (ppm): 8.15 (d, 1H), 8.05 (d, 1H), 7.7 (bs, 1H), 7.6-7.50 (m, 2H), 7.41-7.4 (m, 2H), 7.1 (t, 1H), 6.95 (d, 1H), 6.7-6.65 (dd, 1H), 4.9-4.8 (m, 1H), 4.5-4.4 (m, 1H), 3.8-3.79 (m, 1H), 3.6-3.59 (m, 1H), 3.2 (s, 3H), 2.85-2.8 (m, 1H), 2.6-2.59 (m, 1H), 2.45 (s, 3H).

Example No. 12

Preparation of Compound No. 12

A solution of 2,8-dimethyl-2,3,4,5-tetrahydro-1H-pyrido[4,3-b]indole (0.4 g, 4 mmol), 2-Bromonaphthalene (0.828 g, 4 mmol), $K_3PO_4$ (0.848 g, 4 mmol), CuI (38 mg, 0.2 mmol) and L-Proline (46 mg, 0.39 mmol) in dry DMF (6 mL) was stirred at 150° C. for 16 h. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-naphthalen-2-yl-2,3,4,5-tetrahydro-1H-pyrido[4,3-b]indole as an off white solid (50 mg). $^1$H NMR (HCl salt, $CD_3OD$) δ (ppm): 8.15 (d, 1H), 8.05-7.95 (m, 2H), 7.9 (s, 1H), 7.6 (m, 2H), 7.5 (d, 2H), 7.35 (s, 1H), 7.19 (d, 1H), 7.05 (d, 1H), 4.8 (d, 1H), 4.45 (d, 1H), 3.8-3.79 (m, 1H), 3.6-3.59 (m, 1H), 3.3-3.25 (m, 1H), 3.19 (s, 3H), 3.05-3.0 (m, 1H), 2.45 (s, 3H).

Example No. 13

Preparation of Compound No. 13

To a de-aerated solution of 5-(2-bromo-phenyl)-2,8-dimethyl-2,3,4,5-tetrahydro-1H-pyrido[4,3-b]indole (100 mg, 0.282 mmol), 3-pyridinylboronic acid (51 mg, 0.420 mmol) and $K_3PO_4$ (149 mg, 0.706 mmol) in DMF-water (4:1 mL) was added $PdCl_2(PPh_3)_2$ (10 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-(2-pyridin-3-yl-phenyl)-2,3,4,5-tetrahydro-1H-pyrido[4,3-b]indole as a semisolid (30 mg). $^1$H NMR (Oxalate salt, $CD_3OD$) δ (ppm): 8.30 (s, 1H), 8.10 (s, 1H), 7.70 (m, 3H), 7.56 (d, 1H), 7.50 (d, 1H), 7.24 (m, 2H), 6.98 (d, 1H), 6.82 (d, 1H), 4.50 (m, 2H), 3.60 (m, 2H), 3.05 (s, 3H), 2.95 (m, 1H), 2.62 (m, 1H), 2.40 (s, 3H).

Example No. 14

Preparation of Compound No. 14

A solution of 2,8-dimethyl-2,3,4,5-tetrahydro-1H-pyrido[4,3-b]indole (0.4 g, 2 mmol), 3-bromothiophene (0.347 mL, 4 mmol), $K_3PO_4$ (0.848 g, 4 mmol), CuI (38 mg, 0.2 mmol) and L-Proline (46 mg, 0.39 mmol) in dry DMF (6 mL) was stirred at 150° C. for 16 h. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-thiophen-3-yl-2,3,4,5-tetrahydro-1H-pyrido[4,3-b]indole (25 mg). $^1$H NMR (HCl salt, CD$_3$OD) δ (ppm): 7.65 (m, 1H), 7.50 (s, 1H), 7.30 (s, 1H), 7.21 (d, 1H), 7.19 (d, 1H), 7.02 (d, 1H), 4.76 (d, 1H), 4.40 (d, 1H), 3.82 (m, 1H), 3.60 (m, 1H), 3.2-3.0 (m, 5H), 2.42 (s, 3H).

Example No. 15

Preparation of Compound No. 15

A solution of 2,8-dimethyl-2,3,4,5-tetrahydro-1H-pyrido[4,3-b]indole (0.4 g, 2 mmol), 3-bromofuran (0.35 mL, 4 mmol), K$_3$PO$_4$ (0.848 g, 4 mmol), CuI (38 mg, 0.2 mmol) and L-Proline (46 mg, 0.39 mmol) in dry DMF (6 mL) was stirred at 150° C. for 16 h. The reaction mixture was diluted with water and extracted with EtOAc. The organic layer was dried over anhydrous sodium sulfate and concentrated under reduced pressure to afford crude material, which was purified by reverse phase HPLC to yield 5-furan-3-yl-2,8-dimethyl-2,3,4,5-tetrahydro-1H-pyrido[4,3-b]indole (3 mg). $^1$H NMR (TFA salt, CD$_3$OD) δ (ppm): 7.90 (s, 1H), 7.70 (s, 1H), 7.30 (s, 1H), 7.21 (d, 1H), 7.05 (d, 1H), 6.68 (s, 1H), 4.70 (d, 1H), 4.40 (d, 1H), 3.82 (m, 1H), 3.58 (m, 1H), 3.20-3.0 (m, 5H), 2.42 (s, 3H).

Example No. 16

Preparation of Compound No. 16

A solution of 2,8-dimethyl-2,3,4,5-tetrahydro-1H-pyrido[4,3-b]indole (0.4 g, 2 mmol), 2-bromothiophene (0.347 mL, 4 mmol), K$_3$PO$_4$ (0.848 g, 4 mmol), CuI (38 mg, 0.2 mmol) and L-Proline (46 mg, 0.39 mmol) in dry DMF (6 mL) was stirred at 150° C. for 16 h. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-thiophen-2-yl-2,3,4,5-tetrahydro-1H-pyrido[4,3-b]indole (20 mg). $^1$H NMR (TFA salt, CD$_3$OD) δ (ppm): 7.50 (d, 1H), 7.30 (s, 1H), 7.15 (m, 3H), 7.05 (d, 1H), 4.78 (m, 1H), 4.39 (m, 1H), 3.80 (m, 1H), 3.58 (m, 1H), 3.15 (s, 3H), 3.05 (m, 2H), 2.42 (s, 3H).

Example No. 17

Preparation of Compound No. 17

A solution of 2,8-dimethyl-2,3,4,5-tetrahydro-1H-pyrido[4,3-b]indole (0.4 g, 2 mmol), 5-bromo-2-methoxypyridine (0.752 g, 4 mmol), K$_3$PO$_4$ (0.848 g, 4 mmol), CuI (38 mg, 0.2 mmol) and L-Proline (46 mg, 0.39 mmol) in dry DMF (6 mL) was stirred at 150° C. for 16 h. The reaction mixture was diluted with water and extracted with EtOAc. The organic layer was dried over anhydrous sodium sulfate and concentrated under reduced pressure to afford crude material, which was purified reverse phase HPLC to yield 5-(6-Methoxy-pyridin-3-yl)-2,8-dimethyl-2,3,4,5-tetrahydro-1H-pyrido[4,3-b]indole (35 mg). $^1$H NMR (TFA salt, CD$_3$OD) δ (ppm): 8.20 (s, 1H), 7.74 (d, 1H), 7.32 (s, 1H), 7.0 (m, 3H), 4.78 (m, 1H), 4.40 (m, 1H), 4.0 (s, 3H), 3.82 (m, 1H), 3.60 (m, 1H), 3.16 (s, 3H), 3.10 (m, 1H), 2.98 (m, 1H), 2.42 (s, 3H).

Example No. 18

Preparation of Compound No. 18

A solution of 2,8-dimethyl-2,3,4,5-tetrahydro-1H-pyrido[4,3-b]indole (0.4 g, 2 mmol), 5-bromo-1-methyl-1H-imidazole (0.644 g, 4 mmol), K$_3$PO$_4$ (0.848 g, 4 mmol), CuI (38 mg, 0.2 mmol) and L-Proline (46 mg, 0.39 mmol) in dry DMF (6 mL) was stirred at 150° C. for 16 h. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-(3-methyl-3H-imidazol-4-yl)-2,3,4,5-tetrahydro-1H-pyrido[4,3-b]indole (15 mg). $^1$H NMR (HCl salt, CD$_3$OD) δ (ppm): 9.20 (s, 1H), 8.0 (s, 1H), 7.40 (s, 1H), 7.20 (d, 1H), 7.10 (d, 1H), 4.76 (d, 1H), 4.40 (d, 1H), 3.84 (m, 1H), 3.62 (m, 1H), 3.58 (d, 3H), 3.18 (s, 3H), 3.05 (m, 1H), 2.90 (m, 1H), 2.44 (s, 3H).

Example No. 19

Preparation of Compound No. 19

A solution of 2,8-dimethyl-2,3,4,5-tetrahydro-1H-pyrido[4,3-b]indole (0.2 g, μmol), 4-bromo-thiazole (0.246 g, 1.5 mmol), K$_3$PO$_4$ (0.636 g, 3 mmol), CuI (19 mg, 0.1 mmol) and L-Proline (23 mg, 0.2 mmol) in dry DMF (5 mL) was stirred at 150° C. for 16 h. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-thiazol-4-yl-2,3,4,5-tetrahydro-1H-pyrido[4,3-b]indole (59 mg). $^1$H NMR (TFA salt, CD$_3$OD) δ (ppm): 9.10 (s, 1H), 7.62 (s, 1H), 7.38 (d, 1H), 7.30 (s, 1H), 7.10 (d, 1H), 4.70 (d, 1H), 4.30 (d, 1H), 3.80 (m, 1H), 3.50 (m, 1H), 3.26 (m, 1H), 3.18 (s, 3H), 3.16 (m, 1H), 2.42 (s, 3H).

Example No. 20

Preparation of Compound No. 20

To a de-aerated solution of 5-(4-bromo-thiophen-3-yl)-2,8-dimethyl-2,3,4,5-tetrahydro-1H-pyrido[4,3-b]indole (160 mg, 0.44 mmol), 4-pyridinylboronic acid (81.9 mg, 0.66 mmol) and K$_3$PO$_4$ (235 mg, 1.11 mmol) in DMF-water (4.5:0.5 mL) was added dichlorobis(triphenylphosphine) palladium (II) (15.5 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-(4-pyridin-4-yl-thiophen-3-yl)-2,3,4,5-tetrahydro-1H-pyrido[4,3-b]indole as an off white solid (90 mg). $^1$H NMR (Oxalate salt, CD$_3$OD) δ (ppm): 8.4-8.3 (bs, 2H), 8.19 (s, 1H), 7.8 (s, 1H), 7.35 (s, 1H), 7.05-6.9 (m, 4H), 4.7-4.5 (m, 2H), 3.7-3.5 (m, 2H), 3.1 (s, 3H), 3.05-3.0 (m, 1H), 2.7-2.59 (m, 1H), 2.4 (s, 3H).

Example No. 21

Preparation of Compound No. 21

To a de-aerated solution of 5-(4-bromo-thiophen-3-yl)-2,8-dimethyl-2,3,4,5-tetrahydro-1H-pyrido[4,3-b]indole (40 mg, 0.111 mmol), phenylboronic acid (20 mg, 0.166 mmol) and K$_3$PO$_4$ (58.8 mg, 0.217 mmol) in DMF-water (4.5:0.5 mL) was added PdCl$_2$(PPh$_3$)$_2$ (3.8 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-(4-phenyl-thiophen-3-yl)-2,3,4,5-tetrahydro-1H-pyrido[4,3-b]indole as an off white solid (4 mg). $^1$H NMR (TFA salt, CD$_3$OD) δ (ppm): 7.79-7.65 (m, 2H), 7.3 (s, 1H), 7.2-7.1 (m, 4H), 7.1-7.0 (m, 2H), 6.9 (d, 1H), 4.7 (d, 1H), 4.3 (d, 1H), 3.61-3.60 (m, 1H), 3.25-3.2 (m, 1H), 3.05-3.00 (m, 1H), 2.9 (s, 3H), 2.4 (s, 3H), 2.4-2.39 (m, 1H).

Example No. 22

Preparation of Compound No. 22

To a de-aerated solution of 5-(4-bromo-thiophen-3-yl)-2,8-dimethyl-2,3,4,5-tetrahydro-1H-pyrido[4,3-b]indole (160 mg, 0.44 mmol), 3-pyridinylboronic acid (81.9 mg, 0.66 mmol) and K$_3$PO$_4$ (235 mg, 1.11 mmol) in DMF-water (4.5: 0.5 mL) was added dichlorobis(triphenylphosphine) palladium (II) (15.5 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-(4-pyridin-3-yl-thiophen-3-yl)-2,3,4,5-tetrahydro-1H-pyrido[4,3-b]indole (40 mg). $^1$H NMR (Oxalate salt, CD$_3$OD) δ (ppm): 8.35 (bs, 1H), 8.10 (bs, 1H), 7.95 (s, 1H), 7.8 (s, 1H), 7.45 (bs, 1H), 7.3-7.2 (m, 2H), 6.95 (d, 1H), 6.9 (d, 1H), 4.5 (bs, 2H), 3.6-3.45 (m, 2H), 3.15-3.05 (m, 1H), 3.0 (s, 3H), 2.65-2.59 (m, 1H), 2.4 (s, 3H).

Example No. 23

Preparation of Compound No. 23

A solution of 5-(4-bromo-thiophen-3-yl)-2,8-dimethyl-2,3,4,5-tetrahydro-1H-pyrido[4,3-b]indole (150 mg, 0.416 mmol), 4-fluorophenylboronic acid (87.5 mg, 0.624 mmol), potassium phosphate (220 mg, 1.04 mmol) in DMF-water (9:1) was purged with N$_2$ for 20 min followed by addition of dichlorobis(triphenylphosphine) palladium (II) (14.6 mg, 5 mol %). The reaction mixture was then heated at 95° C. for 30 min under nitrogen atmosphere. After completion of reaction, the reaction mixture was diluted with water and extracted with EtOAc. The organic layer dried over anhydrous sodium sulfate and concentrated under vacuum to obtain crude product which was purified by reverse phase HPLC to yield 15 mg of the title compound. $^1$H NMR (Oxalate salt, CD$_3$OD) δ (ppm): 7.74 (d, 1H), 7.65 (d, 1H), 7.23 (s, 1H), 6.82-7.0 (m, 6H), 4.5 (m, 2H), 3.6 (m, 2H), 2.9-3.0 (m, 5H), 2.4 (s, 3H).

Example No. 24

Preparation of Compound No. 24

A solution of 2,8-dimethyl-2,3,4,5-tetrahydro-1H-pyrido [4,3-b]indole (0.1 g, 0.5 mmol), 6-bromoquinoline (0.135 mL, 1 mmol), K$_3$PO$_4$ (0.318 g, 1.5 mmol), CuI (9.5 mg, 0.05 mmol) and L-Proline (11.5 mg, 0.1 mmol) in dry DMF (5 mL) was stirred at 150° C. for 24 h. The reaction mixture was diluted with water and extracted with EtOAc. The organic layer was dried over anhydrous sodium sulfate and concentrated under reduced pressure to afford crude material, which was purified by reverse phase HPLC to yield 2,8-dimethyl-5-quinolin-6-yl-2,3,4,5-tetrahydro-1H-pyrido[4,3-b]indole as an off white solid (8 mg). $^1$H NMR (Oxalate salt, CD$_3$OD) δ (ppm): 8.92 (d, 1H), 8.43 (d, 1H), 8.2 (dd, 1H), 8.0 (d, 1H), 7.8 (d, 1H), 7.6 (dd, 1H), 7.38 (d, 1H), 7.18 (d, 1H), 7.0 (dd, 1H), 4.42 (s, 2H), 3.5 (m, 2H), 3.1 (m, 5H), 2.4 (s, 3H).

Example No. 25

Preparation of Compound No. 25

A solution of 5-(4-bromo-thiophen-3-yl)-8-chloro-2-methyl-2,3,4,5-tetrahydro-1H-pyrido[4,3-b]indole (100 mg, 0.263 mmol), 4-fluoroboronic acid (55.16 mg, 0.394 mmol) and potassium phosphate (139.39 mg, 0.657 mmol) in DMF (2 mL)-water (0.2 mL) was purged with nitrogen followed by addition of dichlorobis(triphenylphosphine) palladium (II) (9.23 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under vacuum to obtain crude product which was purified by reverse phase HPLC to yield 20 mg of the title compound. $^1$H NMR (Freebase, CDCl$_3$) δ (ppm): 7.42 (d, 1H), 7.18 (m, 2H), 7.0 (m, 2H), 6.8-6.92 (m, 4H), 3.61 (s, 2H), 2.38 (m, 2H), 2.42 (s, 3H), 2.2 (m, 2H).

Example No. 26

Preparation of Compound No. 26

A solution of 5-(4-bromo-thiophen-3-yl)-8-chloro-2-methyl-2,3,4,5-tetrahydro-1H-pyrido[4,3-b]indole (100 mg, 0.263 mmol), phenylboronic acid (48.06 mg, 0.394 mmol) and potassium phosphate (139.39 mg, 0.657 mmol) in DMF (2 mL)-water (0.2 mL) was purged with nitrogen followed by addition of dichlorobis(triphenylphosphine) palladium (II) (9.23 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under vacuum to obtain crude product which was purified by reverse phase HPLC to yield 5 mg of the title compound. $^1$H NMR (TFA salt, CD$_3$OD) δ (ppm): 7.8-7.75 (m, 2H), 7.55 (s, 1H), 7.2-7.1 (m, 5H), 7.0-6.9 (m, 2H), 4.75-4.65 (m, 1H), 4.4-4.3 (m, 1H), 3.7-3.65 (m, 1H), 3.58-3.45 (m, 1H), 2.9 (s, 3H), 2.65-2.59 (m, 1H), 2.5-2.4 (m, 1H).

Example No. 27

Preparation of Compound No. 27

A solution of 5-(4-bromo-thiophen-3-yl)-8-chloro-2-methyl-2,3,4,5-tetrahydro-1H-pyrido[4,3-b]indole (100 mg, 0.263 mmol), 3-pyridinylboronic acid (48.5 mg, 0.394 mmol) and potassium phosphate (139.39 mg, 0.657 mmol), in DMF (2 mL)-water (0.2 mL) was purged with nitrogen followed by addition of dichlorobis(triphenylphosphine) palladium (II) (9.23 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under vacuum to obtain crude product which was purified by reverse phase HPLC to yield 17 mg of the title compound. $^1$H NMR (TFA salt, CD$_3$OD) δ (ppm): 8.59 (bs, 1H), 8.15 (d, 2H), 7.95-7.8 (m, 2H), 7.63-7.59 (m, 2H), 7.1 (d, 1H), 6.95 (d, 1H), 4.8-4.5 (m, 1H), 4.42-4.39 (m, 1H), 3.85-3.75 (m, 1H), 3.61-3.45 (m, 1H), 3.2 (m, 1H), 3.15 (s, 3H), 2.9-2.75 (m, 1H).

Example No. 28

Preparation of Compound No. 28

A solution of 5-(4-bromo-thiophen-3-yl)-8-chloro-2-methyl-2,3,4,5-tetrahydro-1H-pyrido[4,3-b]indole (100 mg, 0.263 mmol), 4-pyridinylboronic acid (48.5 mg, 0.394 mmol) and potassium phosphate (139.39 mg, 0.657 mmol) in DMF (2 mL)-water (0.2 mL) was purged with nitrogen followed by addition of dichlorobis(triphenylphosphine) palladium (II) (9.23 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under vacuum to obtain crude product which was purified by reverse phase HPLC to yield 11 mg of the title compound. $^1$H NMR (TFA salt, CD$_3$OD) δ (ppm): 8.6-8.59 (m, 3H), 8.00 (m, 1H), 7.6 (s, 1H), 7.41 (bs, 2H), 7.1 (d, 1H), 6.95 (bs, 1H), 4.8-4.79 (m, 1H), 4.41-4.39 (m, 1H), 3.81-3.79 (m, 1H), 3.6-3.5 (m, 1H), 3.15 (s, 3H), 3.15-3.00 (m, 1H), 2.85-2.79 (m, 1H).

Example No. 29

Preparation of Compound No. 29

To a de-aerated solution of 5-(4-bromo-thiophen-3-yl)-8-chloro-2-methyl-2,3,4,5-tetrahydro-1H-pyrido[4,3-b]indole (100 mg, 0.263 mmol), 4-pyridinylboronic acid (48.5 mg, 0.394 mmol) and K$_3$PO$_4$ (139.39 mg, 0.657 mmol) in DMF-water (2:0.2 mL) was added dichlorobis(triphenylphosphine) palladium (II) (9.23 mg, 5 mol %). The reaction mixture was heated at 95° C. for 30 min under nitrogen atmosphere. The reaction mixture was diluted with water and extracted with EtOAc. The organic layer was dried over anhydrous sodium sulfate and concentrated under reduced pressure to afford crude material, which was purified by reverse phase HPLC to yield 8-chloro-2-methyl-5-thiophen-3-yl-2,3,4,5-tetrahydro-1H-pyrido[4,3-b]indole (35 mg). $^1$H NMR (TFA salt, CD$_3$OD) δ (ppm): 7.7 (dd, 1H), 7.58 (m, 2H), 7.2 (m, 3H), 4.76 (d, 1H), 4.4 (d, 1H), 3.8 (m, 1H), 3.6 (m, 1H), 3.2 (m, 4H), 3.0 (m, 1H).

Example No. 30

Preparation of Compound No. 30

To a solution of 5-(4-bromothiophen-3-yl)-2,8-dimethyl-2,3,4,5-tetrahydro-1H-pyrido[4,3-b]indole (100 mg, 0.25 mmol) in DME (4 mL) was added Pd(PPh$_3$)$_4$ (15 mg, 0.0128 mmol) and purged with N$_2$. 1-Methylpyrazole-4-boronic acid pinacol ester (108 mg, 0.515 mmol), K$_2$CO$_3$ (36 mg, 0.257 mmol) and water (2 mL) were added followed by N$_2$ purging and the reaction refluxed under N$_2$ for 45 min. The reaction mixture was cooled to RT, and the solvent was removed under reduced pressure. The residue was dissolved in EtOAc and heated at 50° C. along with stirring for 15 min followed by filtration. The filtrate was concentrated under reduced pressure and the product was isolated by reverse phase HPLC. $^1$H NMR (freebase, CDCl$_3$) δ (ppm): 7.41 (d, 1H), 7.38 (m, 2H), 7.20 (d, 1H), 6.82 (m, 2H), 6.38 (s, 1H), 3.78 (s, 3H), 3.61 (s, 3H), 3.80 (s, 2H), 3.60 (d, 2H), 2.41 (s, 3H), 2.39 (d, 2H).

Example No. 31

Preparation of Compound No. 31

A solution of 5-(2-bromophenyl)-2,8-dimethyl-2,3,4,5-tetrahydro-1H-pyrido[4,3-b]indole (100 mg, 0.282 mmol), 2-(dimethylamino)pyrimidine-5-boronic acid pinacol ester (105.5 mg, 0.423 mmol) and potassium phosphate (149.7 mg, 0.706 mmol) in DMF (4 mL)-water (1 mL) was purged with nitrogen followed by addition of dichlorobis(triphenylphosphine) palladium (II) (9.91 mg, 5 mol %). The reaction mixture was heated at 95° C. for 30 min under nitrogen atmosphere. The reaction mixture was diluted with water, extracted with EtOAc, the organic layer dried over anhydrous sodium sulfate and concentrated under reduced pressure to obtain crude which was purified by reverse phase HPLC to yield 9 mg of the title compound. $^1$H NMR (TFA salt, CD$_3$OD) δ (ppm): 8.03 (s, 1H), 7.98 (s, 1H), 7.60-7.68 (m, 3H), 7.43 (d, 1H), 7.30 (s, 1H), 7.0 (d, 1H), 6.80 (m, 1H), 4.78 (m, 2H), 4.40 (d, 2H), 3.70 (m, 1H), 3.40-3.51 (m, 1H), 3.11 (m, 9H), 2.40 (s, 3H).

Example No. 32

Preparation of Compound No. 32

A solution of 5-(2-bromophenyl)-2,8-dimethyl-2,3,4,5-tetrahydro-1H-pyrido[4,3-b]indole (100 mg, 0.282 mmol), 1-methyl-1H-pyrazole-5-boronic acid pinacol ester (88 mg, 0.423 mmol) and potassium phosphate (149.7 mg, 0.706 mmol), in DMF (4 mL)-water (1 mL) was purged with nitrogen followed by addition of dichlorobis(triphenylphosphine) palladium (II) (9.91 mg, 5 mol %). The reaction mixture was heated at 95° C. for 30 min under nitrogen atmosphere. The reaction mixture was diluted with water, extracted with EtOAc, organic layer dried over anhydrous sodium sulfate and concentrated under vacuum to obtain crude which was purified by reverse phase HPLC to yield 3 mg of the title compound. $^1$H NMR (TFA salt, CD$_3$OD) δ (ppm): 7.78 (m, 3H), 7.55 (m, 1H), 7.23 (m, 2H), 7.0 (d, 1H), 6.83 (d, 1H), 5.80 (d, 1H), 4.70 (d, 1H), 4.38 (d, 1H), 3.70 (m, 4H), 3.40 (m, 2H), 2.97-3.14 (m, 4H), 2.40 (s, 3H).

Example No. 33

Preparation of Compound No. 33

To a solution of [5-(4-bromothiophen-3-yl)-2,8-dimethyl-2,3,4,5-tetrahydro-1H-pyrido[4,3-b]indole] (100 mg, 0.25 mmol) in DME (2 mL) were added water (1 mL) and K$_2$CO$_3$ (110 mg, 0.77 mmol) and purged solution with N$_2$. Pd(PPh$_3$)$_4$ (20 mg, 0.017 mmol) and 1-methylindole-5-boronic acid pinacol ester (140 mg, 0.546 mmol) were added to the reaction mixture which was refluxed under N$_2$ for 45 min. The reaction mixture was cooled to RT and diluted with EtOAc. The aqueous layer was extracted with EtOAc (3×6 mL) and the combined organic layer dried over sodium sulfate. The solvent was removed under reduced pressure to afford crude product which was purified by reverse phase HPLC. $^1$H NMR (TFA salt, CD$_3$OD) δ (ppm): 7.62 (d, 2H), 7.31 (d, 1H), 7.10 (m, 4H), 6.77 (m, 2H), 6.20 (d, 1H), 4.60 (d, 1H), 4.23 (d, 1H), 3.65 (s, 3H), 3.51 (m, 2H), 3.37 (s, 3H), 3.02 (m, 1H), 2.80 (m, 1H), 2.44 (s, 3H).

Example No. 34

Preparation of Compound No. 34

To a solution of [5-(4-bromothiophen-3-yl)-2,8-dimethyl-2,3,4,5-tetrahydro-1H-pyrido[4,3-b]indole] (100 mg, 0.25 mmol) in DME (2 mL) were added water (1 mL) and K$_2$CO$_3$ (110 mg, 0.77 mmol) and purged the solution with N$_2$. Pd(PPh$_3$)$_4$ (20 mg, 0.017 mmol) and isoquinoline-4-boronic acid (70 mg, 0.404 mmol) were added to the reaction mixture which was refluxed under N₂ for 45 min. The reaction mixture was cooled to RT and diluted with EtOAc. Aqueous layer was extracted with EtOAc (3×6 mL) and the combined organic layer dried over sodium sulfate. The solvent was removed under reduced pressure to afford crude product which was purified by reverse phase HPLC. ¹H NMR (TFA salt, CD₃OD) δ (ppm): 9.5 (s, 1H), 8.40 (m, 1H), 8.17 (m, 3H), 8.05 (s, 1H), 7.95 (m, 2H), 7.10 (d, 1H), 6.60-6.95 (m, 2H), 4.60 (dd, 1H), 4.20 (dd, 1H), 3.80 (m, 1H), 3.50 (m, 1H), 3.17 (m, 4H), 2.83 (m, 1H), 2.23 (s, 3H).

Example No. 35

Preparation of Compound No. 35

To a solution of [5-(4-bromothiophen-3-yl)-2,8-dimethyl-2,3,4,5-tetrahydro-1H-pyrido[4,3-b]indole] (100 mg, 0.25 mmol) in DME (2 mL) were added water (1 mL) and K₂CO₃ (110 mg, 0.77 mmol) and purged the solution with N₂. Pd(PPh₃)₄ (20 mg, 0.017 mmol) and 2-fluoropyridine-5-boronic acid pinacol ester (140 mg, 0.626 mmol) were added to the reaction mixture which was refluxed under N₂ for 45 min. The reaction mixture was cooled to RT and diluted with EtOAc. The aqueous layer was extracted with EtOAc (3×6 mL) and the combined organic layer dried over sodium sulfate. The solvent was removed under reduced pressure to afford crude product which was purified by reverse phase HPLC. ¹H NMR (TFA salt, CD₃OD) δ (ppm): 7.96 (s, 1H), 7.78 (d, 1H), 7.70 (d, 1H), 7.44 (dd, 1H), 7.31 (d, 1H), 6.98 (d, 1H), 6.82 (m, 2H), 4.71 (d, 1H), 4.40 (d, 1H), 3.78 (m, 1H), 3.57 (m, 1H), 3.15 (m, 5H), 2.40 (s, 3H).

Example No. 36

Preparation of Compound No. 36

A solution of 5-(2-bromophenyl)-2,8-dimethyl-2,3,4,5-tetrahydro-1H-pyrido[4,3-b]indole (100 mg, 0.282 mmol), 4-methylthiophene-2-boronic acid pinacol ester (94 mg, 0.419 mmol) and potassium phosphate (148 mg, 0.702 mmol) in DMF (4 mL)-water (1 mL) was purged with nitrogen followed by addition of dichlorobis(triphenylphosphine) palladium (II) (9.91 mg, 5 mol %). The reaction mixture was heated at 95° C. for 30 min under nitrogen atmosphere. The reaction mixture was diluted with water, extracted with EtOAc, organic layer dried over anhydrous sodium sulfate and concentrated under vacuum to obtain crude product which was purified by reverse phase HPLC to yield 8 mg of the title compound. ¹H NMR (TFA salt, CD₃OD) δ (ppm): 7.84 (d, 1H), 7.60 (dd, 1H), 7.57 (dd, 1H), 7.37 (m, 2H), 7.0 (m, 1H), 6.80 (m, 2H), 6.57 (d, 1H), 4.40 (d, 2H), 3.63 (m, 1H), 4.43 (m, 1H), 3.38 (s, 3H), 2.7-2.9 (m, 2H), 2.41 (s, 3H), 2.04 (s, 3H).

Example No. 37

Preparation of Compound No. 37

To a solution of [5-(4-bromothiophen-3-yl)-2,8-dimethyl-2,3,4,5-tetrahydro-1H-pyrido[4,3-b]indole] (100 mg, 0.25 mmol) in DME (2 mL) were added water (1 mL) and K₂CO₃ (110 mg, 0.77 mmol) and purged the solution with N₂. Pd(PPh₃)₄ (20 mg, 0.017 mmol) and 4-methoxyphenylboronic acid (70 mg) were added to the reaction mixture which was refluxed under N₂ for 45 min. The reaction mixture was cooled to RT and diluted with EtOAc. The aqueous layer was extracted with EtOAc (3×6 mL) and the combined organic layer dried over sodium sulfate. The solvent was removed under reduced pressure to afford crude product which was purified by reverse phase HPLC. ¹H NMR (TFA salt, CD₃OD) δ (ppm): 7.61 (m, 2H), 7.30 (s, 1H), 7.0 (d, 2H), 6.91 (d, 1H), 6.80 (d, 1H), 6.71 (dd, 2H), 4.71 (d, 1H), 4.38 (d, 1H), 3.78 (s, 3H), 3.62 (m, 1H), 3.23 (m, 1H), 2.87 (m, 5H), 2.40 (s, 3H).

Example 38

Preparation of Compound No. 38

To a solution of 6-bromoisoquinoline (124 mg, 0.6 mmol) in DMF (2 mL) were added potassium phosphate (212 mg, 1 mmol), CuI (9.5 mg, 0.05 mmol) and L-proline (11.5 mg, 0.1 mmol) and purged the solution with nitrogen. 2,3,4,5-Tetrahydro-2,8-dimethyl-1H-pyrido[4,3-b]indole (100 mg, 0.5 mmol) was added and again purged the reaction mixture with nitrogen followed by overnight heating at 140° C. Ice water was added to the reaction mixture and extracted the organic part into EtOAc (3×15 mL). The combined organic layer was washed with water (2×10 mL) and concentrated. The crude product was purified by column chromatography using silica (100-200 mesh) in 0-7% MeOH:DCM to yield 29 mg of the desired compound as free base. ¹H NMR (HCl salt, CD₃OD) δ (ppm): 9.82 (s, 1H), 8.78 (d, 1H), 8.62 (d, 1H), 8.57 (d, 1H), 8.4 (s, 1H), 8.2 (d, 1H), 7.41 (m, 2H), 7.18 (d, 1H), 4.78 (d, 1H), 4.43 (d, 1H), 3.82 (m, 1H), 3.6 (m, 1H), 3.58-3.5 (m, 1H), 3.1-3.2 (m, 4H), 2.42 (s, 3H).

Example No. 39

Preparation of Compound No. 39

To a solution of 5-(4-bromothiophen-3-yl)-2,8-dimethyl-2,3,4,5-tetrahydro-1H-pyrido[4,3-b]indole (100 mg, 0.25 mmol) in DME (2 mL) were added water (1 mL) and K₂CO₃ (110 mg, 0.77 mmol) and purged the solution with N₂. Pd(PPh₃)₄ (20 mg, 0.017 mmol) and 3-methylthiophene-2-boronic acid pinacol ester (100 mg, 0.367 mmol) were added to the reaction mixture, which was refluxed under N₂ for 45 min. The reaction mixture was cooled to RT and diluted with EtOAc. Aqueous layer was extracted with EtOAc (3×6 mL) and the combined organic layer dried over sodium sulfate. The solvent was removed under reduced pressure to afford crude material, which was purified by reverse phase HPLC. ¹H NMR (TFA salt, CD₃OD) δ (ppm): 7.61-7.72 (m, 2H), 7.23 (s, 1H), 7.07 (d, 1H), 6.91 (m, 2H), 6.78 (d, 1H), 4.68 (d, 1H), 4.32 (d, 1H), 3.70 (m, 1H), 3.42 (m, 1H), 3.32 (s, 3H), 2.97 (m, 2H), 2.4 (s, 3H), 2.07 (s, 3H).

Example No. 40

Preparation of Compound No. 40

To a solution of 5-(4-bromothiophen-3-yl)-2,8-dimethyl-2,3,4,5-tetrahydro-1H-pyrido[4,3-b]indole (100 mg, 0.25 mmol) in DME (2 mL) were added water (1 mL) and K₂CO₃ (110 mg, 0.77 mmol) and purged solution with N₂. Pd(PPh₃)₄ (20 mg, 0.017 mmol) and 2-(dimethylamino) pyrimidine-5-boronic acid pinacol ester (140 mg, 0.563 mmol) were added to the reaction mixture, which was refluxed under N₂ for 45 min. The reaction mixture was cooled to RT and diluted with EtOAc. Aqueous layer was extracted with EtOAc (3×6 mL) and the combined organic layer dried over sodium sulfate. The solvent was removed under reduced pressure to afford crude material, which was purified by reverse phase HPLC. ¹H NMR (TFA salt, CD₃OD) δ (ppm): 8.0 (m, 3H), 7.80 (dd, 1H), 7.38 (s, 1H), 7.0 (m, 1H), 6.82 (m, 1H), 4.77 (d, 1H), 4.40 (d, 1H), 3.80 (m, 1H), 3.58 (m, 1H), 3.20 (s, 6H), 3.18 (s, 3H), 3.0 (m, 1H), 2.76 (m, 1H), 2.40 (s, 3H).

Example No. 41

Preparation of Compound No. 41

To a solution of 5-(4-bromothiophen-3-yl)-2,8-dimethyl-2,3,4,5-tetrahydro-1H-pyrido[4,3-b]indole (100 mg, 0.25 mmol) in DME (2 mL) were added water (1 mL) and K₂CO₃ (110 mg, 0.77 mmol) and purged the solution with N₂. Pd(PPh₃)₄ (20 mg, 0.017 mmol) and indazole-4-boronic acid.HCl (102 mg, 0.515 mmol) were added to the reaction mixture, which was refluxed under N₂ for 45 min. The reaction mixture was cooled to RT and diluted with EtOAc. Aqueous layer was extracted with EtOAc (3×6 mL) and the combined organic layer dried over sodium sulfate. The solvent was removed under reduced pressure to afford crude product which was purified by reverse phase HPLC. ¹H NMR (TFA salt, CD₃OD) δ (ppm): 7.83-7.98 (m, 2H), 7.77 (dd, 1H), 7.4 (d, 1H), 7.23 (s, 1H), 7.05-7.16 (m, 2H), 7.0 (d, 1H), 6.4 (dd, 1H), 4.61 (m, 1H), 4.24 (m, 1H), 3.58 (m, 1H), 3.38 (m, 4H), 3.10 (m, 1H), 2.8 (m, 1H), 2.4 (s, 3H).

Example No. 42

Preparation of Compound No. 42

To a de-aerated solution of 5-(3-bromophenyl)-2,8-dimethyl-2,3,4,5-tetrahydro-1H-pyrido[4,3-b]indole (100 mg, 0.281 mmol), 2-(dimethylamino)pyrimidine-5-boronic acid pinacol ester (140 mg, 0.561 mmol) and K₂CO₃ (120 mg, 0.845 mmol) in DME (4 mL)-water (2 mL) was added Pd(PPh₃)₄ (16 mg, 0.013 mmol). The reaction mixture was stirred at 90° C. for 45 min. The solvent was removed under reduced pressure, residue diluted with water (20 mL) and extracted with EtOAc (50 mL). The organic layer was dried over anhydrous sodium sulfate, concentrated under reduced pressure to obtain crude, which was purified by reverse phase HPLC to yield 5-(3-(2,8-dimethyl-3,4-dihydro-1H-pyrido[4,3-b]indol-5(2H)-yl)phenyl)-N,N-dimethylpyrimidin-2-amine. ¹H NMR (TFA salt, CD₃OD) δ (ppm): 8.8 (s, 2H), 7.6-7.77 (m, 3H), 7.4 (d, 1H), 7.3 (s, 1H), 7.1 (d, 1H), 6.97 (d, 1H), 4.77 (d, 1H), 4.4 (d, 1H), 3.8 (m, 1H), 3.5 (m, 1H), 3.3 (s, 6H), 3.1 (m, 4H), 3.0 (m, 1H), 2.4 (s, 3H).

Example No. 43

Preparation of Compound No. 43

To a de-aerated solution of 5-(3-bromophenyl)-2,8-dimethyl-2,3,4,5-tetrahydro-1H-pyrido[4,3-b]indole (100 mg, 0.281 mmol), 3-methylthiophene-2-boronic acid pinacol ester (125 mg, 0.557 mmol) and K₂CO₃ (120 mg, 0.845 mmol) in DME (4 mL)-water (2 mL) was added Pd(PPh₃)₄ (16 mg, 0.013 mmol). The reaction mixture was stirred at 90° C. for 45 min. The solvent was removed under reduced pressure, residue diluted with water (20 mL) and extracted with EtOAc (50 mL). The organic layer was dried over anhydrous sodium sulfate, concentrated under reduced pressure to obtain crude, which was purified by reverse phase HPLC to yield 2,8-dimethyl-5-(3-(3-methylthiophen-2-yl)phenyl)-2,3,4,5-tetrahydro-1H-pyrido[4,3-b]indole. ¹H NMR (TFA salt, CD₃OD) δ (ppm): 7.52-7.71 (m, 2H), 7.42 (s, 1H), 7.4 (m, 2H), 7.35 (s, 1H), 7.18 (d, 1H), 7.04 (d, 1H), 6.97 (d, 1H), 4.7 (m, 1H), 4.4 (m, 1H), 3.82 (m, 1H), 3.58 (m, 1H), 3.2 (m, 4H), 3.0 (m, 1H), 2.42 (s, 3H), 2.38 (s, 3H).

Example No. 44

Preparation of Compound No. 44

To a de-aerated solution of 5-(3-bromophenyl)-2,8-dimethyl-2,3,4,5-tetrahydro-1H-pyrido[4,3-b]indole (100 mg, 0.281 mmol), 2-fluoropyridine-5-boronic acid pinacol ester (125 mg, 0.560 mmol) and K₂CO₃ (120 mg, 0.845 mmol) in DME (4 mL)-water (2 mL) was added Pd(PPh₃)₄ (16 mg, 0.013 mmol). The reaction mixture was stirred at 90° C. for 45 min. The solvent was removed under reduced pressure, residue diluted with water (20 mL) and extracted with EtOAc (50 mL). The organic layer was dried over anhydrous sodium sulfate, concentrated under reduced pressure to obtain crude, which was purified by reverse phase HPLC to yield 5-(3-(6-fluoropyridin-3-yl)phenyl)-2,8-dimethyl-2,3,4,5-tetrahydro-1H-pyrido[4,3-b]indole. ¹H NMR (TFA salt, CD₃OD) δ (ppm): 8.5 (s, 1H), 8.21 (dd, 1H), 7.72 (m, 2H), 7.62 (s, 1H), 7.5 (d, 1H), 7.3 (s, 1H), 7.17 (m, 2H), 7.06 (d, 1H), 4.8 (d, 1H), 4.4 (d, 1H), 3.8 (m, 1H), 3.56 (m, 1H), 3.21 (m, 1H), 3.18 (s, 3H), 3.1 (m, 1H), 2.4 (s, 3H).

Example No. 45

Preparation of Compound No. 45

To a de-aerated solution of 5-(3-bromophenyl)-2,8-dimethyl-2,3,4,5-tetrahydro-1H-pyrido[4,3-b]indole (100 mg, 0.281 mmol), 2-acetamidopyridine-5-boronic acid pinacol ester (147 mg, 0.560 mmol) and K₂CO₃ (120 mg, 0.845 mmol) in DME (4 mL)-water (2 mL) was added Pd(PPh₃)₄ (16 mg, 0.013 mmol). The reaction mixture was stirred at 90° C. for 45 min. The solvent was removed under reduced pressure, residue diluted with water (20 mL) and extracted with EtOAc (50 mL). The organic layer was dried over anhydrous sodium sulfate, concentrated under reduced pressure to obtain crude, which was purified by reverse phase HPLC to yield N-(5-(3-(2,8-dimethyl-3,4-dihydro-1H-pyrido[4,3-b]indol-5(2H)-yl)phenyl)pyridin-2-yl)acetamide. ¹H NMR (TFA salt, CD₃OD) δ (ppm): 8.6 (s, 1H), 8.18 (s, 2H), 7.8 (d, 1H), 7.62-7.77 (m, 2H), 7.42 (d, 1H), 7.3 (s, 1H), 7.17 (d, 1H), 7.03 (d, 1H), 4.7 (d, 1H), 4.42 (d, 1H), 3.8 (m, 1H), 3.58 (m, 1H), 3.0-3.2 (m, 5H), 2.41 (s, 3H), 2.2 (s, 3H).

Example No. 46

Preparation of Compound No. 46

To a de-aerated solution of 5-(3-bromophenyl)-2,8-dimethyl-2,3,4,5-tetrahydro-1H-pyrido[4,3-b]indole (100 mg, 0.281 mmol), 1-methylpyrazole-4-boronic acid pinacol ester (116 mg, 0.557 mmol) and K₂CO₃ (120 mg, 0.845 mmol) in DME (4 mL)-water (2 mL) was added Pd(PPh₃)₄ (16 mg, 0.013 mmol). The reaction mixture was stirred at 90° C. for 45 min. The solvent was removed under reduced pressure, residue diluted with water (20 mL) and extracted with EtOAc (50 mL). The organic layer was dried over anhydrous sodium sulfate, concentrated under reduced pressure to obtain crude, which was purified by reverse phase HPLC to yield 2,8-dimethyl-5-(3-(1-methyl-1H-pyrazol-4-yl)phenyl)-2,3,4,5-tetrahydro-1H-pyrido[4,3-b]indole. ¹H NMR (TFA salt, CD₃OD) δ (ppm): 8.02 (s, 1H), 7.84 (s, 1H), 7.64 (d, 1H), 7.58 (m, 2H), 7.52 (s, 1H), 7.22 (d, 1H), 7.14 (d, 1H), 7.02 (d, 1H), 4.4 (m, 2H), 3.96 (s, 3H), 3.8 (m, 1H), 3.58 (m, 1H), 3.0-3.2 (m, 5H), 2.41 (s, 3H).

Example No. 47

Preparation of Compound No. 47

To a solution of 5-bromoquinoline (100 mg, 0.469 mmol) in DMF (2 mL) were added potassium phosphate (198 mg, 0.938 mmol), CuI (8 mg, 0.046 mmol) and L-proline (10 mg, 0.938 mmol) and purged the solution with nitrogen. 2,3,4,5-Tetrahydro-2,6,8-trimethyl-1H-pyrido[4,3-b]indole (100 mg, 0.469 mmol) was added and again purged the reaction mixture with nitrogen followed by overnight heating at 140° C. Ice water was added to the reaction mixture and extracted the organic part into EtOAc (3×15 mL). The combined organic layer was washed with water (2×10 mL) and concentrated under reduced pressure. The crude obtained was purified by column chromatography using silica (100:200 mesh) in 0-7% MeOH-DCM. The compound was further purified through reverse phase HPLC to yield: 1.88 mg of the desired compound as the TFA salt. $^1$H NMR (TFA salt, CD$_3$OD) δ (ppm): 9.0 (d, 1H), 8.3 (d, 1H), 8.0 (dd, 1H), 7.42-7.81 (m, 3H), 7.31 (s, 1H), 6.9 (d, 1H), 4.4 (m, 2H), 3.7 (m, 1H), 3.5 (m, 1H), 3.17 (m, 5H), 2.4 (m, 6H).

Example No. 48

Preparation of Compound No. 48

To a solution of 6-bromoquinoline (0.059 mL, 0.431) in DMF (2 mL) were added potassium phosphate (152 mg, 1 mmol), CuI (6.8 mg, 0.0359 mmol), L-proline (8 mg, 0.0718 mmol) and 2,3,4,5-tetrahydro-2,6,8-trimethyl-1H-pyrido[4,3-b]indole (100 mg, 0.359 mmol). The reaction mixture was purged with nitrogen and stirred at 140° C. for overnight. Ice water (5 mL) was added into the reaction mixture and the solid obtained was filtered. The residue was dissolved in EtOAc and washed with water (2×10 mL). The organic layer was dried over anhydrous sodium sulfate and concentrated under reduced pressure. The crude was purified by column chromatography using silica (100:200) and 0-6% MeOH-DCM. The compound was further purified by reverse phase HPLC to yield 19 mg of the desired compound as the TFA salt. $^1$H NMR (TFA salt, CD$_3$OD) δ (ppm): 9.18 (d, 1H), 8.9 (d, 1H), 8.2-8.37 (m, 2H), 7.97 (m, 2H), 7.2 (s, 1H), 6.81 (s, 1H), 4.76 (d, 1H), 4.4 (d, 1H), 3.8 (m, 1H), 3.5 (m, 1H), 3.18 (s, 3H), 2.9 (m, 1H), 2.8 (m, 1H), 2.4 (s, 3H), 1.9 (s, 3H).

Example No. 49

Preparation of Compound No. 49

To a solution of [5-(4-bromothiophen-3-yl)-2,8-dimethyl-2,3,4,5-tetrahydro-1H-pyrido[4,3-b]indole] (100 mg, 0.25 mmol) in DME (2 mL) were added water (1 mL) and K$_2$CO$_3$ (110 mg, 0.77 mmol) and purged the solution with N$_2$. Pd(PPh$_3$)$_4$ (20 mg, 0.017 mmol) and 6-hydroxypyridine-3-boronic acid pinacol ester (114 mg, 0.515 mmol) were added to the reaction mixture, which was refluxed under N$_2$ for 45 min. The reaction mixture was cooled to RT and diluted with EtOAc. The aqueous layer was extracted with EtOAc (3×6 mL) and the combined organic layer dried over anhydrous sodium sulfate. The solvent was removed under reduced pressure to afford crude material, which was purified by reverse phase HPLC. $^1$H NMR (TFA salt, CD$_3$OD) δ (ppm): 7.78 (d, 1H), 7.72 (d, 1H), 7.38 (s, 1H), 7.2 (d, 1H), 7.02 (d, 1H), 6.92 (d, 1H), 6.82 (s, 1H), 6.3 (d, 1H), 4.5 (m, 2H), 3.6 (m, 2H), 3.0-3.17 (m, 4H), 2.7 (m, 1H), 2.41 (s, 3H).

Example No. 50

Preparation of Compound No. 50

To a solution of [5-(4-bromothiophen-3-yl)-2,8-dimethyl-2,3,4,5-tetrahydro-1H-pyrido[4,3-b]indole] (100 mg, 0.25 mmol) in DME (2 mL) were added water (1 mL) and K$_2$CO$_3$ (110 mg, 0.77 mmol) and purged the solution with N$_2$. Pd(PPh$_3$)$_4$ (20 mg, 0.017 mmol) and 4-methylthiophene-2-boronic acid pinacol ester (70 mg, 0.257 mmol) were added to the reaction mixture, which was refluxed under N$_2$ for 45 min. The reaction mixture was cooled to RT and diluted with EtOAc. Aqueous layer was extracted with EtOAc (3×6 mL) and the combined organic layer dried over anhydrous sodium sulfate. The solvent was removed under reduced pressure to afford crude material, which was purified by reverse phase HPLC. $^1$H NMR (TFA salt, CD$_3$OD) δ (ppm): 7.8 (d, 1H), 7.62 (d, 1H), 7.3 (s, 1H), 7.0 (d, 1H), 6.9 (d, 1H), 6.78 (s, 1H), 6.43 (s, 1H), 4.61 (s, 2H), 3.5-3.7 (m, 2H), 3.02 (s, 3H), 2.9 (m, 1H), 2.6 (m, 1H), 2.4 (s, 3H), 2.0 (s, 3H).

Example No. 51

Preparation of Compound No. 51

To a de-aerated solution of 5-(3-bromophenyl)-2,8-dimethyl-2,3,4,5-tetrahydro-1H-pyrido[4,3-b]indole (100 mg, 0.281 mmol), benzo[b]thien-2-ylboronic acid (100 mg, 0.557 mmol) and K$_2$CO$_3$ (116 mg, 0.845 mmol) in DME (4 mL)-water (2 mL) was added Pd(PPh$_3$)$_4$ (16 mg, 0.013 mmol). The reaction mixture was stirred at 90° C. for 45 min. The reaction mixture was concentrated under reduced pressure. The residue was dissolved in EtOAc (50 mL) and washed with water (20 mL). The organic layer was dried over anhydrous sodium sulfate, concentrated under reduced pressure to obtain crude, which was purified by reverse phase HPLC to yield 5-(3-(benzo[b]thiophen-2-yl)phenyl)-2,8-dimethyl-2,3,4,5-tetrahydro-1H-pyrido[4,3-b]indole. $^1$H NMR (TFA salt, CD$_3$OD) δ (ppm): 7.8-7.91 (m, 3H), 7.78 (s, 2H), 7.61-7.7 (t, 1H), 7.3-7.4 (m, 4H), 7.18 (d, 1H), 7.02 (d, 1H), 4.8 (d, 1H), 4.4 (d, 1H), 3.81 (m, 1H), 3.5 (m, 1H), 3.2 (m, 1H), 3.18 (s, 3H), 3.01 (m, 1H), 2.41 (s, 3H).

Example No. 52

Preparation of Compound No. 52

To a de-aerated solution of 5-(3-bromophenyl)-2,8-dimethyl-2,3,4,5-tetrahydro-1H-pyrido[4,3-b]indole (100 mg, 0.281 mmol), 6-hydroxypyridine-3-boronic acid pinacol ester (124 mg, 0.557 mmol) and K$_2$CO$_3$ (116 mg, 0.845 mmol) in DME (4 mL)-water (2 mL) was added Pd(PPh$_3$)$_4$ (16 mg, 0.013 mmol). The reaction mixture was stirred at 90° C. for 45 min. The reaction mixture concentrated under reduced pressure. The residue was dissolved in EtOAc (50 mL) and washed with water (20 mL). The organic layer was dried over anhydrous sodium sulfate, concentrated under reduced pressure to afford crude material, which was purified by reverse phase HPLC to yield 5-(3-(2,8-dimethyl-3,4-dihydro-1H-pyrido[4,3-b]indol-5(2H)-yl)phenyl)pyridin-2-ol.
$^1$H NMR (TFA salt, CD$_3$OD) δ (ppm): 8.0 (d, 1H), 7.8 (d, 1H), 7.68 (m, 2H), 7.6 (s, 1H), 7.4 (dd, 1H), 7.36 (s, 1H), 7.17

(d, 1H), 7.08 (d, 1H), 6.62 (d, 1H), 4.7 (d, 1H), 4.4 (d, 1H), 3.8 (m, 1H), 3.56 (m, 1H), 3.18 (m, 4H), 3.02 (m, 1H), 2.4 (s, 3H).

Example No. 53

Preparation of Compound No. 53

To a de-aerated solution of 5-(3-bromophenyl)-2,8-dimethyl-2,3,4,5-tetrahydro-1H-pyrido[4,3-b]indole (100 mg, 0.281 mmol), 1-methylindole-5-boronic acid pinacol ester (144 mg, 0.560 mmol) and $K_2CO_3$ (116 mg, 0.845 mmol) in DME (4 mL)-water (2 mL) was added $Pd(PPh_3)_4$ (16 mg, 0.013 mmol). The reaction mixture was stirred at 90° C. for 45 min. The reaction mixture was concentrated under reduced pressure. The residue was dissolved in EtOAc (50 mL) and washed with water (20 mL). The organic layer was dried over anhydrous sodium sulfate, concentrated under reduced pressure to obtain crude, which was purified by reverse phase HPLC to yield 2,8-dimethyl-5-(3-(1-methyl-1H-indol-5-yl)phenyl)-2,3,4,5-tetrahydro-1H-pyrido[4,3-b]indole. $^1$H NMR (TFA salt, $CD_3OD$) δ (ppm): 7.82 (s, 1H), 7.8 (d, 1H), 7.62 (dd, 2H), 7.46 (dd, 2H), 7.35 (m, 2H), 7.2 (m, 2H), 7.04 (d, 1H), 6.5 (d, 1H), 4.6 (m, 2H), 3.8 (s, 3H), 3.7 (m, 2H), 3.11 (m, 5H), 2.41 (s, 3H).

Example No. 54

Preparation of Compound No. 54

To a de-aerated solution of 5-(3-bromophenyl)-2,8-dimethyl-2,3,4,5-tetrahydro-1H-pyrido[4,3-b]indole (100 mg, 0.281 mmol), 1H-benzimidazole-5-boronic acid pinacol ester (137 mg, 0.561 mmol) and $K_2CO_3$ (116 mg, 0.845 mmol) in DME (4 mL)-water (2 mL) was added $Pd(PPh_3)_4$ (16 mg, 0.013 mmol). The reaction mixture was stirred at 90° C. for 45 min. The reaction mixture was concentrated under reduced pressure. The residue was dissolved in EtOAc (50 mL) and washed with water (20 mL). The organic layer was dried over anhydrous sodium sulfate, concentrated under reduced pressure to obtain crude, which was purified by reverse phase HPLC to yield 5-(3-(1H-benzo[d]imidazol-5-yl)phenyl)-2,8-dimethyl-2,3,4,5-tetrahydro-1H-pyrido[4,3-b]indole. $^1$H NMR (TFA salt, $CD_3OD$) δ (ppm): 9.08 (s, 1H), 8.02 (s, 1H), 7.86 (m, 3H), 7.72 (m, 2H), 7.48 (d, 1H), 7.37 (s, 1H), 7.18 (d, 1H), 7.0 (d, 1H), 4.4 (m, 2H), 3.8 (m, 1H), 3.6 (m, 1H), 3.02-3.2 (m, 5H), 2.41 (s, 3H).

Example No. 55

Preparation of Compound No. 55

To a de-aerated solution of 5-(3-bromophenyl)-2,8-dimethyl-2,3,4,5-tetrahydro-1H-pyrido[4,3-b]indole (100 mg, 0.281 mmol), indazole-4-boronic acid hydrochloride (111 mg, 0.559 mmol) and $K_2CO_3$ (116 mg, 0.845 mmol) in DME (4 mL)-water (2 mL) was added $Pd(PPh_3)_4$ (16 mg, 0.013 mmol). The reaction mixture was stirred at 90° C. for 45 min. The reaction mixture was concentrated under reduced pressure. The residue was dissolved in EtOAc (50 mL) and washed with water (20 mL). The organic layer was dried over anhydrous sodium sulfate, concentrated under reduced pressure to obtain crude, which was purified by reverse phase HPLC to yield 5-(3-(1H-indazol-4-yl)phenyl)-2,8-dimethyl-2,3,4,5-tetrahydro-1H-pyrido[4,3-b]indole. $^1$H NMR (TFA salt, $CD_3OD$) δ (ppm): 8.18 (s, 1H), 7.82 (d, 1H), 7.78 (t, 1H), 7.7 (s, 1H), 7.6 (d, 1H), 7.5 (m, 2H), 7.34 (m, 2H), 7.21 (d, 1H), 7.1 (d, 1H), 4.7 (d, 1H), 4.4 (d, 1H), 3.8 (m, 1H), 3.6 (m, 1H), 3.04-3.18 (m, 5H), 2.4 (s, 3H).

Example No. 56

Preparation of Compound No. 56

To a solution of 5-(4-bromothiophen-3-yl)-2,8-dimethyl-2,3,4,5-tetrahydro-1H-pyrido[4,3-b]indole (100 mg, 0.25 mmol) in DME (2 mL) were added water (1 mL) and $K_2CO_3$ (110 mg, 0.77 mmol) and purged the solution with $N_2$. $Pd(PPh_3)_4$ (20 mg, 0.017 mmol) and 2-acetamidopyridine-5-boronic acid pinacol ester (140 mg, 0.515 mmol) were added to the reaction mixture, which was refluxed under $N_2$ for 45 min. The reaction mixture was cooled to RT and diluted with EtOAc. Aqueous layer was extracted with EtOAc (3×6 mL) and the combined organic layer dried over anhydrous sodium sulfate. The solvent was removed under reduced pressure to afford crude material, which was purified by reverse phase HPLC. $^1$H NMR (TFA salt, $CD_3OD$) δ (ppm): 8.0 (s, 1H), 7.8 (m, 2H), 7.68 (m, 1H), 7.51 (m, 1H), 7.33 (s, 1H), 6.82-7.0 (m, 2H), 4.77 (d, 1H), 4.4 (d, 1H), 3.78 (m, 1H), 3.5 (m, 1H), 3.1 (m, 4H), 2.7 (m, 1H), 2.4 (s, 3H), 2.2 (s, 3H).

Example No. 57

Preparation of Compound No. 57

To a de-aerated solution of 5-(3-bromophenyl)-2,6,8-trimethyl-2,3,4,5-tetrahydro-1H-pyrido[4,3-b]indole (80 mg, 0.217 mmol), pyridine-4-boronic acid (53 mg, 0.431 mmol) and $K_2CO_3$ (116 mg, 0.845 mmol) in DME (4 mL)-water (2 mL) was added $Pd(PPh_3)_4$ (12 mg, 0.013 mmol). The reaction mixture was heated at 90° C. for 45 min. The reaction mixture was concentrated under reduced pressure. The residue was dissolved in EtOAc (50 mL) and washed with water (20 mL). The organic layer was dried over anhydrous sodium sulfate, concentrated under reduced pressure to obtain crude, which was purified by reverse phase HPLC to yield 2,6,8-trimethyl-5-(3-(pyridin-4-yl)phenyl)-2,3,4,5-tetrahydro-1H-pyrido[4,3-b]indole. $^1$H NMR (TFA salt, $CD_3OD$) δ (ppm): 8.78 (d, 2H), 8.1 (m, 3H), 7.9 (m, 1H), 7.8 (t, 1H), 7.6 (m, 1H), 7.2 (s, 1H), 6.8 (s, 1H), 4.76 (m, 1H), 4.4 (m, 1H), 3.8 (m, 1H), 3.5 (m, 1H), 3.1 (s, 3H), 2.8-3.03 (m, 2H), 2.4 (s, 3H), 1.93 (s, 3H).

Example No. 58

Preparation of Compound No. 58

A solution of 2,8-dimethyl-2,3,4,5-tetrahydro-1H-pyrido[4,3-b]indole (0.1 g, 0.499 mmol), 8-bromoisoquinoline (0.155 g, 0.748 mmol), potassium phosphate (0.317 g, 1.495 mmol), CuI (9 mg, 0.047 mmol) and L-Proline (11 mg, 0.095 mmol) in dry DMF (3 mL) was heated at 150° C. for 16 h. The reaction mixture was diluted with water and extracted with EtOAc. The organic layer was dried over anhydrous sodium sulfate and concentrated under reduced pressure to obtain crude, which was purified by reverse phase HPLC to yield 5-(isoquinolin-8-yl)-2,8-dimethyl-2,3,4,5-tetrahydro-1H-pyrido[4,3-b]indole. $^1$H NMR (TFA salt, $CD_3OD$) δ (ppm): 8.8 (d, 1H), 8.62 (d, 1H), 8.42 (bs, 1H), 8.4 (d, 1H), 8.3 (t, 1H), 8.0 (d, 1H), 7.42 (s, 1H), 7.0 (d, 1H), 6.87 (bs, 1H), 4.7 (d, 1H), 4.3 (d, 1H), 3.8 (m, 1H), 3.6 (m, 1H), 3.16 (m, 4H), 2.8 (m, 1H), 2.4 (s, 3H).

Example No. 59

Preparation of Compound No. 59

To a de-aerated solution of 5-(2-bromophenyl)-2,8-dimethyl-2,3,4,5-tetrahydro-1H-pyrido[4,3-b]indole (200 mg, 0.564 mmol), 2-methyl-5-(4,4,5,5-tetramethyl-1,3,2-dioxaborolan-2-yl)pyridine (247 mg, 1.12 mmol) and $K_2CO_3$ (233.48 mg, 0.845 mmol) in DME-water (2:1) was added $Pd(PPh_3)_4$ (32.58 mg, 0.028 mmol). The reaction mixture was stirred at 90° C. for 45 min. The reaction mixture concentrated under reduced pressure. The residue obtained was dissolved in EtOAc (50 mL) and washed with water (20 mL). The organic layer was dried over anhydrous sodium sulfate and concentrated under reduced pressure to obtain crude, which was purified by reverse phase HPLC to yield 2,8-dimethyl-5-(2-(6-methylpyridin-3-yl)phenyl)-2,3,4,5-tetrahydro-1H-pyrido[4,3-b]indole. $^1$H NMR (TFA salt, $CD_3OD$) δ (ppm): 8.18 (s, 1H), 7.74 (m, 4H), 7.38-7.58 (m, 2H), 7.28 (s, 1H), 6.93 (d, 1H), 6.78 (d, 1H), 4.4 (m, 2H), 3.7 (m, 2H), 3.1 (s, 3H), 2.8 (m, 2H), 2.57 (s, 3H), 2.38 (s, 3H).

Example No. 60

Preparation of Compound No. 60

To a de-aerated solution of 5-(3-bromophenyl)-2,8-dimethyl-2,3,4,5-tetrahydro-1H-pyrido[4,3-b]indole (100 mg, 0.281 mmol), 2-methyl-5-(4,4,5,5-tetramethyl-1,3,2-dioxaborolan-2-yl)pyridine (124 mg, 0.564 mmol) and $K_2CO_3$ (116 mg, 0.845 mmol) in DME-water (2:1) was added $Pd(PPh_3)_4$ (16 mg, 0.013 mmol). The reaction mixture was stirred at 90° C. for 45 min. The reaction mixture was concentrated under reduced pressure. The residue obtained was dissolved in EtOAc (50 mL) and washed with water (20 mL). The organic layer was dried over anhydrous sodium sulfate and concentrated under reduced pressure to obtain crude, which was purified by reverse phase HPLC to yield 2,8-dimethyl-5-(3-(6-methylpyridin-3-yl)phenyl)-2,3,4,5-tetrahydro-1H-pyrido[4,3-b]indole. $^1$H NMR (TFA salt, $CD_3OD$) δ (ppm): 8.84 (s, 1H), 8.56 (d, 1H), 7.83 (d, 1H), 7.75-7.8 (m, 3H), 7.57 (d, 1H), 7.38 (s, 1H), 7.18 (d, 1H), 7.04 (d, 1H), 4.7 (m, 1H), 4.4 (m, 1H), 3.8 (m, 1H), 3.6 (m, 1H), 3.0-3.22 (m, 5H), 2.77 (s, 3H), 2.4 (s, 3H).

Example No. 61

Preparation of Compound No. 61

To a de-aerated solution of 5-(3-bromophenyl)-2,8-dimethyl-2,3,4,5-tetrahydro-1H-pyrido[4,3-b]indole (100 mg, 0.281 mmol), 4-fluoroboronic acid (79 mg, 0.564 mmol) and $K_2CO_3$ (116 mg, 0.845 mmol) in DME-water (2:1) was added $Pd(PPh_3)_4$ (16 mg, 0.013 mmol). The reaction mixture was stirred at 90° C. for 45 min. The reaction mixture was concentrated under reduced pressure. The residue obtained was dissolved in EtOAc (50 mL) and washed with water (20 mL). The organic layer was dried over anhydrous sodium sulfate and concentrated under reduced pressure to obtain crude, which was purified by reverse phase HPLC to yield 5-(4'-fluorobiphenyl-3-yl)-2,8-dimethyl-2,3,4,5-tetrahydro-1H-pyrido[4,3-b]indole. $^1$H NMR (TFA salt, $CD_3OD$) δ (ppm): 7.63-7.38 (m, 4H), 7.61 (s, 1H), 7.4 (d, 1H), 7.36 (s, 1H), 7.1-7.23 (m, 3H), 7.04 (d, 1H), 4.7 (m, 1H), 4.4 (m, 1H), 3.8 (m, 1H), 3.58 (m, 1H), 3.2 (m, 4H), 3.03 (m, 1H), 2.4 (s, 3H).

Example No. 62

Preparation of Compound No. 62

To a solution of 5-(4-bromothiophen-3-yl)-2,8-dimethyl-2,3,4,5-tetrahydro-1H-pyrido[4,3-b]indole (100 mg, 0.25 mmol) in DME (2 mL) were added water (1 mL) and $K_2CO_3$ (110 mg, 0.77 mmol) and purged the solution with $N_2$. $Pd(PPh_3)_4$ (20 mg, 0.017 mmol) and 3,5-dimethylisoxazole-4-boronic acid pinacol ester (140 mg, 0.626 mmol) were added to the reaction mixture, which was refluxed under $N_2$ for 45 min. The reaction mixture was cooled to RT and extracted with EtOAc. The combined organic layer was dried over sodium sulfate and concentrated under reduced pressure to afford crude material, which was purified by reverse phase HPLC. $^1$H NMR (TFA salt, $CD_3OD$) δ (ppm): 7.7 (s, 2H), 7.22 (s, 1H), 6.8-7.0 (m, 2H), 4.65 (m, 1H), 4.38 (m, 1H), 3.8 (m, 1H), 3.4 (m, 1H), 2.95-3.2 (m, 4H), 2.63 (m, 1H), 2.41 (s, 3H), 2.0 (s, 3H), 1.8 (s, 3H).

Example No. 63

Preparation of Compound No. 63

To a de-aerated solution of 5-(3-bromophenyl)-2,8-dimethyl-2,3,4,5-tetrahydro-1H-pyrido[4,3-b]indole (100 mg, 0.281 mmol), 4-methylthiophene-2-boronic acid pinacol ester (175 mg, 0.784 mmol) and $K_2CO_3$ (162 mg, 1.1 mmol) in DME-water (2:1) was added $Pd(PPh_3)_4$ (22 mg, 0.019 mmol). The reaction mixture was stirred at 90° C. for 45 min. The reaction mixture was concentrated under reduced pressure. The residue obtained was dissolved in EtOAc (50 mL) and washed with water (20 mL). The organic layer was dried over anhydrous sodium sulfate and concentrated under reduced pressure to obtain crude, which was purified by reverse phase HPLC to yield 2,8-dimethyl-5-(3-(4-methylthiophen-2-yl)phenyl)-2,3,4,5-tetrahydro-1H-pyrido[4,3-b]indole. $^1$H NMR (TFA salt, $CD_3OD$) δ (ppm): 7.78 (d, 1H), 7.6 (m, 2H), 7.3-7.38 (m, 3H), 7.17 (d, 1H), 7.02 (d, 1H), 7.0 (s, 1H), 4.4 (m, 2H), 3.8 (m, 1H), 3.6 (m, 1H), 3.2 (s, 4H), 3.1 (m, 1H), 2.41 (s, 3H), 2.27 (s, 3H).

Example No. 64

Preparation of Compound No. 64

To a de-aerated solution of 5-(3-bromophenyl)-2,8-dimethyl-2,3,4,5-tetrahydro-1H-pyrido[4,3-b]indole (100 mg, 0.281 mmol), 5-methylthiophene-2-boronic acid pinacol ester (175 mg, 0.784 mmol) and $K_2CO_3$ (162 mg, 1.1 mmol) in DME-water (2:1) was added $Pd(PPh_3)_4$ (22 mg, 0.019 mmol). The reaction mixture was stirred at 90° C. for 45 min. The reaction mixture was concentrated under reduced pressure. The residue obtained was dissolved in EtOAc (50 mL) and washed with water (20 mL). The organic layer was dried over anhydrous sodium sulfate and concentrated under reduced pressure to obtain crude, which was purified by reverse phase HPLC to yield 2,8-dimethyl-5-(3-(5-methylthiophen-2-yl)phenyl)-2,3,4,5-tetrahydro-1H-pyrido[4,3-b]indole. $^1$H NMR (TFA salt, $CD_3OD$) δ (ppm): 7.7 (d, 1H), 7.6 (m, 2H), 7.37 (s, 1H), 7.23 (m, 2H), 7.19 (d, 1H), 7.03 (d, 1H), 6.8 (s, 1H), 4.6 (m, 2H), 3.7 (m, 2H), 3.3 (m, 1H), 3.1-3.2 (m, 4H), 2.5 (s, 3H), 2.42 (s, 3H).

Example No. 65

Preparation of Compound No. 65

To a de-aerated solution of 5-(3-bromophenyl)-2,8-dimethyl-2,3,4,5-tetrahydro-1H-pyrido[4,3-b]indole (100 mg, 0.281 mmol), 3,5-dimethylisoxazole-4-boronic acid pinacol ester (125 mg, 0.56 mmol) and $K_2CO_3$ (116 mg, 0.84 mmol) in DME-water (2:1) was added $Pd(PPh_3)_4$ (16 mg, 0.014 mmol). The reaction mixture was stirred at 90° C. for 45 min. The reaction mixture was concentrated under reduced pressure. The residue obtained was dissolved in EtOAc (50 mL) and washed with water (20 mL). The organic layer was dried over anhydrous sodium sulfate and concentrated under reduced pressure to obtain crude, which was purified by reverse phase HPLC to yield 4-(3-(2,8-dimethyl-3,4-dihydro-1H-pyrido[4,3-b]indol-5(2H)-yl)phenyl)-3,5-dimethylisoxazole. $^1$H NMR (TFA salt, $CD_3OD$) δ (ppm): 7.7 (t, 1H), 7.41-7.5 (m, 2H), 7.4 (s, 1H), 7.37 (s, 1H), 7.18 (d, 1H), 7.03 (d, 1H), 4.7 (m, 1H), 4.4 (m, 1H), 3.8 (m, 1H), 3.6 (m, 1H), 3.2 (m, 4H), 3.01 (m, 1H), 3.43 (m, 6H), 2.31 (s, 3H).

Example No. 66

Preparation of Compound No. 66

To a de-aerated solution of 5-(3-bromophenyl)-2,8-dimethyl-2,3,4,5-tetrahydro-1H-pyrido[4,3-b]indole (100 mg, 0.281 mmol), 1-methyl-1H-pyrazole-5-boronic acid pinacol ester (116 mg, 0.56 mmol) and $K_2CO_3$ (116 mg, 0.84 mmol) in DME-water (2:1) was added $Pd(PPh_3)_4$ (16 mg, 0.014 mmol). The reaction mixture was stirred at 90° C. for 45 min. The reaction mixture was concentrated under reduced pressure. The residue obtained was dissolved in EtOAc (50 mL) and washed with water (20 mL). The organic layer was dried over anhydrous sodium sulfate and concentrated under reduced pressure to obtain crude, which was purified by reverse phase HPLC to yield 2,8-dimethyl-5-(3-(1-methyl-1H-pyrazol-5-yl)phenyl)-2,3,4,5-tetrahydro-1H-pyrido[4,3-b]indole. $^1$H NMR (TFA salt, $CD_3OD$) δ (ppm): 7.78 (t, 1H), 7.62 (d, 1H), 7.57 (m, 3H), 7.37 (d, 1H), 7.18 (d, 1H), 7.02 (d, 1H), 6.43 (d, 1H), 4.76 (d, 1H), 4.4 (d, 1H), 3.93 (s, 3H), 3.8 (m, 1H), 3.57 (m, 1H), 3.2 (m, 4H), 3.0 (m, 1H), 2.42 (s, 3H).

Example No. 67

Preparation of Compound No. 67

To a de-aerated solution of 5-(3-bromophenyl)-2,8-dimethyl-2,3,4,5-tetrahydro-1H-pyrido[4,3-b]indole (100 mg, 0.281 mmol), 4-isoquinolineboronic acid (96.8 mg, 0.56 mmol) and $K_2CO_3$ (116 mg, 0.84 mmol) in DME-water (2:1) was added $Pd(PPh_3)_4$ (16 mg, 0.014 mmol). The reaction mixture was heated at 90° C. for 45 min. The reaction mixture was concentrated under reduced pressure. The residue obtained was dissolved in EtOAc (50 mL) and washed with water (20 mL). The organic layer was dried over anhydrous sodium sulfate and concentrated under reduced pressure to obtain crude, which was purified by reverse phase HPLC to yield 5-(3-(isoquinolin-4-yl)phenyl)-2,8-dimethyl-2,3,4,5-tetrahydro-1H-pyrido[4,3-b]indole. $^1$H NMR (TFA salt, $CD_3OD$) δ (ppm): 9.5 (s, 1H), 8.57 (s, 1H), 8.4 (d, 1H), 8.09 (d, 1H), 8.0 (dd, 1H), 7.8-7.95 (m, 2H), 7.7 (d, 1H), 7.6 (m, 2H), 7.37 (s, 1H), 7.21 (d, 1H), 7.07 (d, 1H), 4.7 (m, 1H), 4.4 (m, 1H), 3.81 (m, 1H), 3.61 (m, 1H), 3.1-3.3 (m, 5H), 2.4 (s, 3H).

Example No. 68

Preparation of Compound No. 68

To a solution of 5-(4-bromothiophen-3-yl)-2,8-dimethyl-2,3,4,5-tetrahydro-1H-pyrido[4,3-b]indole (100 mg, 0.25 mmol) in DME-water (2:1) was added $K_2CO_3$ (110 mg, 0.77 mmol) and the solution purged with $N_2$. $Pd(PPh_3)_4$ (20 mg, 0.017 mmol) and 6-(4,4,5,5-tetramethyl-1,3,2-dioxaborolan-2-yl)isoquinoline (100 mg, 0.392 mmol) were added to the reaction mixture, which was refluxed under $N_2$ for 45 min. The reaction mixture was cooled to RT and extracted with EtOAc. The combined organic layer was dried over anhydrous sodium sulfate and concentrated under reduced pressure to afford crude material, which was purified by reverse phase HPLC. $^1$H NMR (TFA salt, $CD_3OD$) δ (ppm): 9.07 (s, 1H), 8.27 (d, 1H), 7.97 (d, 1H), 7.8 (d, 1H), 7.64 (d, 1H), 7.42 (d, 1H), 7.35 (s, 1H), 7.26 (d, 1H), 7.19 (s, 1H), 6.9 (d, 1H), 6.8 (d, 1H), 3.6 (m, 2H), 2.63 (m, 2H), 2.5 (m, 1H), 2.4 (m, 6H), 2.2 (m, 1H).

Example No. 69

Preparation of Compound No. 69

To a degassed solution of 5-(3-bromophenyl)-2,8-dimethyl-2,3,4,5-tetrahydro-1H-pyrido[4,3-b]indole (100 mg, 0.281 mmol), 1-methyl-2-pyrroleboronic acid pinacol ester (96.8 mg, 0.56 mmol) and $K_2CO_3$ (116 mg, 0.84 mmol) in DME (4 mL)-water (2 mL) was added $Pd(PPh_3)_4$ (16 mg, 0.014 mmol). The reaction mixture was stirred at 90° C. for 45 min. The reaction mixture concentrated under reduced pressure. The residue was dissolved in EtOAc (50 mL) and washed with water (20 mL). The organic layer was dried over anhydrous sodium sulfate and concentrated under reduced pressure to afford crude material, which was purified by reverse phase HPLC to yield 2,8-dimethyl-5-(3-(1-methyl-1H-pyrrol-2-yl)phenyl)-2,3,4,5-tetrahydro-1H-pyrido[4,3-b]indole. $^1$H NMR (TFA salt, $CD_3OD$) δ (ppm): 7.61 (dd, 1H), 7.57 (d, 1H), 7.4 (s, 1H), 7.37 (m, 2H), 7.17 (d, 1H), 7.07 (d, 1H), 6.8 (d, 1H), 6.21 (d, 1H), 6.1 (dd, 1H), 4.76 (m, 1H), 4.4 (m, 1H), 3.8 (m, 1H), 3.7 (m, 3H), 3.57 (m, 1H), 3.2 (m, 4H), 3.03 (m, 1H), 2.42 (s, 3H).

Example No. 70

Preparation of Compound No. 70

To a de-aerated solution of 5-(3-bromophenyl)-2,8-dimethyl-2,3,4,5-tetrahydro-1H-pyrido[4,3-b]indole (100 mg, 0.281 mmol), 1H-pyrazole-4-boronic acid (62 mg, 0.56 mmol) and $K_2CO_3$ (116 mg, 0.84 mmol) in DME (4 mL)-water (2 mL) was added $Pd(PPh_3)_4$ (16 mg, 0.014 mmol). The reaction mixture was stirred at 90° C. for 45 min. The reaction mixture was concentrated under reduced pressure and residue and dissolved in EtOAc (30 mL). The organic layer was washed with water (20 mL), dried over anhydrous sodium sulfate and concentrated under reduced pressure to afford crude material, which was purified by reverse phase HPLC to yield 5-(3-(1H-pyrazol-4-yl)phenyl)-2,8-dimethyl-2,3,4,5-tetrahydro-1H-pyrido[4,3-b]indole. $^1$H NMR (TFA salt, $CD_3OD$) δ (ppm): 8.03 (s, 2H), 7.7 (d, 1H), 7.58 (m, 2H), 7.3 (s, 1H), 7.22 (d, 1H), 7.1 (d, 1H), 7.0 (d, 1H), 4.8 (d, 1H), 4.4 (d, 1H), 3.8 (m, 1H), 3.57 (m, 1H), 3.2 (m, 1H), 3.17 (s, 3H), 3.0 (m, 1H), 2.42 (s, 3H).

Example No. 71

Preparation of Compound No. 71

To a de-aerated solution of 5-(2-bromophenyl)-2,8-dimethyl-2,3,4,5-tetrahydro-1H-pyrido[4,3-b]indole (100 mg, 0.28 mmol), N-methyl-5-(4,4,5,5-tetramethyl-1,3,2-dioxaborolan-2-yl)picolinamide (148 mg, 0.56 mmol) and K₂CO₃ (115 mg, 0.84 mmol) in DME-water (2:1) was added Pd(PPh₃)₄ (16 mg, 0.014 mmol). The reaction mixture was stirred at 90° C. for 2 h, additional Pd (PPh₃)₄ (16 mg, 0.014 mmol) was added into the reaction mixture and stirring continued at 90° C. for 12 h. The reaction mixture was concentrated under reduced pressure. The residue was dissolved in EtOAc (30 mL) and washed with water (20 mL). The organic layer was dried over anhydrous sodium sulfate and concentrated under reduced pressure to afford crude material, which was purified by reverse phase HPLC to yield 5-(2-(2,8-dimethyl-3,4-dihydro-1H-pyrido[4,3-b]indol-5(2H)-yl)phenyl)-N-methylpicolinamide as an off-white solid. ¹H NMR (TFA salt, CD₃OD) δ (ppm): 8.21 (d, 1H), 7.82 (d, 1H), 7.76 (m, 3H), 7.6 (d, 2H), 7.23 (s, 1H), 6.9 (d, 2H), 4.7 (m, 1H), 4.3 (m, 1H), 3.63 (m, 1H), 3.42 (m, 1H), 2.8-3.1 (m, 7H), 2.6 (m, 1H), 2.4 (s, 3H).

Example No. 72

Preparation of Compound No. 72

To a degassed solution of 5-(2-bromophenyl)-2,8-dimethyl-2,3,4,5-tetrahydro-1H-pyrido[4,3-b]indole (300 mg, 0.84 mmol), N-methyl-4-(4,4,5,5-tetramethyl-1,3,2-dioxaborolan-2-yl)benzamide (328 mg, 1.27 mmol) and K₃PO₄ (445 mg, 0.706 mmol), in DMF (6 mL)-water (0.6 mL) was added dichlorobis (triphenylphosphine) palladium (II) (30 mg, 0.042 mmol). The reaction mixture was heated at 90° C. for 95 min under nitrogen atmosphere. The reaction mixture was diluted with water and extracted with EtOAc. The organic layer was dried over anhydrous sodium sulfate and concentrated under reduced pressure to afford crude material, which was purified by reverse HPLC to yield 2'-(2,8-dimethyl-3,4-dihydro-1H-pyrido[4,3-b]indol-5(2H)-yl)-N-methylbiphenyl-4-carboxamide. ¹H NMR (TFA salt, CD₃OD) δ (ppm): 7.57-7.78 (m, 5H), 7.4 (dd, 1H), 7.25 (s, 1H), 6.92-7.2 (m, 4H), 4.6 (m, 1H), 4.2 (m, 1H), 3.6 (m, 1H), 3.4 (m, 1H), 3.1 (m, 1H), 2.83 (m, 6H), 2.5 (m, 1H), 2.4 (s, 3H).

Example No. 73

Preparation of Compound No. 73

To a solution of 5-(4-bromothiophen-3-yl)-2,8-dimethyl-2,3,4,5-tetrahydro-1H-pyrido[4,3-b]indole (100 mg, 0.276 mmol) in DME-water (2:1) was added K₂CO₃ (110 mg, 0.77 mmol) and the solution purged with N₂. Pd(PPh₃)₄ (20 mg, 0.017 mmol) and N-methyl-5-(4,4,5,5-tetramethyl-1,3,2-dioxaborolan-2-yl)pyridine-2-carboxamide (145 mg, 0.552 mmol) were added to the reaction mixture, which was refluxed under N₂ for 45 min. The reaction mixture was cooled to RT and extracted with EtOAc. The combined organic layer was dried over anhydrous sodium sulfate and concentrated under reduced pressure to afford crude material, which was purified by reverse phase HPLC. ¹H NMR (TFA salt, CD₃OD) δ (ppm): 8.1-8.27 (m, 1H), 8.0 (s, 1H), 7.8 (m, 2H), 7.42 (m, 1H), 7.3 (s, 1H), 6.9-7.0 (m, 2H), 4.76 (d, 1H), 4.38 (d, 1H), 3.7 (m, 1H), 3.5 (m, 1H), 3.0 (m, 4H), 2.88 (s, 3H), 2.93 (m, 1H), 2.4 (s, 3H).

Example No. 74

Preparation of Compound No. 74

A solution of 2,8-dimethyl-2,3,4,5-tetrahydro-1H-pyrido[4,3-b]indole (100 mg, 0.499 mmol), 7-bromoisoquinoline (155 mg, 0.748 mmol), K₃PO₄ (317 mg, 1.495 mmol), CuI (9 mg, 0.047 mmol) and L-Proline (11 mg, 0.095 mmol) in dry DMF (2 mL) was stirred at 150° C. for 16 h. The reaction mixture was diluted with water and extracted with EtOAc. The organic layer was dried over anhydrous sodium sulfate and concentrated under reduced pressure to afford crude material, which was purified by reverse phase HPLC to yield 5-(isoquinolin-7-yl)-2,8-dimethyl-2,3,4,5-tetrahydro-1H-pyrido[4,3-b]indole as a yellow solid. ¹H NMR (TFA salt, CD₃OD) δ (ppm): 9.57 (s, 1H), 8.6 (d, 1H), 8.37 (m, 2H), 8.2 (d, 1H), 8.0 (d, 1H), 7.4 (s, 1H), 7.21 (d, 1H), 7.1 (d, 1H), 4.76 (m, 1H), 4.42 (m, 1H), 3.82 (m, 1H), 3.61 (m, 1H), 3.21 (s, 3H), 3.1 (m, 2H), 2.42 (s, 3H).

Example No. 75

Preparation of Compound No. 75

To a degassed solution of 5-(3-bromophenyl)-2,8-dimethyl-2,3,4,5-tetrahydro-1H-pyrido[4,3-b]indole (101 mg, 0.286 mmol), N-methyl-5-(4,4,5,5-tetramethyl-1,3,2-dioxaborolan-2-yl)picolinamide (150 mg, 0.57 mmol) and K₂CO₃ (236 mg, 1.71 mmol) in DME-water (2:1) was added Pd(PPh₃)₄ (33 mg, 0.028 mmol). The reaction mixture was stirred at 90° C. for 45 min. The reaction mixture concentrated under reduced pressure. The residue was dissolved in EtOAc (50 mL) and washed with water (20 mL). The organic layer was dried over anhydrous sodium sulfate and concentrated under reduced pressure to afford crude material, which was purified by reverse phase HPLC to yield 5-(3-(2,8-dimethyl-3,4-dihydro-1H-pyrido[4,3-b]indol-5(2H)-yl)phenyl)-N-methylpicolinamide. ¹H NMR (TFA salt, CD₃OD) δ (ppm): 8.97 (s, 1H), 8.23 (d, 1H), 8.12 (d, 1H), 7.85 (d, 1H), 7.78 (m, 2H), 7.5 (d, 1H), 7.37 (s, 1H), 7.21 (d, 1H), 7.04 (d, 1H), 4.76 (m, 1H), 4.4 (m, 1H), 3.8 (m, 1H), 3.6 (m, 1H), 3.08-3.21 (m, 5H), 3.0 (s, 3H), 2.4 (s, 3H).

Example No. 76

Preparation of Compound No. 76

To a solution of 5-(4-bromothiophen-3-yl)-2,8-dimethyl-2,3,4,5-tetrahydro-1H-pyrido[4,3-b]indole (100 mg, 0.276 mmol) in DME-water (2:1) was added K₂CO₃ (110 mg, 0.77 mmol) and the solution purged with N₂. Pd(PPh₃)₄ (20 mg, 0.017 mmol) and 4-(methylsulfonyl)phenylboronic acid (110 mg, 0.552 mmol) were added to the reaction mixture, which was refluxed under N₂ for 45 min. The reaction mixture was cooled to RT and extracted with EtOAc. The combined organic layer was dried over anhydrous sodium sulfate and concentrated under reduced pressure to afford crude material, which was purified by reverse phase HPLC. ¹H NMR (TFA salt, CD₃OD) δ (ppm): 7.98 (s, 1H), 7.7 (m, 3H), 7.3 (s, 1H), 7.2 (m, 2H), 6.9 (m, 2H), 4.7 (d, 1H), 4.3 (d, 1H), 3.67 (m, 1H), 3.5 (m, 1H), 2.9-3.1 (m, 8H), 2.4 (s, 3H).

Example No. 77

Preparation of Compound No. 77

To a de-aerated solution of 5-isoquinolin-6-yl-2,8-dimethyl-2,3,4,5-tetrahydro-1H-pyrido[4,3-b]indole (35 mg, 0.10 mmol) in MeOH (5 mL) were added 10% Pd—C (18 mg) and ammonium formate (68 mg, 1.07 mmol). The reaction mixture was refluxed for 15 h and filtered through Celite. The filtrate was concentrated under reduced pressure to afford crude material, which was purified by column chromatography using silica (100:200) and 3% MeOH-DCM to yield 6-(2,8-dimethyl-1,2,3,4-tetrahydro-pyrido[4,3-b]indol-5-yl)-3,4-dihydro-1H-isoquinoline-2-carbaldehyde (10 mg). $^1$H NMR (HCl salt, CD$_3$OD) δ (ppm): 8.2 (s, 1H), 7.41 (s, 1H), 7.3 (s, 1H), 7.25 (m, 2H), 7.1 (d, 1H), 7.03 (d, 1H), 4.7 (d, 1H), 4.4 (d, 1H), 3.8 (m, 3H), 3.57 (m, 3H), 3.17 (s, 3H), 3.0 (m, 4H), 2.4 (s, 3H).

Example No. 78

Preparation of Compound No. 78

To a solution of 3,4-dibromo-N-methylthiophene-2-carboxamide (100 mg, 0.33 mmol) in DMF (2 mL) were added K$_3$PO$_4$ (101 mg, 0.478 mmol), CuI (5 mg, 0.0239 mmol) and L-proline (6 mg, 0.0478 mmol). The solution was purged with nitrogen and 2,3,4,5-tetrahydro-2,8-dimethyl-1H-pyrido[4,3-b]indole (48 mg, 0.239 mmol) was added followed by nitrogen purging for 2 min. The reaction mixture was stirred at 140° C. overnight. Ice water was added into the reaction mixture and extracted the organic part into EtOAc (3×25 mL). The combined organic layer was washed with water (3×10 mL), dried over anhydrous sodium sulfate and concentrated under reduced pressure to afford crude material, which was purified by column chromatography using silica (100:200) and 0-5% MeOH-DCM. $^1$H NMR (TFA salt, CD$_3$OD) δ (ppm): 7.78 (d, 2H), 7.38 (s, 1H), 7.2 (d, 1H), 7.1 (d, 1H), 4.77 (d, 1H), 4.4 (d, 1H), 3.8 (m, 1H), 3.58 (m, 1H), 3.27 (m, 1H), 3.19 (m, 1H), 3.16 (s, 3H), 2.95 (s, 3H), 2.43 (s, 3H).

Example No. 79

Preparation of Compound No. 79

To a solution of [5-(4-bromothiophen-3-yl)-2,8-dimethyl-2,3,4,5-tetrahydro-1H-pyrido[4,3-b]indole (100 mg, 0.25 mmol) in DME (2 mL) were added water (1 mL) and K$_2$CO$_3$ (110 mg, 0.77 mmol) and purged the solution with N$_2$. Pd(PPh$_3$)$_4$ (20 mg, 0.017 mmol) and 5-methylthiophene-2-boronic acid pinacol ester (0.15 mL, 0.628 mmol) were added to the reaction mixture which was refluxed under N$_2$ for 45 min. The reaction mixture was cooled to RT and diluted with EtOAc. The aqueous layer was extracted with EtOAc (3×6 mL) and the combined organic layer dried over sodium sulfate. The solvent was removed under reduced pressure to afford crude material, which was purified by reverse phase HPLC. $^1$H NMR (TFA salt, CD$_3$OD) δ (ppm): 7.78 (d, 1H), 7.62 (d, 1H), 7.37 (s, 1H), 7.0 (d, 1H), 6.91 (d, 1H), 6.42 (d, 1H), 6.22 (d, 1H), 4.73 (m, 1H), 4.40 (m, 1H), 3.63 (m, 1H), 3.41 (m, 1H), 3.11 (s, 3H), 2.85 (m, 2H), 2.91 (s, 3H), 2.32 (s, 3H).

Example No. 80

Preparation of Compound No. 80

To a de-aerated solution of 5-(2-bromophenyl)-2,8-dimethyl-2,3,4,5-tetrahydro-1H-pyrido[4,3-b]indole (100 mg, 0.281 mmol), 6-hydroxypyridine-3-boronic acid pinacol ester (124 mg, 0.562 mmol) and K$_2$CO$_3$ (120 mg, 0.845 mmol) in DME (4 mL)-water (2 mL) was added Pd(PPh$_3$)$_4$ (16 mg, 0.013 mmol). The reaction mixture was stirred at 90° C. for 45 min. The reaction mixture was concentrated under reduced pressure to dryness. The residue was dissolved in EtOAc (50 mL) and washed with water (20 mL). The organic layer was dried over anhydrous sodium sulfate and concentrated under reduced pressure to afford crude material, which was purified by reverse phase HPLC to yield 5-(2-(2,8-dimethyl-3,4-dihydro-1H-pyrido[4,3-b]indol-5(2H)-yl)phenyl)pyridin-2-ol. $^1$H NMR (TFA salt, CD$_3$OD) δ (ppm): 7.59-7.68 (m, 3H), 7.4 (s, 1H), 7.3 (s, 1H), 6.98-7.18 (m, 3H), 6.82 (d, 1H), 6.23 (d, 1H), 4.7 (d, 1H), 4.37 (d, 1H), 3.7 (m, 1H), 3.4 (m, 1H), 3.0 (m, 4H), 2.8 (m, 1H), 2.4 (s, 3H).

Example No. 81

Preparation of Compound No. 81

To a de-aerated solution of 5-(2-bromophenyl)-2,8-dimethyl-2,3,4,5-tetrahydro-1H-pyrido[4,3-b]indole (100 mg, 0.281 mmol), 5-methylthiophene-2-boronic acid pinacol ester (0.13 ml, 0.562 mmol) and K$_2$CO$_3$ (116 mg, 0.845 mmol) in DME (4 mL)-water (2 mL) was added Pd(PPh$_3$)$_4$ (16 mg, 0.013 mmol). The reaction mixture was stirred at 90° C. for 45 min. The reaction mixture was concentrated under reduced pressure to dryness. The residue was dissolved in EtOAc (50 mL) and washed with water (20 mL). The organic layer was dried over anhydrous sodium sulfate and concentrated under reduced pressure to afford crude material, which was purified by reverse phase HPLC to yield 2,8-dimethyl-5-(2-(5-methylthiophen-2-yl)phenyl)-2,3,4,5-tetrahydro-1H-pyrido[4,3-b]indole as a TFA salt. $^1$H NMR (TFA salt, CD$_3$OD) δ (ppm): 7.8 (d, 1H), 7.6 (t, 1H), 7.5 (t, 1H), 7.26-7.37 (m, 2H), 7.0 (d, 1H), 6.8 (d, 1H), 6.43-6.57 (m, 2H), 4.7 (m, 1H), 4.4 (m, 1H), 3.65 (m, 1H), 3.42 (m, 1H), 3.3 (m, 4H), 2.8 (m, 1H), 2.4 (s, 3H), 2.27 (s, 3H).

Example No. 82

Preparation of Compound No. 82

To a de-aerated solution of 5-(2-bromophenyl)-2,8-dimethyl-2,3,4,5-tetrahydro-1H-pyrido[4,3-b]indole (100 mg, 0.281 mmol), 3,5-dimethylisoxazole-4-boronic acid pinacol ester (125 mg, 0.562 mmol) and K$_2$CO$_3$ (116 mg, 0.845 mmol) in DME (4 mL)-water (2 mL) was added Pd(PPh$_3$)$_4$ (16 mg, 0.013 mmol). The reaction mixture was stirred at 90° C. for 45 min. The reaction mixture was concentrated under reduced pressure to dryness. The residue was dissolved in EtOAc (50 mL) and washed with water (20 mL). The organic layer was dried over anhydrous sodium sulfate and concentrated under reduced pressure to afford crude material, which was purified by reverse phase HPLC to yield 4-(2-(2,8-dimethyl-3,4-dihydro-1H-pyrido[4,3-b]indol-5(2H)-yl)phenyl)-3,5-dimethylisoxazole as a TFA salt. $^1$H NMR (TFA salt, CD$_3$OD) δ (ppm): 7.62 (bs, 2H), 7.58 (t, 1H), 7.42 (bs, 1H), 7.22 (s, 1H), 6.9-7.1 (m, 2H), 4.65 (m, 1H), 4.27 (m, 1H), 3.7 (m, 1H), 3.4 (m, 1H), 3.08 (s, 3H), 2.8 (m, 1H), 2.6 (m, 1H), 2.4 (s, 3H), 2.0 (s, 3H), 1.8 (s, 3H).

Example No. 83

Preparation of Compound No. 83

To a de-aerated solution of 5-(2-bromophenyl)-2,8-dimethyl-2,3,4,5-tetrahydro-1H-pyrido[4,3-b]indole (100 mg, 0.281 mmol), 2-acetamidopyridine-5-boronic acid pinacol ester (147 mg, 0.562 mmol) and K$_2$CO$_3$ (116 mg, 0.845 mmol) in DME (4 mL)-water (2 mL) was added Pd(PPh$_3$)$_4$ (16 mg, 0.013 mmol). The reaction mixture was stirred at 90° C. for 45 min. The reaction mixture was concentrated under reduced pressure to dryness. The residue was dissolved in EtOAc (50 mL) and washed with water (20 mL). The organic layer was dried over anhydrous sodium sulfate and concentrated under reduced pressure to afford crude material, which was purified by reverse phase HPLC to yield N-(5-(2-(2,8-dimethyl-3,4-dihydro-1H-pyrido[4,3-b]indol-5(2H)-yl)phenyl)pyridin-2-yl)acetamide as a TFA salt. $^1$H NMR (TFA salt, CD$_3$OD) δ (ppm): 7.8-8.0 (m, 2H), 7.6-7.78 (m, 3H), 7.35-7.48 (m, 2H), 7.27 (s, 1H), 7.0 (d, 1H), 6.9 (d, 1H), 4.63 (d, 1H), 4.3 (d, 1H), 3.64 (m, 1H), 3.42 (m, 1H), 2.92-3.1 (m, 4H), 2.8 (m, 1H), 2.4 (s, 3H), 2.1 (s, 3H).

Example No. 84

Preparation of Compound No. 84

To a de-aerated solution of 5-(2-bromophenyl)-2,8-dimethyl-2,3,4,5-tetrahydro-1H-pyrido[4,3-b]indole (100 mg, 0.281 mmol), 2-fluoropyridine-5-boronic acid pinacol ester (125 mg, 0.562 mmol) and K$_2$CO$_3$ (116 mg, 0.845 mmol) in DME (4 mL)-water (2 mL) was added Pd(PPh$_3$)$_4$ (16 mg, 0.013 mmol). The reaction mixture was stirred at 90° C. for 45 min. The reaction mixture was concentrated under reduced pressure to dryness. The residue was dissolved in EtOAc (50 mL) and washed with water (20 mL). The organic layer was dried over anhydrous sodium sulfate and concentrated under reduced pressure to afford crude material, which was purified by reverse phase HPLC to yield 5-(2-(6-fluoropyridin-3-yl)phenyl)-2,8-dimethyl-2,3,4,5-tetrahydro-1H-pyrido[4,3-b]indole as a TFA salt. $^1$H NMR (TFA salt, CD$_3$OD) δ (ppm): 7.79 (d, 1H), 7.7 (m, 3H), 7.57 (bs, 1H), 7.5 (d, 1H), 7.17 (s, 1H), 7.0 (d, 1H), 6.82 (d, 2H), 4.65 (m, 1H), 4.3 (m, 1H), 3.7 (m, 1H), 3.47 (m, 1H), 3.0 (m, 4H), 2.87 (m, 1H), 2.3 (s, 3H).

Example No. 85

Preparation of Compound No. 85

To a de-aerated solution of 5-(2-bromophenyl)-2,8-dimethyl-2,3,4,5-tetrahydro-1H-pyrido[4,3-b]indole (100 mg, 0.281 mmol), 1-methylindole-5-boronic acid pinacol ester (144 mg, 0.562 mmol) and K$_2$CO$_3$ (116 mg, 0.845 mmol) in DME (4 mL)-water (2 mL) was added Pd(PPh$_3$)$_4$ (16 mg, 0.013 mmol). The reaction mixture was stirred at 90° C. for 45 min. The reaction mixture was concentrated under reduced pressure to dryness. The residue was dissolved in EtOAc (50 mL) and washed with water (20 mL). The organic layer was dried over anhydrous sodium sulfate and concentrated under reduced pressure to afford crude material, which was purified by reverse phase HPLC to yield 2,8-dimethyl-5-(2-(1-methyl-1H-indol-5-yl)phenyl)-2,3,4,5-tetrahydro-1H-pyrido[4,3-b]indole as a TFA salt. $^1$H NMR (TFA salt, CD$_3$OD) δ (ppm): 7.7 (d, 1H), 7.62 (t, 1H), 7.38 (t, 1H), 7.4 (bs, 1H), 7.3 (s, 2H), 7.08-7.17 (m, 4H), 6.8 (bs, 1H), 6.21 (s, 1H), 4.5 (bs, 2H), 4.2 (bs, 2H), 3.7 (s, 3H), 3.4 (m, 1H), 2.68 (bs, 3H), 2.4 (m, 4H).

Example No. 86

Preparation of Compound No. 86

To a de-aerated solution of 5-(2-bromophenyl)-2,8-dimethyl-2,3,4,5-tetrahydro-1H-pyrido[4,3-b]indole (100 mg, 0.281 mmol), 1-methylpyrazole-4-boronic acid pinacol ester (116 mg, 0.562 mmol) and K$_2$CO$_3$ (116 mg, 0.845 mmol) in DME (4 mL)-water (2 mL) was added Pd(PPh$_3$)$_4$ (16 mg, 0.013 mmol). The reaction mixture was stirred at 90° C. for 45 min. The reaction mixture was concentrated under reduced pressure to dryness. The residue was dissolved in EtOAc (50 mL) and washed with water (20 mL). The organic layer was dried over anhydrous sodium sulfate and concentrated under reduced pressure to afford crude material, which was purified by reverse phase HPLC to yield 2,8-dimethyl-5-(2-(1-methyl-1H-pyrazol-4-yl)phenyl)-2,3,4,5-tetrahydro-1H-pyrido[4,3-b]indole as a TFA salt. $^1$H NMR (TFA salt, CD$_3$OD) δ (ppm): 7.8 (d, 1H), 7.6 (t, 1H), 7.42 (t, 1H), 7.27 (m, 2H), 7.1 (s, 1H), 7.0 (d, 1H), 6.62-6.83 (m, 2H), 4.4 (m, 2H), 3.43-3.8 (m, 5H), 2.8-3.1 (m, 5H), 2.4 (s, 3H).

Example No. 87

Preparation of Compound No. 87

To a de-aerated solution of 5-(2-bromophenyl)-2,8-dimethyl-2,3,4,5-tetrahydro-1H-pyrido[4,3-b]indole (100 mg, 0.281 mmol), 4-isoquinolineboronic acid (97 mg, 0.562 mmol) and K$_2$CO$_3$ (116 mg, 0.845 mmol) in DME (4 mL)-water (2 mL) was added Pd(PPh$_3$)$_4$ (16 mg, 0.013 mmol). The reaction mixture was stirred at 90° C. for 45 min. The reaction mixture was concentrated under reduced pressure to dryness. The residue was dissolved in EtOAc (50 mL) and washed with water (20 mL). The organic layer was dried over anhydrous sodium sulfate and concentrated under reduced pressure to afford crude material, which was purified by reverse phase HPLC to yield 5-(2-(isoquinolin-4-yl)phenyl)-2,8-dimethyl-2,3,4,5-tetrahydro-1H-pyrido[4,3-b]indole as a TFA salt. $^1$H NMR (TFA salt, CD$_3$OD) δ (ppm): 9.08-9.2 (m, 1H), 7.85-8.21 (m, 3H), 7.8 (m, 5H), 7.5-7.62 (m, 1H), 6.97-7.2 (m, 2H), 6.41-6.63 (m, 1H), 4.7 (m, 1H), 4.4 (m, 1H), 3.8 (m, 1H), 3.5 (m, 1H), 2.77-3.1 (m, 5H), 2.2 (s, 3H).

Example No. 88

Preparation of Compound No. 88

A solution of 2,8-dimethyl-2,3,4,5-tetrahydro-1H-pyrido[4,3-b]indole (500 mg, 2.50 mmol), 3-bromoquinoline (1.040 g, 5.0 mmol), potassium phosphate tribasic (1.325 g, 6.25 mmol), L-proline (87 mg, 0.756 mmol) and copper iodide (143 mg, 0.752 mmol) in DMF (4 mL) was stirred at 150° C. for 14 h. The reaction mixture was diluted with water and extracted with EtOAc (3×50 mL). The combined organic layer was dried over anhydrous sodium sulfate and concentrated under reduced pressure to afford crude material, which was re-crystallized from MeOH-ether (1:99) to afford 2,8-dimethyl-5-quinolin-3-yl-2,3,4,5-tetrahydro-1H-pyrido[4,3-b]indole (350 mg). $^1$H NMR (Freebase, CDCl$_3$) δ (ppm): 9.0 (s, 1H), 8.2 (d, 1H), 8.17 (s, 1H), 7.82 (t, 1H), 7.68 (t, 1H), 7.61 (t, 1H), 7.25 (s, 1H), 7.18 (d, 1H), 7.0 (d, 1H), 3.7 (s, 2H), 2.8 (m, 4H), 2.58 (s, 3H), 2.4 (s, 3H).

Example No. 89

Preparation of 5-(2-bromophenyl)-2,8-dimethyl-2,3,4,5-tetrahydro-1H-pyrido[4,3-b]indole

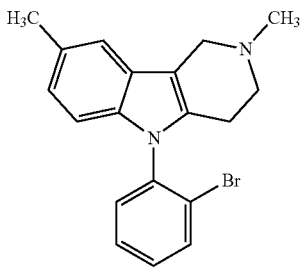

A solution of 2,8-dimethyl-2,3,4,5-tetrahydro-1H-pyrido [4,3-b]indole (2 g, 9.986 mmol), 1,2-dibromobenzene (1.7 mL, 14.97 mmol), $K_3PO_4$ (6.35 g, 29.95 mmol), CuI (189 mg, 0.99 mmol) and L-proline (229 mg, 1.99 mmol) in dry DMF (20 mL) was stirred at 150° C. for 24 h. The reaction mixture was diluted with water (150 mL) and extracted with EtOAc (250 mL). The organic layer was washed with water (10×100 mL), dried over anhydrous sodium sulfate and evaporated to afford crude material, which was purified by column chromatography using neutral alumina and 3% EtOAc-hexane, to yield 5-(2-bromophenyl)-2,8-dimethyl-2,3,4,5-tetrahydro-1H-pyrido[4,3-b]indole.

Example No. 90

Preparation of 5-(3-bromophenyl)-2,8-dimethyl-2,3,4,5-tetrahydro-1H-pyrido[4,3-b]indole

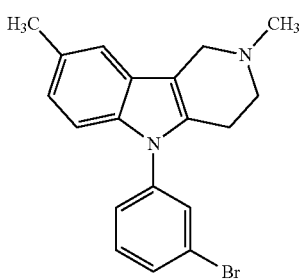

A solution of 2,8-dimethyl-2,3,4,5-tetrahydro-1H-pyrido [4,3-b]indole (1 g, 5 mmol), 1,3-dibromobenzene (1.7 g, 7.2 mmol), $K_3PO_4$ (3.18 g, 15 mmol), CuI (95 mg, 0.5 mmol) and L-proline (115 mg, 1 mmol) in dry DMF (5 mL) was stirred at 150° C. for 16 h. The reaction mixture was diluted with water (100 mL) and extracted with EtOAc (150 mL). The organic layer was washed with water (6×30 mL), dried over anhydrous sodium sulfate and evaporated to afford crude material, which was purified by column chromatography using neutral alumina and 5% EtOAc-hexane to yield 5-(3-bromophenyl)-2,8-dimethyl-2,3,4,5-tetrahydro-1H-pyrido[4,3-b]indole.

Example No. 91

Preparation of 5-(5-bromopyridin-2-yl)-2,8-dimethyl-2,3,4,5-tetrahydro-1H-pyrido[4,3-b]indole

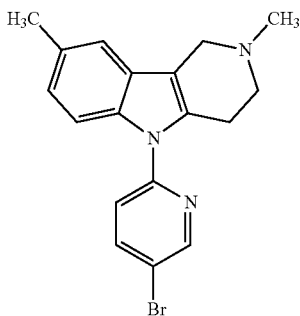

A solution of 2,8-dimethyl-2,3,4,5-tetrahydro-1H-pyrido [4,3-b]indole (1 g, 5 mmol), 2,5-dibromopyridine (1.78 g, 7.5 mmol), $K_3PO_4$ (3.18 g, 15 mmol), CuI (95 mg, 0.5 mmol) and L-proline (115 mg, 1 mmol) in dry DMF (10 mL) was stirred at 150° C. for 16 h. The reaction mixture was diluted with water (100 mL) and extracted with EtOAc (300 mL). The organic layer was washed with water (8×50 mL), dried over anhydrous sodium sulfate and evaporated to afford crude material, which was purified by column chromatography using neutral alumina and 5% EtOAc-hexane, to yield 5-(5-bromopyridin-2-yl)-2,8-dimethyl-2,3,4,5-tetrahydro-1H-pyrido[4,3-b]indole.

Example No. 92

Preparation of Compound No. 100

To a de-aerated solution of 5-(2-bromophenyl)-2,8-dimethyl-2,3,4,5-tetrahydro-1H-pyrido[4,3-b]indole[4,3-b]indole (100 mg, 0.282 mmol), 1-methyl-2-pyrroleboronic acid pinacol ester (87.7 mg, 00.423 mmol) and $K_3PO_4$ (149.5 mg, 0.705 mmol) in DMF (2 mL) and water (0.2 mL) was added dichloro bis-(triphenylphosphine) palladium (II) (9.89 mg, 0.014 mmol). The reaction mixture was stirred at 95° C. for 30 min under nitrogen atmosphere. The reaction mixture was diluted with water and extracted with EtOAc. The organic layer was dried over anhydrous sodium sulfate and concentrated under reduced pressure to afford crude material, which was purified by reverse HPLC to yield 2,8-dimethyl-5-(2-(1-methyl-1H-pyrrol-2-yl)phenyl)-2,3,4,5-tetrahydro-1H-pyrido[4,3-b]indole as the TFA salt. $^1$H NMR ($CD_3OD$, TFA salt) δ (ppm): 7.6 (m, 3H), 7.4 (m, 1H), 7.26 (s, 1H), 7.0 (q, 2H), 6.6 (s, 1H), 5.83 (s, 1H), 5.4 (m, 1H), 4.65 (d, 1H), 4.3 (d, 1H), 3.6 (bs, 1H), 3.38 (m, 4H), 3.07 (bs, 1H), 2.9 (s, 3H), 2.8 (m, 1H), 2.4 (s, 3H).

Example No. 93

Preparation of Compound No. 102

To a de-aerated solution of 5-(2-bromophenyl)-2,8-dimethyl-2,3,4,5-tetrahydro-1H-pyrido[4,3-b]indole (100 mg, 0.281 mmol), 3-methylthiophene-2-boronic acid pinacol ester (125 mg, 0.562 mmol) and $K_2CO_3$ (116 mg, 0.845 mmol) in DME (4 mL) and water (2 mL) was added $Pd(PPh_3)_4$ (16 mg, 0.013 mmol). The reaction mixture was stirred at 90° C. for 45 min. The solvent was removed under reduced pressure. The residue was diluted with water (20 mL) and extracted with EtOAc (50 mL). The organic layer was dried over anhydrous sodium sulfate and concentrated under reduced pressure to afford crude material, which was purified by reverse HPLC to yield 2,8-dimethyl-5-(2-(3-methylthiophen-2-yl)phenyl)-2,3,4,5-tetrahydro-1H-pyrido[4,3-b]indole as the TFA salt. $^1$H NMR ($CD_3OD$, TFA salt) δ (ppm): 7.6 (m, 3H), 7.4 (m, 1H), 7.21 (s, 1H), 7.1 (m, 1H), 6.93 (d, 1H), 6.81 (t, 1H), 6.78 (d, 1H), 4.65 (d, 1H), 4.37 (d, 1H), 3.7 (m, 1H), 3.42 (m, 1H), 3.04 (s, 1H), 2.97 (s, 3H), 2.8 (m, 1H), 2.4 (s, 3H), 2.17 (s, 3H).

Example No. 94

Preparation of Compound No. 103

To a de-aerated solution of 5-(2-bromophenyl)-2,8-dimethyl-2,3,4,5-tetrahydro-1H-pyrido[4,3-b]indole (100 mg, 0.281 mmol), benzo[b]thien-2-ylboronic acid (100 mg, 0.562 mmol) and $K_2CO_3$ (116 mg, 0.845 mmol) in DME (4 mL) and water (2 mL) was added $Pd(PPh_3)_4$ (16 mg, 0.013 mmol). The reaction mixture was stirred at 90° C. for 45 min. The solvent was removed under reduced pressure. The residue was diluted with water (20 mL) and extracted with EtOAc (50 mL). The organic layer was dried over anhydrous sodium sulfate and concentrated under reduced pressure to afford crude material, which was purified by reverse HPLC to yield 5-(2-(benzo[b]thiophen-2-yl)phenyl)-2,8-dimethyl-2,3,4,5-tetrahydro-1H-pyrido[4,3-b]indole as the TFA salt. $^1$H NMR (CD$_3$OD, TFA salt) δ (ppm): 8.0 (d, 1H), 7.65 (t, 2H), 7.6 (d, 2H), 7.35-7.42 (m, 2H), 7.22-7.3 (m, 2H), 7.0 (m, 2H), 6.9 (d, 1H), 4.72 (d, 1H), 4.4 (d, 1H), 3.62 (m, 1H), 3.4 (m, 1H), 3.0 (bs, 1H), 2.87 (s, 3H), 2.7 (m, 1H), 2.4 (s, 3H).

Example No. 95

Preparation of Compound No. 104

To a de-aerated solution of 5-(2-bromophenyl)-2,8-dimethyl-2,3,4,5-tetrahydro-1H-pyrido[4,3-b]indole (100 mg, 0.281 mmol), 1H-pyrazole-4-boronic acid (62 mg, 0.554 mmol) and K$_2$CO$_3$ (116 mg, 0.845 mmol) in DME (4 mL) and water (2 mL) was added Pd(PPh$_3$)$_4$ (16 mg, 0.013 mmol). The reaction mixture was stirred at 90° C. for 45 min. The solvent was removed under reduced pressure. The residue was diluted with water (20 mL) and extracted with EtOAc (50 mL). The organic layer was dried over anhydrous sodium sulfate and concentrated under reduced pressure to afford crude material, which was purified by reverse HPLC to yield 5-(2-(1H-pyrazol-4-yl)phenyl)-2,8-dimethyl-2,3,4,5-tetrahydro-1H-pyrido[4,3-b]indole as the TFA salt. $^1$H NMR (CD$_3$OD, TFA salt) δ (ppm): 7.82 (d, 1H), 7.6 (t, 1H), 7.5 (t, 1H), 7.38 (bs, 2H), 7.0 (m, 3H), 6.83 (bs, 1H), 4.4 (bs, 2H), 3.63 (m, 1H), 3.42 (m, 1H), 3.0 (m, 4H), 2.8 (m, 1H), 2.42 (s, 3H).

Example No. 96

Preparation of Compound No. 105

To a de-aerated solution of 5-(2-bromophenyl)-2,8-dimethyl-2,3,4,5-tetrahydro-1H-pyrido[4,3-b]indole (100 mg, 0.281 mmol), indazole-4-boronic acid hydrochloride (111 mg, 0.559 mmol) and K$_2$CO$_3$ (116 mg, 0.845 mmol) in DME (4 mL) and water (2 mL) was added Pd (PPh$_3$)$_4$ (16 mg, 0.013 mmol). The reaction mixture was stirred at 90° C. for 45 min. The solvent was removed under reduced pressure. The residue was diluted with water (20 mL) and extracted with EtOAc (50 mL). The organic layer was dried over anhydrous sodium sulfate and concentrated under reduced pressure to afford crude material, which was purified by reverse HPLC to yield 5-(2-(1H-indazol-4-yl)phenyl)-2,8-dimethyl-2,3,4,5-tetrahydro-1H-pyrido[4,3-b]indole as the TFA salt. $^1$H NMR (CD$_3$OD, TFA salt) δ (ppm): 7.8-7.97 (m, 2H), 7.7 (m, 2H), 7.42-7.57 (m, 1H), 7.4 (d, 1H), 7.2 (s, 1H), 6.96-7.16 (m, 3H), 6.5-6.7 (m, 1H), 4.57 (m, 1H), 4.2 (m, 1H), 3.5 (m, 1H), 3.0 (m, 2H), 2.8 (m, 1H), 2.7 (s, 3H), 2.4 (s, 3H).

Example No. 97

Preparation of Compound No. 131

To a de-aerated solution of 5-(3-bromophenyl)-2,8-dimethyl-2,3,4,5-tetrahydro-1H-pyrido[4,3-b]indole (100 mg, 0.281 mmol), 4-(methylsulfonyl)phenylboronic acid (111 mg, 0.563 mmol) and K$_2$CO$_3$ (116 mg, 0.845 mmol) in DME (4 mL) and water (2 mL) was added Pd(PPh$_3$)$_4$ (16 mg, 0.013 mmol). The reaction mixture was stirred at 90° C. for 45 min. The solvent was removed under reduced pressure. The residue was diluted with water (20 mL) and extracted with EtOAc 50 mL). The organic layer was dried over anhydrous sodium sulfate and concentrated under reduced pressure to afford crude material, which was purified by reverse HPLC to yield 2,8-dimethyl-5-(4'-(methylsulfonyl)biphenyl-3-yl)-2,3,4,5-tetrahydro-1H-pyrido[4,3-b]indole as the TFA salt. $^1$H NMR (CD$_3$OD, TFA salt) δ (ppm): 8.03 (d, 2H), 7.97 (d, 2H), 7.85 (d, 1H), 7.78 (t, 2H), 7.5 (d, 1H), 7.38 (s, 1H), 7.2 (d, 1H), 7.08 (d, 1H), 4.7 (m, 1H), 4.4 (m, 1H), 3.8 (m, 1H), 3.6 (m, 1H), 3.2 (m, 7H), 3.1 (m, 1H), 2.47 (s, 3H).

Example No. 98

Preparation of Compound No. 132

To a de-aerated solution of 5-(5-bromopyridin-2-yl)-2,8-dimethyl-2,3,4,5-tetrahydro-1H-pyrido[4,3-b]indole (90 mg, 0.253 mmol), pyridin-4-ylboronic acid (111 mg, 0.507 mmol) and K$_2$CO$_3$ (104.6 mg, 0.757 mmol) in DME (4 mL) and water (2 mL) was added Pd(PPh$_3$)$_4$ (14.6 mg, 0.0126 mmol). The reaction mixture was stirred at 90° C. for 45 min. The solvent was removed under reduced pressure. The residue was diluted with water (20 mL) and extracted with EtOAc (50 mL). The organic layer was dried over anhydrous sodium sulfate and concentrated under reduced pressure to afford crude material, which was purified by reverse HPLC to yield 5-(3,4'-bipyridin-6-yl)-2,8-dimethyl-2,3,4,5-tetrahydro-1H-pyrido[4,3-b]indole as the TFA salt. $^1$H NMR (CD$_3$OD, TFA salt) δ (ppm): 9.2 (s, 1H), 8.9 (bs, 2H), 8.6 (d, 1H), 8.43 (d, 2H), 7.9 (d, 1H), 7.62 (d, 1H), 7.38 (s, 1H), 7.18 (d, 1H), 4.73 (d, 1H), 4.4 (d, 1H), 3.85 (m, 1H), 3.6 (m, 2H), 3.4 (m, 1H), 3.18 (s, 3H), 2.43 (s, 3H).

Example No. 99

Preparation of Compound No. 133

To a de-aerated solution of 5-(5-bromopyridin-2-yl)-2,8-dimethyl-2,3,4,5-tetrahydro-1H-pyrido[4,3-b]indole (100 mg, 0.280 mmol), pyridin-3-ylboronic acid (68 mg, 0.553 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse HPLC to yield 5-(3,3'-bipyridin-6-yl)-2,8-dimethyl-2,3,4,5-tetrahydro-1H-pyrido[4,3-b]indole as the TFA salt. $^1$H NMR (CD$_3$OD, TFA salt) δ (ppm): 9.02 (s, 1H), 8.98 (s, 1H), 8.7 (s, 1H), 8.4 (d, 2H), 7.8 (d, 1H), 7.77 (m, 1H), 7.57 (d, 1H), 7.27 (s, 1H), 7.18 (d, 1H), 4.7 (d, 1H), 4.4 (d, 1H), 3.8 (bs, 1H), 3.44-3.6 (m, 3H), 3.18 (s, 3H), 2.46 (s, 3H).

Example No. 100

Preparation of Compound No. 134

To a de-aerated solution of 5-(5-bromopyridin-2-yl)-2,8-dimethyl-2,3,4,5-tetrahydro-1H-pyrido[4,3-b]indole (100 mg, 0.280 mmol), 1-methylpyrazole-4-boronic acid pinacol ester (116 mg, 0.557 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse HPLC to 2,8-dimethyl-5-(5-(1-methyl-1H-pyrazol-4-yl)pyridin-2-yl)-2,3,4,5-tetrahydro-1H-pyrido[4,3-b]indole as the TFA salt. $^1$H NMR (CD$_3$OD, TFA salt) δ (ppm): 8.8 (s, 1H), 8.2 (d, 1H), 8.18 (s, 1H), 7.98 (s, 1H), 7.6 (d, 1H), 7.42 (d, 1H), 7.37 (s, 1H), 7.1 (d, 1H), 4.7 (m, 1H), 4.4 (d, 1H), 4.0 (s, 3H), 3.8 (bs, 1H), 3.6 (bs, 1H), 3.4 (m, 2H), 3.18 (s, 3H), 2.42 (s, 3H).

Example No. 101

Preparation of Compound No. 135

To a de-aerated solution of 5-(5-bromopyridin-2-yl)-2,8-dimethyl-2,3,4,5-tetrahydro-1H-pyrido[4,3-b]indole (100 mg, 0.280 mmol), 4-isoquinolineboronic acid (96 mg, 0.554 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse HPLC to yield 5-(5-(isoquinolin-4-yl)pyridin-2-yl)-2,8-dimethyl-2,3,4,5-tetrahydro-1H-pyrido[4,3-b]indole as the TFA salt. $^1$H NMR (CD$_3$OD, TFA salt) δ (ppm): 9.6 (s, 1H), 8.8 (s, 1H), 8.6 (s, 1H), 8.46 (d, 1H), 8.3 (d, 1H), 8.1 (m, 2H), 7.82 (d, 1H), 7.9 (d, 1H), 7.62 (d, 1H), 7.4 (s, 1H), 7.2 (d, 1H), 4.7 (m, 1H), 4.4 (bs, 1H), 3.8 (bs, 1H), 3.4-3.66 (m, 3H), 3.18 (s, 3H), 2.46 (s, 3H).

Example No. 102

Preparation of Compound No. 136

To a de-aerated solution of 5-(5-bromopyridin-2-yl)-2,8-dimethyl-2,3,4,5-tetrahydro-1H-pyrido[4,3-b]indole (100 mg, 0.280 mmol), 1-methylindole-5-boronic acid pinacol ester (143 mg, 0.556 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse HPLC to yield 2,8-dimethyl-5-(5-(1-methyl-1H-indol-5-yl)pyridin-2-yl)-2,3,4,5-tetrahydro-1H-pyrido[4,3-b]indole as the TFA salt. $^1$H NMR (CD$_3$OD, TFA salt) δ (ppm): 8.88 (s, 1H), 8.3 (d, 1H), 7.94 (s, 1H), 7.64 (d, 1H), 7.57 (s, 2H), 7.51 (d, 1H), 7.38 (s, 1H), 7.24 (d, 1H), 7.16 (d, 1H), 6.58 (d, 1H), 4.7 (m, 1H), 4.4 (bs, 1H), 3.84 (s, 3H), 3.8 (m, 1H), 3.4-3.62 (m, 3H), 3.18 (s, 3H), 2.42 (s, 3H).

Example No. 103

Preparation of Compound No. 137

To a de-aerated solution of 5-(5-bromopyridin-2-yl)-2,8-dimethyl-2,3,4,5-tetrahydro-1H-pyrido[4,3-b]indole (100 mg, 0.280 mmol), 3,5-dimethylisoxazole-4-boronic acid pinacol ester (124 mg, 0.556 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse HPLC to yield 4-(6-(2,8-dimethyl-3,4-dihydro-1H-pyrido[4,3-b]indol-5(2H)-yl)pyridin-3-yl)-3,5-dimethylisoxazole as the TFA salt. $^1$H NMR (CD$_3$OD, TFA salt) δ (ppm): 8.6 (s, 1H), 8.06 (d, 1H), 7.78 (d, 1H), 7.57 (d, 1H), 7.38 (s, 1H), 7.17 (d, 1H), 4.7 (m, 1H), 4.4 (d, 1H), 3.82 (bs, 1H), 3.46-3.62 (m, 2H), 3.2 (s, 3H), 3.17 (m, 1H), 2.51 (s, 3H), 2.47 (s, 3H), 2.36 (s, 3H).

Example No. 104

Preparation of Compound No. 138

To a de-aerated solution of 5-(5-bromopyridin-2-yl)-2,8-dimethyl-2,3,4,5-tetrahydro-1H-pyrido[4,3-b]indole (100 mg, 0.280 mmol), 2-(dimethylamino)pyrimidine-5-boronic acid pinacol ester (139 mg, 0.557 mmol) and K$_2$CO$_3$ (116 mg, 0.839 mmol) in mixture of DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate and evaporated to afford crude material, which was purified by reverse HPLC to yield 5-(6-(2,8-dimethyl-3,4-dihydro-1H-pyrido[4,3-b]indol-5(2H)-yl)pyridin-3-yl)-N,N-dimethylpyrimidin-2-amine as the TFA Salt. $^1$H NMR (CD$_3$OD, TFA salt) δ (ppm): 8.8 (s, 1H), 8.71 (s, 2H), 8.24 (d, 1H), 7.68 (d, 1H), 7.48 (d, 1H), 7.37 (s, 1H), 7.17 (d, 1H), 4.7 (d, 1H), 4.3 (d, 1H), 3.81 (bs, 1H), 3.4-3.6 (m, 3H), 3.3 (s, 6H), 3.18 (s, 3H), 2.42 (s, 3H).

Example No. 105

Preparation of Compound No. 139

To a de-aerated solution of 5-(5-bromopyridin-2-yl)-2,8-dimethyl-2,3,4,5-tetrahydro-1H-pyrido[4,3-b]indole (100 mg, 0.280 mmol), 2-acetamidopyridine-5-boronic acid pinacol ester (146 mg, 0.557 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse HPLC to yield N-(6'-(2,8-dimethyl-3,4-dihydro-1H-pyrido[4,3-b]indol-5(2H)-yl)-3,3'-bipyridin-6-yl)acetamide as the TFA salt. $^1$H NMR (CD$_3$OD, TFA salt) δ (ppm): 8.9 (s, 1H), 8.63 (s, 1H), 8.3 (d, 1H), 8.22 (d, 1H), 8.18 (d, 1H), 7.76 (d, 1H), 7.5 (d, 1H), 7.38 (s, 1H), 7.13 (d, 1H), 4.7 (d, 1H), 4.4 (d, 1H), 3.82 (bs, 1H), 3.42-3.6 (m, 3H), 3.18 (s, 3H), 2.42 (s, 3H), 2.2 (s, 3H).

Example No. 106

Preparation of Compound No. 140

To a de-aerated solution of 5-(5-bromopyridin-2-yl)-2,8-dimethyl-2,3,4,5-tetrahydro-1H-pyrido[4,3-b]indole (100 mg, 0.280 mmol), 4-fluorophenylboronic acid (146 mg, 0.557 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse HPLC to yield 5-(5-(4-fluorophenyl)pyridin-2-yl)-2,8-dimethyl-2,3,4,5-tetrahydro-1H-pyrido[4,3-b]indole as the TFA salt. $^1$H NMR (CD$_3$OD, TFA salt) δ (ppm): 8.82 (s, 1H), 8.3 (d, 1H), 7.79 (t, 2H), 7.7 (d, 1H), 7.5 (d, 1H), 7.37 (s, 1H), 7.3 (t, 2H), 7.17 (d, 1H), 4.7 (m, 1H), 4.4 (bs, 1H), 3.8 (bs, 1H), 3.4-3.6 (m, 3H), 3.18 (s, 3H), 2.42 (s, 3H).

Example No. 107

Preparation of Compound No. 141

To a de-aerated solution of 5-(5-bromopyridin-2-yl)-2,8-dimethyl-2,3,4,5-tetrahydro-1H-pyrido[4,3-b]indole (100 mg, 0.280 mmol), naphthalene-1-boronic acid (96 mg, 0.558 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse HPLC to yield 2,8-dimethyl-5-(5-(naphthalen-1-yl)pyridin-2-yl)-2,3,4,5-tetrahydro-1H-pyrido[4,3-b]indole as the TFA salt. $^1$H NMR (CD$_3$OD, TFA salt) δ (ppm): 8.7 (s, 1H), 8.2 (d, 1H), 8.0 (d, 2H), 7.88 (d, 1H), 7.8 (d, 1H), 7.5-7.62 (m, 5H), 7.38 (s, 1H), 7.18 (d, 1H), 4.7 (m, 1H), 4.4 (s, 1H), 3.9 (bs, 1H), 3.3 (m, 3H), 3.18 (s, 3H), 2.47 (s, 3H).

Example No. 108

Preparation of Compound No. 142

To a de-aerated solution of 5-(5-bromopyridin-2-yl)-2,8-dimethyl-2,3,4,5-tetrahydro-1H-pyrido[4,3-b]indole (100 mg, 0.280 mmol), 2-fluoropyridine-5-boronic acid pinacol ester (124 mg, 0.556 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material which, was purified by reverse HPLC to yield 5-(6'-fluoro-3,3'-bipyridin-6-yl)-2,8-dimethyl-2,3,4,5-tetrahydro-1H-pyrido[4,3-b]indole as the TFA salt. $^1$H NMR (CD$_3$OD, TFA salt) δ (ppm): 8.9 (s, 1H), 8.6 (s, 1H), 8.3 (m, 2H), 7.77 (d, 1H), 7.56 (d, 1H), 7.28 (s, 1H), 7.25 (d, 1H), 7.17 (d, 1H), 4.7 (m, 1H), 4.4 (bs, 1H), 3.82 (bs, 1H), 3.46-3.62 (m, 3H), 3.18 (s, 3H), 2.44 (s, 3H).

Example No. 109

Preparation of Compound No. 143

To a de-aerated solution of 5-(5-bromopyridin-2-yl)-2,8-dimethyl-2,3,4,5-tetrahydro-1H-pyrido[4,3-b]indole (100 mg, 0.280 mmol), N-methyl-3-(4,4,5,5-tetramethyl-1,3,2-dioxaborolan-2-yl)benzamide (146 mg, 0.559 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse HPLC to yield 3-(6-(2,8-dimethyl-3,4-dihydro-1H-pyrido[4,3-b]indol-5(2H)-yl)pyridin-3-yl)-N-methylbenzamide as the TFA salt $^1$H NMR (CD$_3$OD, TFA salt) δ (ppm): 8.96 (s, 1H), 8.37 (d, 1H), 8.2 (s, 1H), 7.9 (m, 2H), 7.76 (d, 1H), 7.64 (t, 1H), 7.56 (d, 1H), 7.38 (s, 1H), 7.18 (d, 1H), 4.7 (bs, 1H), 4.4 (bs, 1H), 3.82 (bs, 1H), 3.45-3.62 (m, 3H), 3.2 (s, 3H), 3.0 (s, 3H), 2.45 (s, 3H).

Example No. 110

Preparation of Compound No. 144

To a de-aerated solution of 5-(5-bromopyridin-2-yl)-2,8-dimethyl-2,3,4,5-tetrahydro-1H-pyrido[4,3-b]indole (100 mg, 0.280 mmol), 4-methylthiophene-2-boronic acid pinacol ester (125 mg, 0.557 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse phase HPLC to yield 2,8-dimethyl-5-(5-(4-methylthiophen-2-yl)pyridin-2-yl)-2,3,4,5-tetrahydro-1H-pyrido[4,3-b]indole as the TFA salt. $^1$H NMR (CD$_3$OD, TFA salt) δ (ppm): 8.82 (s, 1H), 8.21 (d, 1H), 7.61 (d, 1H), 7.48 (d, 1H), 7.4 (s, 1H), 7.38 (s, 1H), 7.13 (m, 2H), 4.7 (bs, 1H), 4.4 (bs, 1H), 3.8 (bs, 1H), 3.56 (bs, 1H), 4.4 (m, 2H), 3.18 (s, 3H), 2.42 (s, 3H), 2.3 (s, 3H).

Example No. 111

Preparation of Compound No. 145

To a de-aerated solution of 5-(5-bromopyridin-2-yl)-2,8-dimethyl-2,3,4,5-tetrahydro-1H-pyrido[4,3-b]indole (100 mg, 0.280 mmol), 4-(4,4,5,5-tetramethyl-1,3,2-dioxaborolan-2-yl)benzenesulfonamide (158 mg, 0.558 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL), The organic layer was dried over anhydrous sodium sulfate, concentrated under reduced pressure to afford crude material, which was purified by reverse phase HPLC to yield 4-(6-(2,8-dimethyl-3,4-dihydro-1H-pyrido[4,3-b]indol-5(2H)-yl)pyridin-3-yl)benzenesulfonamide as the TFA salt. $^1$H NMR (CD$_3$OD, TFA salt) δ (ppm): 8.96 (s, 1H), 8.38 (d, 1H), 8.08 (d, 2H), 7.95 (d, 2H), 7.77 (d, 1H), 7.57 (d, 1H), 7.37 (s, 1H), 7.18 (d, 1H), 4.7 (bs, 1H), 4.4 (bs, 1H), 3.8 (bs, 1H), 3.5 (m, 3H), 3.2 (s, 3H), 2.42 (s, 3H).

Example No. 112

Preparation of Compound No. 146

To a de-aerated solution of 5-(5-bromopyridin-2-yl)-2,8-dimethyl-2,3,4,5-tetrahydro-1H-pyrido[4,3-b]indole (100 mg, 0.280 mmol), 1-methyl-1H-pyrazole-5-boronic acid pinacol ester (116 mg, 0.557 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse phase HPLC to yield 2,8-dimethyl-5-(5-(1-methyl-1H-pyrazol-5-yl)pyridin-2-yl)-2,3,4,5-tetrahydro-1H-pyrido[4,3-b]indole as the TFA salt. $^1$H NMR (CD$_3$OD, TFA salt) δ (ppm): 8.77 (s, 1H), 8.18 (d, 1H), 7.8 (d, 1H), 7.6 (d, 1H), 7.58 (s, 1H), 7.36 (s, 1H), 7.16 (d, 1H), 6.58 (s, 1H), 4.7 (bs, 1H), 4.4 (bs, 1H), 3.98 (s, 3H), 3.8 (bs, 1H), 3.5 (m, 3H), 3.2 (s, 3H), 2.45 (s, 3H).

Example No. 113

Preparation of Compound No. 147

To a de-aerated solution of 5-(5-bromopyridin-2-yl)-2,8-dimethyl-2,3,4,5-tetrahydro-1H-pyrido[4,3-b]indole (100 mg, 0.280 mmol), indazole-4-boronic acid hydrochloride (111 mg, 0.559 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse phase HPLC to yield 5-(5-(1H-indazol-4-yl)pyridin-2-yl)-2,8-dimethyl-2,3,4,5-tetrahydro-1H-pyrido[4,3-b]indole as the TFA salt. $^1$H NMR (CD$_3$OD, TFA salt) δ (ppm): 8.97 (s, 1H), 8.4 (d, 1H), 8.2 (s, 1H), 7.8 (d, 1H), 7.62 (d, 1H), 7.5 (m, 2H), 7.4 (s, 1H), 7.38 (d, 1H), 7.17 (d, 1H), 3.6-4.0 (m, 4H), 3.2 (s, 3H), 3.18 (m, 2H), 2.41 (s, 3H).

Example No. 114

Preparation of Compound No. 148

To a de-aerated solution of 5-(5-bromopyridin-2-yl)-2,8-dimethyl-2,3,4,5-tetrahydro-1H-pyrido[4,3-b]indole (100 mg, 0.280 mmol), 3-methylthiophene-2-boronic acid pinacol ester (125 mg, 0.557 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h. The reaction mixture was concentrated under reduced pressure. The residue was diluted with water (30 mL) and extracted with EtOAc (50 mL). The organic layer was dried over anhydrous sodium sulfate, concentrated under reduced pressure to afford crude material, which was purified by reverse phase HPLC to yield 2,8-dimethyl-5-(5-(3-methylthiophen-2-yl)pyridin-2-yl)-2,3,4,5-tetrahydro-1H-pyrido[4,3-b]indole as the TFA salt. $^1$H NMR (CD$_3$OD, TFA salt) δ (ppm): 8.7 (s, 1H), 8.14 (d, 1H), 7.7 (d, 1H), 7.5 (d, 1H), 7.42 (d, 1H), 7.37 (s, 1H), 7.1 (d, 1H), 7.03 (d, 1H), 4.7 (bs, 1H), 4.4 (bs, 1H), 3.8 (bs, 1H), 3.5 (m, 3H), 3.18 (s, 3H), 2.42 (s, 3H), 2.38 (s, 3H).

Example No. 115

Preparation of Compound No. 149

To a de-aerated solution of 5-(4-bromothiophen-3-yl)-2,6,8-trimethyl-2,3,4,5-tetrahydro-1H-pyrido[4,3-b]indole (250 mg, 0.668 mmol), pyridine-4-boronic acid (165 mg, 1.33 mmol) and K$_2$CO$_3$ (277 mg, 2.0 mmol) in DME-water (2:1) was added Pd(PPh$_3$)$_4$ (46 mg, 0.04 mmol). The reaction mixture was stirred at 90° C. for 45 min and concentrated under reduced pressure. The residue was dissolved in EtOAc (50 mL) and washed with water (20 mL). The organic layer was dried over anhydrous sodium sulfate, concentrated and the residue purified by reverse phase HPLC. $^1$H NMR (CD$_3$OD, TFA salt) δ (ppm): 8.8 (d, 2H), 8.6 (s, 1H), 8.38 (d, 2H), 8.1 (s, 1H), 6.8 (s, 1H), 6.2 (s, 1H), 3.82 (bs, 1H), 3.7 (m, 1H), 3.4 (m, 3H), 3.07 (s, 3H), 2.43 (s, 3H), 2.22 (m, 1H), 2.2 (s, 3H).

Example No. 116

Preparation of Compound No. 150

To a de-aerated solution of 5-(4-bromothiophen-3-yl)-2,6,8-trimethyl-2,3,4,5-tetrahydro-1H-pyrido[4,3-b]indole (100 mg, 0.276 mmol), 1-methyl-1H-pyrazole-5-boronic acid pinacol ester (86 mg, 0.413 mmol) and K$_2$CO$_3$ (110 mg, 0.8 mmol) in DME-water (2:1) was added Pd(PPh$_3$)$_4$ (20 mg, 0.016 mmol). The reaction mixture was stirred at 90° C. for 45 min and concentrated under reduced pressure. The residue was dissolved in EtOAc (50 mL) and washed with water (20 mL). The organic layer was dried over anhydrous sodium sulfate, concentrated and residue purified by reverse phase HPLC. $^1$H NMR (CD$_3$OD, TFA salt) δ (ppm): 7.96 (s, 1H), 7.79 (d, 1H), 7.08 (s, 1H), 7.01 (s, 1H), 7.0 (m, 2H), 5.6 (m, 1H), 4.7 (d, 1H), 4.36 (m, 1H), 3.7 (m, 4H), 3.5 (m, 1H), 3.05 (m, 5H), 2.4 (s, 3H).

Example No. 117

Preparation of Compound No. 151

To a de-aerated solution of 5-(4-bromothiophen-3-yl)-2,8-dimethyl-2,3,4,5-tetrahydro-1H-pyrido[4,3-b]indole (100 mg, 0.25 mmol), benzo[b]thiophen-2-ylboronic acid (100 mg, 0.367 mmol) and K$_2$CO$_3$ (110 mg, 0.77 mmol) in DME-water (2:1) was added Pd(PPh$_3$)$_4$ (20 mg, 0.017 mmol). The reaction mixture was stirred at 90° C. for 45 min and concentrated under reduced pressure. The residue was dissolved in EtOAc (50 mL) and washed with water (20 mL). The organic layer was dried over anhydrous sodium sulfate, concentrated and residue purified by reverse phase HPLC. $^1$H NMR (CD$_3$OD, TFA salt) δ (ppm): 7.99 (s, 1H), 7.65 (s, 1H), 7.6 (d, 1H), 7.5 (d, 1H), 7.37 (s, 1H), 7.2 (m, 2H), 7.0 (d, 1H), 6.95 (d, 1H), 6.76 (d, 1H), 4.7 (m, 1H), 4.4 (m, 1H), 3.68 (bs, 1H), 3.42 (bs, 1H), 3.0 (m, 5H), 2.4 (s, 3H).

Example No. 118

Preparation of Compound No. 152

To a solution of 4-bromo-N,N-dimethylthiophene-3-carboxamide (100 mg, 0.434 mmol) in DMF (1 mL) were added K$_3$PO$_4$ (5.31 mg, 2 mmol), CuI (5.9 mg, 0.031 mmol), L-proline (7.13 mg, 0.062 mmol) and 2,3,4,5-tetrahydro-2,8-dimethyl-1H-pyrido[4,3-b]indole (62 mg, 0.31 mmol) and stirred at 140° C. overnight. Ice water was added into the reaction mixture and extracted with EtOAc (2×25 mL). The organic layer was washed with water (2×10 mL), dried over anhydrous sodium sulfate, concentrated under reduced pressure, and the residue purified by silica column chromatography (0-3% MeOH-DCM) followed by reverse phase HPLC. $^1$H NMR (CD$_3$OD, TFA salt) δ (ppm): 7.83 (d, 1H), 7.68 (d, 1H), 7.3 (s, 1H), 7.0 (d, 1H), 6.98 (d, 1H), 4.7 (d, 1H), 4.38 (d, 1H), 3.8 (m, 1H), 3.57 (m, 1H), 3.02-3.17 (m, 5H), 2.85 (d, 3H), 2.7 (d, 3H), 2.4 (s, 3H).

Example No. 119

Preparation of Compound No. 153

To a de-aerated solution of 2,8-dimethyl-5-quinolin-3-yl-2,3,4,5-tetrahydro-1H-pyrido[4,3-b]indole (50 mg, 0.152 mmol) in methanol (5 mL) were added palladium hydroxide (50 mg, 100% w/w) and ammonium formate (48 mg, 0.761 mmol). The reaction mixture was stirred at 100° C. for 2 h then cooled to RT. The mixture was filtered through Celite and washed with MeOH (5 mL). The filtrate was concentrated under reduced pressure and the residue purified by reverse phase HPLC to yield 2,8-dimethyl-5-(1,2,3,4-tetrahydro-quinolin-3-yl)-2,3,4,5-tetrahydro-1H-pyrido[4,3-b]indole as the TFA salt (15 mg). $^1$H NMR (CD$_3$OD, TFA salt) δ (ppm): 8.62 (s, 1H), 8.19 (s, 1H), 7.38 (s, 1H), 7.2 (d, 1H), 7.1 (d, 1H), 4.76 (m, 1H), 4.4 (bs, 1H), 3.8 (bs, 1H), 3.56 (bs, 1H), 3.28 (m, 6H), 3.01 (t, 3H), 2.43 (s, 3H), 2.01 (t, 2H), 1.95 (t, 2H).

Example No. 120

Preparation of Compound No. 154

To a degassed solution of 5-(4-bromothiophen-3-yl)-2,3,4,5-tetrahydro-2,8-dimethyl-1H-pyrido[4,3-b]indole (50 mg, 0.138 mmol) and K$_2$CO$_3$ (8 mg, 0.07 mmol) in DME-water (1:1) were added Pd(PPh$_3$)$_4$ (19 mg, 0.138 mmol) and N-methyl-3-(4,4,5,5-tetramethyl-1,3,2-dioxaborolan-2-yl)benzamide (109 mg, 0.417 mmol). The reaction mixture was stirred at 85° C. for 1 h then diluted with EtOAc (20 mL). The organic layer was washed with water (2×5 mL), dried over anhydrous sodium sulfate, concentrated under reduced pressure, and the residue was purified by silica gel column chromatography (0-1.5% MeOH-DCM) followed by reverse phase HPLC purification. $^1$H NMR (CD$_3$OD, HCl salt) δ (ppm): 7.82 (dd, 1H), 7.77 (dd, 1H), 7.58 (d, 1H), 7.4 (d, 1H), 7.28 (d, 1H), 7.2 (m, 1H), 7.18 (d, 1H), 7.0 (m, 2H), 4.7 (d, 1H), 4.37 (d, 1H), 3.7 (m, 1H), 3.5 (m, 1H), 3.1 (s, 2H), 2.94 (s, 3H), 2.82 (s, 3H), 2.41 (d, 3H).

Example No. 121

Preparation of Compound No. 155

To a degassed solution of 5-(4-bromothiophen-3-yl)-2,3,4,5-tetrahydro-2,8-dimethyl-1H-pyrido[4,3-b]indole (50 mg, 0.138 mmol) and K$_2$CO$_3$ (8 mg, 0.07 mmol) in DME:water (2:1) were added Pd(PPh$_3$)$_4$ (19 mg, 0.138 mmol) and N-methyl-4-(4,4,5,5-tetramethyl-1,3,2-dioxaborolan-2-yl)benzamide (109 mg, 0.417 mmol). The reaction mixture was stirred at 85° C. for 1 h, and diluted with EtOAc (20 mL). The organic layer was washed with water (2×5 mL), dried over anhydrous sodium sulfate, concentrated under reduced pressure, and the residue was purified by silica gel column chromatography (0-2% MeOH-DCM) followed by reverse phase HPLC purification. $^1$H NMR (CD$_3$OD, HCl salt) δ (ppm): 7.83 (dd, 1H), 7.7 (dd, 1H), 7.58 (d, 2H), 7.3 (d, 1H), 7.07 (d, 1H), 7.0 (d, 3H), 4.7 (d, 1H), 4.38 (d, 1H), 3.62 (m, 1H), 3.52 (m, 1H), 3.03 (s, 2H), 2.9 (s, 3H), 2.83 (s, 3H), 2.4 (s, 3H).

Example No. 122

Preparation of Compound No. 156

To a de-aerated solution of 5-(5-bromopyridin-2-yl)-2,8-dimethyl-2,3,4,5-tetrahydro-1H-pyrido[4,3-b]indole (100 mg, 0.280 mmol), 2-methyl-5-(4,4,5,5-tetramethyl-1,3,2-dioxaborolan-2-yl)pyridine (122 mg, 0.557 mmol) and K$_2$CO$_3$ (116 mg, 0.839 mmol) in DME (4 mL) and water (2 mL) was added Pd(PPh$_3$)$_4$ (16 mg, 0.013 mmol). The reaction mixture was stirred at 90° C. for 2 h and concentrated under reduced pressure. The residue was diluted with water (30 mL) and extracted with EtOAc (50 mL). The organic layer was dried over anhydrous sodium sulfate, concentrated under reduced pressure, and the residue purified by reverse phase HPLC to yield 2,8-dimethyl-5-(6'-methyl-3,3'-bipyridin-6-yl)-2,3,4,5-tetrahydro-1H-pyrido[4,3-b]indole as the TFA salt. $^1$H NMR (CD$_3$OD, TFA salt) δ (ppm): 8.9 (s, 1H), 8.82 (s, 1H), 8.37 (d, 1H), 8.22 (d, 1H), 7.78 (d, 1H), 7.58 (d, 1H), 7.5 (d, 1H), 7.38 (s, 1H), 7.17 (d, 1H), 4.5 (bs, 2H), 3.7 (bs, 2H), 3.4 (bs, 2H), 3.17 (s, 3H), 2.68 (s, 3H), 2.42 (s, 3H).

Example No. 123

Preparation of Compound No. 157

A solution of 2,8-dimethyl-2,3,4,5-tetrahydro-1H-pyrido[4,3-b]indole (300 mg, 1.50 mmol), 6-bromo-2-methylquinoline (600 mg, 2.7 mmol), potassium phosphate tribasic (954 mg, 4.50 mmol), L-proline (87 mg, 0.75 mmol) and copper iodide (143 mg, 0.75 mmol) in DMF (3 mL) was stirred at 100° C. for 16 h. The reaction mixture was diluted with water and extracted with EtOAc (3×50 mL). The organic layer was washed with water (5×50 mL), dried over anhydrous sodium sulfate, concentrated and the residue obtained was purified by flash chromatography using silica gel (100-200 mesh) and 4% MeOH-DCM to yield of 2,8-dimethyl-5-(2-methyl-quinolin-6-yl)-2,3,4,5-tetrahydro-1H-pyrido[4,3-b]indole (130 mg). $^1$H NMR (CD$_3$OD, di-HCl salt) δ (ppm): 9.1 (d, 1H), 8.4 (m, 2H), 8.23 (d, 1H), 8.03 (d, 1H), 7.4 (s, 1H), 7.26 (d, 1H), 7.1 (d, 1H), 4.7 (d, 1H), 4.42 (d, 1H), 3.82 (m, 1H), 3.6 (m, 1H), 3.37 (m, 1H), 3.2 (s, 3H), 3.1 (m, 1H), 3.08 (s, 3H), 2.45 (s, 3H).

Example No. 124

Preparation of Compound No. 158

To a de-aerated solution of 5-(3-bromophenyl)-2,8-dimethyl-2,3,4,5-tetrahydro-1H-pyrido[4,3-b]indole (300 mg, 0.845 mmol), 4-(4,4,5,5-tetramethyl-[1,3,2]dioxaborolan-2-yl)-benzenesulfonamide (478 mg, 1.689 mmol) and K$_2$CO$_3$ (350 mg, 2.532 mmol) in DME (10 mL) and water (5 mL) was added Pd(PPh$_3$)$_4$ (48 mg, 0.041 mmol). The reaction mixture was stirred at 90° C. for 2 h and concentrated under reduced pressure. The residue was diluted with water (60 mL) and extracted with EtOAc (100 mL). The organic layer was dried over anhydrous sodium sulfate, concentrated under reduced pressure and residue was purified by reverse phase HPLC to yield 3'-(2,8-dimethyl-3,4-dihydro-1H-pyrido[4,3-b]indol-5 (2H)-yl)biphenyl-4-sulfonamide as the TFA salt. $^1$H NMR (CD$_3$OD, TFA salt) δ (ppm): 8.0 (d, 2H), 7.84 (m, 3H), 7.7 (m, 2H), 7.46 (d, 1H), 7.27 (s, 1H), 7.18 (d, 1H), 7.04 (d, 1H), 4.7 (bs, 1H), 4.4 (bs, 1H), 3.8 (bs, 1H), 3.6 (bs, 1H), 3.2 (m, 1H), 3.17 (s, 3H), 3.07 (m, 1H), 2.42 (s, 3H).

Example No. 125

Preparation of Compound No. 159

To a de-aerated solution of 5-(2-bromophenyl)-2,8-dimethyl-2,3,4,5-tetrahydro-1H-pyrido[4,3-b]indole (100 mg, 0.281 mmol), 4-methyl-3-(4,4,5,5-tetramethyl-1,3,2-dioxaborolan-2-yl)pyridine (124 mg, 0.563 mmol) and $K_2CO_3$ (116 mg, 0.843 mmol) in DME (4 mL) and water (0.4 mL) was added $Pd(PPh_3)_4$ (16 mg, 0.014 mmol). The reaction mixture was stirred at 90° C. for 2 h and concentrated under reduced pressure. The residue was diluted with water (20 mL) and extracted with EtOAc (40 mL). The organic layer was dried over anhydrous sodium sulfate, evaporated and the residue obtained was purified by reverse phase HPLC to yield 2,8-dimethyl-5-(2-(4-methylpyridin-3-yl)phenyl)-2,3,4,5-tetrahydro-1H-pyrido[4,3-b]indole as the TFA salt. $^1$H NMR ($CDCl_3$, freebase) δ (ppm): 8.2 (d, 2H), 7.5 (m, 2H), 7.4 (t, 1H), 7.38 (t, 1H), 7.1 (s, 1H), 6.9 (s, 1H), 6.8 (s, 2H), 3.6 (q, 2H), 2.7 (t, 2H), 2.6 (t, 2H), 2.5 (s, 3H), 2.38 (s, 3H), 2.0 (bs, 3H).

Example No. 126

Preparation of Compound No. 160

To a degassed solution of 5-(2-bromophenyl)-2,8-dimethyl-2,3,4,5-tetrahydro-1H-pyrido[4,3-b]indole (200 mg, 0.563 mmol), 4-(methylsulfonyl)phenylboronic acid (169 mg, 0.845 mmol) and $K_3PO_4$ (297 mg, 1.40 mmol) in DMF (6 mL) and water (0.66 mL) was added $Pd(PPh_3)_2Cl_2$ (20 mg, 0.028 mmol), and the reaction mixture heated at 90° C. for 16 h. Water (40 mL) was added to the reaction mixture, which was then extracted with EtOAc. The organic layer was washed with water (10×30 mL), dried over anhydrous sodium sulfate and concentrated under reduced pressure to afford crude material, which was purified by silica gel flash chromatography, followed by reverse phase HPLC to yield 2,8-dimethyl-5-(4'-(methylsulfonyl)biphenyl-2-yl)-2,3,4,5-tetrahydro-1H-pyrido[4,3-b]indole as the TFA salt. $^1$H NMR ($CD_3OD$, TFA salt) δ (ppm): 7.7 (m, 4H), 7.5 (bs, 1H), 7.3 (m, 4H), 7.0 (d, 1H), 6.9 (d, 1H), 4.63 (bs, 1H), 4.3 (bs, 1H), 3.63 (bs, 1H), 3.5 (bs, 1H), 3.0 (m, 5H), 2.9 (s, 3H), 2.4 (s, 3H).

Example No. 127

Preparation of Compound No. 161

To a degassed solution of 5-(3-bromopyridin-2-yl)-2,8-dimethyl-2,3,4,5-tetrahydro-1H-pyrido[4,3b]indole (100 mg, 0.281 mmol), pyridin-4-ylboronic acid (69 mg, 0.563 mmol) and $K_2CO_3$ (116 mg, 0.843 mmol) in DME (0.9 mL) and water (0.1 mL) was added $Pd(PPh_3)_4$ (16 mg, 0.014 mmol). The reaction mixture was irradiated in a microwave reactor at 90° C. for 45 min and concentrated under reduced pressure. The residue was diluted with EtOAc and washed with water (20 mL). The organic layer was dried over anhydrous sodium sulfate and concentrated to afford crude material, which was purified by reverse phase HPLC to yield 5-(3,4'-bipyridin-2-yl)-2,8-dimethyl-2,3,4,5-tetrahydro-1H-pyrido[4,3-b]indole as the TFA salt. $^1$H NMR ($CD_3OD$, TFA salt) δ (ppm): 8.8 (d, 1H), 8.4 (d, 2H), 8.3 (d, 1H), 7.8 (t, 1H), 7.3 (m, 3H), 6.87 (bs, 1H), 6.76 (bs, 1H), 4.7 (m, 1H), 4.4 (m, 1H), 3.8 (bs, 1H), 3.6 (bs, 1H), 3.17 (s, 3H), 2.8 (m, 2H), 2.38 (s, 3H).

Example No. 128

Preparation of Compound No. 162

To a de-aerated solution of 5-(2-bromophenyl)-2,8-dimethyl-2,3,4,5-tetrahydro-1H-pyrido[4,3-b]indole (200 mg, 0.563 mmol), N-methyl-3-(4,4,5,5-tetramethyl-1,3,2-dioxaborolan-2-yl)benzamide (294 mg, 1.126 mmol) and $K_2CO_3$ (233 mg, 1.689 mmol) in DME (8 mL) and water (0.4 mL) was added $Pd(PPh_3)_4$ (33 mg, 0.028 mmol). The reaction mixture was stirred at 90° C. for 45 min and concentrated under reduced pressure. The residue was diluted with water (50 mL) and extracted with EtOAc (60 mL). The organic layer was dried over anhydrous sodium sulfate and evaporated to afford crude material, which was purified by reverse phase HPLC to yield 3'-(2,8-dimethyl-3,4-dihydro-1H-pyrido[4,3-b]indol-5(2H)-yl)-N-methylbiphenyl-3-carboxamide as the TFA salt. $^1$H NMR ($CD_3OD$, TFA salt) δ (ppm): 8.1 (s, 1H), 7.8 (m, 3H), 7.7 (m, 2H), 7.58 (t, 1H), 7.4 (d, 1H), 7.36 (s, 1H), 7.18 (d, 1H), 7.02 (d, 1H), 4.7 (d, 1H), 4.4 (d, 1H), 3.8 (bs, 1H), 3.58 (bs, 1H), 3.2 (m, 1H), 3.1 (s, 3H), 3.0 (m, 1H), 2.9 (s, 3H), 2.4 (s, 3H).

Example No. 129

Preparation of Compound No. 163

To a degassed solution of 5-(2-bromophenyl)-2,8-dimethyl-2,3,4,5-tetrahydro-1H-pyrido[4,3-b]indole (300 mg, 0.845 mmol), 4-(4,4,5,5-tetramethyl-1,3,2-dioxaborolan-2-yl)benzenesulfonamide (478 mg, 1.69 mmol) and $K_2CO_3$ (350 mg, 2.53 mmol) in DME (12 mL) and water (0.6 mL) was added $Pd(PPh_3)_4$ (49 mg, 0.042 mmol). The reaction mixture was stirred overnight at 90° C. and concentrated under reduced pressure. The residue was diluted with water (50 mL) and extracted with EtOAc (60 mL). The organic extract was dried over anhydrous sodium sulfate, and concentrated to afford crude material, which was triturated with diethyl ether and the solid was purified by reverse phase HPLC to yield 2'-(2,8-dimethyl-3,4-dihydro-1H-pyrido[4,3-b]indol-5(2H)-yl)biphenyl-4-sulfonamide as the TFA salt. $^1$H NMR ($CD_3OD$, TFA salt) δ (ppm): 7.62 (m, 5H), 7.38-7.5 (m, 1H), 7.28 (s, 2H), 7.17 (d, 1H), 6.9-7.08 (m, 2H), 4.6 (d, 1H), 4.2 (d, 1H), 3.6 (bs, 1H), 3.52 (bs, 1H), 3.2 (bs, 1H), 2.9 (bs, 1H), 2.8 (s, 3H), 2.4 (s, 3H).

Example No. 130

Preparation of Compound No. 164

A solution of 2,8-dimethyl-2,3,4,5-tetrahydro-1H-pyrido[4,3-b]indole (310 mg, 1.55 mmol), $K_3PO_4$ (0.985 g, 4.65 mmol), CuI (29.4 mg, 0.15 mmol), L-proline (35.6 mg, 0.31 mmol) and 4-bromo-1-methylisoquinoline (0.520 g, 2.35 mmol) in dry DMF (3 mL) was stirred at RT for 10 min and then at 150° C. for 16 h. Water (50 mL) was added to the reaction mixture and then extracted with EtOAc (150 mL). The organic layer was washed with water (6×30 mL), dried over anhydrous sodium sulfate and evaporated to afford crude material, which was purified by reverse phase HPLC to yield 2,8-dimethyl-5-(1-methylisoquinolin-4-yl)-2,3,4,5-tetrahydro-1H-pyrido[4,3-b]indole as the TFA salt. $^1$H NMR ($CD_3OD$, TFA salt) δ (ppm): 8.6-8.74 (m, 2H), 8.0 (m, 2H), 7.41 (s, 1H), 7.38 (bs, 1H), 7.0 (d, 1H), 6.8 (bs, 1H), 4.8 (bs, 1H), 4.5 (bs, 1H), 3.8 (bs, 1H), 3.6 (bs, 1H), 3.3 (s, 3H), 3.18 (s, 3H), 3.0 (bs, 1H), 2.82 (bs, 1H), 2.41 (s, 3H).

Example No. 131

Preparation of N-Methyl and N-Ethyl 9-Chloro-1,2,3,4,5,6-hexhydroazepino[4,3-b]indole

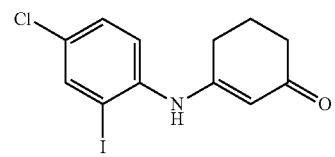 [SMILES: O=C1C=C(Nc2ccc(Cl)cc2I)CCC1]

A mixture of 4-chloro-2-iodoaniline (0.5 g, 1.97 mmol), 1,3-cyclohexanedione (0.22 g, 1.96 mmol) and p-toluenesulfonic acid monohydrate (catalytic) in toluene (6 mL) were heated to reflux for 2 h. The reaction was cooled and EtOAc (50 mL) was added and the organic phase was washed with water (20 mL) and brine (20 mL), dried over sodium sulfate, filtered and evaporated to give a brown solid, which was purified by column chromatography [Silica, eluent: EtOAc:hexane to give 3-(4-chloro-2-iodophenylamino)cyclohex-2-enone as a yellow solid (0.55 g, 80%).

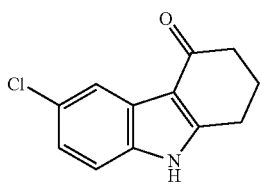 [SMILES: O=C1CCCc2[nH]c3ccc(Cl)cc3c21]

A mixture of 3-(4-chloro-2-iodo-phenylamino)-cyclohex-2-enone (0.5 g, 1.44 mmol), cuprous iodide (27.4 mg, 0.14 mmol), L-proline (33.12 mg, 0.29 mmol) and potassium hydroxide (0.32 g, 5.70 mmol) in DMSO (6 mL) were heated to 90° C. for 24 h. The reaction was cooled and poured into water. The aqueous phase was extracted with EtOAc (3×50 mL). The combined organic phase was washed with brine (25 mL), dried over magnesium sulfate, filtered and the solvent removed under reduced pressure to give a dark brown solid. This was recrystallized using acetonitrile water to give a brown solid (0.17 g, 54%). mp 281-282° C.

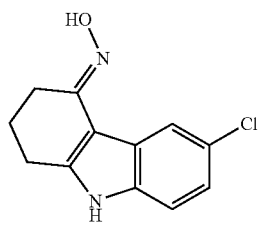 [SMILES: O/N=C1\CCCc2[nH]c3ccc(Cl)cc3c21]

A solution of 6-chloro-2,3-dihydro-1H-carbazol-4(9H)-one (500 mg, 2.27 mmol), hydroxylamine hydrochloride (238 mg, 3.41 mmol) and NaOAc (280 mg, 3.41 mmol) in EtOH:water (4.5:2 mL) was heated to reflux (125° C.) for 5 h. The reaction mixture was concentrated to dryness. Water was added to the residue and the solid filtered, dried under vacuum to yield the title compound.

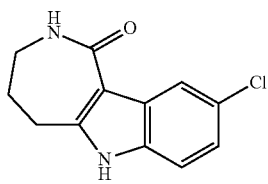 [SMILES: O=C1NCCCc2[nH]c3ccc(Cl)cc3c21]

6-Chloro-2,3-dihydro-1H-carbazol-4(9H)-one oxime (4.39 g, 18.71 mMol) and polyphosphoric acid (119 g) was heated together at 120° C. for 20 min. After cooling to RT, ice-water mixture was added to hydrolyze the mixture and stirred for 2 h. The mixture was filtered and washed with NH₄OH (40 ml) followed by water. The resultant solid was dissolved in MeOH and filtered. The methanolic solution was concentrated to yield 4.7 g of crude as a brown solid. The crude product was purified by flash column chromatography over silica-gel (230-400 mesh) using EtOAc/Hexane followed by MeOH/EtOAc, the product eluting at 2-10% MeOH/EA. Yield: 2.1 g (47.8%).

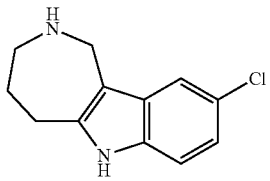 [SMILES: Clc1ccc2[nH]c3c(c2c1)CNCCC3]

To an ice-cooled stirred suspension of lithium aluminum hydride (486 mg, 12.8 mmol) in dry THF (29 mL) was added dropwise a solution of 9-chloro-2,3,4,5-tetrahydroazepino[4,3-b]indol-1(6H)-one (380 mg, 1.62 mmol) in dry THF (20 mL), and the reaction mixture heated to reflux for 15 h (89° C.). The reaction mixture was cooled to RT, quenched with water (3 mL), and 15% NaOH solution (6 mL) and water (9 mL), and then diluted with THF. The reaction mixture was filtered through Celite and the filtrate concentrated under reduced pressure to yield the title compound.

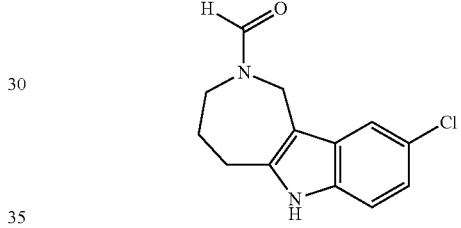

A solution of 9-chloro-1,2,3,4,5,6-hexahydroazepino[4,3-b]indole (360 mg, 1.6 mmol) in THF (1 mL) was added dropwise to ethyl formate (1 mL). The reaction mixture was stirred at RT for 30 min, followed by heating to reflux for 14 h. The solvent was removed under reduced pressure to yield the title compound.

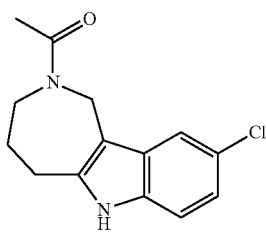 [SMILES: CC(=O)N1CCCc2[nH]c3ccc(Cl)cc3c2C1]

A solution of 9-chloro-1,2,3,4,5,6-hexahydroazepino[4,3-b]indole (360 mg, 1.6 mmol) was stirred in acetic anhydride for 12 h. The solvent was removed under reduced pressure to yield the title compound.

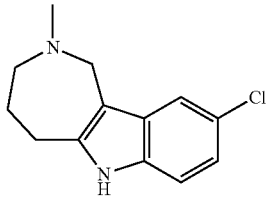 [SMILES: CN1CCCc2[nH]c3ccc(Cl)cc3c2C1]

A solution of 9-chloro-1,2,3,4,5,6-hexahydroazepino[4,3-b]indole (12.3 g, 55.9 mmol) in ethyl formate (369 mL) was stirred at 55° C. for 2 h. The progress of reaction was monitored by TLC. The reaction mixture was concentrated under reduced pressure and the crude product (13.5 g) was used for the next step without purification. To a stirred suspension of lithium aluminum hydride (4.13 g, 108.8 mmol) in dry THF (405 mL) was added portionwise 9-chloro-3,4,5,6-tetrahydroazepino[4,3-b]indole-2(1H)-carbaldehyde (13.5 g) and the mixture heated to reflux for 2 h. The progress of reaction was monitored by TLC. The reaction was quenched with saturated aqueous sodium sulfate solution at 0° C., and the mixture filtered. The filtrate was dried over anhydrous sodium sulfate and evaporated to dryness. The residue was washed with diethyl ether to yield the title compound (9.7 g). $^1$H NMR (DMSO) δ (ppm): 11.02 (s, 1H, D$_2$O exchangeable), 7.45 (s, 1H), 7.25-7.22 (d, 1H), 6.98-6.95 (d, 1H), 3.72 (s, 2H), 2.90-2.80 (m, 4H), 2.30 (s, 3H), 1.82-1.77 (m, 2H).

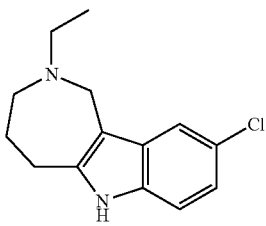 [SMILES: CCN1CCCc2[nH]c3ccc(Cl)cc3c2C1]

To an ice-cooled stirred suspension of lithium aluminum hydride (390 mg, 10.09 mmol) in 1,4-dioxane (15 mL) was added portionwise 1-(9-chloro-4,5-dihydroazepino[4,3-b]indol-2(1H,3H,6H)-yl)ethanone (300 mg, 1.14 mmol), and the reaction mixture heated to reflux for 6 h. The reaction mixture was quenched with water (1 mL), 15% aq. NaOH solution (3 mL) and water (3 mL), and extracted with warm EtOAc (3×50 mL). The combined organic extract was concentrated and the residue purified by silica gel (230-400 mesh) flash column chromatography (100% EtOAc) to yield the title compound (115 mg).

Example No. 132

Preparation of 2,9-dimethyl-1,2,3,4,5,6-hexahydroazepino[4,3-b]indole

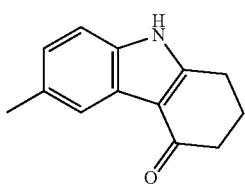

To a solution of p-tolylhydrazine hydrochloride (7.5 g, 47.2 mmol) in 1,4-dioxane:conc. H$_2$SO$_4$ (225:16.5 mL) was added cyclohexane-1,3-dione (4.42 g, 39.4 mmol), and the mixture heated to reflux for 16 h (85-90° C.). The reaction mixture was cooled to RT, basified with 15% aqueous KOH (pH 10) and extracted with EtOAc. The organic layer was washed twice with brine, dried over anhydrous sodium sulfate and concentrated under reduced pressure to yield the title compound (7.7 g, crude).

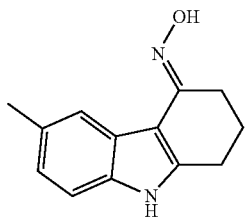 [SMILES: Cc1ccc2[nH]c3c(c2c1)/C(=N/O)CCC3]

A solution of 2,3-dihydro-6-methyl-1H-carbazol-4(9H)-one (5.8 g, 19.1 mmol), hydroxylamine hydrochloride (3.0 g, 43.6 mmol) and NaOAc (3.58 g, 43.6 mmol) in EtOH:water (58:25.3 mL) was heated to reflux (125° C.) for 5 h. The reaction mixture was concentrated to dryness. Water was added to the residue and the solid filtered, dried under vacuum to yield title compound.

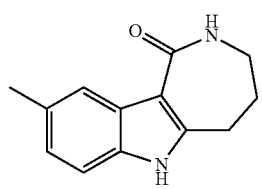 [SMILES: Cc1ccc2[nH]c3c(c2c1)C(=O)NCCC3]

To a preheated (105° C.) solution of polyphosphoric acid (225 g) was added powdered 6-methyl-2,3-dihydro-1H-carbazol-4(9H)-one oxime (10 g) under nitrogen and heating continued for 15 min. The reaction mixture was cooled and to it was added crushed ice water. The crystallized solid obtained was collected by filtration. The solid was washed with water and then by dilute ammonium hydroxide, then dried under vacuum to obtain the desired product (8 g, crude product).

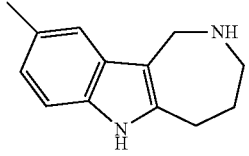

Lithium aluminum hydride (3 g, 78.95 mmol) was placed in 1,4-dioxane (100 mL) under inert atmosphere and 9-methyl-2,3,4,5-tetrahydroazepino[4,3-b]indol-1(6H)-one (3 g, 14.018 mmol) was added, and the mixture heated to reflux for 15 h. The reaction was monitored by TLC. The reaction was quenched with saturated aqueous sodium sulfate at 0° C., and the reaction mixture filtered. The filtrate was dried over anhydrous sodium sulfate and evaporated to dryness to afford solid, which was washed with water followed by EtOAc, and dried to afford 1.25 g of the title compound.

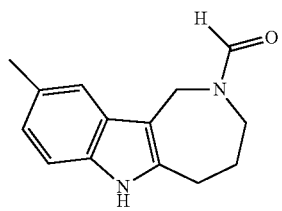 [SMILES: Cc1ccc2[nH]c3c(c2c1)CN(C=O)CCC3]

9-Methyl-1,2,3,4,5,6-hexahydroazepino[4,3-b]indole (0.25 g, 1.25 mmol) was taken in ethyl formate (18 mL, 227 mmol) and stirred at 55° C. for 3 h. The reaction was monitored by TLC. The reaction mixture was evaporated under reduced pressure and used for the next step without purification (0.2 g).

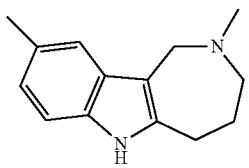 [SMILES: Cc1ccc2[nH]c3c(c2c1)CN(C)CCC3]

To a stirred suspension of lithium aluminum hydride (2 g, 52.63 mmol) in dry THF (150 mL) was added portionwise 9-methyl-3,4,5,6-tetrahydroazepino[4,3-b]indole-2(1H)-carbaldehyde (5.9 g, 25.87 mmol) and the reaction mixture stirred at 55° C. for 2 h. The progress of reaction was monitored by TLC. The reaction mixture was quenched with saturated sodium aqueous sulfate solution at 0° C. and then filtered. The filtrate was dried over anhydrous sodium sulfate and evaporated to dryness to afford the title compound (5.2 g). $^1$H NMR (DMSO) δ (ppm): 7.12-7.05 (m, 2H), 6.80-6.6.76 (d, 1H), 3.65 (s, 2H), 2.90-2.80 (m, 4H), 2.34 (s, 3H), 2.26 (s, 3H), 1.80-1.72 (m, 2H).

Example B1

Determination of the Ability of Compounds of the Invention to Bind an Adrenergic Receptor Adrenergic $\alpha_{2B}$ To evaluate in radioligand binding assays the activity of compounds of the invention, human recombinant adrenergic α2B receptor expressed in Chinese hamster ovary (CHO) K1 cells (Uhlen, S. et al, Eur. J. Pharmacol. 343(1):93, 1998) in a modified Tris-HCl buffer (50 mM Tris-HCl, pH 7.4, 12.5 mM MgCl$_2$, 1 mM EDTA, 0.2% BSA) was used. Compounds of the invention were incubated with 2.5 nM [3H]Rauwolscine for 60 min at 25° C. Non-specific binding was estimated in the presence of 10 μM Prazosin. Receptor proteins were filtered and washed, the filters were then counted to determine [3H] Rauwolscine specifically bound. Compounds were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 2.

Adrenergic $\alpha_{2A}$

To evaluate in radioligand binding assays the activity of compounds of the invention, human recombinant adrenergic $\alpha_{2A}$ receptor expressed in insect Sf9 cells (Uhlen, S. et al, J. Pharmacol. Exp. Ther. 271:1558, 1994) in a modified Tris-HCl buffer (50 mM Tris-HCl, pH 7.4, 12.5 mM MgCl$_2$, 2 mM EDTA) was used. Compounds of invention were incubated with 1 nM [$^3$H]MK-912 for 60 min at 25° C. MK912 is (2S-trans)-1,3,4,5',6,6',7,12b-octahydro-1',3'-dimethyl-spiro[2H-benzofuro[2,3-a]quinolizine-2,4'(1'H)-pyrimidin]-2'(3'H)-one hydrochloride Non-specific binding was estimated in the presence of 10 μM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 2.

Adrenergic $\alpha_{1B}$

To evaluate in radioligand binding assays the activity of compounds of the invention, rat adrenergic $\alpha_{1B}$ receptor obtained from Wistar Rat liver (Garcia-S'ainz, J. et al, Biochem. Biophys. Res. Commun. 186:760, 1992; Michel, A. et al, Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prazosin for 60 min at 25° C. Non-specific binding was estimated in the presence of 10 μM phentolamine. Receptor proteins were filtered and washed, the filters were then counted to determine [$^3$H]Prazosin specifically bound. Compounds were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 2.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. et al, Br. J. Pharmacol. 115(6):981, 1995) in a 50 mM Tris-HCl buffer, pH 7.4, was used. Compounds were incubated with 0.6 nM [3H]Prazosin for 60 min at 25° C. Non-specific binding was estimated in the presence of 10 μM phentolamine. Receptor proteins were filtered and washed, the filters were then counted to determine [3H]Prazosin specifically bound. Compounds were screened at 1 μM or lower, using 1% DMSO as vehicle. Biochemical assay results are presented as the percent inhibition of specific binding in Table 2.

TABLE 2

Percentage inhibition of ligand binding to adrenergic receptors by compounds of the invention:

| Compound | Adrenergic (0.1 μM)* | | | | Adrenergic (0.03 μM)* | | |
|---|---|---|---|---|---|---|---|
| No. | $\alpha_{1B}$ | $\alpha_{1D}$ | $\alpha_{2A}$ | $\alpha_{2B}$ | $\alpha_{1B}$ | $\alpha_{2A}$ | $\alpha_{2B}$ |
| 5 | 52 | 45 | 26 | 78 | — | — | — |
| 10 | 61 | 63 | 88 | 85 | — | — | — |
| 14 | 38 | 20 | 23 | 51 | — | — | — |
| 15 | 35 | 19 | 10 | 30 | — | — | — |
| 16 | 8 | 16 | −1 | 16 | — | — | — |
| 30 | 32 | 17 | 42 | 86 | — | — | — |
| 31 | 36 | 80 | 74 | 67 | — | — | — |
| 32 | 73 | 65 | 72 | 80 | — | — | — |

TABLE 2-continued

Percentage inhibition of ligand binding to adrenergic receptors by compounds of the invention:

| Compound No. | Adrenergic (0.1 μM)* | | | | Adrenergic (0.03 μM)* | | |
|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{2A}$ | $\alpha_{2B}$ |
| 33 | 52, 73 | 69 | 92, 96, 100 | 95, 105, 106 | 46 | 87, 96 | 100, 102 |
| 34 | 16 | 18 | 28 | 1 | — | — | — |
| 35 | 67 | 68 | 84 | 95 | — | — | — |
| 36 | 13 | 26 | 90 | 79 | — | — | — |
| 37 | 77 | 79 | 88, 94 | 96, 104 | — | 81 | 104 |
| 38 | 31 | 32 | 32 | 57 | — | — | — |
| 39 | 67 | 62 | 98 | 70 | — | — | — |
| 40 | 43 | 79 | 91 | 89 | — | — | — |
| 41 | 77 | 76 | 87 | 70 | — | — | — |
| 42 | 10 | −3 | 17 | 7 | — | — | — |
| 43 | 9 | 3 | 31 | 6 | — | — | — |
| 44 | 0 | 2 | 29 | 12 | — | — | — |
| 45 | 1 | 1 | 12 | 6 | — | — | — |
| 46 | −7 | 8 | 48 | 21 | — | — | — |
| 47 | 5 | 3 | 62 | 6 | — | — | — |
| 48 | 1 | −5 | 19 | 16 | — | — | — |
| 49 | 12 | 14 | −3 | 31 | — | — | — |
| 50 | 42 | 51 | 88, 93 | 103 | — | 82 | 97 |
| 51 | 10 | 12 | 27 | 7 | — | — | — |
| 52 | 6 | −3 | 43 | 36 | — | — | — |
| 53 | 8 | 0 | 24 | 15 | — | — | — |
| 54 | 8 | −3 | 23 | 3 | — | — | — |
| 55 | 10 | 9 | 19 | 26 | — | — | — |
| 56 | 36 | 65 | 4 | 90 | — | — | — |
| 57 | 6 | −1 | 7 | 11 | — | — | — |
| 58 | 22 | 24 | 22 | 39 | — | — | — |
| 59 | 47 | 65 | 77 | 91 | — | — | — |
| 60 | 4 | 9 | 62 | 14 | — | — | — |
| 61 | 11 | 5 | 23 | 7 | — | — | — |
| 62 | 32 | 18 | 67 | 19 | — | — | — |
| 63 | 2 | 5 | 30 | 11 | — | — | — |
| 64 | 10 | −1 | 25 | 1 | — | — | — |
| 65 | 14 | 1 | 33 | 46 | — | — | — |
| 66 | 13 | 11 | 39 | 18 | — | — | — |
| 67 | 2 | −1 | 39 | 13 | — | — | — |
| 68 | 61 | 68 | 86, 90 | 86, 93 | — | 76 | 71 |
| 69 | 11 | 9 | 39 | 3 | — | — | — |
| 70 | 18 | 9 | 34 | 19 | — | — | — |
| 71 | 66 | 87 | 11 | 89 | — | — | — |
| 72 | 28 | 56 | 3 | 17 | — | — | — |
| 73 | 64 | 83 | 16 | 94 | — | — | — |
| 74 | 41 | 18 | 38 | 70 | — | — | — |
| 75 | 20 | 15 | 21 | 16 | — | — | — |
| 76 | 68 | 73 | 68, 90 | 94, 100 | — | 44 | 89 |
| 77 | 15 | 6 | 15 | 45 | — | — | — |
| 78 | 8 | 21 | 63 | 86 | — | — | — |
| 79 | 51 | 53 | 90, 92 | 104, 106 | — | 82 | 102 |
| 80 | 9 | 23 | 12 | 27 | — | — | — |
| 81 | 37 | 36 | 88 | 95 | — | — | — |
| 82 | 14 | 14 | 30 | 21 | — | — | — |
| 83 | 18 | 64 | 20 | 71 | — | — | — |
| 84 | 54 | 58 | 68 | 89 | — | — | — |
| 85 | 36 | 62 | 89, 94 | 98, 102 | — | 80 | 89 |
| 86 | 26 | 22 | 33 | 67 | — | — | — |
| 87 | 13 | 16 | 30 | 18 | — | — | — |
| 88 | 36 | 20 | 15 | 80 | — | — | — |
| 100 | 79 | 64 | 84, 95 | 99, 109 | — | 74 | 103 |
| 102 | 57 | 50 | 85 | 90 | — | — | — |
| 103 | 41 | 62 | 98 | 97 | — | — | — |
| 104 | 6, 15 | 22 | 10, 19 | 87 | — | — | 61 |
| 105 | 71 | 65 | 79 | 84 | — | — | — |
| 131 | 0 | 3 | 75 | 28 | — | — | — |
| 132 | 33 | 28 | 17 | 69 | — | — | — |
| 133 | 63 | 53 | 31 | 77 | — | — | — |
| 134 | 43 | 30 | 38 | 73 | — | — | — |
| 135 | 59 | 64 | 56 | 99 | — | — | — |
| 136 | 70 | 59 | 59 | 105 | — | — | — |
| 137 | 72 | 74 | 57 | 92 | — | — | — |
| 138 | 73 | 73 | 40 | 82 | — | — | — |
| 139 | 55 | 45 | 18 | 59 | — | — | — |
| 140 | 69 | 56 | 70 | 96 | — | — | — |
| 141 | 62 | 50 | 69 | 82 | — | — | — |

TABLE 2-continued

Percentage inhibition of ligand binding to adrenergic receptors by compounds of the invention:

| Compound No. | Adrenergic (0.1 µM)* | | | | Adrenergic (0.03 µM)* | | |
|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{2A}$ | $\alpha_{2B}$ |
| 142 | 83 | 78 | 59 | 91 | — | — | — |
| 143 | 83 | 72 | 44 | 77 | — | — | — |
| 144 | 68 | 52 | 72 | 95 | — | — | — |
| 145 | 86 | 73 | 71 | 83 | — | — | — |
| 146 | 70 | 79 | 26 | 54 | — | — | — |
| 147 | 72 | 61 | 46 | 43 | — | — | — |
| 148 | 63 | 68 | 50 | 90 | — | — | — |
| 149 | 16 | 8 | −6 | 14 | — | — | — |
| 150 | 72 | 73 | 55 | 77 | — | — | — |
| 151 | 59 | 67 | 96 | 99 | — | — | — |
| 152 | 10 | 16 | 9 | 51 | — | — | — |
| 153 | 8 | 9 | 1 | 58 | — | — | — |
| 154 | 46 | 70 | 20 | 42 | — | — | — |
| 155 | 43 | 63 | 9 | 74 | — | — | — |
| 156 | 78 | 69 | 40 | 78 | — | — | — |
| 157 | 22 | 13 | 8 | 60 | — | — | — |
| 158 | 7 | 14 | 73 | 60 | — | — | — |
| 159 | — | — | — | 56 | — | — | — |
| 160 | — | — | — | 74 | — | — | — |
| 161 | — | — | — | 26 | — | — | — |
| 162 | — | — | — | 40 | — | — | — |
| 163 | — | — | — | 69 | — | — | — |
| 164 | — | — | — | 3 | — | — | — |

*Where shown, some compounds were tested in repeat assays, each datapoint is shown.

Example B2

Functional Activity on Recombinant Adrenergic $\alpha_{1B}$, Adrenergic $\alpha_{2A}$ Adrenergic $\alpha_{2B}$ and Adrenergic $\alpha_{1D}$ Receptors using Aequorin and GTPγS Functional Assays To study the functional activity of compounds of the invention on the human recombinant adrenergic $\alpha_{2B}$, adrenergic $\alpha_{2A}$, adrenergic $\alpha_{1B}$ or adrenergic $\alpha_{1D}$ with Aequorin functional assays and on the human recombinant adrenergic $\alpha_{2B}$ receptor with GTPγS assay, CHO-K1 cell lines expressing adrenergic $\alpha_{2B}$, adrenergic $\alpha_{2A}$, adrenergic $\alpha_{1B}$ or adrenergic $\alpha_{1D}$ recombinant receptor, mitochondrial apoaequorin and Gα16 are used for the Aequorin assay. CHO-K1 cell line expressing the recombinant $\alpha_{2B}$ receptor is amplified to prepare membranes used for the GTPγS assay.

The following reference agonists are used as both the reference ligand in agonist mode and as the agonist that needs to be inhibited in antagonist mode.

| Assay | $\alpha_{1B}$ (aeq) | $\alpha_{1D}$ (aeq) | $\alpha_{2A}$ (aeq) | $\alpha_{2B}$ (aeq) | $\alpha_{2B}$ (GTPgS) |
|---|---|---|---|---|---|
| Agonist ligand | Cirazoline | Cirazoline | UK 14304 | Oxymetazoline | Guanfacine |

Aequorin Assay Procedure:

Aequorin adrenergic $\alpha_{1B}$ (FAST-008A), adrenergic $\alpha_{2A}$ (FAST-006A) or adrenergic $\alpha_{2B}$ (FAST-007A) cells are grown 18 h prior to the test in media without antibiotics. They are then detached by gentle flushing with PBS-EDTA (5 mM EDTA), recovered by centrifugation and re-suspended in "assay buffer" (DMEM/HAM's F12 with HEPES+0.1% BSA protease free). Cells are incubated at RT for at least 4 h with Coelenterazine h (Molecular Probes). Dose response curves with reference compounds are performed before testing the compounds of the invention. The $\alpha_{1B}$ reference agonist and antagonist are cirazoline and qinazoline, respectively. The $\alpha_{2A}$ reference agonist and antagonist are UK14, 304 and rauwolscine, respectively. The $\alpha_{2B}$ reference agonist and antagonist are oxymetazoline and rauwolscine, respectively.

For agonist testing, 50 µL of cell suspension are injected on 500 µL of test compound or reference agonist plated in a 96-well plate. The resulting emission of light is recorded using the Hamamatsu Functional Drug Screening System 6000 (FDSS 6000). For antagonist testing, following an incubation of 15 min. after the first injection, 100 µL of reference agonist at a concentration corresponding to its $EC_{80}$ is injected on the 100 µL of the mixture of cell suspension and test compound. The resulting emission of light is recorded using the same luminometer as for agonist testing. To standardize the emission of recorded light (determination of the "100% signal") across plates and across different experiments, some of the wells contained 100 µM digitonin or a saturating concentration of ATP (20 µM). Plates also contained the reference agonist at a concentration equivalent to the $EC_{80}$ obtained during the test validation.

Agonist activity of test compound is expressed as a percentage of the activity of the reference agonist at its $EC_{100}$ concentration. Antagonist activity of test compound is expressed as a percentage of the inhibition of reference agonist activity at its $EC_{80}$ concentration.

Test compounds are tested for agonist & antagonist activity at the human adrenergic $\alpha_{1B}$ (FAST-008A), adrenergic $\alpha_{2A}$ (FAST-006A) or adrenergic $\alpha_{2B}$ (FAST-007A) at the following nanomolar concentrations, in duplicate: Agonist (nM): 0.3, 1, 3, 10, 30, 100, 300, 1000, 3000, 10000; Antagonist (nM): 0.15, 0.5, 1.5, 5, 15, 50, 150, 500, 1500, 5000.

GTPγS Assay Procedure:

The procedure is carried out with the following: assay buffer [20 mM HEPES pH 7.4; 100 mM NaCl, 10 µg/mL saponin, 1 mM $MgCl_2$]; membranes [Recombinant CHO-K1-adrenergic $\alpha_{2B}$ membrane extracts thawed on ice and diluted in assay buffer to give 10 µg/well and kept on ice]; GDP [diluted in assay buffer to give 3 µM final concentration]; beads [PVT-WGA (Amersham, RPNQ0001), diluted in assay buffer at 0.5 mg/well]; GTPγ$^{35}$S [(PerkinElmer NEG030X), diluted in assay buffer to give 0.1 nM final concentration]; ligand [Guanfacine (Tocris, 1030) as reference agonist and Rauwolscine (Tocris, 891) as reference antagonist, diluted in assay buffer]. Membranes are mixed with GDP (volume:volume) and incubated for at least 15 min. on ice. In parallel, GTPγ[$^{35}$S] is mixed with the beads (volume:volume) just before starting the reaction.

For agonist testing, the following reagents are successively added in the wells of an Optiplate (Perkin Elmer): 50 µL of test or reference ligand, 20 µL of the membranes:GDP mix, 10 µL of assay buffer and 20 µL of the GTPγ[$^{35}$S]:beads mix. For antagonist testing, the following reagents are successively added in the wells of an Optiplate (Perkin Elmer): 50 µL of test or reference ligand, 20 µL of the membranes:GDP mix, and then after an incubation of 15 min. at RT, 10 µL of reference ligand at historical $EC_{80}$ concentration and 20 µL of the GTPγ[$^{35}$S]:beads mix.

The plates are covered with a top seal, mixed on an orbital shaker for 2 min, and then incubated for 1 h at RT. Then the plates are centrifuged for 10 min. at 2000 rpm, incubated at RT 4 h and counted for 1 min/well with a Perkin Elmer TopCount reader.

Test compounds are tested for antagonist activity at the human adrenergic $\alpha_{2B}$ receptor (FAST-007G) (Figure 4) at the following nanomolar concentrations, in duplicate: Agonist and antagonist (nM): 0.3, 1, 3, 10, 30, 100, 300, 1000, 3000, 10000.

Inverse Agonist Activity

SPA 35S-GTPgS and Radioligand Binding experiments are conducted with Euroscreen membrane preparations. Test compound is tested for inverse agonist activity at the human Adrenergic a2A receptor using GTPg35S binding functional assay (FAST-006G) in dose-response and in duplicates.

Example B3

Cell Culture and Cell Viability Assay

SH-SY5Y cells cultured in DMEM/F12 media supplemented with 10% FBS are seeded in 96-well microplates at 150,000 cells/cm$^2$. After 24 h, cells are depleted from FBS and kept in culture for 24 h before the experiment. Cells are then treated with 4-Br-A23187 (2 µM), hydrogen peroxide (300 µM) or the mitochondrial toxin rotenone (25 µM) in the presence of vehicle or Test compound of the Invention for 24 h. Cell death is determined by measurements of LDH release according to the Cytotoxicity Detection KitPlus (Roche, Mannheim, Germany). Cell viability is determined by measuring the capacity of cells to metabolize MTS tetrazolium (MTS) according to the Cytotoxicity Detection KitPlus (Roche, Mannheim, Germany) and MTS reduction is assessed by the CellTiter 96® AQueous One Solution Cell Proliferation assay (Promega Corporation, Madison, Wis., USA). Test compounds are screened at 10 nM, using DMSO as vehicle. Assay results for the experiments with hydrogen peroxide are presented as the LDH release (cell death) of untreated cells (control), hydrogen peroxide-treated cells (vehicle), and co-incubation of hydrogen peroxide with Compounds of the Invention treated cells normalized to the vehicle. This assay assesses the ability of the test compounds to protect against cell death that is mediated by mitochondrial dysfunction. In the assay, the calcium ionophore 4-Br-A23187 is used to challenge the cells, causing calcium levels to rise in mitochondria, which leads to depolarization and cell death. Test compounds are assessed for their ability to prevent cell death in response to challenge with 4-Br-A23187.

Assay results for the experiments with Br-A23187 are presented as the MTS reduction capacity (cell viability) of untreated cells (control), 4-Br-A23187-treated cells (vehicle), and co-incubation of Br-A23187 with Compounds of the Invention treated cells and using p-trifluoromethoxyphenylhydrazone (FCCP) at 10 µM for 30 min as a control.

Example B4

Cell Culture and Cell Viability Assay

Cell Culture.

SH-SY5Y cells stably transfected with a doxycyline (dox)-inducible wild-type α-synuclein (α-syn) gene along with control SH-SY5Y cells over-expressing the β-galactosidase (β-gal) gene (a gift from L. Stefanis, Division of Basic Neurosciences, Biomedical Research Foundation of the Academy of Athens, Athens, Greece) are cultured as described by Vekrellis et al. (Vekrellis K, Xilouri M, Emmanouilidou E, Stefanis L. (2009). Inducible over-expression of α-syn in human neuronal cells leads to caspase-dependent non-apoptotic death. J Neurochem 109, 1348-1362). In accordance with this method, cells are cultured and maintained in RPMI 1640, 10% fetal bovine serum supplemented with 250 µg/mL G418 and 50 µg/mL Hygromycin B. Expression of α-syn is switched off in stock cultures with doxycycline (2 µg/mL). For experimental procedures, cells are plated at (4–8×10$^4$ cells/cm$^2$) and differentiated in absence of doxycycline and in the presence of 20 µM all-trans retinoic acid (RA) (Sigma, St Louis, Mo., USA).

Viability Assay:

Cells are cultured in 96-well plates. After 24 h, cells are treated with RA and Compounds of Invention at 0.1 and 10 nM in the absence of doxycyline. Culture medium with RA and drugs is fully replaced after 7 days. Cell viability is measured by the release of lactate dehydrogenase (LDH) from necrotic cells into the culture medium and by measuring the capacity of cells to metabolize MTS tetrazolium (MTS) after 14 days in culture. LDH leakage is assessed according to the Cytotoxicity Detection KitPlus (Roche, Mannheim, Germany) and MTS reduction is assessed by the CellTiter 96® AQueous One Solution Cell Proliferation assay (Promega Corporation, Madison, Wis., USA).

Assay results for the experiments with α-syn over-expression are presented as the MTS reduction capacity (cell viability) of control cells (+dox), cells over-expressing α-syn (−dox), and cells over-expressing α-syn incubated with Compounds of the Invention at 0.1 nM or 10 nM.

Immunoblotting of α-Synuclein and α-Synuclein Aggregates:

Cells stably expressing α-synuclein are cultured in 6-well plates at a density of 4×10$^4$ cells/cm$^2$ cells per well. Cells are differentiated and treated with Compound of the Invention at 10 nM in absence of dox after 24 h of plating. Drug treatments are repeated after 7 days in freshly prepared medium containing RA. After 14 days, cells are washed twice with cold PBS and lysed in lysis buffer containing 1% Triton X-100, 20 mM HEPES, 150 mM NaCl, 10% glycerol, 1 mM EGTA, 1.5 mM $MgCl_2$, 1 mM PMSF pH 7.4, and 1× protease inhibitor mixture (Roche, Mannheim, Germany). Lysates are homogenized and subjected to four successive freeze-thaw cycles to disrupt membranes. Triton soluble fractions and triton insoluble pellets are obtained by ultracentrifugation at 100,000×g for 30 min at 4° C. The concentration of protein in each fraction is determined by BCA assay (Thermo Scientific).

Samples from total, soluble and triton insoluble fractions, are boiled in 1× sample buffer (20 mM Tris, 1% glycerol, 180 mM β-mercaptoethanol, 0.003% bromophenol blue, and 2% SDS, pH 6.8), loaded on 12% SDS-PAGE gels, and transferred to polyvinylidene difluoride (PVDF) membranes (0.2 μM-pore immobilon Biorad). Membranes are blocked in 1×TBS-Tween (20 mM Tris, pH 7.4, 150 mM NaCl, and 0.2% Tween 20) containing 5% milk for 1 h and incubated overnight at 4° C. with the following primary antibodies in blocking solution at the indicated dilutions: monoclonal anti-α-synuclein α-syn-1 (1:1000; BD Transduction Laboratories). (Perrin, R. J., Payton, J. E., Barnett, D. H., Wraight, C. L., Woods, W. S., Ye, L., and George, J. M. (2003). Epitope mapping and specificity of the anti-α-synuclein monoclonal antibody Syn-1 in mouse brain and cultured cell lines. Neurosci Lett 349, 133-135), and monoclonal vimentin (1:1000; BD PharMingen). Primary antibodies are detected with secondary anti-mouse antibodies conjugated to HRP (1:5000).

Isolation of RNA and RT-Quantitative PCR(RT-qPCR):
SH-SY5Y cells stably over-expressing α-syn are treated with Compound of the Invention (10 nM). Total RNA from these cells as well as control cells not treated with Compound is extracted using the E.Z.N.A RNA extraction Kit (OMEGAbiotek, Norcross, Ga.). 1 μg of RNA is reverse transcribed to cDNA using the M-Mulv reverse transcriptase enzyme (Promega Corporation, Madison, Wis., USA). RT-qPCR of cDNA templates is carried out using TAQMAN probes for human α-synuclein (Hs00240906_M1) and TAQMAN masterMix (Applied Biosystems) and a Mx3005P real-time PCR system (Agilent Technologies Inc., Santa Clara, Calif.). Levels of alpha-tubulin mRNA are used to normalize the amounts of total RNA between samples. Fold changes are calculated as described by (Pfaffl, M. W. (2001). A new mathematical model for relative quantification in real-time RT-PCR. Nucleic Acids Res 29, e45).

Example B5

$\alpha_{2B}$ Pharmacology: Studies in Spontaneously Hypertensive Rat (SHR) Model of Hypertension Male spontaneously hypertensive rats (SHR), approximately 3 months of age and weighting approximately 250 grams are utilized. Free access to standard lab chow for rats and reverse osmosis (RO) water is granted. All aspects of this work, including housing, experimentation and disposal of animals are performed in general accordance with the Guide for the Care and Use of Laboratory Animals (National Academy Press, Washington, D.C., 1996).

The animals are anaesthetized with sodium pentobarbital (50 mg/kg IP). The left carotid artery when compound dosed orally (PO) or subcutaneously (SC); and both left carotid and femoral artery when compound dosed intravenous (i.v.) are cannulated with a polyethylene catheter (38 cm in length; PE60, Portex, Ltd.) connected with a polyurethane tubing (12 cm in length; PU-40, Cat. # BB520-40, Scientific Commodities, Inc.), which is tunneled under the skin and exited through the nape of the neck. The arterial cannula is connected to a pressure transducer through a swivel system, allowing free roaming during continuous recording of mean arterial pressure and heart rate. The animals are housed individually with food and water freely available during recovery. On the following day, the arterial cannula is connected via a Statham (P23×L) pressure transducer to a NEC/San-Ei amplifier and data acquisition and analysis system (Power Lab 8/SP) for direct mean arterial pressure and heart rate measurements.

The test compounds, dissolved in sterile saline, are administered subcutaneously (SC) or orally (PO), or by intravenous (i.v.) bolus administration in two minutes or the escalating doses of compound administration in every 30 minutes, with each dose and its strength delivered over 2 minutes as shown in the respective figures; the internal standard phentolamine is given by oral gavage. The control group received vehicle alone. Immediately before (−10 min and −5 min) and at 15 min, 30 min, 1 hr, 1.5 hr, 2 hr, 2.5 hr, 3 hr, 3.5 hr, and 4 hr post-dosing, systolic pressure blood pressure values are recorded. Effect of the test compounds on blood pressure is determined.

Example B6

$\alpha_{2B}$ Pharmacology: Studies in Healthy Dogs and Dexmedetomidine (DEX) Induced Beagle Dog Model of Hypertension These studies are conducted in both acute and chronic modes.

Four adult beagle dogs of both sex and weighted around 10 kg are chosen for the acute studies after a preliminary qualitative electrocardiogram/ECG, clinical pathology and physical examination. Upon arrival at the laboratory, the dogs are weighed and acclimated for a period of one week. Lab Diet certified canine diet #5007, PMI Nutrition International Inc is made available ad libitum to all dogs except during fasting periods. The dogs are surgically implanted with a pressure transducer equipped telemetry transmitter under sodium pentobarbitone anesthesia. The transmitter assembly is secured internally and the fluid-filled catheter is placed into an appropriate artery.

In the acute studies, the test compounds at different doses is administered by oral gavage, 30 minutes prior to intravenous dexmedetomidine (5 μg/kg) challenge. Dexmedetomidine administration is enabled by prior placement of a peripheral intravenous line. The same four dogs are received all four treatments in the order noted in the table below, with at least a 3-day washout period between treatments.

In another acute study, the test agent is administered a dose of 6 mg/kg by oral gavage to 4 healthy dogs; and the blood pressure monitored for a period of 4 hours.

For the chronic study mode (see Table B9), the test compound at 3 doses is administered by oral gavage once on day 1 and then twice/day on days 2 to 14, and finally once on day 15. The dexmedetomidine is administered on day −4 to check its effectiveness in inducing blood pressure, and once following the morning dose of test compound or vehicle on days 2, 7 and 14. Blood pressure and heart rate data are collected 1 h prior & 4 h post-morning dose on days 1, 2, 7, 14 and 15 to allow the appropriate data comparisons. Blood aliquots are saved at 4 h post-morning dose for exposure determination.

TABLE B9

Chronic dosing sequence and study design for test compound

| Test compound - 30 minute Pretreatment (mg/kg, p.o.) with b.i.d. regimen for 14 days | Dexmedetomidine Challenge (μg/kg, i.v.) | Number of Dogs |
|---|---|---|
| 0 | 5 | 6 |
| 6 | 5 | 6 |
| 18 | 5 | 6 |

| | Day | | | | | |
|---|---|---|---|---|---|---|
| | −4 | 1 | 2 | 7 | 14 | 15 |
| Compound dosed on | — | am | am/pm | from day 2 am/pm | to day 14 am/pm | Am |
| DEX* | Am | — | Am | am | Am | — |

*DEX administered 30 min following am dose of test compound.

In both acute and chronic studies, dogs are weighed before dosing. Cardiovascular evaluations at each dose of test compound are collected with animals gently restrained in a sling. Dogs are placed in the sling at least 1 hour prior to dose administration, and after at least 30 minutes of stable baseline data collection. The dogs are monitored continuously for 3-4 hours subsequent to test compound administration and summarized in 5-minute bins. The systolic blood pressure is collected. Data is reported as mean±SEM or mean.

In acute studies, oral administration of test compound dose-dependently reduced systolic blood pressure in both healthy and dexmedetomidine induced dogs that are tested in the acute mode.

Adrenergic receptors $\alpha_{2B}$ and $\alpha_{2A}$ mixed inhibitor's pharmacology—Studies in Spontaneously Hypertensive Rat (SHR) Model of Hypertension: Similar to dosing regimen for selective antagonists of adrenergic receptor $\alpha_{2B}$, the mixed inhibitors is dosed orally (PO) or intravenous (i.v bolus or escalating doses) to SHR rats. A compound that is an adrenergic receptor $\alpha_{2B}$ antagonist also showing adrenergic receptor $\alpha_{2A}$ antagonist and/or inverse agonist activity can be useful for reducing blood pressure in an individual with hypertension who is also suffering from metabolic syndrome.

Example B7

Peripheral and Central Effects of Test Compound on Blood Pressure in Conscious Rabbits Four adult New Zealand White rabbits of both sexes are chosen for these studies. The experiments are conducted in accordance with the Australian code of Practice for the Care and use of Animals for Scientific Purposes and approval is sought from the Animal Experimental Committee of Alfred Hospital, Baker IDI, Melbourne, Australia. The conscious rabbits are implanted with an intravenous catheter in marginal ear vein or by centrally by intracisternal catheter interfaced to a pressure transducer connected to a suitable recorder. To unveil peripheral effects of test compound, two sets of acute studies are conducted in rabbits. In the first set of studies, test compound is dosed to rabbit intravenously for a dose-response study with cumulative doses starting 0 (Ringer's Lock solution as a vehicle), 0.1, 0.3, 1, 3.2 and 10 mg/kg where each dose is tested on a separate day. A single intravenous bolus dose at 3 mg/kg is given and a time-course study is conducted in the second set of studies. Systolic, diastolic, mean and diastolic blood pressures are recorded in both the studies. Data collections are made for 3 hours in the second set of studies. Heart rate (HR) is derived electronically using an algorithm to determine HR from pulse interval. In a separate set of studies, Clonidine (positive control) is tested where all experimental procedures including dose-regimen are identical to that of the studies with test compound.

The mean arterial pressure responses to test compound is dose-dependent in the dose-response study with cumulative doses. Under similar conditions, Clonidine produces a maximum drop of arterial blood pressure of −6 mmHg before the blood pressure reversed back.

The cardiovascular effects of intracranial administration of test compound are tested in rabbits. Test compound is administered by infusion directly into the brain with the cannula delivering the compound placed directly into the 4th ventrical of the brain. Several doses are tested for cardiovascular effects, including effects on blood pressure and heart rate, following direct brain infusion. The blood pressure effects following intravenous and ventricular infusion provides the effect of the compound on the peripheral and central nervous systems respectively.

Example B8

Renal Effects of Compounds of the Invention in Conscious Rabbits

The long duration of blood pressure effect of Compounds of the invention results in a reduction in blood volume that can result from diueresis and/or the movement of fluid from the vascular space to the extravascular space. The effect of test compound on hematocrit levels is measured, compounds that reduce blood volume increase hematocrit. Characterization of the effect of $\alpha_{2B}$ antagonists on renal function is determined by measuring urine volume, urine sodium and urine potassium using methods described by Burke et al. (Effects of chronic sympatho-inhibition on renal excretory function in renovascular hypertension Sandra L. Burke, Roger G. Evans and Geoffrey A. Head. Journal of Hypertens 29:945-952 (2011).

Example B9

Human Clinical Studies

The compound is studied in a clinical trial of hypertensive patients who have not reached their blood pressure goals on current therapy. The target patient population are patients with refractory hypertension that have not reached their blood pressure goals despite use of at least 3 different blood pressure agents. The study compares the active compound against a matched placebo compound with the primary objective of comparing mean blood pressure change from baseline to the end of the study between the active compound and placebo.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of lowering blood pressure in an individual in need thereof comprising administering to the individual an effective amount of a compound of formulae (IA), (IB), (J-1) or (K-1), or a salt, solvate or N-oxide thereof, wherein:
formula (IA) is:

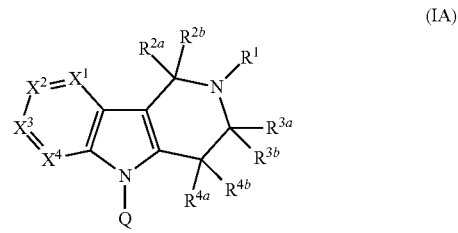

(IA)

wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^{2a}$ and $R^{4a}$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2CH_2$—) moiety or a propylene (—$CH_2CH_2CH_2$—) moiety, or $R^{4a}$ and $R^{2a}$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $X^1$, $X^2$, $X^3$ and $X^4$ is independently N, CH or $CR^6$;

Q is a substituted or unsubstituted aryl, substituted or unsubstituted heteroaryl, or substituted of unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and $R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, provided that:

(1) at least one of $X^1$, $X^2$, $X^3$ and $X^4$ is CH or $CR^6$;

(2) when each $X^1$, $X^2$, $X^3$ and $X^4$ is independently CH or $CR^6$, none of $R^1$, $R^{2a}$, $R^{2b}$, $R^{3a}$, $R^{3b}$, $R^{4a}$ and $R^{4b}$ are taken together to form a ring and Q is an unsubstituted 6-membered aryl or an unsubstituted 6-membered heteroaryl, then Q is other than unsubstituted phenyl, unsubstituted pyridyl and unsubstituted pyrimidyl;

(3) when each $X^1$, $X^2$, $X^3$ and $X^4$ is independently CH or $CR^6$, none of $R^1$, $R^{2a}$, $R^{2b}$, $R^{3a}$, $R^{3b}$, $R^{4a}$ and $R^{4b}$ are taken together to form a ring and Q is a substituted phenyl, then Q is a phenyl substituted with a substituent selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl; and (4) when each $X^1$, $X^2$, $X^3$ and $X^4$ is independently CH or $CR^6$, and $R^{2a}$ and $R^{3a}$ are taken together to form an ethylene (—$CH_2CH_2$—) moiety, then Q is a substituted aryl or substituted heteroaryl, where the substituted aryl or substituted heteroaryl is substituted with at least one substituent selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl;

formula (IB) is:

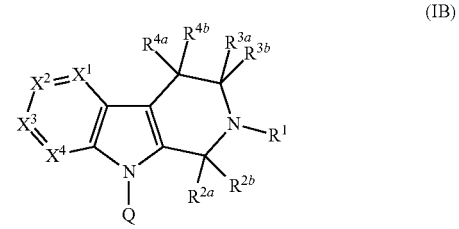

(IB)

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—CH₂CH₂—) moiety or a propylene (—CH₂CH₂CH₂—) moiety;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety, or $R^{2a}$ and $R^1$ are taken together to form a propylene (—CH₂CH₂CH₂—) moiety or a butylene (—CH₂CH₂CH₂CH₂—) moiety, or $R^{2a}$ and $R^{3a}$ are taken together to form an ethylene (—CH₂CH₂—) moiety or a propylene (—CH₂CH₂CH₂—) moiety, or $R^{2a}$ and $R^{4a}$ are taken together to form a methylene (—CH₂—) moiety or an ethylene (—CH₂CH₂—) moiety;

each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH₂CH₂CH₂—) moiety or a butylene (—CH₂CH₂CH₂CH₂—) moiety, or $R^{3a}$ and $R^{2a}$ are taken together to form an ethylene (—CH₂CH₂—) moiety or a propylene (—CH₂CH₂CH₂—) moiety, or $R^{3a}$ and $R^{4a}$ are taken together to form a propylene (—CH₂CH₂CH₂—) moiety or a butylene (—CH₂CH₂CH₂CH₂—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH₂CH₂—) moiety or a propylene (—CH₂CH₂CH₂—) moiety, or $R^{4a}$ and $R^{2a}$ are taken together to form a methylene (—CH₂—) moiety or an ethylene (—CH₂CH₂—) moiety, or $R^{4a}$ and $R^{3a}$ are taken together to form a propylene (—CH₂CH₂CH₂—) moiety or a butylene (—CH₂CH₂CH₂CH₂—) moiety;

each $X^1$, $X^2$, $X^3$ and $X^4$ is independently N, CH or $CR^6$;

Q is a substituted or unsubstituted aryl, substituted or unsubstituted heteroaryl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and $R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

provided that:

(1) at least one of $X^1$, $X^2$, $X^3$ and $X^4$ is $CR^6$;
(2) when none of $X^1$, $X^2$ and $X^3$ is N, and none of $R^1$, $R^{2a}$, $R^{2b}$, $R^{3a}$, $R^{3b}$, $R^{4a}$ and $R^{4b}$ are taken together to form a ring, then Q is other than an unsubstituted phenyl;
(3) when none of $X^1$, $X^2$, $X^3$ and $X^4$ is N, and $R^{2a}$ and $R^{2b}$ are taken together with the carbon to which they are attached to form a carbonyl moiety, then Q is other than a 4-substituted phenyl group; and
(4) when each $X^1$, $X^3$ and $X^4$ is CH, $X^2$ is $CR^6$ where $R^6$ is fluoro, and each $R^{2a}$, $R^{2b}$, $R^{3a}$, $R^{3b}$, $R^{4a}$ and $R^{4b}$ is H, then Q is other than 4-fluorophenyl;

formula (J-1) is:

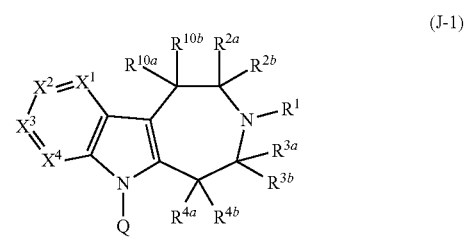

(J-1)

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{2(a/b)}$, $R^{3(a/b)}$, $R^{4(a/b)}$ or $R^{10(a/b)}$ to form a carbonyl moiety or a cycloalkyl moiety;

each $X^1$, $X^2$ and $X^3$ is independently N, CH or $CR^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and $R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;
provided that at least one of $X^1$, $X^2$, $X^3$ and $X^4$ is CH or $CR^6$;
and formula (K-1) is:

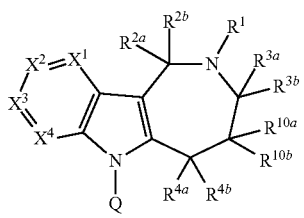

(K-1)

wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;
each $R^{2a}$, $R^{2b}$ $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{2(a/b)}$, $R^{3(a/b)}$, $R^{4(a/b)}$ or $R^{10(a/b)}$ to form a carbonyl moiety or a cycloalkyl moiety;
each $X^1$, $X^2$ and $X^3$ is independently N, CH or $CR^6$;
Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and
$R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;
provided that at least one of $X^1$, $X^2$, $X^3$ and $X^4$ is CH or $CR^6$;
and wherein the individual has high blood pressure or has one or more risk factors for developing high blood pressure.

2. The method of claim 1, wherein the individual has high blood pressure.

3. The method of claim 2, wherein the method reduces systolic blood pressure of the individual.

4. The method of claim 2, wherein the method reduces diastolic blood pressure of the individual.

5. The method of claim 2, wherein the method reduces (i) mean arterial blood pressure, or (ii) pulse pressure, of the individual.

6. The method of claim 3, wherein the method does not substantially increase heart rate of the individual.

7. The method of claim 1, wherein the individual has one or more risk factors for developing high blood pressure.

8. A method of (i) increasing renal blood flow, and/or (ii) decreasing sodium reabsorption, in an individual in need thereof comprising administering to the individual an effective amount of a compound of the formula (IA), (TB), (J-1) or (K-1), or a salt, solvate or N-oxide thereof, wherein:
formula (IA) is:

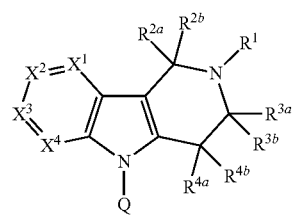

(IA)

wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;
each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or R$^{2a}$ and R$^{4a}$ are taken together to form a methylene (—CH$_2$—) moiety or an ethylene (—CH$_2$CH$_2$—) moiety;

each R$^{3a}$ and R$^{3b}$ is independently H, substituted or unsubstituted C$_1$-C$_8$ alkyl, halo, cyano, hydroxyl, alkoxy, nitro or R$^{3a}$ and R$^{3b}$ are taken together with the carbon to which they are attached to form a carbonyl moiety or a cycloalkyl moiety, or R$^{3a}$ and R$^1$ are taken together to form a propylene (—CH$_2$CH$_2$CH$_2$—) moiety or a butylene (—CH$_2$CH$_2$CH$_2$CH$_2$—) moiety, or R$^{3a}$ and R$^{2a}$ are taken together to form an ethylene (—CH$_2$CH$_2$—) moiety or a propylene (—CH$_2$CH$_2$CH$_2$—) moiety, or R$^{3a}$ and R$^{4a}$ are taken together to form a propylene (—CH$_2$CH$_2$CH$_2$—) moiety or a butylene (—CH$_2$CH$_2$CH$_2$CH$_2$—) moiety;

each R$^{4a}$ and R$^{4b}$ is independently H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or R$^{4a}$ and R$^{4b}$ are taken together with the carbon to which they are attached to form a carbonyl moiety or a cycloalkyl moiety, or R$^{4a}$ and R$^1$ are taken together to form an ethylene (—CH$_2$CH$_2$—) moiety or a propylene (—CH$_2$CH$_2$CH$_2$—) moiety, or R$^{4a}$ and R$^{2a}$ are taken together to form a methylene (—CH$_2$—) moiety or an ethylene (—CH$_2$CH$_2$—) moiety, or R$^{4a}$ and R$^{3a}$ are taken together to form a propylene (—CH$_2$CH$_2$CH$_2$—) moiety or a butylene (—CH$_2$CH$_2$CH$_2$CH$_2$—) moiety;

each X$^1$, X$^2$, X$^3$ and X$^4$ is independently N, CH or CR$^6$;

Q is a substituted or unsubstituted aryl, substituted or unsubstituted heteroaryl, or substituted of unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and R$^6$ is hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, provided that:
(1) at least one of X$^1$, X$^2$, X$^3$ and X$^4$ is CH or CR$^6$;
(2) when each X$^1$, X$^2$, X$^3$ and X$^4$ is independently CH or CR$^6$, none of R$^1$, R$^{2a}$, R$^{2b}$, R$^{3a}$, R$^{3b}$, R$^{4a}$ and R$^{4b}$ are taken together to form a ring and Q is an unsubstituted 6-membered aryl or an unsubstituted 6-membered heteroaryl, then Q is other than unsubstituted phenyl, unsubstituted pyridyl and unsubstituted pyrimidyl;
(3) when each X$^1$, X$^2$, X$^3$ and X$^4$ is independently CH or CR$^6$, none of R$^1$, R$^{2a}$, R$^{2b}$, R$^{3a}$, R$^{3b}$, R$^{4a}$ and R$^{4b}$ are taken together to form a ring and Q is a substituted phenyl, then Q is a phenyl substituted with a substituent selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl; and
(4) when each X$^1$, X$^2$, X$^3$ and X$^4$ is independently CH or CR$^6$, and R$^{2a}$ and R$^{3a}$ are taken together to form an ethylene (—CH$_2$CH$_2$—) moiety, then Q is a substituted aryl or substituted heteroaryl, where the substituted aryl or substituted heteroaryl is substituted with at least one substituent selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl;

formula (IB) is:

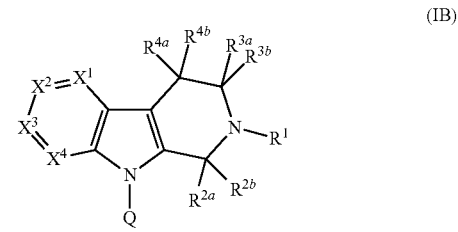

(IB)

wherein:
R$^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or R$^1$ and R$^{2a}$ are taken together to form a propylene (—CH$_2$CH$_2$CH$_2$—) moiety or a butylene (—CH$_2$CH$_2$CH$_2$CH$_2$—) moiety, or R$^1$ and R$^{3a}$ are taken together to form a propylene (—CH$_2$CH$_2$CH$_2$—) moiety or a butylene (—CH$_2$CH$_2$CH$_2$CH$_2$—) moiety, or R$^1$ and R$^{4a}$ are taken together to form an ethylene (—CH$_2$CH$_2$—) moiety or a propylene (—CH$_2$CH$_2$CH$_2$—) moiety;

each R$^{2a}$ and R$^{2b}$ is independently H, substituted or unsubstituted C$_1$-C$_8$ alkyl, halo, cyano, hydroxyl, alkoxy, nitro or R$^{2a}$ and R$^{2b}$ are taken together with the carbon to which they are attached to form a carbonyl moiety or a cycloalkyl moiety, or R$^{2a}$ and R$^1$ are taken together to form a propylene (—CH$_2$CH$_2$CH$_2$—) moiety or a butylene (—CH$_2$CH$_2$CH$_2$CH$_2$—) moiety, or R$^{2a}$ and R$^{3a}$ are taken together to form an ethylene (—CH$_2$CH$_2$—) moiety or a propylene (—CH$_2$CH$_2$CH$_2$—) moiety, or R$^{2a}$ and R$^{4a}$ are taken together to form a methylene (—CH$_2$—) moiety or an ethylene (—CH$_2$CH$_2$—) moiety;

each R$^{3a}$ and R$^{3b}$ is independently H, substituted or unsubstituted C$_1$-C$_8$ alkyl, halo, cyano, hydroxyl, alkoxy, nitro or R$^{3a}$ and R$^{3b}$ are taken together with the carbon to which they are attached to form a carbonyl moiety or a cycloalkyl moiety, or R$^{3a}$ and R$^1$ are taken together to form a propylene (—CH$_2$CH$_2$CH$_2$—) moiety or a butylene (—CH$_2$CH$_2$CH$_2$CH$_2$—) moiety, or R$^{3a}$ and R$^{2a}$ are taken together to form an ethylene (—CH$_2$CH$_2$—) moiety or a propylene (—CH$_2$CH$_2$CH$_2$—) moiety, or R$^{3a}$ and R$^{4a}$ are taken together to form a propylene (—CH$_2$CH$_2$CH$_2$—) moiety or a butylene (—CH$_2$CH$_2$CH$_2$CH$_2$—) moiety;

each R$^{4a}$ and R$^{4b}$ is independently H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or R$^{4a}$ and R$^{4b}$ are taken together with the carbon to which they are attached to form a carbonyl moiety or a cycloalkyl moiety, or R$^{4a}$ and R$^1$ are taken together to form an ethylene (—CH$_2$CH$_2$—) moiety or a propylene (—CH$_2$CH$_2$CH$_2$—) moiety, or R$^{4a}$ and R$^{2a}$ are taken together to form a methylene (—CH$_2$—) moiety or an ethylene (—CH$_2$CH$_2$—) moiety, or R$^{4a}$ and R$^{3a}$ are taken together to form a propylene (—CH$_2$CH$_2$CH$_2$—) moiety or a butylene (—CH$_2$CH$_2$CH$_2$CH$_2$—) moiety;

each X$^1$, X$^2$, X$^3$ and X$^4$ is independently N, CH or CR$^6$;

Q is a substituted or unsubstituted aryl, substituted or unsubstituted heteroaryl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and R$^6$ is hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

provided that:
(1) at least one of X$^1$, X$^2$, X$^3$ and X$^4$ is CR$^6$;
(2) when none of X$^1$, X$^2$ and X$^3$ is N, and none of R$^1$, R$^{2a}$, R$^{2b}$, R$^{3a}$, R$^{3b}$, R$^{4a}$ and R$^{4b}$ are taken together to form a ring, then Q is other than an unsubstituted phenyl;
(3) when none of X$^1$, X$^2$, X$^3$ and X$^4$ is N, and R$^{2a}$ and R$^{2b}$ are taken together with the carbon to which they are attached to form a carbonyl moiety, then Q is other than a 4-substituted phenyl group; and
(4) when each X$^1$, X$^3$ and X$^4$ is CH, X$^2$ is CR$^6$ where R$^6$ is fluoro, and each R$^{2a}$, R$^{2b}$, R$^{3a}$, R$^{3b}$, R$^{4a}$ and R$^{4b}$ is H, then Q is other than 4-fluorophenyl;

formula (J-1) is:

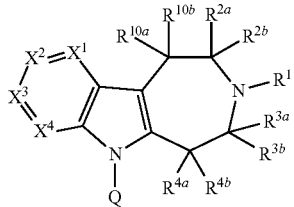

(J-1)

wherein:
R$^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each R$^{2a}$, R$^{2b}$ R$^{3a}$, R$^{3b}$, R$^{4a}$, R$^{4b}$, R$^{10a}$ and R$^{10b}$ is independently H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal R$^{2(a/b)}$, R$^{3(a/b)}$, R$^{4(a/b)}$ or R$^{10(a/b)}$ to form a carbonyl moiety or a cycloalkyl moiety;

each X$^1$, X$^2$ and X$^3$ is independently N, CH or CR$^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and R$^6$ is hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

provided that at least one of X$^1$, X$^2$, X$^3$ and X$^4$ is CH or CR$^6$;

and formula (K-1) is:

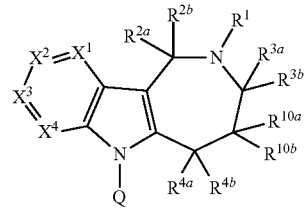

(K-1)

wherein:
R$^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{2(a/b)}$, $R^{3(a/b)}$, $R^{4(a/b)}$ or $R^{10(a/b)}$ to form a carbonyl moiety or a cycloalkyl moiety;

each $X^1$, $X^2$ and $X^3$ is independently N, CH or $CR^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and $R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

provided that at least one of $X^1$, $X^2$, $X^3$ and $X^4$ is CH or $CR^6$;

and wherein the method results in increase in renal blood flow or results in decrease in sodium reabsorption.

9. The method of claim 8, wherein the method results in increase in renal blood flow.

10. The method of claim 8, wherein the method results in decrease in sodium reabsorption.

11. The method of claim 9, wherein the method results in increase in urine sodium content and/or increase in urine volume.

12. The method of claim 9, wherein the method results in any one or more of: (i) reducing edema, (ii) reducing elevated blood urea nitrogen to creatinine (BUN/Cr) ratio, and (iii) decreasing creatinine levels.

13. The method of claim 1, wherein the individual has or is at risk of developing acute or chronic congestive heart failure, acute decompensated congestive heart failure, acute or chronic renal failure, or acute or chronic renal failure due to renal insufficiency.

14. A method of treating a disease or condition that is responsive to any one or more of: (i) a decrease in blood pressure; (ii) an increase in renal blood flow; and (iii) a decrease of sodium reabsorption, comprising administering to an individual in need thereof an effective amount of a compound of formula (IA), (IB), (J-1) or (K-1), or a salt, solvate or N-oxide thereof, wherein:

formula (IA) is:

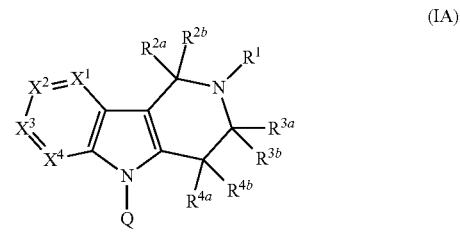

(IA)

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^{4a}$ are taken together to form an ethylene (—CH$_2$CH$_2$—) moiety or a propylene (—CH$_2$CH$_2$CH$_2$—) moiety;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety, or $R^{2a}$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^{2a}$ and $R^{4a}$ are taken together to form a methylene (—CH$_2$—) moiety or an ethylene (—CH$_2$CH$_2$—) moiety;

each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$CH$_2$—) moiety or a propylene (—CH$_2$CH$_2$CH$_2$—) moiety, or R$^{4a}$ and R$^{2a}$ are taken together to form a methylene (—CH$_2$—) moiety or an ethylene (—CH$_2$CH$_2$—) moiety, or R$^{4a}$ and R$^{3a}$ are taken together to form a propylene (—CH$_2$CH$_2$CH$_2$—) moiety or a butylene (—CH$_2$CH$_2$CH$_2$CH$_2$—) moiety;
each X$^1$, X$^2$, X$^3$ and X$^4$ is independently N, CH or CR$^6$;
Q is a substituted or unsubstituted aryl, substituted or unsubstituted heteroaryl, or substituted of unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and
R$^6$ is hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl,
provided that:
(1) at least one of X$^1$, X$^2$, X$^3$ and X$^4$ is CH or CR$^6$;
(2) when each X$^1$, X$^2$, X$^3$ and X$^4$ is independently CH or CR$^6$, none of R$^1$, R$^{2a}$, R$^{2b}$, R$^{3a}$, R$^{3b}$, R$^{4a}$ and R$^{4b}$ are taken together to form a ring and Q is an unsubstituted 6-membered aryl or an unsubstituted 6-membered heteroaryl, then Q is other than unsubstituted phenyl, unsubstituted pyridyl and unsubstituted pyrimidyl;
(3) when each X$^1$, X$^2$, X$^3$ and X$^4$ is independently CH or CR$^6$, none of R$^1$, R$^{2a}$, R$^{2b}$, R$^{3a}$, R$^{3b}$, R$^{4a}$ and R$^{4b}$ are taken together to form a ring and Q is a substituted phenyl, then Q is a phenyl substituted with a substituent selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl; and
(4) when each X$^1$, X$^2$, X$^3$ and X$^4$ is independently CH or CR$^6$, and R$^{2a}$ and R$^{3a}$ are taken together to form an ethylene (—CH$_2$CH$_2$—) moiety, then Q is a substituted aryl or substituted heteroaryl, where the substituted aryl or substituted heteroaryl is substituted with at least one substituent selected from the group consisting of substituted or unsubstituted aryl, substituted or unsubstituted heteroaryl, substituted or unsubstituted cycloalkyl, substituted or unsubstituted cycloalkenyl, substituted or unsubstituted heterocyclyl, and substituted or unsubstituted aralkyl;
formula (IB) is:

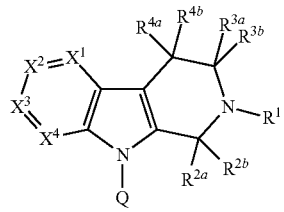

(IB)

wherein:
R$^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or R$^1$ and R$^{2a}$ are taken together to form a propylene (—CH$_2$CH$_2$CH$_2$—) moiety or a butylene (—CH$_2$CH$_2$CH$_2$CH$_2$—) moiety, or R$^1$ and R$^{3a}$ are taken together to form a propylene (—CH$_2$CH$_2$CH$_2$—) moiety or a butylene (—CH$_2$CH$_2$CH$_2$CH$_2$—) moiety, or R$^1$ and R$^{4a}$ are taken together to form an ethylene (—CH$_2$CH$_2$—) moiety or a propylene (—CH$_2$CH$_2$CH$_2$—) moiety;
each R$^{2a}$ and R$^{2b}$ is independently H, substituted or unsubstituted C$_1$-C$_8$ alkyl, halo, cyano, hydroxyl, alkoxy, nitro or R$^{2a}$ and R$^{2b}$ are taken together with the carbon to which they are attached to form a carbonyl moiety or a cycloalkyl moiety, or R$^{2a}$ and R$^1$ are taken together to form a propylene (—CH$_2$CH$_2$CH$_2$—) moiety or a butylene (—CH$_2$CH$_2$CH$_2$CH$_2$—) moiety, or R$^{2a}$ and R$^{3a}$ are taken together to form an ethylene (—CH$_2$CH$_2$—) moiety or a propylene (—CH$_2$CH$_2$CH$_2$—) moiety, or R$^{2a}$ and R$^{4a}$ are taken together to form a methylene (—CH$_2$—) moiety or an ethylene (—CH$_2$CH$_2$—) moiety;
each R$^{3a}$ and R$^{3b}$ is independently H, substituted or unsubstituted C$_1$-C$_8$ alkyl, halo, cyano, hydroxyl, alkoxy, nitro or R$^{3a}$ and R$^{3b}$ are taken together with the carbon to which they are attached to form a carbonyl moiety or a cycloalkyl moiety, or R$^{3a}$ and R$^1$ are taken together to form a propylene (—CH$_2$CH$_2$CH$_2$—) moiety or a butylene (—CH$_2$CH$_2$CH$_2$CH$_2$—) moiety, or R$^{3a}$ and R$^{2a}$ are taken together to form an ethylene (—CH$_2$CH$_2$—) moiety or a propylene (—CH$_2$CH$_2$CH$_2$—) moiety, or R$^{3a}$ and R$^{4a}$ are taken together to form a propylene (—CH$_2$CH$_2$CH$_2$—) moiety or a butylene (—CH$_2$CH$_2$CH$_2$CH$_2$—) moiety;
each R$^{4a}$ and R$^{4b}$ is independently H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or R$^{4a}$ and R$^{4b}$ are taken together with the carbon to which they are attached to form a carbonyl moiety or a cycloalkyl moiety, or R$^{4a}$ and R$^1$ are taken together to form an ethylene (—CH$_2$CH$_2$—) moiety or a propylene (—CH$_2$CH$_2$CH$_2$—) moiety, or R$^{4a}$ and R$^{2a}$ are taken together to form a methylene (—CH$_2$—) moiety or an ethylene (—CH$_2$CH$_2$—) moiety, or R$^{4a}$ and R$^{3a}$ are taken together to form a propylene (—CH$_2$CH$_2$CH$_2$—) moiety or a butylene (—CH$_2$CH$_2$CH$_2$CH$_2$—) moiety;
each X$^1$, X$^2$, X$^3$ and X$^4$ is independently N, CH or CR$^6$;
Q is a substituted or unsubstituted aryl, substituted or unsubstituted heteroaryl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and
R$^6$ is hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

provided that:
(1) at least one of $X^1$, $X^2$, $X^3$ and $X^4$ is $CR^6$;
(2) when none of $X^1$, $X^2$ and $X^3$ is N, and none of $R^1$, $R^{2a}$, $R^{2b}$, $R^{3a}$, $R^{3b}$, $R^{4a}$ and $R^{4b}$ are taken together to form a ring, then Q is other than an unsubstituted phenyl;
(3) when none of $X^1$, $X^2$, $X^3$ and $X^4$ is N, and $R^{2a}$ and $R^{2b}$ are taken together with the carbon to which they are attached to form a carbonyl moiety, then Q is other than a 4-substituted phenyl group; and
(4) when each $X^1$, $X^3$ and $X^4$ is CH, $X^2$ is $CR^6$ where $R^6$ is fluoro, and each $R^{2a}$, $R^{3b}$, $R^{4a}$ and $R^{4b}$ is H, then Q is other than 4-fluorophenyl;

formula (J-1) is:

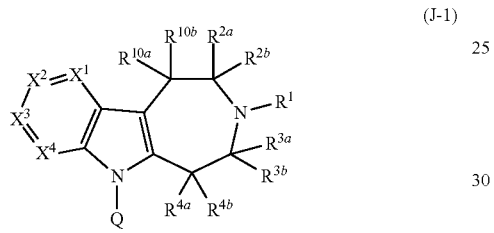

(J-1)

wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$ $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{2(a/b)}$, $R^{3(a/b)}$, $R^{4(a/b)}$ or $R^{10(a/b)}$ to form a carbonyl moiety or a cycloalkyl moiety;

each $X^1$, $X^2$ and $X^3$ is independently N, CH or $CR^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and $R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

provided that at least one of $X^1$, $X^2$, $X^3$ and $X^4$ is CH or $CR^6$;

and formula (K-1) is:

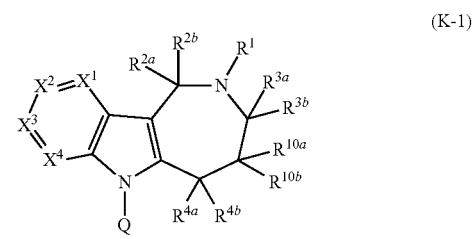

(K-1)

wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$ $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{2(a/b)}$, $R^{3(a/b)}$, $R^{4(a/b)}$ or $R^{10(a/b)}$ to form a carbonyl moiety or a cycloalkyl moiety;

each $X^1$, $X^2$ and $X^3$ is independently N, CH or $CR^6$;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, or substituted or unsubstituted aralkyl, wherein the aralkyl is a fused ring system where at least one cycloalkyl moiety is fused with at least one aryl moiety and wherein the aralkyl is attached to the parent structure via the cycloalkyl moiety or the aryl moiety; and $R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

provided that at least one of $X^1$, $X^2$, $X^3$ and $X^4$ is CH or $CR^6$;

and wherein the disease or condition is hypertension, hypertensive emergency, or a cardiac or renal disease or condition.

15. The method of claim 14, wherein the disease or condition is hypertension.

16. The method of claim 15, wherein the disease or condition is treatment-resistant hypertension.

17. The method of claim 14, wherein the disease or condition is hypertensive emergency.

18. The method of claim 14, wherein the disease or condition is a cardiac or renal disease or condition.

19. The method of claim 1, wherein the compound is selected from the group consisting of Compound Nos. 1-231 as depicted in Table 1 and salts thereof.

20. The method of claim 1, wherein the compound is of the formula (IA5):

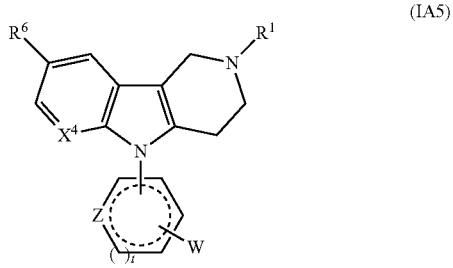

(IA5)

or a salt thereof, where $R^6$ and $X^4$ are as defined in claim 1 for formula (IA) and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

Z is C, NH, N—CH$_3$, O or S;

t is 0 or 1;

W is: (i) a substituted or unsubstituted aryl, or a substituted or unsubstituted heteroaryl that is bound to the Z-containing ring via a single bond at any available position or is fused to the Z-containing ring at two adjacent positions, (ii) a substituted amino, provided that $R^1$ is a $C_1$-$C_8$ alkyl when W is a substituted amino, or (iii) H, provided that W is only H when the Z-containing ring is a 5-membered heteroaryl moiety; and wherein the Z-containing ring is aromatic and is attached to the parent structure at any available ring position.

21. The method of claim 1, wherein the compound is of the formula (A1) or (A2):

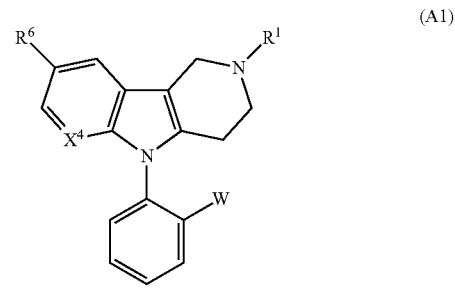

(A1)

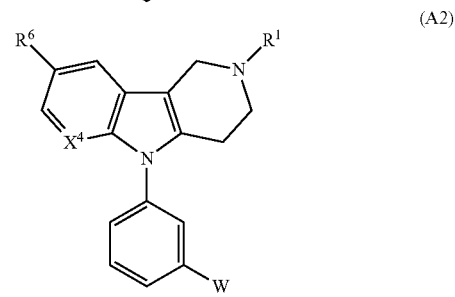

(A2)

or a salt thereof; wherein $R^6$ and $X^4$ are as defined in claim 1 for formula (IA), and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy; and W is a substituted amino, substituted or unsubstituted aryl, or substituted or unsubstituted heteroaryl.

22. The method of claim 1, wherein the compound is of the formula (IA7):

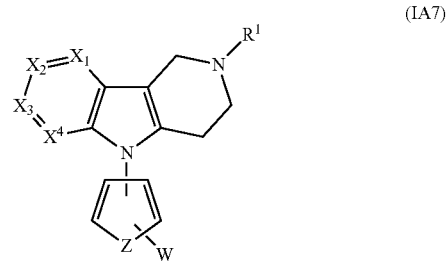

(IA7)

or a salt thereof, where $X^1$, $X^2$, $X^3$ and $X^4$ are as defined in claim 1 for formula (IA) and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

W is H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl or sulfonylamino; and Z is NH, N—$CH_3$, O or S.

23. The method of claim 1, wherein the compound is of the formula (B1), (B2), (B3), (B4), (B5) or (B6):

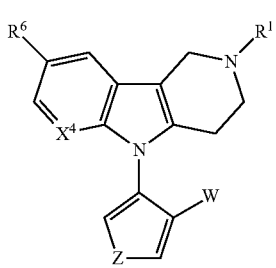
(B1)

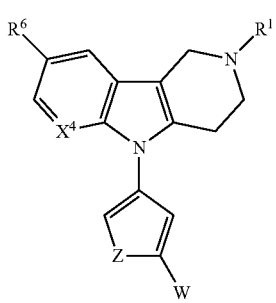
(B2)

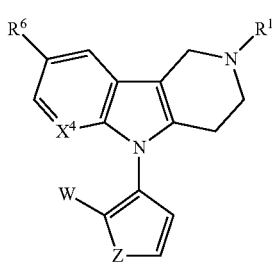
(B3)

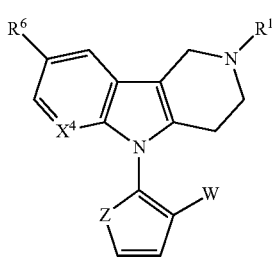
(B4)

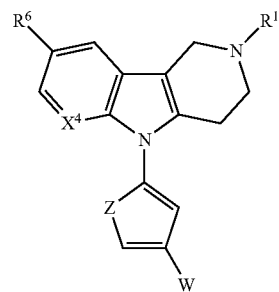
(B5)

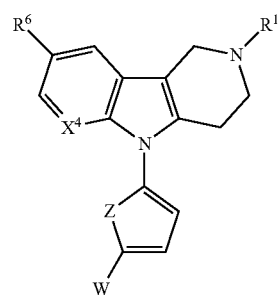
(B6)

or a salt thereof; wherein $R^6$ and $X^4$ are as defined in claim 1 for formula (IA), and wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

Z is NH, N—$CH_3$, O or S; and

W is H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl or sulfonylamino.

24. The method of claim 8, wherein the compound is selected from the group consisting of Compound Nos. 1-231 as depicted in Table 1 and salts thereof.

25. The method of claim 14, wherein the compound is selected from the group consisting of Compound Nos. 1-231 as depicted in Table 1 and salts thereof.

* * * * *